(12) United States Patent
Qing et al.

(10) Patent No.: US 12,247,990 B2
(45) Date of Patent: Mar. 11, 2025

(54) MOLECULAR HOPPER

(71) Applicant: OXFORD UNIVERSITY INNOVATION LIMITED, Oxford (GB)

(72) Inventors: Yujia Qing, Oxford (GB); John Hagan Pryce Bayley, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1003 days.

(21) Appl. No.: 17/260,110

(22) PCT Filed: Jul. 16, 2019

(86) PCT No.: PCT/GB2019/051990
§ 371 (c)(1),
(2) Date: Jan. 13, 2021

(87) PCT Pub. No.: WO2020/016573
PCT Pub. Date: Jan. 23, 2020

(65) Prior Publication Data
US 2021/0318340 A1    Oct. 14, 2021

(30) Foreign Application Priority Data
Jul. 16, 2018 (GB) .................................. 1811623

(51) Int. Cl.
*G01N 35/00* (2006.01)
*C12Q 1/6869* (2018.01)
*G01N 33/487* (2006.01)

(52) U.S. Cl.
CPC ..... *G01N 35/00029* (2013.01); *C12Q 1/6869* (2013.01); *G01N 33/48721* (2013.01); *G01N 35/00584* (2013.01)

(58) Field of Classification Search
None
See application file for complete search history.

(56) References Cited

U.S. PATENT DOCUMENTS

| 6,464,842 B1 | 10/2002 | Golovchenko et al. |
| 7,253,434 B2 | 8/2007 | Golovchenko et al. |
| 7,258,838 B2 | 8/2007 | Li et al. |

(Continued)

FOREIGN PATENT DOCUMENTS

| CN | 102834527 A | 12/2012 |
| CN | 102 890 474 A | 1/2013 |

(Continued)

OTHER PUBLICATIONS

Alegre-Cebollada et al., "Direct observation of disulfide isomerization in a single protein," Nat. Chem., vol. 3: 882-887 (2011).

(Continued)

*Primary Examiner* — J. Christopher Ball
(74) *Attorney, Agent, or Firm* — Nelson Mullins Riley & Scarborough LLP; Jane E. Remillard, Esq.; Christopher L. Frank

(57) ABSTRACT

Provided herein are methods for moving molecular hoppers along tracks; methods of characterising an analyte using molecular hoppers; kits for characterising an analyte; and molecule hoppers per se and systems comprising such hoppers. The invention particularly relates to the use of such methods and kits in the characterisation of analytes.

33 Claims, 33 Drawing Sheets
Specification includes a Sequence Listing.

(56) References Cited

U.S. PATENT DOCUMENTS

| | | | |
|---|---|---|---|
| 7,466,069 | B2 | 12/2008 | Golovchenko et al. |
| 7,468,271 | B2 | 12/2008 | Golovchenko et al. |

FOREIGN PATENT DOCUMENTS

| | | |
|---|---|---|
| WO | 00/28312 A1 | 5/2000 |
| WO | 03/003446 A2 | 1/2003 |
| WO | 2005/061383 A1 | 7/2005 |
| WO | 2006/028508 A2 | 3/2006 |
| WO | 2006/100484 A2 | 9/2006 |
| WO | 2008/102120 A1 | 8/2008 |
| WO | 2008/102121 A1 | 8/2008 |
| WO | 2009/035647 A1 | 3/2009 |
| WO | 2009/077734 A2 | 6/2009 |
| WO | 2011/067559 A1 | 6/2011 |
| WO | 2013/083983 A1 | 6/2013 |

OTHER PUBLICATIONS

Altschul S. F., "A protein alignment scoring system sensitive at all evolutionary distances," J Mol Evol., vol. 36: 290-300 (1993).

Altschul, S.F et al., "Basic local alignment search tool," J Mol Biol., vol. 215:403-410 (1990).

Bach, R. et al., "Mechanism of thiolate-disulfide interchange reactions in biochemistry," J. Org. Chem., vol. 73: 12-21 (2008).

Barrell, M. et al., "Light-driven transport of a molecular walker in either direction along a molecular track," Angew. Chem. Int. Ed., vol. 50: 2 pages (2011).

Bayley, H. et al., Chapter 10: Single-Molecule Covalent chemistry in a Protein Nanoreactor, Single Molecules and Nanotechnology, Springer Series in Biophysics 12 (eds. Rigler, R. & Vogel, H.) 251-277 (2008).

Bayley, H., "Nanopore sequencing: from imagination to reality," Clin. Chem, vol. 61: 25-31 (2015).

Beedle, A. et al., "Protein S-sulfenylation is a fleeting molecular switch that regulates non-enzymatic oxidative folding" Nat. Commun., vol. 7: 12490 (2016).

Beedle, A. et al., "Forcing the reversibility of a mechanochemical reaction," Nat. Commun, vol. 9: 3155 (2018).

Beedle, A. et al., "Tailoring protein nanomechanics with chemical reactivity," Nat. Commun., vol. 8: 15658 (2017).

Garcia-Manyes and Beedle, "Steering chemical reactions with force," Nat. Rev. Chem.1, 0083 (2017).

Belowich M. et al., "Dynamic imine chemistry," Chem Soc Rev., vol. 41: 2003-2024 (2012).

Beves, J. et al., "Toward metal complexes that can directionally walk along tracks: controlled stepping of a molecular biped with a palladium(II) foot," J. Am. Chem. Soc., vol. 136: 2094-2100 (2014).

Booth, M. et al., "Light-activated communication in synthetic tissues," Sci. Adv, vol. 2: e1600056 (2016).

Bosco, A. et al., "Elastic properties and secondary structure formation of single-stranded DNA at monovalent and divalent salt conditions," Nucleic Acids Res., vol. 42: 2064-2074 (2014).

Braha, O. et al., "Designed protein pores as components for biosensors," Chem Biol., vol. 4(7):497-505 (1997).

Breyer, W.A., "A structural basis for processivity," Protein Sci., vol. 10:1699-1711 (2001).

Campaña, A. et al., "A small molecule that walks non-directionally along a track without external intervention" Angew. Chem. Int. Ed., vol. 51: 5480-5483 (2012).

Campaña, A., et al. "One-dimensional random walk of a synthetic small molecule toward a thermodynamic sink," J. Am. Chem. Soc., vol. 135: 8639-45 (2013).

Carson, S. et al., "Challenges in DNA motion control and sequence readout using nanopore devices," Nanotehcnology, vol. 26: 074004 (2015).

Case, R. et al., "The directional preference of kinesin motors is specified by an element outside of the motor catalytic domain," Cell, vol. 90:959-966 (1997).

Cha, T-G. et al., "A synthetic DNA motor that transports nanoparticles along carbon nanotubes," .Nat. Nanotechnol., vol. 9: 39-43 (2014).

Cheng, C. et al., "An artificial molecular pump," Nat. Nanotechnol., vol. 10: 547-553 (2015).

Chin, J. et al., "Expanding and reprogramming the genetic code of cells and animals," Annu. Rev. Biochem., vol. 83: 379-408 (2014).

Cross, R., "Prime movers: the mechanochemistry of mitotic kinesins," Nat. Rev. Mol. Cell Biol., vol. 15: 257-271 (2014).

Davis, H. et al., "Harnessing non-covalent interactions to exert control over regioselectivity and site-selectivity in catalytic reactions" Chem. Sci., vol. 8: 864-877 (2017).

De Poli, M. et al. "Conformational photoswitching of a synthetic peptide foldamer bound within a phospholipid bilayer," Science, vol. 352:575-580 (2016).

Depuydt, M. et al., "How proteins form disulfide bonds," Antioxid. Redox Signal., vol. 15: 49-66 (2011).

Deutman, A. et al., "Mechanism of threading a polymer through a macrocyclic ring," Science, vol. 322: 1668-1671 (2008).

Devereux, J. et al., "A comprehensive set of sequence analysis programs for the VAX," Nucleic Acids Research, vol. 12: 387-395 (1984).

Diehl et al., "Click and chemically triggered declick reactions through reversible amine and thiol coupling via a conjugate acceptor," Nat Chem., vol. 8: 968-973 (2016).

Dodani, S. et al., "Discovery of a regioselectivity switch in nitrating P450s guided by molecular dynamics simulations and Markov models," Nat. Chem., vol. 8: 419-425 (2016).

Erbas-Cakmak, S. et al., "Artificial Molecular Machines," Chem. Rev., vol. 115: 10081-10206 (2015).

Erbas-Cakmak, S. et al., "Rotary and linear molecular motors driven by pulses of a chemical fuel," Science, vol. 358: 340-343 (2017).

Fernandes, P. et al., "Theoretical insights into the mechanism for thiol/disulfide exchange," Chem. Eur. J., vol. 10: 257-266 (2004).

Frisch, H. et al., "Wavelength Gated Dynamic Covalent Chemistry," Angew Chem Int Ed Engl., vol. 57: 2036-2045 (2018).

Gennerich, A. et al., "Walking the walk: how kinesin and dynein coordinate their steps," (2009) Curr. Opin. Cell Biol., vol. 21:59-67 (2009).

Gonzalez-Perez, A. et al., "Biomimetic triblock copolymer membrane arrays: a stable template for functional membrane proteins," Langmuir, vol. 25: 10447-10450 (2009).

Gu, H. et al., "A proximity-based programmable DNA nanoscale assembly line," Nature, vol. 465: 202-205 (2010).

Gyarfas, B. et al., "Mapping the position of DNA polymerase-bound DNA templates in a nanopore at 5 A resolution," ACS Nano, vol. 3: 1457-1466 (2009).

Hammerstein, A. et al., "Single-molecule kinetics of two-step divalent cation chelation," Angew. Chem. Int. Ed, vol. 49: 5085-5090 (2010).

He, Y. et al., "Autonomous multistep organic synthesis in a single isothermal solution mediated by a DNA walker," Nat. Nanotechnol., vol. 5: 778-782 (2010).

Henikoff, S. et al., "Amino acid substitution matrices from protein blocks," Proc. Natl. Acad. Sci. USA, vol. 89: 10915-10919 (1992).

Holden, M et al., "Direct introduction of single protein channels and pores into lipid bilayers," J. Am. Chem. Soc., vol. 127:6502-6503(2005).

Holden, M. et al., "Functional bionetworks from nanoliter water droplets," J Am Chem Soc.. vol. 129(27): 8650-8655 (2007).

Howorka, S. et al., "Probing distance and electrical potential within a protein pore with tethered DNA," Biophys. J., vol. 83: 3202-3210 (2002).

Huang, S. et al., "High-throughput optical sensing of nucleic acids in a nanopore array," Nature Nanotechnology, vol. 10: 986-992 (2015).

Hunter, C. et al., "What is cooperativity?," Angew. Chem. Int. Ed., vol. 48: 7488-7499 (2009).

Huxley, M. et al., "Protecting-Group-Free Site-Selective Reactions in a Metal-Organic Framework Reaction Vessel," J. Am. Chem. Soc., vol. 140: 6416-6425 (2018).

Iacovache, I. et al., "Cryo-EM structure of aerolysin variants reveals a novel protein fold and the pore-formation process," Nat. Commun., vol. 7: 12062 (2016).

(56) References Cited

OTHER PUBLICATIONS

Ibarra, B. et al., "Proofreading dynamics of a processive DNA polymerase," EMBO J., vol. 28: 2794-2802 (2009).
International Preliminary Report on Patentability, PCT/GB2019/051990, dated Jan. 19, 2021, 7 pages.
International Search Report and Written Opinion, PCT/GB2019/051990, dated Aug. 27, 2019, 12 pages.
Janout, V. et al., "Bioconjugate-based molecular umbrellas," Bioconjug. Chem, vol. 20: 183-92 (2009).
Janout, V. et al., "Molecular umbrella-assisted transport of thiolated AMP and ATP across phospholipid bilayers," Bioconjug. Chem., vol. 13: 351-356 (2012).
Jiang, J. et al., "Atomic structure of anthrax protective antigen pore elucidates toxin translocation," Nature, vol. 521: 545-549 (2015).
Jin, Y. et al., "Recent advances in dynamic covalent chemistry," Chem Soc Rev, vol. 42: 6634-6654 (2013).
Joshi, G, et al., "Dynamic thiol exchange with ß-sulfido-a,ß-unsaturated carbonyl compounds and dithianes," Org Lett, vol. 14: 4714-4717 (2012).
Karlin, S. et al., "Applications and statistics for multiple high-scoring segments in molecular sequences," Proc. Natl. Acad. Sci. USA, vol. 90: 5873-5787 (1993).
Kassem, S. et al., "Stereodivergent synthesis with a programmable molecular machine," Nature, vol. 549: 374-378 (2017).
Keire et al. (1992) J. Org. Chem. 57, 123-127.
Kolšek, K. et al., "Accessibility explains preferred thiol-disulfide isomerization in a protein domain," Sci. Rep., vol. 7: 9858 (2017).
Koumura, L. et al., "Light-driven monodirectional molecular rotor," Nature, vol. 401: 152-155 (1999).
Krishnamurthy, V. et al., "Dependence of effective molarity on linker length for an intramolecular protein-ligand system," J. Am. Chem. Soc., vol. 129,:1312-1320 (2007).
Langecker, M. et al., "Synthetic lipid membrane channels formed by designed DNA nanostructures," Science, vol. 338: 932-936 (2012).
Langton, M. et al. "Langton et al. (2017) Nat. Chem. 9, 426-430," Nat. Chem., vol. 9; 426-430 (2017).
Lee, J. et al., "Semisynthetic Nanoreactor for Reversible Single-Molecule Covalent Chemistry," ACS Nano, vol. 10: 8843-8850 (2016).
Lentini, R. et al., "Integrating artificial with natural cells to translate chemical messages that direct E. coli behaviour," Nat. Commun. 5, pp. 1-6 (2014).
Lieberman KR et al., "Processive replication of single DNA molecules in a nanopore catalyzed by phi29 DNA polymerase," J Am Chem Soc., vol. 132(50): 17961-17972 (2010).
Lister et al. (2017) Nat. Chem. 9, 420-425.
Lu, B. et al., "Thermal Motion of DNA in an MspA Pore," Biophys. J., vol. 109: 1439-1445 (2015).
Luchian, T. et al., "Single-molecule covalent chemistry with spatially separated reactants," Angew. Chem. Int. Ed., vol. 42: 3766-3771 (2003).
Mahatthananchai, J. et al., "Catalytic selective synthesis," Angew. Chem. Int. Ed, vol. 51: 10954-10990 (2012).
Messens, J. et al., "How thioredoxin can reduce a buried disulphide bond," J. Mol. Biol., vol. 339:527-537 (2004).
Miles, G. et al., "Properties of Bacillus cereus hemolysin II: a heptameric transmembrane pore," Protein Sci., vol. 11: 1813-1824 (2009).
Montal, M. et al., "Formation of bimolecular membranes from lipid monolayers and a study of their electrical properties," Proc. Natl. Acad. Sci. USA, vol. 69: 3561-3566 (1972).
Murzin, A. et al., "Principles determining the structure of beta-sheet barrels in proteins. II. The observed structures," J Mol Biol., vol. 236:1382-1400 (1994).
Nakane, J. et al., "A nanosensor for transmembrane capture and identification of single nucleic Acid molecules," Biophys. J., vol. 87: 615-621 (2004).
Nicolai and Sachs (2013) Biophys. Rev. Lett. 08, 191-211.

Noireaux, V. et al., "A vesicle bioreactor as a step toward an artificial cell assembly," Proc. Natl. Acad. Sci., vol. 101: 17669-17674 (2004).
Pace, C. et al., "Protein ionizable groups: pK values and their contribution to protein stability and solubility," J. Biol. Chem., vol. 284, 13285-13289 (2009).
Pulcu, G. et al., "Continuous observation of the stochastic motion of an individual small-molecule walker," Nat. Nanotechnol., vol. 10: 76-83 (2015).
Qin, F. et al., "Estimating single-channel kinetic parameters from idealized patch-clamp data containing missed events," Biophys. J., vol. 70: 264-280 (1996).
Qing, Y. et al., "Directional control of a processive molecular hopper," Science, vol. 361: 908-912 (2018).
Roos, G. et al., "How thioredoxin dissociates its mixed disulfide," PLoS Comput. Biol., vol. 5: e1000461 (2009).
Roos, G., et al., "Understanding the pK(a) of redox cysteines: the key role of hydrogen bonding," Antioxid. Redox Signal., vol. 18, 94-127 (2013).
Rothwarf, D. et al., "Equilibrium and kinetic constants for the thiol-disulfide interchange reaction between glutathione and dithiothreitol," Proc. Natl. Acad. Sci. U.S.A., vol. 89: 7944-7948 (1992).
Rouseau, G. et al., "Removable directing groups in organic synthesis and catalysis," Angew. Chem. Int. Ed.50, 2, vol. 2450-2494 (2011).
Roy, N. et al., "Dynamic covalent chemistry: a facile room-temperature, reversible, Diels-Alder reaction between anthracene derivatives and N-phenyltriazolinedione," Chem Asian J., vol. 6: 2419-2425 (2011).
Shin, J. et al., "A synthetic DNA walker for molecular transport," J. Am. Chem. Soc., vol. 126, 10834-10835 (2004).
Shiu, H-Y, et al., "Electron-deficient alkynes as cleavable reagents for the modification of cysteine-containing peptides in aqueous medium," Chem Eur J., vol. 15: 3839-3850 (2009).
Singh, R. & Whitesides, (1993). in Sulphur-Containing Functional Groups (John Wiley & Sons, Inc) 633-658.
Smith, M. et al., "Protein modification, bioconjugation, and disulfide bridging using bromomaleimides," J Am Chem Soc. vol. 132: 1960-1965 (2010).
Song, L. et al., "Structure of staphylococcal alpha-hemolysin, a heptameric transmembrane pore," Science, vol. 274: 1859-1866 (1996).
Spruijt, E. et al., "DNA scaffolds support stable and uniform peptide nanopores," Nature Nanotechnology, vol. 13: 739-745 (2018).
Stoddart, D. S. et al., "Single-nucleotide discrimination in immobilized DNA oligonucleotides with a biological nanopore," Proc. Natl. Acad. Sci. USA, vol. 106: 7702-7707 (2009).
Su et al., "High regioselectivity in the Diels-Alder reaction of a surfactant 1,3-diene with a surfactant dienophile resulting from a short tether between their functional groups and head groups" Tetrahedron Lett., vol. 40: 7871-7874 (1999).
Szajewski and Whitesides, "Rate Constants and Equilibrium Constants for Thiol-Disulfide Interchange Reactions Involvins Oxidized Glutathione," J. Am. Chem. Soc., vol. 102: 2011-2026 (1980).
Tian, Y. et al., "A DNAzyme that walks processively and autonomously along a one-dimensional track," Angew. Chem., vol. 117: 4429-4432(2005).
Ukuwela, A. et al., "Glutaredoxins employ parallel monothiol-dithiol mechanisms to catalyze thiol-disulfide exchanges with protein disulfides," Chem. Sci., vol. 9: 1173-1183 (2018).
Vale, R. et al., "Direct observation of single kinesin molecules moving along microtubules," Nature, vol. 380:451-453 (1996).
Venkatraman, J., et al. "Design and construction of an open multistranded beta-sheet polypeptide stabilized by a disulfide bridge," J. Am. Chem. Soc., vol. 124: 4987-4994 (2002).
Villar, G. et al., "A tissue-like printed material," Science, vol. 340: 48-52 (2013).
Von Delius, M. et al., "A synthetic small molecule that can walk down a track," Nat. Chem., vol. 2: 96-101 (2010).
Von Delius, M. et al., "Design, synthesis, and operation of small molecules that walk along tracks," J. Am. Chem. Soc., vol. 132: 16134-16145 (2010).

(56) References Cited

OTHER PUBLICATIONS

Walter, W. et al., "Two independent switches regulate cytoplasmic dynein's processivity and directionality," Proc. Natl. Acad. Sci. U.S.A., vol. 109: 5289-5293 (2012).

Wang, J-B. et al, "Enzymatic site-selectivity enabled by structure-guided directed evolution," Chem. Commun., vol. 53, 3916-3928 (2017).

Wang, Y. et al., "Probing molecular pathways for DNA orientational trapping, unzipping and translocation in nanopores by using a tunable overhang sensor," Nanoscale, vol. 1:1-32(2014).

Whitesides et al., "Rates of Thiol-Disulfide Interchange Reactions between Mono- and Dithiols and Ellman's Reagen," J. Org. Chem., vol. 42: 332-338 (1977).

Wickham, S. et al., "Direct observation of stepwise movement of a synthetic molecular transporter," Nat. Nanotechnol., vol. 6:166-169 (2011).

Wiita, A., et al. "Probing the chemistry of thioredoxin catalysis with force," Nature, vol. 450: 124-127 (2007).

Wilson, M. et al. "An autonomous chemically fuelled small-molecule motor," Nature, vol. 534: 235-240 (2016).

Wollman, A. et al., "Transport and self-organization across different length scales powered by motor proteins and programmed by DNA," Nature Nanotechnology, vol. 9: 44-47 (2014).

Yehl, K. et al., "High-speed DNA-based rolling motors powered by RNase H," Nat. Nanotechnol., vol. 11: 184-190 (2016).

Ying, H. et al., "Dynamic urea bond for the design of reversible and self-healing polymers," Nat Commun, vol. 5: 3218 (2014).

Yoshizawa, M. et al., "Diels-alder in aqueous molecular hosts: unusual regioselectivity and efficient catalysis" Science, vol. 312, 251-254 (2006).

You, M. et al., "An autonomous and controllable light-driven DNA walking device," Angew. Chem. Int. Ed, vol. 51:2457-2460 (2012).

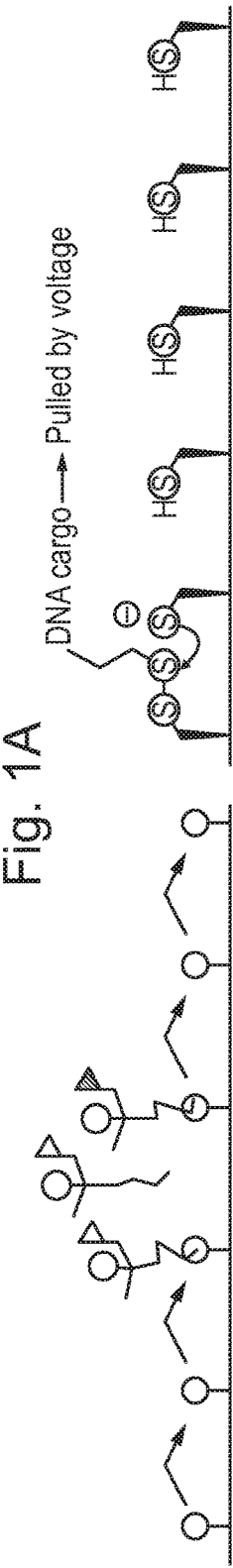
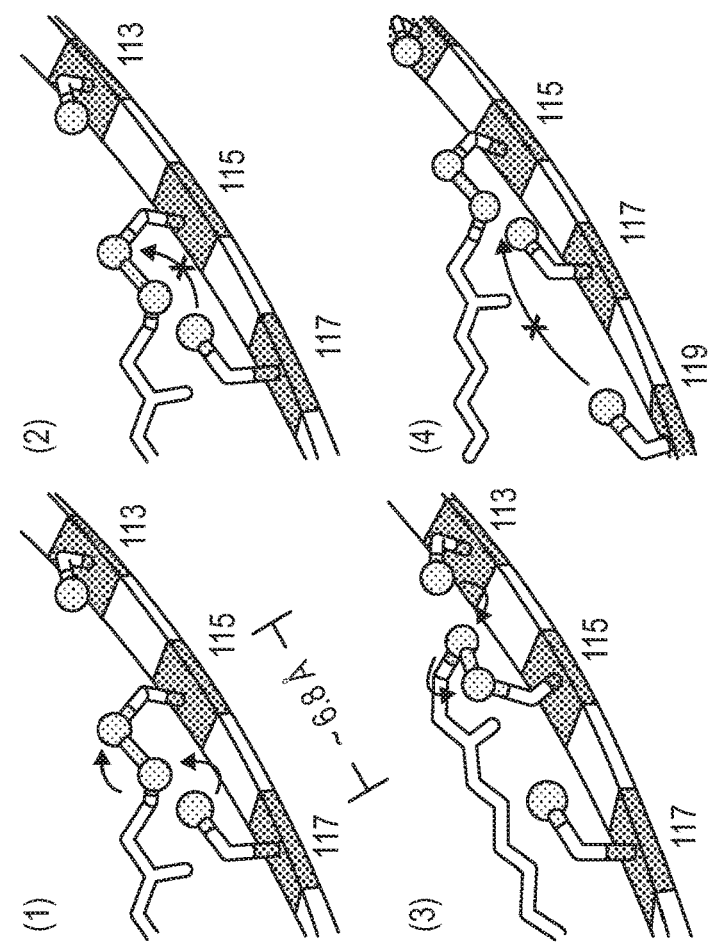
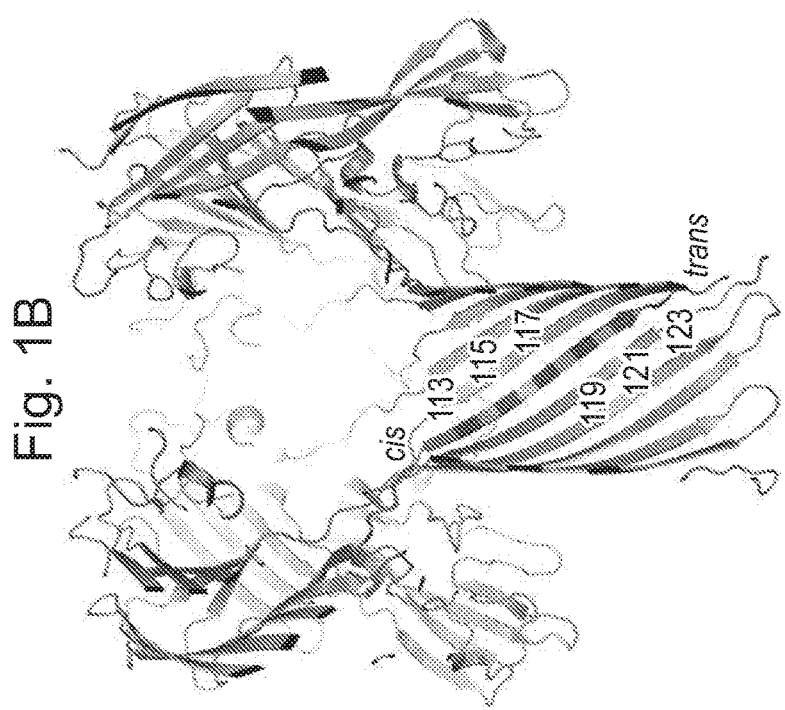
Fig. 1A
Fig. 1C
Fig. 1B

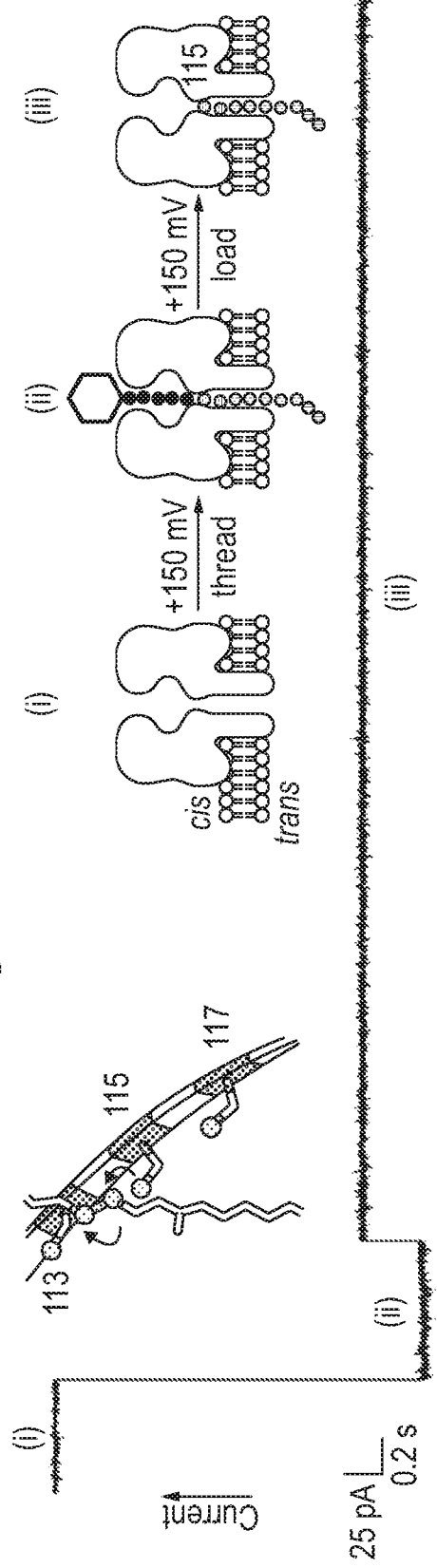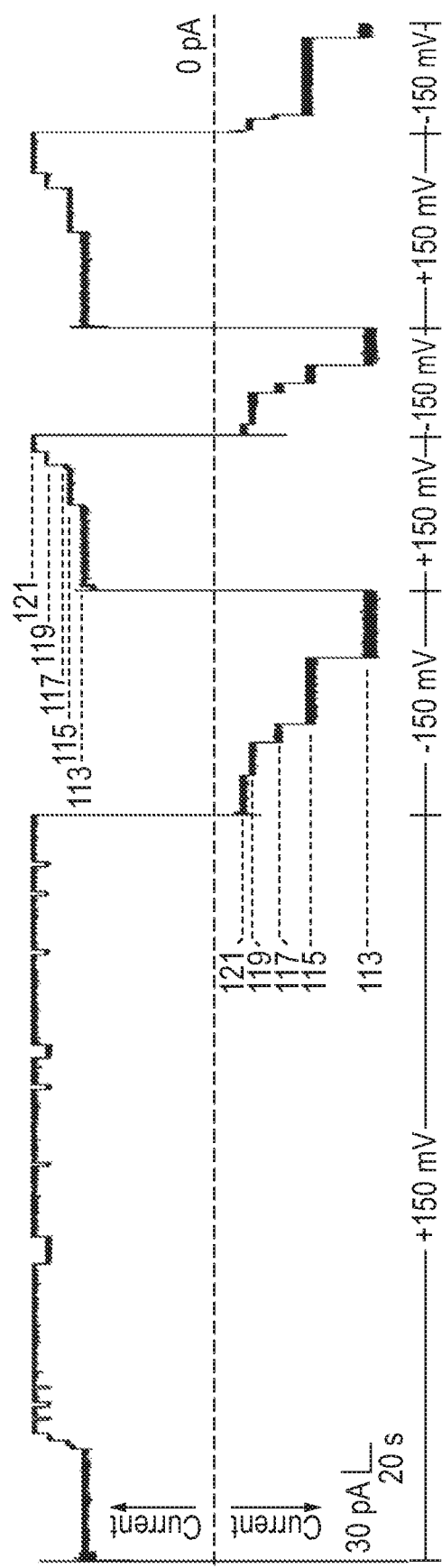

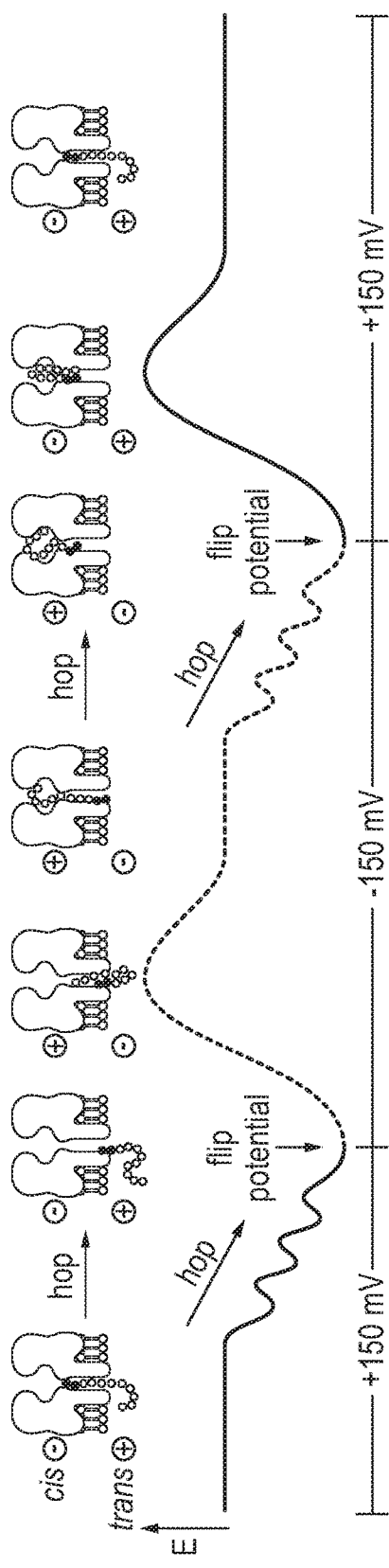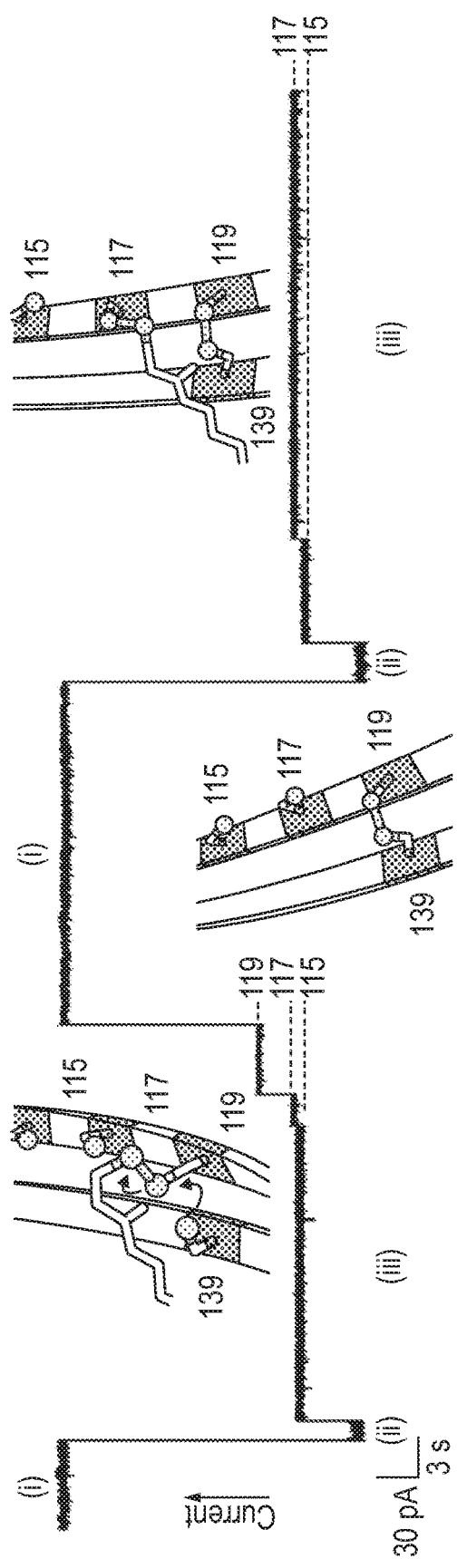

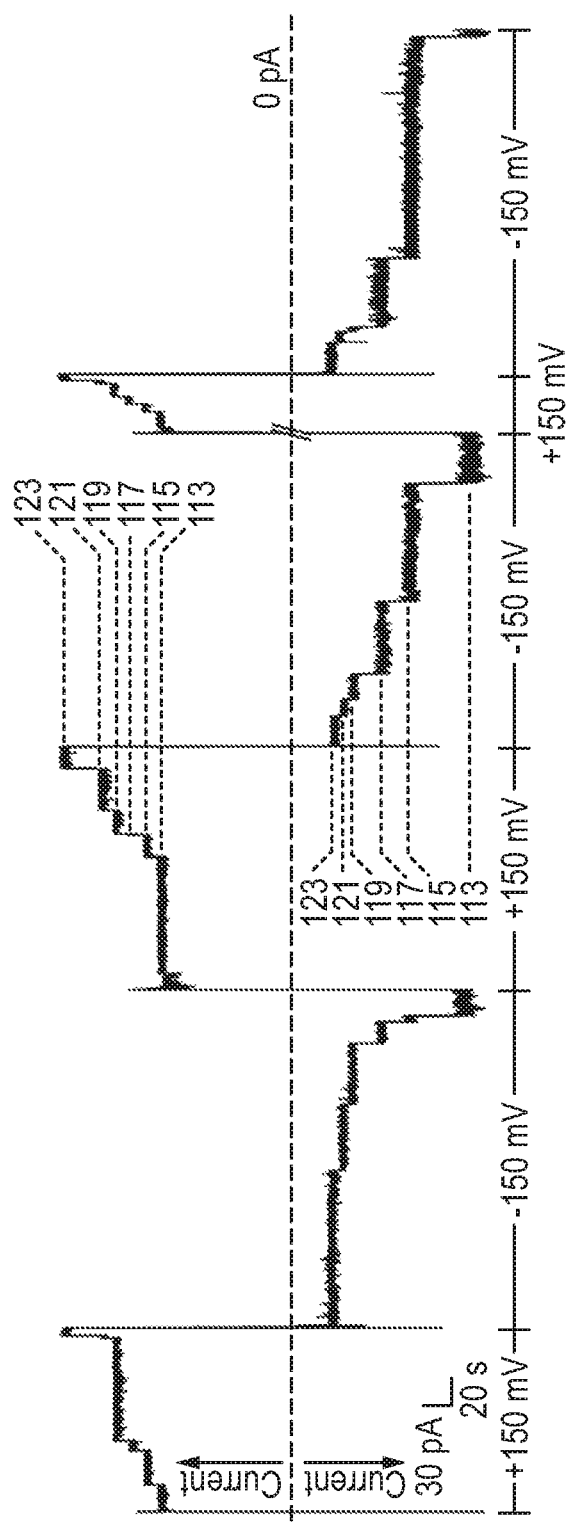

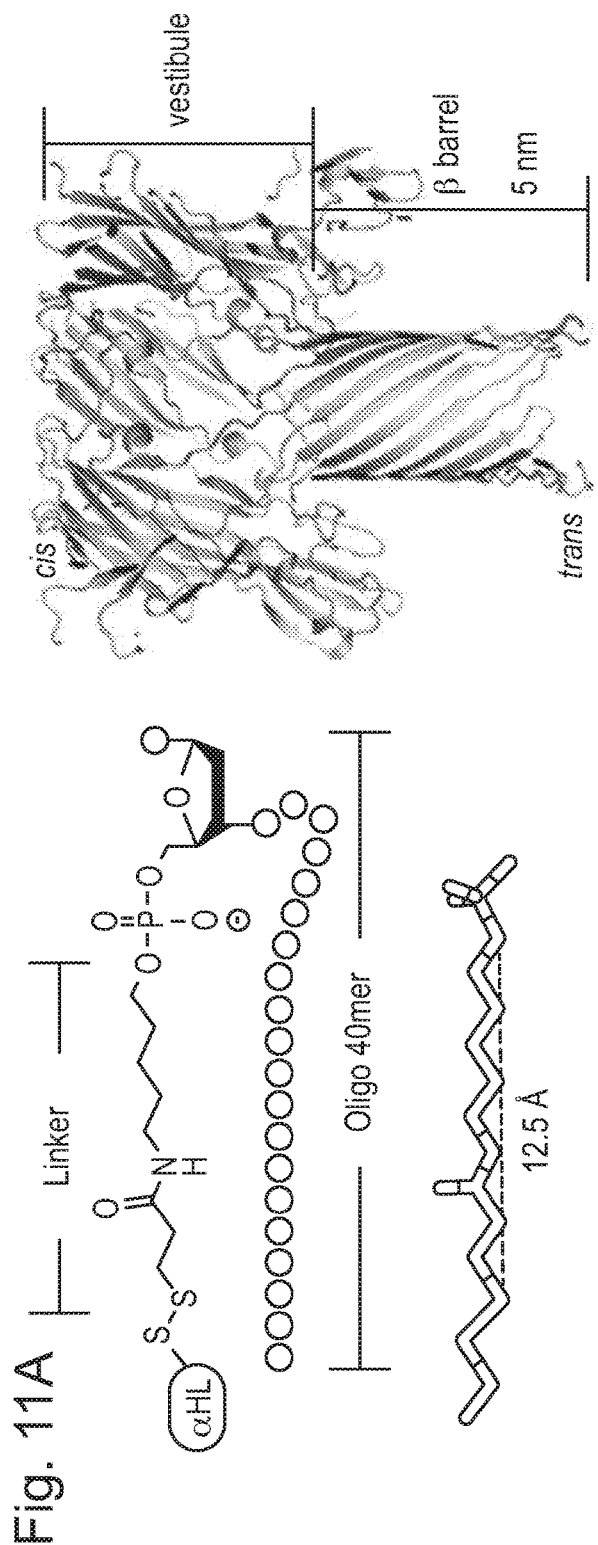
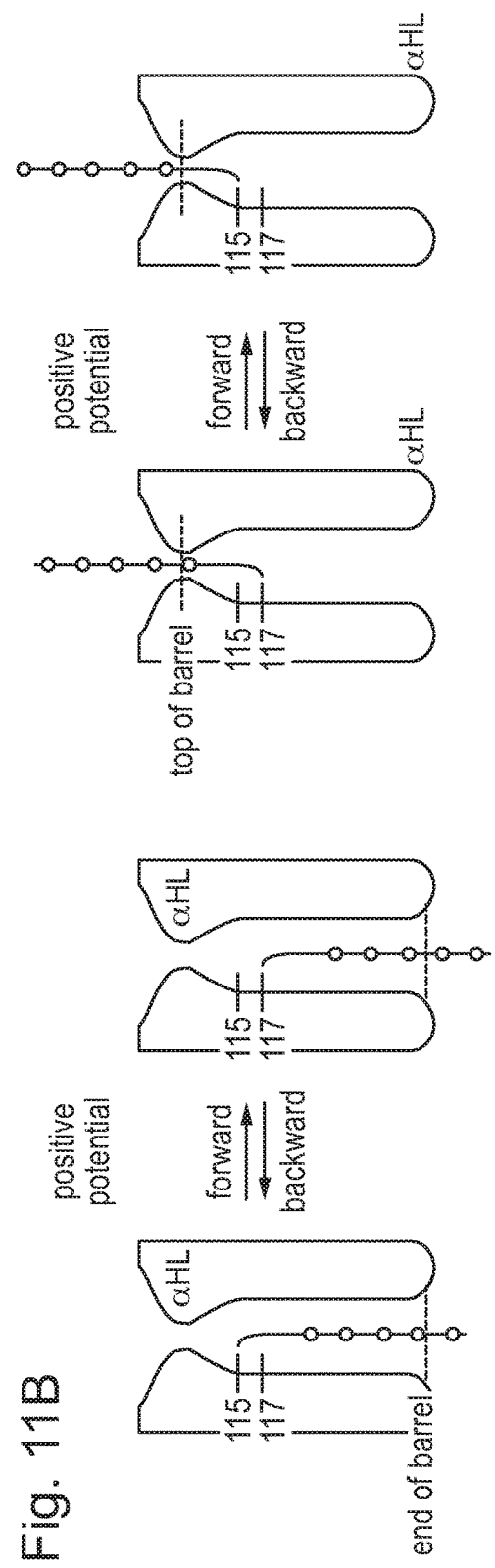
Fig. 11A
Fig. 11B

Fig. 13
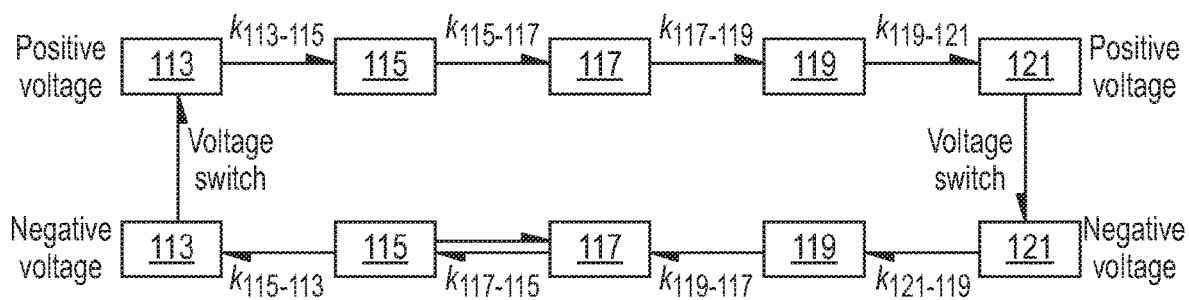
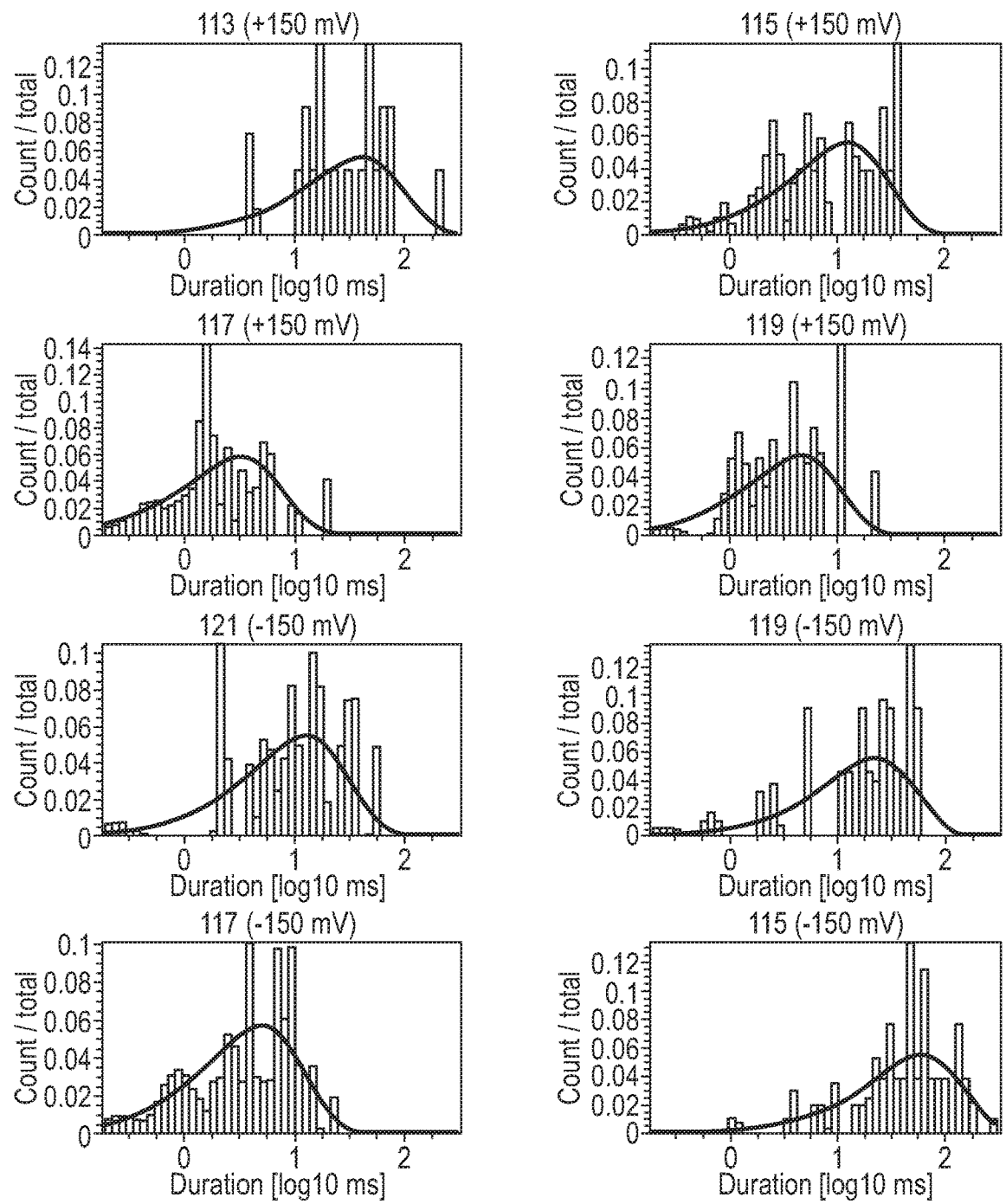

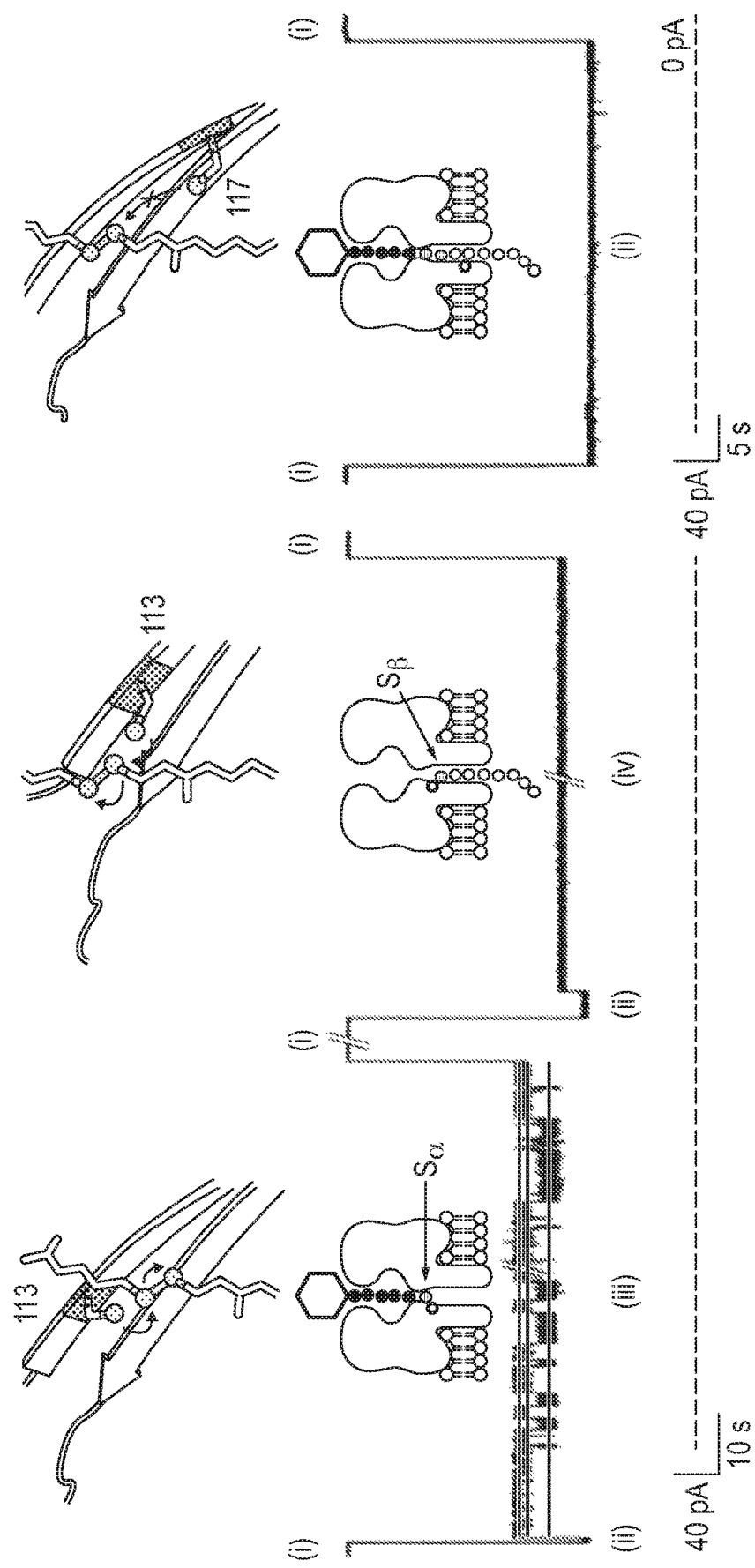

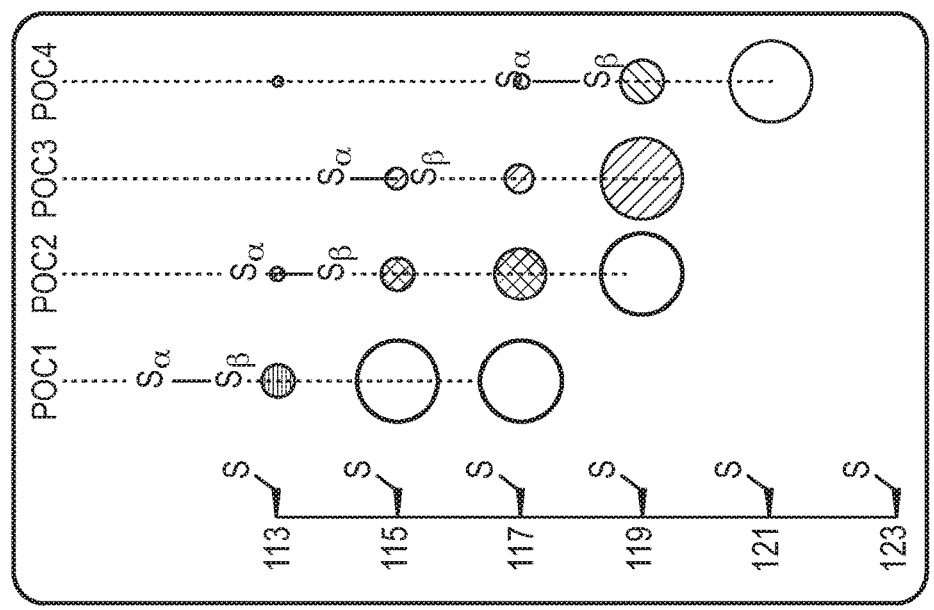
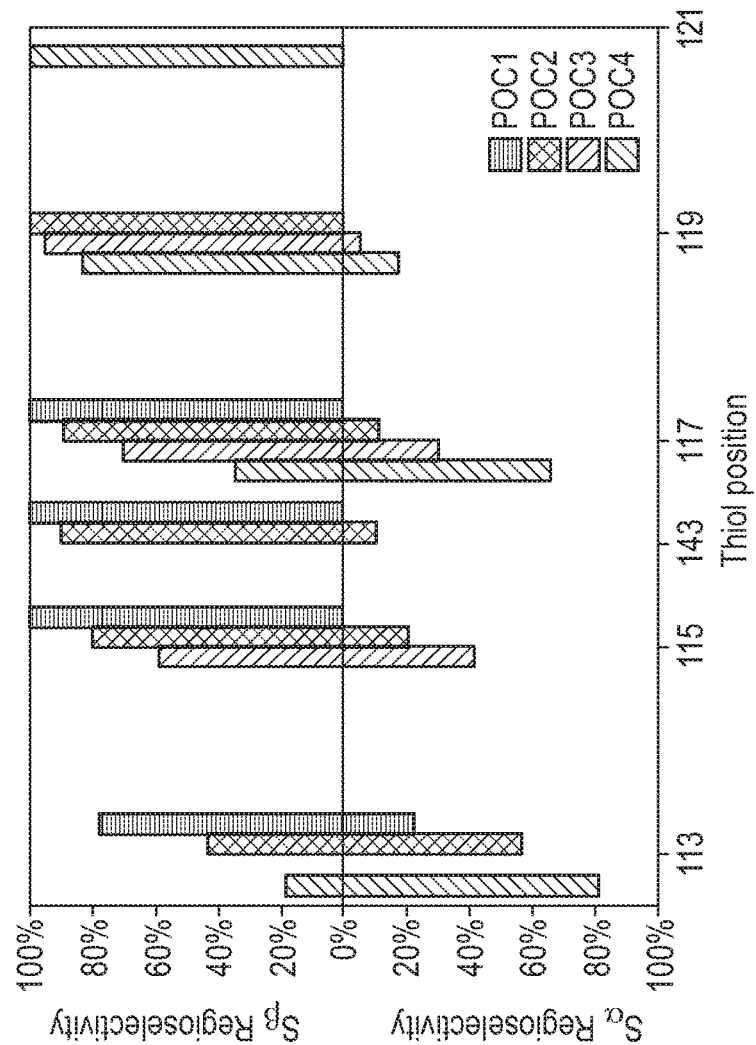

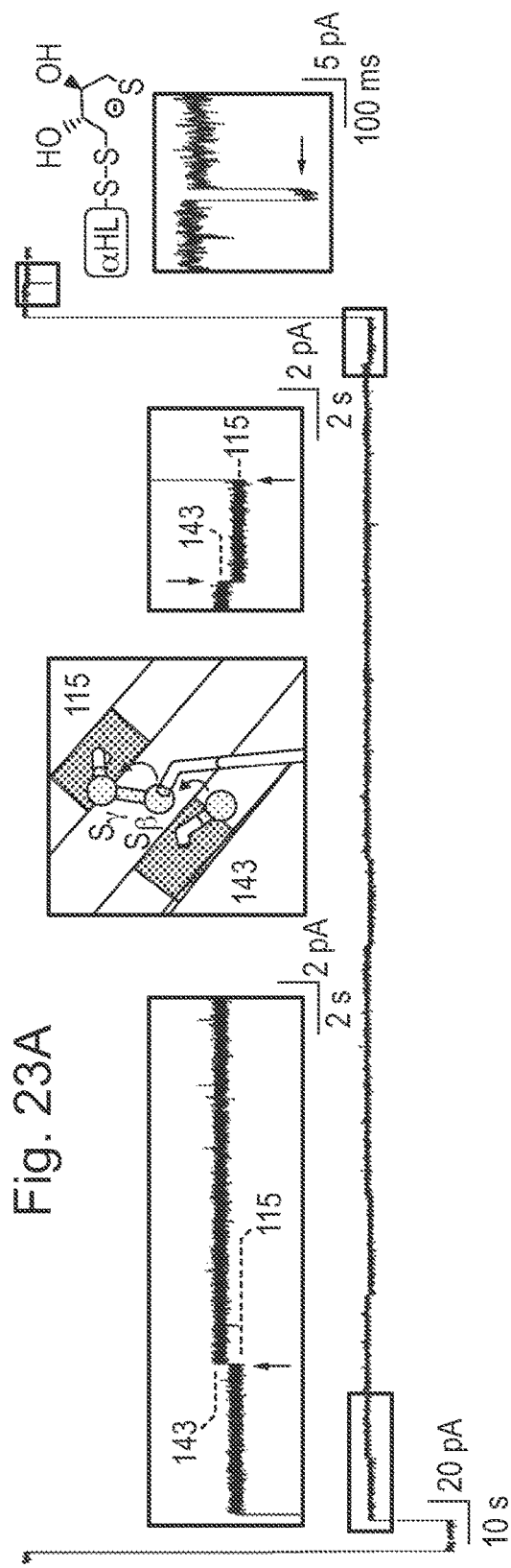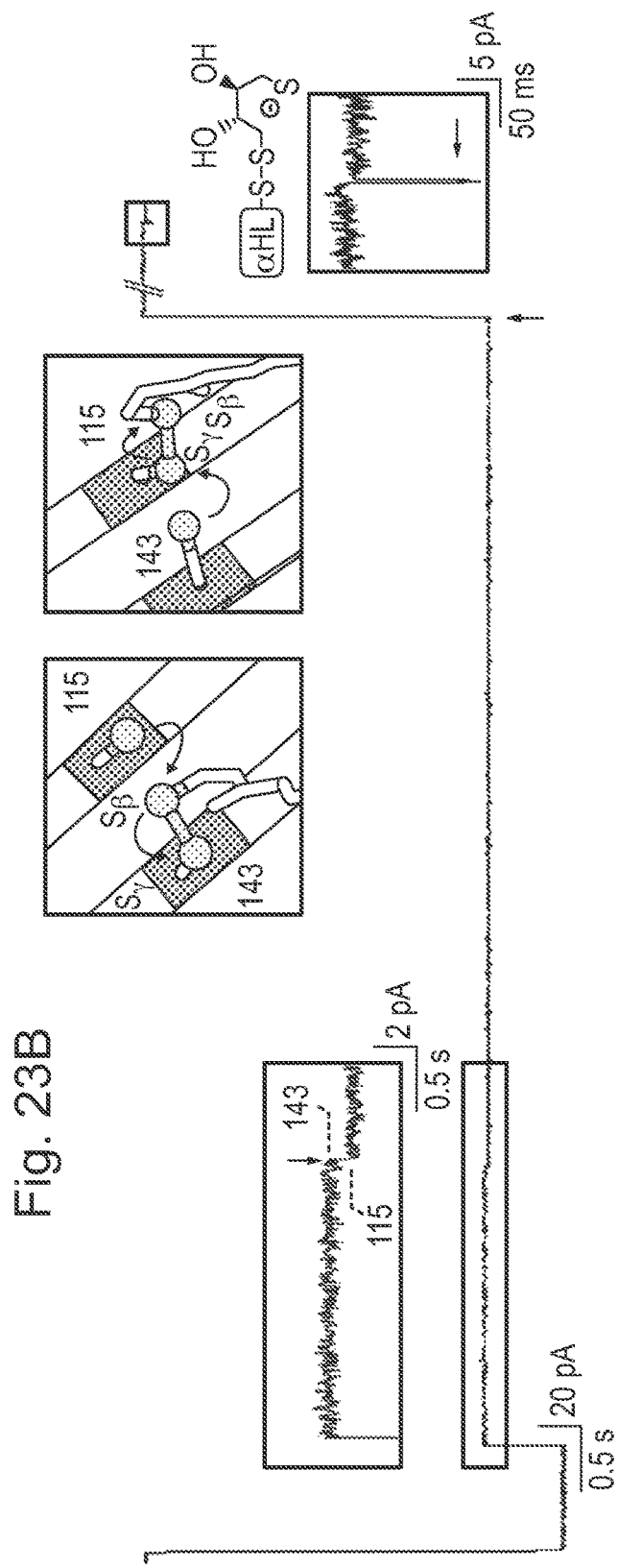

SEQUENCE LISTING

```
<160> NUMBER OF SEQ ID NOS: 15

<210> SEQ ID NO 1
<211> LENGTH: 293
<212> TYPE: PRT
<213> ORGANISM: Staphylococcus aureus

<400> SEQUENCE: 1

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 2
<211> LENGTH: 307
<212> TYPE: PRT
<213> ORGANISM: Artificial Sequence
<220> FEATURE:
<223> OTHER INFORMATION: alpha hemolysin mutant (WT-D8H6)

<400> SEQUENCE: 2

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Asp Asp Asp Asp Asp Asp His His His
    290                 295                 300

His His His
305
```

<210> SEQ ID NO 3
<211> LENGTH: 307
<212> TYPE: PRT
<213> ORGANISM: Artificial Sequence
<220> FEATURE:
<223> OTHER INFORMATION: alpha hemolysin mutant (115C117C-D8H6)

```
<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Cys Leu Cys Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Thr Asp Arg Ser Glu Arg Tyr Lys Ile Asp Trp Glu Lys
    275                 280                 285

Glu Glu Met Thr Asn Asp Asp Asp Asp Asp Asp His His His
290                 295                 300

His His His
305

<210> SEQ ID NO 4
<211> LENGTH: 307
<212> TYPE: PRT
<213> ORGANISM: Artificial Sequence
<220> FEATURE:
<223> OTHER INFORMATION: alpha hemolysin mutant (115C117C119C-D8H6)

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
```

```
                35                  40                  45
Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Cys Leu Cys Tyr Cys Phe Asn Gly Asn Val Thr Gly Asp Asp
                115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn Asp Asp Asp Asp Asp Asp His His His
        290                 295                 300

His His His
305

<210> SEQ ID NO 5
<211> LENGTH: 307
<212> TYPE: PRT
<213> ORGANISM: Artificial Sequence
<220> FEATURE:
<223> OTHER INFORMATION: alpha hemolysin mutant (113C115C117C119C121C-
      D8H6)

<400> SEQUENCE: 5

Ala Asp Ser Asp Ile Asn Ile Lys Thr Gly Thr Thr Asp Ile Gly Ser
 1               5                  10                  15

Asn Thr Thr Val Lys Thr Gly Asp Leu Val Thr Tyr Asp Lys Glu Asn
                 20                  25                  30

Gly Met His Lys Lys Val Phe Tyr Ser Phe Ile Asp Asp Lys Asn His
             35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80
```

```
Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Cys Ser Cys Leu Cys Tyr Cys Phe Cys Gly Asn Val Thr Gly Asp Asp
            115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn Asp Asp Asp Asp Asp Asp His His His
290                 295                 300

His His His
305

<210> SEQ ID NO 6
<211> LENGTH: 307
<212> TYPE: PRT
<213> ORGANISM: Artificial Sequence
<220> FEATURE:
<223> OTHER INFORMATION: alpha hemolysin mutant
      (113C115C117C119C121C123C-D8H6)

<400> SEQUENCE: 6

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Cys Ser Cys Leu Cys Tyr Cys Phe Cys Gly Cys Val Thr Gly Asp Asp
            115                 120                 125
```

```
Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
            275                 280                 285

Glu Glu Met Thr Asn Asp Asp Asp Asp Asp Asp His His His
            290                 295                 300

His His His
305

<210> SEQ ID NO 7
<211> LENGTH: 307
<212> TYPE: PRT
<213> ORGANISM: Artificial Sequence
<220> FEATURE:
<223> OTHER INFORMATION: alpha hemolysin mutant (115C117C119C139C-D8H6)

<400> SEQUENCE: 7

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Cys Leu Cys Tyr Cys Phe Asn Gly Asn Val Thr Gly Asp Asp
            115                 120                 125

Thr Gly Lys Ile Gly Gly Leu Ile Gly Ala Cys Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175
```

```
Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Asp Asp Asp Asp Asp Asp His His His
    290                 295                 300

His His His
305

<210> SEQ ID NO 8
<211> LENGTH: 36
<212> TYPE: DNA
<213> ORGANISM: Artificial Sequence
<220> FEATURE:
<223> OTHER INFORMATION: forward mutagenic primer

<400> SEQUENCE: 8
ctgcttctgc ggttgtgtta ctggtgatga tacagg                              36

<210> SEQ ID NO 9
<211> LENGTH: 23
<212> TYPE: DNA
<213> ORGANISM: Artificial Sequence
<220> FEATURE:
<223> OTHER INFORMATION: reverse non-mutagenic primer (SC47)

<400> SEQUENCE: 9
cagaagtggt cctgcaactt tat                                            23

<210> SEQ ID NO 10
<211> LENGTH: 36
<212> TYPE: DNA
<213> ORGANISM: Artificial Sequence
<220> FEATURE:
<223> OTHER INFORMATION: reverse mutagenic primer

<400> SEQUENCE: 10
cctgtatcat caccagtaac acaaccgcag aagcag                              36

<210> SEQ ID NO 11
<211> LENGTH: 23
<212> TYPE: DNA
<213> ORGANISM: Artificial Sequence
<220> FEATURE:
<223> OTHER INFORMATION: forward non-mutagenic primer (SC46)

<400> SEQUENCE: 11
ataaagttgc aggaccactt ctg                                            23

<210> SEQ ID NO 12
<211> LENGTH: 39
```

```
<212> TYPE: DNA
<213> ORGANISM: Artificial Sequence
<220> FEATURE:
<223> OTHER INFORMATION: forward mutagenic primer

<400> SEQUENCE: 12
caaaagagta tatgagttgc ttatgctatt gcttcaacg                          39

<210> SEQ ID NO 13
<211> LENGTH: 39
<212> TYPE: DNA
<213> ORGANISM: Artificial Sequence
<220> FEATURE:
<223> OTHER INFORMATION: reverse mutagenic primer

<400> SEQUENCE: 13
cgttgaagca atagcataag caactcatat actcttttg                          39

<210> SEQ ID NO 14
<211> LENGTH: 37
<212> TYPE: DNA
<213> ORGANISM: Artificial Sequence
<220> FEATURE:
<223> OTHER INFORMATION: forward mutagenic primer

<400> SEQUENCE: 14
ccttattggt gcatgtgttt cgattggtca tacactg                            37

<210> SEQ ID NO 15
<211> LENGTH: 37
<212> TYPE: DNA
<213> ORGANISM: Artificial Sequence
<220> FEATURE:
<223> OTHER INFORMATION: reverse mutagenic primer

<400> SEQUENCE: 15
cagtgtatga ccaatcgaaa cacatgcacc aataagg                            37
```

MOLECULAR HOPPER

CROSS-REFERENCE TO RELATED APPLICATIONS

This application is a 35 U.S.C. 371 national stage filing of International Application No. PCT/GB2019/051990, filed Jul. 16, 2019, which claims priority to British Patent Application No. 1811623.6, filed Jul. 16, 2018. The contents of the aforementioned applications are hereby incorporated by reference.

SEQUENCE LISTING

The instant application contains a substitute Sequence Listing which has been submitted electronically in ASCII format and is hereby incorporated by reference in its entirety. Said ASCII copy, created on Jan. 31, 2025, is named JKJ_071US_SubstituteSequenceListing.txt and is 21,798 bytes in size.

FIELD OF THE INVENTION

The invention relates to methods for moving molecular hoppers along tracks; to methods of characterising an analyte using molecular hoppers; to kits for characterising an analyte; and to molecular hoppers per se and systems comprising such hoppers. The invention particularly relates to the use of such methods and kits in the characterisation of analytes such as polynucleotides, polypeptides, and polysaccharides.

BACKGROUND OF THE INVENTION

Many desirable technological applications require precise control of molecular motion. For example, characterization of analytes at the single molecule level requires the precise manipulation of the analytes with nanometer precision. Attempts have long been made to achieve this goal and have typically focused on controlling analytes using complex systems such as molecular or optical tweezers or other physical means. However, the possibility of controlling molecular motion without recourse to such equipment has major potential in many fields of nanotechnology, especially in the field of single-molecule analyte characterisation.

Some attempts to control molecular motion have been inspired by the processivity demonstrated by biological machines. For example, a replicative DNA polymerase can incorporate thousands of nucleotides before dissociating from its template (1). Molecular motors, such as kinesin and dynein, can travel directionally along microtubules over hundreds of steps without detaching from the track (2-4). However, these systems are very complicated and are typically not readily susceptible to application in biotechnology.

There is a need for methods and systems for moving molecules which resemble their biomolecular counterparts but use simpler components (5). The ultimate goals are to achieve true processivity, which can be defined as directional motion without leaving a track, and the performance of useful work such as the transport of a cargo. Ideally, a synthetic system should exhibit the reversibility of stepping seen in various biological systems (6, 7) to enable the direction of motion to be switched through external control.

SUMMARY OF THE INVENTION

The inventors have developed a molecular hopper which is capable of moving along a track comprising a plurality of primary functional groups aligned along a substrate. The hopper itself comprises a secondary functional group capable of binding to each of the plurality of primary functional groups on the track, such that application of a driving force causes the hopper to be directionally transferred between primary functional groups on the track, thereby causing the hopper to move along the track. The inventors have recognised that there is a clear need for methods and systems which are simple and capable of demonstrating improved processivity, autonomous movement, directional control including the ability to reverse direction, ability to move cargo and/or selective loading/unloading. The methods and systems provided in the present invention address some or all of these needs.

Accordingly, the invention provides a method of moving a molecular hopper along a track; wherein:
  (a) the track comprises a plurality of primary functional groups aligned along a substrate;
  (b) the hopper comprises a secondary functional group capable of binding to each of the plurality of primary functional groups on the track; and
  (c) the hopper optionally comprises a cargo moiety;
the method comprising the steps of:
  (i) contacting the hopper with the track such that the secondary functional group of the hopper binds to a first primary functional group on the track;
  (ii) applying a driving force so as to cause the hopper to be directionally transferred from the first primary functional group to a second primary functional group on the track thereby causing the hopper to move along the track.

Typically, the substrate is a surface of a transmembrane pore such as an internal surface of a transmembrane pore. The hopper may comprise a cargo moiety. Prior to contacting the hopper with the track the hopper can be attached to a positioning moiety which positions the hopper relative to the track such that the first primary functional group on the track binds to the secondary functional group on the hopper. The method may further comprise, after movement of the hopper along the track, the step of (iii) contacting the primary functional group of the track bonded to the secondary functional group of the hopper with a tertiary functional group on the substrate such that the tertiary functional group bonds to the primary functional group thereby displacing the secondary functional group and so releasing the hopper. The method may further comprise reversing the direction of the driving force relative to the track so as to cause the direction of the movement of the hopper along the track to be reversed.

The invention also provides a method of characterising an analyte, the method comprising:
  (i) providing (A) a detector; (B) a track comprising a plurality of primary functional groups aligned along a substrate; and (C) a molecular hopper attached to the analyte, wherein the hopper comprises a secondary functional group capable of binding to each of the plurality of primary functional groups on the track;
  (ii) contacting the hopper with the track such that the secondary functional group of the hopper binds to a first primary functional group on the track;
  (iii) applying a driving force so as to cause the hopper to be directionally transferred from the first primary functional group to a second primary functional group on the track thereby causing the hopper to move along the track;

wherein the track is positioned such that the movement of the hopper along the track causes the analyte to interact with the detector, thereby characterising the analyte.

The invention further provides a kit for characterising an analyte, the kit comprising: (A) a detector; (B) a track comprising a plurality of primary functional groups aligned along a substrate; and (C) a molecular hopper for conjugating to the analyte; wherein the hopper comprises a secondary functional group capable of binding to each of the plurality of primary functional groups on the track; wherein preferably the analyte is a polynucleotide, a polypeptide or a polysaccharide.

The invention further provides a system comprising (A) a detector; (B) a track comprising a plurality of primary functional groups aligned along a substrate; and (C) a molecular hopper conjugated to a polynucleotide, polypeptide or polysaccharide analyte; wherein the hopper comprises a secondary functional group bonded to at least one of the plurality of primary functional groups on the track.

The invention further provides a molecular hopper comprising:
a secondary functional group for bonding to a primary functional group on a track;
a polynucleotide, polypeptide or polysaccharide cargo moiety;
a linking moiety between the secondary functional group and the cargo moiety.

BRIEF DESCRIPTION OF THE FIGURES

FIGS. 1A-1D show a molecular hopper on a protein track. (FIG. 1A) A hopper carrying a cargo (red flag) moves along a track, by employing consecutive thiol-disulfide interchange reactions. The overall direction is set by the applied voltage. (FIG. 1B) A six-foothold track comprising odd-numbered cysteine residues on a β strand inside the αHL protein nanopore. (FIG. 1C) The applied potential exerts a force on the DNA cargo, which helps align the three sulfur atoms (yellow) participating in the interchange. The colinear geometry promotes hopping (1) but not the formation of an intra-strand disulfide, which would release the hopper from the track (2). Occasionally, back-stepping is observed (3). Over-stepping (4) does not occur. (FIG. 1D) The hopper enters the nanopore as a carrier-hopper disulfide conjugate. More details are set out in the Example.

FIGS. 2A-2D show the monitoring of individual hopper steps. (FIG. 2A) Under +150 mV, a hopper-carrier conjugate capped with traptavidin was pulled from the cis compartment into an αHL nanopore containing cysteines at positions 113, 115, 117, 119, and 121 in one of the seven subunits. The resultant blockade reduced the ionic current from (i) to (ii). Reaction of the disulfide in the hopper-carrier with Cys-115 covalently attached the hopper to the track, and the ionic current increased to (iii). (FIG. 2B) With a five-cysteine track, four hopping steps were observed at ±150 mV. Every forward step moved part of the DNA cargo outside the β barrel, producing an increase in conductance. Alternation of the applied potential drove the hopper repeatedly up and down the track. (FIG. 2C) A hypothetical free energy diagram (not to scale) of the controlled hopping motion. (FIG. 2D) On an L-shaped track consisting of cysteines at positions 115, 117, 119, and 139, the hopper moved along the track from Cys-115 to Cys-119, where it was released by the side chain of Cys-139. Subsequently, a second hopper became loaded at Cys-115, but its motion was arrested at Cys-117 because Cys-119 was now engaged in an inter-strand disulfide bond. Conditions: 2 M KCl, 20 mM HEPBS, 20 μM EDTA, pH 8.5, 20±1° C. Data are described in the Example.

(FIG. 3A) Two sequential abasic nucleotides (dSdS) were substituted at positions 3 and 4 (hopper 2) or at positions 2 and 3 (hopper 3). The numbers of nucleotides (brown circles, dA; red circles dS) placed inside the β barrel are based on PyMOL modelling. (FIG. 3B) With a five-cysteine track, four-step hopping was observed with hopper 2 at ±150 mV. The current decreases for hops from 115 to 117 and from 121 to 119 are marked (green arrows). (FIG. 3C) Four-step hopping with hopper 3 at ±150 mV. The current transitions for hops from 117 to 119 and from 119 to 117 are marked (red arrows). (FIG. 3D) Top: Overlaid current traces of hoppers 1, 2, and 3 with step durations normalized. The current levels are given as the residual current with respect to the open pore level (Ires %). Bottom: Step sizes of hoppers 2 and 3 plotted as ΔIres %. Minima in the plots showing the single nucleotide offset are marked. Conditions: 2 M KCl, 20 mM HEPBS, 20 μM EDTA, pH 8.5, 20±1° C. Data are described in the Example.

(FIG. 4A) Structure of the carrier. (FIG. 4B) The carrier mass ([M+H]$^+$) was calculated to be 1243.7 g mol$^{-1}$ and found to be 1244.6 g mol$^{-1}$. (FIG. 4C) The purity of the carrier was confirmed by analytical HPLC. Data are described in the Example.

(FIG. 6B) a three-cysteine track (Footholds: Cys-115, 117, 119); (FIG. 6C) a five-cysteine track (Footholds: Cys-113, 115, 117, 119, 121). The movement of the hopper was tracked from locations ascertained from the residual current passing through the nanopore. With the five-cysteine track, only three steps were seen in the first excursion at +150 mV. Following the four-step hopping at −150 mV, the second excursion at +150 mV on the same track exhibited four steps, indicating that the initial attachment was on Cys-115. The trace was filtered at 200 Hz. Conditions: 2 M KCl, 20 mM HEPBS, 20 μM EDTA, pH 8.5, 20±1° C. Data are described in the Example.

(FIG. 8A) Complete cycles at ±150 mV are shown, from which the kinetic rate constants were derived by using QuB (see section 11). (FIG. 8B) External manipulation of voltage to various values (e.g. +100 mV) was applied at non-terminating footholds as well (e.g. Cys-115) in the same experiment. The total number of steps was 282 (only back-steps at the non-terminating footholds were counted; steps after reaching the final footholds and before the voltage switch were discounted). Traces were filtered at 200 Hz. Conditions: 2 M KCl, 20 mM HEPBS, 20 µM EDTA, pH 8.5, 20±1° C. Data are described in the Example.

FIG. 9 shows hopping on a six-cysteine track. Five hopping steps were recorded for hopper 1 on a six-cysteine track (Footholds: Cys-113, 115, 117, 119, 121, 123) at ±150 mV. Every forward step moved part of the DNA cargo outside the β barrel, producing an increase in conductance. Alternation of the applied potential drove the hopper repeatedly up and down the track. The trace was filtered at 200 Hz. Conditions: 2 M KCl, 20 mM HEPBS, 20 µM EDTA, pH 8.5, 20±1° C. Data are described in the Example.

FIGS. 11A and 11B show estimating the number of nucleotides inside the αHL barrel during forward and backward stepping between footholds 115 and 117. (FIG. 11A) Length of the fully stretched linker (left) and the αHL β barrel (from residue 111 to 129) (right). Given that the average vertical distance between footholds is 5.6 Å, the linker spans a distance of about two steps. (FIG. 11B) Under a positive potential, hopper 1 moved forward from foothold 115 to 117 and backward from 117 to 115 (left). Four negative charges are estimated to be moved within the β barrel during the forward step 115 to 117 (see section 12). Under a negative potential, the hopper moved forward from foothold 117 to 115 and backward from 115 to 117 (right). In this case, there is little charge movement within the β barrel, because most of the DNA has exited into the vestibule. Data are described in the Example.

FIG. 13 shows kinetic model and duration histograms for the four steps on the five-cysteine track (Footholds: Cys-113, 115, 117, 119, 121). The kinetic model (top) links the four steps at positive voltages with the four at negative voltages to form a closed cycle. Two voltage-switch transitions were built into the model by assigning an arbitrary duration of 1 s to the final foothold of the track (Cys-121 at +150 mV; Cys-113 at −150 mV). QuB was set to treat the forward steps as irreversible apart from 117-115, where back-stepping occurred 29 times. Back-steps after reaching the final footholds were discounted. The derived kinetic rate constants are given in Table S3 and S5. Data were collected from a single αHL pore. Data are described in the Example.

FIG. 17A, Cysteines (pink) on one of the seven α-hemolysin (αHL) subunits provide nucleophilic thiolates at defined sites within the transmembrane β barrel. Six single-cysteine mutants (113, 115, 117, 119, 121, 143) and two double-cysteine mutants (115/117 and 115/143) were used. FIG. 17B, Substrates consisted of a biotin at one terminus followed by a peptide-oligonucleotide junction formed by click chemistry. The cleavable disulfide bond was installed between the click product and the oligo. The peptide length was manipulated by adding two amino acids (glycine or serine, Δn=2) at a time, following the PEG unit: POC1 (n=0); POC2 (n=2), POC3 (n=4), POC4 (n=6). FIG. 17C, A molecule of traptavidin-capped substrate threads into the nanopore (i) from the cis side under an applied potential (+150 mV, trans), and translocation is arrested by the traptavidin stopper (ii). Favorable alignment enables thiol-disulfide interchange between the cysteine thiolate and the substrate disulfide, generating either an αHL-peptide adduct (top, iv) or an αHL-oligo adduct (bottom, iii). Reduction of the newly formed disulfide by DTT (5 mM in the trans compartment) returns the nanopore to its open state (i) to initiate the next reaction cycle. Results are described in Example 2.

FIG. 18A, The computed transition state for a thiol-disulfide interchange has a S—S bond length of ~2.5 Å and a S—S—S bond angle of ~180°. This creates a reactive zone of 2.5 Å at either end of a disulfide (shown as arbitrary 100 blue wedges) and a forbidden zone of 2 Å in the middle (red). Assuming free rotation of the cysteine (Cys) side chains, a thiolate can access 3 Å in the vertical dimension (blue triangle). Overlap between the disulfide reactive zone and the thiolate-accessible region leads to thiol-disulfide interchange. FIG. 18B, The reactivity between different substrates and single-cysteine nanoreactors, represented by the ratio of thiol-disulfide interchange events to the total number of threading incidents (reactivity=ninterchange/nthread) expressed as a percentage. Blue indicates that threading led to adduct formation. Red indicates that the substrate was directly cleaved by DTT (5 mM, trans) without adduct formation. All threading events resulted in either adduct formation or cleavage. White indicates an untested combination. FIG. 18C, The relative positions of the substrates and the cysteines within single-cysteine nanoreactors. Accessible positions of the disulfide are indicated with dashed lines, which are inferred from the reactivity results. Successive nanoreactor cysteines are separated by ~5.6 Å vertically, due to the inclination of the β strand with respect to the barrel axis. The disulfide in POC1 was aligned based on based on its reactivity with Cys-113 and Cys-115. Assuming the force produced by the electric field is enough to fully elongate the substrates, two additional amino acids create a ~7 Å shift in disulfide depth inside the barrel, in a static model, and the disulfides in POC2, POC3 and POC4 were subsequently aligned on this basis. Results are described in Example 2.

FIGS. 19A-19C show Regioselectivity of single-molecule thiol-disulfide interchange. FIG. 19A, Identification of turnover intermediates from current signatures. Threading of POC1 into nanoreactor 113 from the cis compartment (i) led to partial blockade of the ion flow (Ires %=33%) (ii). Thiol-disulfide interchange between nanoreactor 113 and POC1 produced two types of electrical pattern (iii, iv) corresponding to the formation of two different covalent adducts within the nanopore (see SI section 1): the αHL-peptide adduct offered three sub-conductance states (iii: pink lines: Ires %=43%, 48%, 51%); the αHL-oligo adduct gave a single current state (iv: Ires %=39%). Subsequent adduct release by DTT returned the system to its initial state (i). Misalignment of the substrate disulfide and the thiolate disfavoured the reaction between nanoreactor 117 and POC1, resulting mainly in direct cleavage of the substrate disulfide by DTT rather than adduct formation (4.5% reactivity). Traces were filtered at 200 Hz. Conditions: 2 M KCl, 20 mM HEPBS, 20 μM EDTA, 5 mM DTT (trans), pH 8.5, 20±1° C. FIG. 19B, The sulfur regioselectivity of thiol-disulfide interchange between substrates POC1 (red), POC2 (blue), POC3 (yellow), and POC4 (green) and nanoreactors 113, 115, 143, 117, 119, and 121, expressed as a percentage of the total number of adducts formed (reaction at Sα and Sβ). FIG. 19C, The relative positions of the substrates and the cysteines within single-cysteine nanoreactors inferred from the regioselectivity data. The area of each solid circle is scaled to the regioselectivity ratio (Sβ/Sα) for the corresponding combination of substrate and nanoreactor. Empty circles indicate a complete Sβ regioselectivity. The disulfides are placed where Sβ/Sα regioselectivity=1, as extrapolated from the regioselectivity data. Accessible positions of the disulfide are indicated with dashed lines based on the reactivity data (FIG. 18c). Results are described in Example 2.

FIG. 20A, With nanoreactor 115/117, POC1 reacted site-selectively and regioselectively with cysteine 115 to form an αHL-oligo adduct (iv). Subsequent regioselective attack on Sβ initiated intramolecular thiol-disulfide interchange to transfer the adduct to cysteine 117 (pink arrow). The adduct moved back and forth between the two sites on the same β strand before it was eventually released by DTT, which was evidenced by an intermediate αHL-DTT adduct (blue arrow). FIG. 20B, With nanoreactor 115/143, POC1 reacted with 81% site-selectivity and 100% regioselectivity at cysteine 115 to form an αHL-oligo adduct (iv). Attack on Sγ by Cys-143 on the antiparallel strand cleaved the adduct from the nanoreactor (pink arrow). Consequently, a cross-strand disulfide bridge was generated, prohibiting turnover of a new substrate (ii, substrate within pore) until DTT regenerated the two free cysteines through an intermediate αHL-DTT adduct (blue arrow). Attack on Sβ by Cys-143 was seen occasionally, resulting in adduct transfer (see SI section 2). Traces were filtered at 200 Hz. Insets showing αHL-DTT adducts were filtered at 1000 Hz. Conditions: 2 M KCl, 20 mM HEPBS, 20 μM EDTA, 5 mM DTT (trans), pH 8.5, 20±1° C. Results are described in Example 2.

FIG. 22A, An αHL-oligo adduct was formed after thiol-disulfide interchange between POC2 and nanoreactor 119. A step to +50 mV produced a different level of current blockade depending on whether the step was made from −150 mV or from +150 mV (purple arrows), indicating that a switch in oligonucleotide orientation occurs at high applied potentials. FIG. 22B, An αHL-peptide adduct was formed after thiol-disulfide interchange between POC2 and nanoreactor 113. After a step to −50 mV, the current levels of the three sub-conductance levels were the same whether the step came from +150 mV or from −150 mV (green arrows), in keeping with the presence of a covalent adduct locked inside the vestibule of the αHL pore by the traptavidin stopper. Traces were filtered at 200 Hz. Conditions: 2 M KCl, 20 mM HEPBS, 20 μM EDTA, 5 mM DTT (trans), pH 8.5, 20±1° C. Results are described in Example 2.

FIGS. 23A-23C show Thiol-disulfide interchanges between nanoreactor 115/143 and POC1. FIG. 23A, An αHL-oligo adduct was formed at Cys-115 following threading. The oligonucleotide transferred between Cys-115 and Cys-143 by Sβ attack (orange: transfer from 115 to 143; brown: transfer from 143 to 115) until Sγ was attacked to form the cross-strand disulfide (purple). Here, we show an unusual example in which six transfers were observed, the most we recorded. An αHL-DTT adduct was subsequently observed (blue) as DTT reduced the disulfide to regenerate the two free cysteine residues. FIG. 23B, An αHL-oligo adduct was formed at Cys-143 following threading. The oligonucleotide transferred to Cys-115 (brown) from which release took place through Sγ attack by Cys-143 (purple). Traces were filtered at 50 Hz. Insets showing αHL-DTT adducts were filtered at 1000 Hz. Conditions: 2 M KCl, 20 mM HEPBS, 20 μM EDTA, 5 mM DTT (trans), pH 8.5, 20±1° C. FIG. 23C, The kinetic model and the derived rate constants for the thiol-disulfide interchanges observed with nanoreactor 115/143 and POC1. Dwell time analysis and rate constant estimations were performed by using the maximum interval likelihood algorithm of QuB. Results are described in Example 2.

(FIG. 26A) Structure of the peptide segment. (FIG. 26B) The mass of the peptide segment ([M+H]+) was calculated to be 1243.7 g mol-1 and found to be 1244.6 g mol-1. (FIG. 26C) The purity of peptide segment was confirmed by analytical HPLC. Results are described in Example 2.

(FIG. 27A) Structure of the peptide segment. (FIG. 27B) The mass of the peptide segment ([M+H]+) was calculated to be 1358.8 g mol-1 and found to be 1358.8 g mol-1. (FIG. 27C) The purity of the peptide segment was confirmed by analytical HPLC. Results are described in Example 2.

DESCRIPTION OF THE SEQUENCE LISTING

Figure 1D:
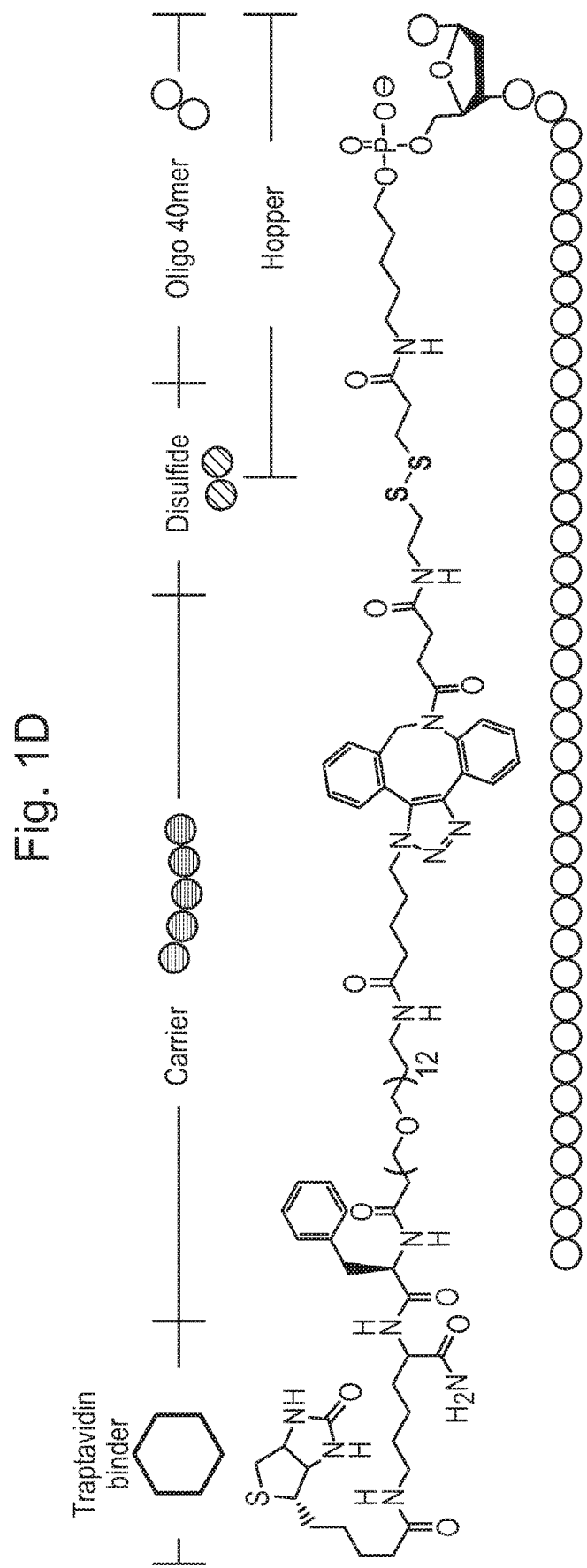

SEQ ID NO: 1 shows the amino acid sequence of one subunit of wild type α-HL. Amino acids 2 to 6, 73 to 75, 207 to 209, 214 to 216 and 219 to 222 form α-helices. Amino acids 22 to 30, 35 to 44, 52 to 62, 67 to 71, 76 to 91, 98 to 103, 112 to 123, 137 to 148, 154 to 159, 165 to 172, 229 to 235, 243 to 261, 266 to 271, 285 to 286 and 291 to 293 form β-strands. All the other non-terminal amino acids, namely 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274 and 287 to 290 form loop regions. Amino acids 1 and 293 are terminal amino acids.

SEQ ID NO: 2 shows the amino acid sequence of one subunit of wild type α-HL-D8H6. The same amino acids that form α-helices, β-strands and loop regions in wild type α-HL form the corresponding regions in this subunit.

SEQ ID NO: 3 shows the amino acid sequence of one subunit of 115C117C-α-HL-D8H6. The same amino acids that form α-helices, β-strands and loop regions in wild type α-HL form the corresponding regions in this subunit.

SEQ ID NO: 4 shows the amino acid sequence of one subunit of 115C117C119C-α-HL-D8H6. The same amino acids that form α-helices, β-strands and loop regions in wild type α-HL form the corresponding regions in this subunit.

SEQ ID NO: 5 shows the amino acid sequence of one subunit of 113C115C117C119C121C-α-HL-D8H6. The same amino acids that form α-helices, β-strands and loop regions in wild type α-HL form the corresponding regions in this subunit.

SEQ ID NO: 6 shows the amino acid sequence of one subunit of 113C115C117C119C121C123C-α-HL-D8H6. The same amino acids that form α-helices, β-strands and loop regions in wild type α-HL form the corresponding regions in this subunit.

SEQ ID NO: 7 shows the amino acid sequence of one subunit of C115C117C119C139C-α-HL-D8H6. The same amino acids that form α-helices, β-strands and loop regions in wild type α-HL form the corresponding regions in this subunit.

DETAILED DESCRIPTION OF THE INVENTION

Definitions

The following substituent definitions apply with respect to the compounds defined herein: An alkyl group is an unsubstituted or substituted, straight or branched chain saturated hydrocarbon radical. Typically the alkyl group has from 1 to 20 carbon atoms, i.e. it is a $C_{1-20}$ alkyl group. Usually, it is $C_{1-10}$ alkyl. The alkyl group may for instance be a $C_{1-6}$ alkyl, for example methyl, ethyl, propyl, butyl, pentyl or hexyl, or $C_{1-4}$ alkyl, for example methyl, ethyl, i-propyl, n-propyl, t-butyl, s-butyl or n-butyl. When an alkyl group is substituted it typically bears one or more substituents selected from substituted or unsubstituted $C_{1-10}$ alkyl, substituted or unsubstituted aryl (as defined herein), cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-10}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Examples of substituted alkyl groups include haloalkyl, hydroxyalkyl, aminoalkyl, alkoxyalkyl and alkaryl groups. The term alkaryl, as used herein, pertains to a $C_{1-10}$ alkyl group in which at least one hydrogen atom has been replaced with an aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, $Ph$-$CH_2CH_2$—), styryl ($Ph$-$CH$=$CH$—), cinnamyl (Ph-CH=CH—CH$_2$—). Typically a substituted C$_{1-10}$ alkyl group carries 1, 2 or 3 substituents, for instance 1 or 2.

An alkenyl group is an unsubstituted or substituted, straight or branched chain unsaturated hydrocarbon radical having one or more, e.g. one or two, double bonds. Typically the alkenyl group has from 2 to 20 carbon atoms, i.e. it is a C$_{2-20}$ alkenyl group. Usually, it is C$_{2-10}$ alkenyl. The alkenyl group may for instance be C$_{2-6}$ alkenyl, for example ethenyl, propenyl, butenyl, pentenyl or hexenyl, or C$_{2-4}$ alkenyl, for example ethenyl, i-propenyl, n-propenyl, t-butenyl, s-butenyl or n-butenyl. When an alkenyl group is substituted it typically bears one or more substituents selected from substituted or unsubstituted C$_{1-10}$ alkyl, substituted or unsubstituted aryl (as defined herein), cyano, amino, C$_{1-10}$ alkylamino, di(C$_{1-10}$)alkylamino, arylamino, diarylamino, arylalkylamino, amido, acylamido, hydroxy, oxo, halo, carboxy, ester, acyl, acyloxy, C$_{1-10}$ alkoxy, aryloxy, haloalkyl, sulfonic acid, sulfhydryl (i.e. thiol, —SH), C$_{1-10}$ alkylthio, arylthio, sulfonyl, phosphoric acid, phosphate ester, phosphonic acid and phosphonate ester. Examples of substituted alkenyl groups include haloalkenyl, hydroxyalkenyl, aminoalkenyl, alkoxyalkenyl and alkenaryl groups. The term alkenaryl, as used herein, pertains to a C$_{2-10}$ alkenyl group in which at least one hydrogen atom has been replaced with an aryl group. Examples of such groups include, but are not limited to, styryl (PhCH=CH—), Ph$_2$C=CH—, PhCH=C(Ph)-, and cinnamyl (Ph-CH=CH—CH$_2$—). Typically a substituted C$_{2-10}$ alkenyl group carries 1, 2 or 3 substituents, for instance 1 or 2.

An alkynyl group is an unsubstituted or substituted, straight or branched chain unsaturated hydrocarbon radical having one or more, e.g. one or two, triple bonds. Typically the alkynyl group has from 2 to 20 carbon atoms, i.e. it is a C$_{2-20}$ alkynyl group. Usually, it is C$_{2-10}$ alkynyl. The alkynyl group may for instance be C$_{2-6}$ alkynyl, for example ethynyl, propynyl, butynyl, pentynyl or hexynyl, or C$_{2-4}$ alkynyl, for example ethynyl, i-propynyl, n-propynyl, t-butynyl, s-butynyl or n-butynyl. When an alkynyl group is substituted it typically bears one or more substituents selected from substituted or unsubstituted C$_{1-10}$ alkyl, substituted or unsubstituted aryl (as defined herein), cyano, amino, C$_{1-10}$ alkylamino, di(C$_{1-10}$)alkylamino, arylamino, diarylamino, arylalkylamino, amido, acylamido, hydroxy, oxo, halo, carboxy, ester, acyl, acyloxy, C$_{1-10}$ alkoxy, aryloxy, haloalkyl, sulfonic acid, sulfhydryl (i.e. thiol, —SH), C$_{1-10}$ alkylthio, arylthio, sulfonyl, phosphoric acid, phosphate ester, phosphonic acid and phosphonate ester. Examples of substituted alkynyl groups include haloalkynyl, hydroxyalkynyl, aminoalkynyl, alkoxyalkynyl and alkynaryl groups. The term alkynaryl, as used herein, pertains to a C$_{2-10}$ alkyl group in which at least one hydrogen atom has been replaced with an aryl group. Examples of such groups include, but are not limited to, Ph-C≡C—, Ph-C≡C—CH$_2$—, H—C≡C—CH(Ph)-, and H—C≡C—CPh$_2$-. Typically a substituted C$_{2-10}$ alkynyl group carries 1, 2 or 3 substituents, for instance 1 or 2.

A cycloalkyl group, which may also be referred to as a carbocyclyl group, is an unsubstituted or substituted alkyl group which is also a cyclyl group; that is, a monovalent moiety obtained by removing a hydrogen atom from an alicyclic ring atom of a carbocyclic ring of a carbocyclic compound. Typically, the moiety has from 3 to 10 carbon atoms (unless otherwise specified), including from 3 to 10 ring atoms, in which case it is referred to as a C$_{3-10}$ cycloalkyl group or a C$_{3-10}$ carbocyclyl group. Thus, the term "cycloalkyl" includes the sub-classes cycloalkyenyl and cycloalkynyl. Examples of groups of C$_{3-10}$ cycloalkyl groups include C$_{3-7}$ cycloalkyl. When a C$_{3-10}$ cycloalkyl group is substituted it typically bears one or more substituents selected from C$_{1-6}$ alkyl which is unsubstituted, aryl (as defined herein), cyano, amino, C$_{1-10}$ alkylamino, di(C$_{1-10}$) alkylamino, arylamino, diarylamino, arylalkylamino, amido, acylamido, hydroxy, oxo, halo, carboxy, ester, acyl, acyloxy, C$_{1-20}$ alkoxy, aryloxy, haloalkyl, sulfonic acid, sulfhydryl (i.e. thiol, —SH), C$_{1-10}$ alkylthio, arylthio, phosphoric acid, phosphate ester, phosphonic acid and phosphonate ester and sulfonyl. Typically a substituted C$_{3-10}$ cycloalkyl group carries 1, 2 or 3 substituents, for instance 1 or 2.

Examples of C$_{3-10}$ cycloalkyl groups include, but are not limited to, those derived from saturated monocyclic hydrocarbon compounds, which C$_{3-10}$ cycloalkyl groups are unsubstituted or substituted as defined above: cyclopropane (C$_3$), cyclobutane (C$_4$), cyclopentane (C$_5$), cyclohexane (C$_6$), cycloheptane (C$_7$), methylcyclopropane (C$_4$), dimethylcyclopropane (C$_5$), methylcyclobutane (C$_5$), dimethylcyclobutane (C$_6$), methylcyclopentane (C$_6$), dimethylcyclopentane (C$_7$), methylcyclohexane (C$_7$), dimethylcyclohexane (C$_8$), menthane (C$_{10}$);

unsaturated monocyclic hydrocarbon compounds: cyclopropene (C$_3$), cyclobutene (C$_4$), cyclopentene (C$_5$), cyclohexene (C$_6$), methylcyclopropene (C$_4$), dimethylcyclopropene (C$_5$), methylcyclobutene (C$_5$), dimethylcyclobutene (C$_6$), methylcyclopentene (C$_6$), dimethylcyclopentene (C$_7$), methylcyclohexene (C$_7$), dimethylcyclohexene (C$_8$);

saturated polycyclic hydrocarbon compounds: thujane (C$_{10}$), carane (C$_{10}$), pinane (C$_{10}$), bornane (C$_{10}$), norcarane (C$_7$), norpinane (C$_7$), norbornane (C$_7$), adamantane (C$_{10}$), decalin (decahydronaphthalene) (C$_{10}$);

unsaturated polycyclic hydrocarbon compounds: camphene (C$_{10}$), limonene (C$_{10}$), pinene (C$_{10}$), polycyclic hydrocarbon compounds having an aromatic ring: indene (C$_9$), indane (e.g., 2,3-dihydro-1H-indene) (C$_9$), tetraline (1,2,3,4-tetrahydronaphthalene) (C$_{10}$).

A heterocyclyl group is an unsubstituted or substituted monovalent moiety obtained by removing a hydrogen atom from a ring atom of a heterocyclic compound. Typically, the moiety has from 3 to 10 ring atoms (unless otherwise specified), of which from 1 to 5 are ring heteroatoms, in which case it is referred to as a C$_{3-10}$ heterocyclyl group. Preferably, each ring has from 3 to 7 ring atoms, of which from 1 to 4 are ring heteroatoms. When a C$_{3-10}$ heterocyclyl group is substituted it typically bears one or more substituents selected from C$_{1-6}$ alkyl which is unsubstituted, aryl (as defined herein), cyano, amino, C$_{1-10}$ alkylamino, di(C$_{1-10}$) alkylamino, arylamino, diarylamino, arylalkylamino, amido, acylamido, hydroxy, oxo, halo, carboxy, ester, acyl, acyloxy, C$_{1-20}$ alkoxy, aryloxy, haloalkyl, sulfonic acid, sulfhydryl (i.e. thiol, —SH), C$_{1-10}$ alkylthio, arylthio, phosphoric acid, phosphate ester, phosphonic acid and phosphonate ester and sulfonyl. Typically a substituted C$_{3-10}$ heterocyclyl group carries 1, 2 or 3 substituents, for instance 1 or 2.

Examples of groups of heterocyclyl groups include C$_{5-10}$ heterocyclyl, C$_{3-7}$ heterocyclyl, C$_{5-7}$ heterocyclyl, and C$_{5-6}$ heterocyclyl.

Examples of (non-aromatic) monocyclic C$_{3-10}$ heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of $C_{3-10}$ heterocyclyl groups which are also aryl groups are described below as heteroaryl groups.

An aryl group is a substituted or unsubstituted, monocyclic or fused polycyclic aromatic group which typically contains from 6 to 14 carbon atoms, preferably from 6 to 10 carbon atoms, in the ring portion. Examples include phenyl (i.e. monocyclic), naphthyl, indenyl and indanyl (i.e. fused bicyclic), anthracenyl (i.e. fused tricyclic), and pyrenyl (i.e. fused tetracyclic) groups. An aryl group is unsubstituted or substituted. When an aryl group as defined above is substituted it typically bears one or more substituents selected from $C_1$-$C_6$ alkyl which is unsubstituted (to form an aralkyl group), aryl which is unsubstituted, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfhydryl (i.e. thiol, —SH), $C_{1-10}$ alkylthio, arylthio, sulfonic acid, phosphoric acid, phosphate ester, phosphonic acid and phosphonate ester and sulfonyl. Typically it carries 0, 1, 2 or 3 substituents. A substituted aryl group may be substituted in two positions with a single $C_{1-6}$ alkylene group, or with a bidentate group represented by the formula —X—$C_{1-6}$ alkylene, or —X—$C_{1-6}$ alkylene-X—, wherein X is selected from O, S and NR, and wherein R is H, aryl or $C_{1-6}$ alkyl. Thus a substituted aryl group may be an aryl group fused with a cycloalkyl group or with a heterocyclyl group. The term aralkyl as used herein, pertains to an aryl group in which at least one hydrogen atom (e.g., 1, 2, 3) has been substituted with a $C_{1-6}$ alkyl group. Examples of such groups include, but are not limited to, tolyl (from toluene), xylyl (from xylene), mesityl (from mesitylene), and cumenyl (or cumyl, from cumene), and duryl (from durene).

As used herein, a heteroaryl group is a substituted or unsubstituted monocyclic or fused polycyclic (e.g. bicyclic or tricyclic) aromatic group which typically contains from 5 to 14 atoms in the ring portion including at least one heteroatom, for example 1, 2 or 3 heteroatoms, selected from O, S, N, P, Se and Si, more typically from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, thiazolyl, imidazolyl, triazolyl, pyrazolyl, oxazolyl, isothiazolyl, benzofuranyl, isobenzofuranyl, benzothiophenyl, indolyl, indazolyl, carbazolyl, acridinyl, purinyl, cinnolinyl, quinoxalinyl, naphthyridinyl, benzimidazolyl, benzoxazolyl, quinolinyl, quinazolinyl and isoquinolinyl. A heteroaryl group is often a 5- or 6-membered ring. However, as used herein, references to a heteroaryl group also include fused polycyclic ring systems, including for instance fused bicyclic systems in which a heteroaryl group is fused to an aryl group. When the heteroaryl group is such a fused heteroaryl group, preferred examples are fused ring systems wherein a 5- to 6-membered heteroaryl group is fused to a phenyl group. Examples of such fused ring systems are benzofuranyl, isobenzofuranyl, benzothiophenyl, indolyl, indazolyl, benzimidazolyl, benzoxazolyl, quinolinyl, quinazolinyl and isoquinolinyl moieties.

A heteroaryl group may be unsubstituted or substituted, for instance, as specified above for aryl. Typically it carries 0, 1, 2 or 3 substituents.

An alkylene group is an unsubstituted or substituted bidentate moiety obtained by removing two hydrogen atoms, either both from the same carbon atom, or one from each of two different carbon atoms, of a hydrocarbon compound which may be aliphatic or alicyclic, and which may be saturated, partially unsaturated, or fully unsaturated. The hydrocarbon compound may have from 1 to 20 carbon atoms, in which case the alkylene group is a $C_{1-20}$ alkylene. It may for instance have from 1 to 10 carbon atoms in which case the alkylene group is $C_{1-10}$ alkylene. Thus, the term "alkylene" includes the sub-classes alkenylene, alkynylene, cycloalkylene, etc., discussed below. Usually, however, it is a saturated aliphatic (non-cyclic) group. Typically it is $C_{1-6}$ alkylene, or $C_{1-4}$ alkylene, for example methylene, ethylene, i-propylene, n-propylene, t-butylene, s-butylene or n-butylene. It may for instance be $C_{2-4}$ alkylene. Or, for instance, it may be $C_{2-3}$ alkylene, for example ethylene, n-propylene or i-propylene. (Although usually, herein, a $C_{2-3}$ alkylene refers to ethylene or n-proylene.) It may also be pentylene, hexylene, heptylene, octylene and the various branched chain isomers thereof. An alkylene group may be unsubstituted or substituted, for instance, as specified above for alkyl. Typically a substituted alkylene group carries 1, 2 or 3 substituents, for instance 1 or 2.

Usually, an alkylene group is an unsubstituted or substituted bidentate moiety obtained by removing two hydrogen atoms, either both from the same carbon atom, or one from each of two different carbon atoms, from an alkyl group as defined herein, for instance from a $C_{1-10}$ alkyl group as defined herein. Usually, an alkenylene group is an unsubstituted or substituted bidentate moiety obtained by removing two hydrogen atoms, either both from the same carbon atom, or one from each of two different carbon atoms, from an alkenyl group as defined herein, for instance from a $C_{2-10}$ alkenyl group as defined herein. Usually, an alkynylene group is an unsubstituted or substituted bidentate moiety obtained by removing two hydrogen atoms, either both from the same carbon atom, or one from each of two different carbon atoms, from an alkynyl group as defined herein, for instance from a $C_{2-10}$ alkynyl group as defined herein.

In this context, the prefixes (e.g., $C_{1-4}$, $C_{1-7}$, $C_{1-10}$, $C_{2-7}$, $C_{3-7}$, etc.) denote the number of carbon atoms, or range of number of carbon atoms. For example, the term "$C_{1-4}$ alkylene," as used herein, pertains to an alkylene group having from 1 to 4 carbon atoms. Examples of groups of alkylene groups include $C_{1-4}$ alkylene ("lower alkylene"), $C_{1-7}$ alkylene, and $C_{1-10}$ alkylene.

Examples of linear saturated $C_{1-7}$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but is not limited to, —CH=CH— (vinylene), —CH=CH—$CH_2$—, —$CH_2$—CH=$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—.

Examples of branched partially unsaturated $C_{1-7}$ alkylene groups include, but is not limited to, —$C(CH_3)$=CH—, —$C(CH_3)$=CH—$CH_2$—, and —CH=CH—$CH(CH_3)$—.

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

Alkylene, alkenylene, alkynylene and alkyl groups as defined herein are either uninterrupted or interrupted by one or more heteroatoms or heterogroups, such as S, O or N(R'') wherein R'' is H, $C_{1-6}$ alkyl, $C_{2-6}$ alkenyl, $C_{2-6}$ alkynyl, aryl (typically phenyl), or heteroaryl, or by one or more arylene or heteroarylene (typically arylene, more typically phenylene) groups, or by one or more —C(O)—, —C(O)O— or —C(O)N(R'')— groups, or for instance by one or more carbocyclylene or heterocyclylene groups, each of which may be unsubstituted or substituted. The phrase "optionally interrupted" as used herein thus refers to an alkylene, alkenylene, alkynylene or alkyl group, as defined above, which is uninterrupted or which is interrupted between adjacent carbon atoms by a heteroatom such as oxygen or sulfur, by a heterogroup such as N(R'') wherein R'' is as defined above, or by an arylene or heteroarylene (typically arylene, more typically phenylene) group, or by a —C(O)—, —C(O)O— or —C(O)N(R'')— group, again wherein R'' is as defined above, or for instance by one or more carbocyclylene or heterocyclylene groups, each of which may be unsubstituted or substituted.

For instance, a $C_{1-10}$ alkyl group such as n-butyl may be interrupted by the heterogroup N(R'') as follows: —$CH_2$N(R'')$CH_2CH_2CH_3$, —$CH_2CH_2$N(R'')$CH_2CH_3$, or —$CH_2CH_2CH_2$N(R'')$CH_3$. Similarly, an alkylene group such as n-butylene may be interrupted by the heterogroup N(R'') as follows: —$CH_2$N(R'')$CH_2CH_2CH_2$—, —$CH_2CH_2$N(R'')$CH_2CH_2$—, or —$CH_2CH_2CH_2$N(R'')$CH_2$—. Typically an interrupted group, for instance an interrupted $C_{1-10}$ alkylene or $C_{1-10}$ alkyl group, is interrupted by 1, 2 or 3 heteroatoms or heterogroups or by 1, 2 or 3 arylene (typically phenylene) groups. More typically, an interrupted group, for instance an interrupted $C_{1-10}$ alkylene or $C_{1-10}$ alkyl group, is interrupted by 1 or 2 heteroatoms or heterogroups or by 1 or 2 arylene (typically phenylene) groups. For instance, a $C_{1-20}$ alkyl group such as n-butyl may be interrupted by 2 heterogroups N(R'') as follows: —$CH_2$N(R'')$CH_2$N(R'')$CH_2CH_3$.

An arylene group is an unsubstituted or substituted monocyclic or fused polycyclic bidentate moiety obtained by removing two hydrogen atoms, one from each of two different aromatic ring atoms of an aromatic compound, which moiety has from 5 to 14 ring atoms (unless otherwise specified). Typically, each ring has from 5 to 7 or from 5 to 6 ring atoms. An arylene group may be unsubstituted or substituted, for instance, as specified above for aryl.

In this context, the prefixes (e.g., $C_{5-20}$, $C_{6-20}$, $C_{5-14}$, $C_{5-7}$, $C_{5-6}$, etc.) denote the number of ring atoms, or range of number of ring atoms, whether carbon atoms or heteroatoms. For example, the term "$C_{5-6}$ arylene," as used herein, pertains to an arylene group having 5 or 6 ring atoms. Examples of groups of arylene groups include $C_{5-20}$ arylene, $C_{6-20}$ arylene, $C_{5-14}$ arylene, $C_{6-14}$ arylene, $C_{6-10}$ arylene, $C_{5-12}$ arylene, $C_{5-10}$ arylene, $C_{5-7}$ arylene, $C_{5-6}$ arylene, $C_5$ arylene, and $C_6$ arylene.

The ring atoms may be all carbon atoms, as in "carboarylene groups" (e.g., $C_{6-20}$ carboarylene, $C_{6-14}$ carboarylene or $C_{6-10}$ carboarylene).

Examples of $C_{6-20}$ arylene groups which do not have ring heteroatoms (i.e., $C_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_{5-14}$ heteroarylene). Examples of $C_{5-14}$ heteroarylene groups include, but are not limited to, those derived from the compounds discussed above in regard to heteroaryl groups.

A carbocyclylene group is an unsubstituted or substituted divalent moiety obtained by removing two hydrogen atoms from the same or different ring carbon atoms of a carbocyclic compound. Typically, the moiety has from 3 to 10 carbon atoms, including from 3 to 10 ring atoms, in which case it is referred to as a $C_{3-10}$ carbocyclylene group. The carbocyclylene group may be unsaturated or saturated and therefore includes the sub-classes cycloalkenylene and cycloalkynylene. It may also be unsubstituted or substituted, as specified above for carbocyclyl and cycloalkyl groups.

A heterocyclylene group is an unsubstituted or substituted divalent moiety obtained by removing two hydrogen atoms from the same or different ring carbon atoms of a heterocyclic compound. Typically, the moiety has from 3 to 10 carbon atoms, including from 3 to 10 ring atoms, of which from 1 to 5 are ring heteroatoms, in which case it is referred to as a $C_{3-10}$ heterocyclylene group. Where a heterocyclylene group is substituted, it typically bears one or more, typically 1, 2 or 3, substituents as defined above for heterocyclic groups.

As used herein the term oxo represents a group of formula: =O

As used herein the term acyl represents a group of formula: —C(=O)R, wherein R is an acyl substituent, for example, a substituted or unsubstituted $C_{1-20}$ alkyl group, a $C_{1-20}$ perfluoroalkyl group, a substituted or unsubstituted $C_{3-10}$ cycloalkyl group, a substituted or unsubstituted $C_{3-10}$ heterocyclyl group, a substituted or unsubstituted aryl group, a perfluoroaryl group, or a substituted or unsubstituted heteroaryl group. Examples of acyl groups include, but are not limited to, —C(=O)CH₃ (acetyl), —C(=O)CH₂CH₃ (propionyl), —C(=O)C(CH₃)₃ (t-butyryl), and —C(=O)Ph (benzoyl, phenone).

As used herein the term acyloxy (or reverse ester) represents a group of formula: —OC(=O)R, wherein R is an acyloxy substituent, for example, substituted or unsubstituted $C_{1-10}$ alkyl group, a substituted or unsubstituted $C_{3-10}$ heterocyclyl group, or a substituted or unsubstituted aryl group, typically a $C_{1-6}$ alkyl group. Examples of acyloxy groups include, but are not limited to, —OC(=O)CH₃ (acetoxy), —OC(=O)CH₂CH₃, —OC(=O)C(CH₃)₃, —OC(=O)Ph, and —OC(=O)CH₂Ph.

As used herein the term ester (or carboxylate, carboxylic acid ester or oxycarbonyl) represents a group of formula: —C(=O)OR, wherein R is an ester substituent, for example, a substituted or unsubstituted $C_{1-10}$ alkyl group, a substituted or unsubstituted $C_{3-20}$ heterocyclyl group, or a substituted or unsubstituted aryl group (typically a phenyl group). Examples of ester groups include, but are not limited to, —C(=O)OCH₃, —C(=O)OCH₂CH₃, —C(=O)OC(CH₃)₃, and —C(=O)OPh.

As used herein the term amino represents a group of formula —NH₂. The term $C_{1-10}$ alkylamino represents a group of formula —NHR' wherein R' is a $C_{1-10}$ alkyl group, preferably a $C_{1-6}$ alkyl group, as defined previously. The term di($C_{1-10}$)alkylamino represents a group of formula —NR'R" wherein R' and R" are the same or different and represent $C_{1-10}$ alkyl groups, preferably $C_{1-6}$ alkyl groups, as defined previously. The term arylamino represents a group of formula —NHR' wherein R' is an aryl group, preferably a phenyl group, as defined previously. The term diarylamino represents a group of formula —NR'R" wherein R' and R" are the same or different and represent aryl groups, preferably phenyl groups, as defined previously. The term arylalkylamino represents a group of formula —NR'R" wherein R' is a $C_{1-10}$ alkyl group, preferably a $C_{1-6}$ alkyl group, and R" is an aryl group, preferably a phenyl group.

A halo group is chlorine, fluorine, bromine or iodine (a chloro group, a fluoro group, a bromo group or an iodo group). It is typically chlorine, fluorine or bromine.

As used herein the term amido represents a group of formula: —C(=O)NR'R", wherein R' and R" are independently selected from H, $C_{1-10}$ alkyl and aryl. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R' and R", together with the nitrogen atom to which they are attached, form a heterocyclic structure as in, for example, piperidinocarbonyl, morpholinocarbonyl, thiomorpholinocarbonyl, and piperazinocarbonyl.

As used herein the term acylamido represents a group of formula: —NR¹C(=O)R², wherein R¹ is an amide substituent, for example, hydrogen, a $C_{1-10}$ alkyl group, a $C_{3-20}$ heterocyclyl group, an aryl group, preferably hydrogen or a $C_{1-10}$ alkyl group, and R² is an acyl substituent, for example, a $C_{1-10}$ alkyl group, a $C_{3-20}$ heterocyclyl group, or an aryl group. Preferably R¹ is hydrogen and R² is a $C_{1-10}$ alkyl group. Examples of acylamide groups include, but are not limited to, —NHC(=O)CH₃, —NHC(=O)CH₂CH₃, —NHC(=O)Ph, —NHC(=O)C₁₅H₃₁ and —NHC(=O)C₉H₁₉. Thus, a substituted $C_{1-10}$ alkyl group may comprise an acylamido substituent defined by the formula —NHC(=O)—$C_{1-10}$ alkyl, such as —NHC(=O)C₅H₁₁ or —NHC(=O)C₉H₁₉. R¹ and R² may together form a cyclic structure, as in, for example, succinimidyl, maleimidyl, and phthalimidyl:

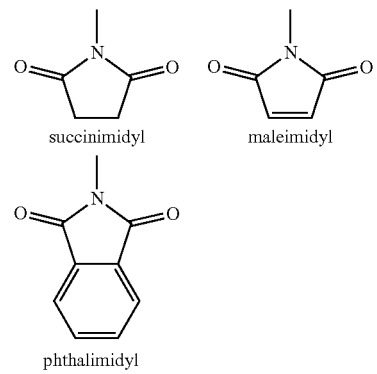

A $C_{1-10}$ alkylthio group is a said $C_{1-10}$ alkyl group, preferably a $C_{1-6}$ alkyl group, attached to a thio group. An arylthio group is an aryl group, preferably a phenyl group, attached to a thio group.

A $C_{1-10}$ alkoxy group is a said substituted or unsubstituted $C_{1-10}$ alkyl group attached to an oxygen atom. A $C_{1-6}$ alkoxy group is a said substituted or unsubstituted $C_{1-6}$ alkyl group attached to an oxygen atom. A $C_{1-4}$ alkoxy group is a substituted or unsubstituted $C_{1-4}$ alkyl group attached to an oxygen atom. Said $C_{1-10}$, $C_{1-6}$ and $C_{1-4}$ alkyl groups are optionally interrupted as defined herein. Examples of $C_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of $C_{1-20}$ alkoxy groups are —O(Adamantyl), —O—CH₂-Adamantyl and —O—CH₂—CH₂-Adamantyl. An aryloxy group is a substituted or unsubstituted aryl group, as defined herein, attached to an oxygen atom. An example of an aryloxy group is —OPh (phenoxy).

Unless otherwise specified, included in the above are the well known ionic, salt, solvate, and protected forms of these substituents. For example, a reference to carboxylic acid, carboxy or carboxyl group (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxy or hydroxyl group (—OH) also includes the anionic form (—O⁻), a salt or solvate thereof, as well as conventional protected forms.

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH₃, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto, enol, and enolate forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

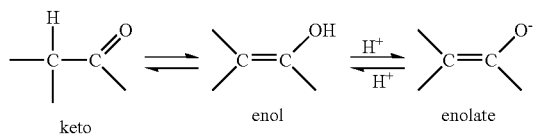

keto     enol     enolate

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting known methods, in a known manner.

Unless otherwise specified, a reference to a particular compound or complex also includes ionic, salt, solvated and protected forms.

Molecular Hoppers

As explained above, the invention provides a method of moving a molecular hopper along a track; wherein:
  (a) the track comprises a plurality of primary functional groups aligned along a substrate;
  (b) the hopper comprises a secondary functional group capable of binding to each of the plurality of primary functional groups on the track; and
  (c) the hopper optionally comprises a cargo moiety;
the method comprising the steps of:
  (i) contacting the hopper with the track such that the secondary functional group of the hopper binds to a first primary functional group on the track;
  (ii) applying a driving force so as to cause the hopper to be directionally transferred from the first primary functional group to a second primary functional group on the track thereby causing the hopper to move along the track.

Movement of the Hopper

Advantageously, in the invention, the motion of the hopper along the track can be controlled. In other words, the movement of the hopper along the track is not merely a random walk. Rather, the movement of the hopper can be determined by application of a driving force as described herein. In such a manner the hopper can perform useful work such as by directing the movement of a cargo molecule towards a desired destination or in a desired direction. Non-directional random walks of molecules along tracks and capture by thermodynamic sinks have been described in the literature but the provision of a directed system wherein direction is determined by the application of a driving force is a significantly more complex challenge addressed by the present invention.

Typically, in the invention, the direction of the driving force relative to the track determines the overall direction of the movement of the hopper along the track. Usually, the hopper moves in the same direction along the track as the direction of the applied force. For example, if the driving force is applied in a direction from the start of the track to the end of the track then the overall movement of the hopper is typically likewise from the start of the track to the end of the track. In the same way, if the direction of the driving force is reversed such that the driving force is applied in a direction from the end of the track to the start of the track then the overall movement of the hopper is likewise reversed, i.e. from the end of the track to the start of the track. However, the invention also embraces methods wherein the movement of the hopper is determined by the direction of the driving force relative to the track and the overall movement of the hopper is opposite to the driving force.

In the invention, the transfer of the hopper from the first primary functional group to the second primary functional group on the track is typically independent of the addition of exogenous fuel such as a chemical reagent. In other words, there is typically no requirement for a catalyst for transfer of the hopper from the first primary functional group to a second primary functional group on the track, although the use of such a catalyst is not excluded in the invention. When no catalyst or exogenous "fuel" is present, the movement of the hopper along the track is said to be autonomous. Such movement contrasts with systems which require the use of a sacrificial fuel molecule to cause movement.

Typically, in the invention, step (ii) of the method comprises applying a driving force to the hopper so as to cause the hopper to be sequentially transferred between each of the plurality of primary functional groups on the track thereby causing the hopper to move along the track. Those skilled in the art will recognise that the driving force may be applied directly to the hopper or may be applied to the hopper via the track. For example, if the track is a surface of a pore and the hopper moves along the track, the force may be for example an physical or chemical potential applied from one side of the pore to the other. For example, an electrical potential may be applied across the pore. Such a driving force acts on the hopper thereby causing the hopper to be sequentially transferred between each of the functional groups on the track and thus to move along the track. It will be apparent from the above discussion that the direction of the movement of the hopper is typically the same as the direction of the applied force. By way of non-limiting example, if an electrical potential is applied across a track comprised in a pore from the "cis" side to the "trans" side of the pore then the movement of the hopper along the track is typically likewise in a "cis-to-trans" direction. The applied force causes the hopper to move in a defined direction and so the overall movement of the hopper is not random.

The movement of the hopper is typically highly processive. Backstepping is highly disfavoured and is typically not observed. The hopper does not spontaneously dissociate from the track, although as described herein release from the track can be controlled by appropriate design of the track to provide a release point. Typically, a hopper may be capable of completing more than 10 steps, e.g. more than 20 steps, for example more than 30 steps, such as more than 50 steps, e.g. more than 100 steps, for example more than 150 steps, e.g. more than 200 steps, such as more than 250 steps, e.g. more than 500 steps, such as more than 1000 steps without dissociating from the track Substrate In the invention, the track comprises a plurality of primary functional groups aligned along a substrate.

Typically, the substrate is an organic or inorganic surface comprising plurality of primary functional groups. Any suitable organic or inorganic surface can be used in such methods. The substrate can be a surface of an inorganic substance such as the surface of a metal with e.g. an oxide coating or a semiconductor material e.g. silicon or compounds thereof. The substrate may be organic, e.g the substrate may be a polymer or a protein or any other organic substrate. A polymeric substrate may comprise a naturally occurring or non-naturally occurring polymer. In the same way, a protein substrate may comprise a naturally occurring protein or a non-naturally occurring protein.

A non-naturally occurring protein may comprise only naturally occurring amino acids, or may comprise one or more non-naturally occurring amino acids (also known as non-canonical amino acids). Naturally occurring proteins can be produced in a variety of ways known in the art, and the methods used for their production are not limiting on the invention. Known methods include expression in bacteria, yeast or insect cells from a suitable plasmid, followed by appropriate processing as required, for example purification. Non-cellular expression systems (e.g. in vitro transcription/translation systems) can also be used. Synthetic routes such as native chemical ligation can also be used. Similar processes can also be used to generate non-naturally occurring proteins, either using appropriate plasmids to encode the desired protein sequence or with non-natural amino acids incorporated either by synthetic or biological means. Methods for producing proteins are described in references known to those skilled in the art, such as Green and Sambrook, *Molecular Cloning*, Cold Spring Harbor Laboratory Press (4$^{th}$ edition).

Often, in the invention, the substrate is a surface of a transmembrane pore. The surface may be an internal or external surface. Usually, in the invention, the substrate is an internal surface of a transmembrane pore.

As explained below, any suitable transmembrane pore can be used in the invention. A nanopore can be naturally occurring (e.g. a pore-forming protein) or can be synthetically produced e.g. as a hole (a pore) generated in a synthetic material such as silicon compound (e.g. silicon nitride) or graphene. For example, the transmembrane pore may be a protein nanopore, a solid state nanopore, a DNA nanopore, a polymer nanopore, or a synthetic or semi-synthetic nanopore. A first transmembrane pore may be comprised in a second transmembrane pore; for example, a protein nanopore may be located in a solid state nanopore. When the substrate is an organic or inorganic surface, the pore may be a well, gap, channel, trench or slit in the surface. Typically, in the invention, a transmembrane pore is a protein or solid state nanopore. More often, a transmembrane pore is a transmembrane β-barrel protein nanopore. Typical transmembrane pores are described in more detail below.

When the substrate is a surface of a transmembrane pore, the pore may be comprised in an array of pores. Thus, an array of tracks may be formed in an array of pores. The pores may be the same or different. The array may, for example, be formed by localising protein nanopores in an array formed on a solid state surface; for example in an array of solid state nanopores.

Pores

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end.

A transmembrane pore suitable for use in the invention may be a solid state pore. A solid-state nanopore is typically a nanometer-sized hole formed in a synthetic membrane. Suitable solid state pores include, but are not limited to, silicon nitride pores, silicon dioxide pores and graphene pores. Solid state nanopores may be fabricated e.g. by focused ion or electron beams, so the size of the pore can be tuned freely. Suitable solid state pores and methods of producing them are discussed in U.S. Pat. No. 6,464,842, WO 03/003446, WO 2005/061373, U.S. Pat. Nos. 7,258, 838, 7,466,069, 7,468,271 and 7,253,434.

A transmembrane pore may be a DNA origami pore (Langecker et al., Science, 2012; 338: 932-936). DNA origami pores are disclosed in WO2013/083983.

A transmembrane pore may be a polymer-based pore. Suitable pores can be made from polymer-based plastics such as a polyester e.g. polyethylene terephthalate (PET) via track etching.

A transmembrane pore suitable for use in the invention may be a transmembrane protein pore. A transmembrane protein pore is a polypeptide or a collection of polypeptides that permits ions driven by an applied potential to flow from one side of a membrane to the other side of the membrane. Transmembrane protein pores are particularly suitable for use in the invention.

A transmembrane protein pore may be isolated, substantially isolated, purified or substantially purified. A pore is isolated or purified if it is completely free of any other components, such as lipids or other pores. A pore is substantially isolated if it is mixed with carriers or diluents which will not interfere with its intended use. For instance, a pore is substantially isolated or substantially purified if it present in a form that comprises less than 10%, less than 5%, less than 2% or less than 1% of other components, such as lipids or other pores. The pore is typically present in a membrane, for example a lipid bilayer or a synthetic membrane e.g. a block-copolymer membrane.

A transmembrane protein pore may be a monomer or an oligomer. A transmembrane protein pore is often made up of several repeating subunits, such as at least 6, at least 7, at least 8, at least 9, at least 10, at least 11, at least 12, at least 13, at least 14, at least 15, or at least 16 subunits. The pore is typically a hexameric, heptameric, octameric or nonameric pore.

The pore may be a homo-oligomer or a hetero-oligomer. A transmembrane protein pore may be a heptameric pore. A transmembrane protein pore may typically comprises a barrel or channel through which the ions may flow. The subunits of the pore typically surround a central axis and contribute strands to a transmembrane β barrel or channel or a transmembrane α-helix bundle or channel.

Suitable transmembrane pores for use in accordance with the invention can be β-barrel pores, α-helix bundle pores or solid state pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smeg-* matis porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner α-helix bundle proteins and a outer membrane proteins, such as Wza and ClyA toxin. For example, the transmembrane pore may be derived from or based on Msp, α-hemolysin (α-HL), lysenin, CsgG, ClyA, Sp1 and haemolytic protein fragaceatoxin C (FraC).

For example, the pore may be derived from α-hemolysin (α-HL). The wild type α-HL pore is formed of seven identical monomers or subunits (i.e. it is heptameric). The sequence of one wild type monomer or subunit of α-hemolysin is shown in SEQ ID NO: 1. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 293 of SEQ ID NO: 1 form loop regions. Residues 111, 113 and 147 of SEQ ID NO: 1 form part of a constriction of the barrel or channel of α-HL.

In some embodiments, the transmembrane protein pore is chemically modified. For example, the pore (e.g. the monomers derived from α-HL (i.e. SEQ ID NO: 1 or a variant thereof)) may be modified to assist their identification or purification, for example by the addition of histidine residues (a His tag), an aspartic acid residues (an Asp tag), a streptavidin tag and/or a flag tag, or by the addition of a signal sequence to promote their secretion from a cell where the polypeptide does not naturally contain such a sequence. For example, a His tag and an Asp tag can be included in a transmembrane pore to aid purification. Such a strategy is used in the Examples wherein the α-HL monomers described are modified with 8 aspartate and 6 histidine (D8H6) residues to aid in purification and characterisation. The sequence of WT α-HL-D8H6 is given in SEQ ID NO: 2. An alternative to introducing a genetic tag is to chemically react a tag onto a native or engineered position on the pore. An example of this would be to react a gel-shift reagent to a cysteine engineered on the outside of the pore. This has been demonstrated as a method for separating α-HL heterooligomers (Chem Biol. 1997 July; 4(7):497-505).

As described above, a track may be present in a transmembrane protein pore (i.e. the substrate may comprise a surface of a transmembrane protein pore). The substrate may thus be an internal surface of a barrel or channel or lumen of a transmembrane protein nanopore such as a transmembrane protein nanopore described herein. Often, the substrate is an internal surface of the barrel or channel of the pore. The barrel or the channel of the pore is the portion of the pore through which ions travel through the pore across the membrane. When the track is in the barrel or channel of the pore, the hopper typically moves along the track through the barrel or the channel. The barrel or channel may be formed from α-helices or β-strands depending on the type of pore. The track may be positioned near or may span a constriction of the barrel or channel. In another embodiment, the track may be positioned at the entrance of the pore. An entrance of the pore is the portion of the pore through which the analyte enters into the barrel or channel. Entrances are typically formed primarily from loop regions in the pore.

The track may be natively present in a naturally occurring protein or may be introduced. For example, as described in more detail in the Example, a track may be generated in a transmembrane protein pore such as α-hemolysin, Msp, lysenin, CsgG, ClyA, Sp1 or haemolytic protein fragaceatoxin C (FraC) by introducing appropriate amino acid residues at appropriate points in the amino acid sequence of the monomer and then oligomerising the monomer to form a heterooligomeric or homooligomeric pore. For example, with reference to the example protein α-HL, positions 113, 115, 117, 119, 121 and/or 123 of SEQ ID NO: 1 can be modified for example to contain amino acid residues such as cysteine residues (as in SEQ ID NOs: 3 to 7) in order that a thiol-containing track is generated in the SEQ ID NO: 1 monomer; the monomer can then be oligomerised to form a transmembrane pore containing the track. Typically such monomers are oligomerised to form a heteroligomeric pore.

As will be apparent from the above discussion, the invention comprises the use of a track comprising a plurality of primary functional groups aligned along a substrate. Often, the track comprises an array of natural and/or unnatural amino acid residues comprised in the barrel and/or lumen of a transmembrane β-barrel protein nanopore, wherein each amino acid residue in the track comprises a primary functional group. Natural and non-natural amino acids are mentioned herein. As used herein, the term "natural amino acid"s refers to one of the 20 canonical amino acids: i.e., alanine, arginine, asparagine, aspartic acid, cysteine, glutamic acid, glutamine, glycine, histidine, isoleucine, leucine, lyseine, methionine, phenylalanine, proline, serine, threonine, tryptophan, tyrosine and valine. Selenocysteine can also be considered as a naturally occurring amino acid. When the track comprises natural amino acids, it often comprises cysteine and/or selenocysteine residues. The amino acids in the track can be D- or L-amino acids, typically L-amino acids. Non-natural (non-canonical) amino acids can be made synthetically and introduced into proteins as described above. Those skilled in the art will appreciate that a protein comprising one or more non-natural amino acids is still referred to as a protein despite incorporating such non-naturally occurring (non-canonical) amino acids.

When the track is comprised on a protein substrate, the track may typically comprise an array of amino acids. The amino acids need not be identical although identical amino acids are within the scope of the invention. Non-identical amino acids may be different residues (for example cysteine and selenocysteine) or may be the same residue (e.g. cysteine) but in a different chemical environment, for example due to differences in local pH or the pKa values of surrounding amino acid residues.

An array of amino acids is typically a 1 dimensional array, e.g. a line of amino acids with equal or approximately equal spacing between the amino acids. For more complex movement, an array of amino acids may be a 2 dimensional array e.g. a grid of amino acids, or a non-linear arrangement such as a "U", "V", "L" or "Z" shape. Many other track geometries are possible and the invention is not limited in this regard.

Often, in the invention, the track comprises an array of amino acid residues approximately evenly spaced along one or more β-strands in the barrel of a transmembrane β-barrel protein nanopore, wherein each amino acid residue in the track comprises a primary functional group. The amino acids may be natural or unnatural amino acids, and may be the same or different. Those skilled in the art will appreciate that by "evenly spaced" it is meant that the "step" size between adjacent amino acid residues in the track is approximately constant; for example the step size may be consistently between about 5 Å and about 10 Å such as between about 6 Å and about 8 Å e.g. about 7 Å. Without being bound by theory, the inventors believe that when the hopper comprises a polymeric cargo, the "step" size between adjacent footholds e.g. amino acid residues in the track can advantageously be selected to be similar to the distance between adjacent monomer units on the cargo. For example, when the hopper comprises a polynucleotide cargo, the inventors believe (without being bound by theory) that the distance between adjacent footholds e.g. amino acid residues in the track can advantageously be selected to be similar to the internucleotide spacing in the polynucleotide.

An exemplary track with two footholds can be produced through use of positions 113 and 115; 115 and 117; 117 and 119; 119 and 121; or 121 and 123 of the SEQ ID NO: 1 or 2 monomer. For example, appropriate amino acid residues such as cysteine or selenocysteine (e.g. cysteine) residues can be located at such points in the amino acid sequence of the protein monomer and then the monomer can be oligomerised to form a heterooligomeric or homooligomeric pore. An example of an track with two footholds is provided in SEQ ID NO: 3 wherein the track is aligned along the internal surface of an α-HL β-barrel protein nanopore.

A track with three footholds can be produced for example through use of positions 113, 115 and 117; 115, 117 and 119; 117, 119 and 121; or 119, 121 and 123 of the SEQ ID NO: 1 or 2 monomer. For example, appropriate amino acid residues such as cysteine or selenocysteine (e.g. cysteine) residues can be located at such points in the amino acid sequence of the protein monomer and then the monomer can be oligomerised to form a heterooligomeric or homooligomeric pore. An example of an track with three footholds is provided in SEQ ID NO: 4 wherein the track is aligned along the internal surface of an α-HL β-barrel protein nanopore.

A track with four footholds can be produced for example through use of positions 113, 115, 117 and 119; 115, 117, 119 and 121; or 117, 119, 121 and 123 of the SEQ ID NO: 1 or 2 monomer. For example, appropriate amino acid residues such as cysteine or selenocysteine (e.g. cysteine) residues can be located at such points in the amino acid sequence of the protein monomer and then the monomer can be oligomerised to form a heterooligomeric or homooligomeric pore. An example of an track with four footholds is provided in SEQ ID NO: 5 wherein the track is aligned along the internal surface of an α-HL β-barrel protein nanopore.

A track with five footholds can be produced for example through use of positions 113, 115, 117, 119 and 121; or 115, 117, 119, 121 and 123 of the SEQ ID NO: 1 or 2 monomer. For example, appropriate amino acid residues such as cysteine or selenocysteine (e.g. cysteine) residues can be located at such points in the amino acid sequence of the protein monomer and then the monomer can be oligomerised to form a heterooligomeric or homooligomeric pore. An example of an track with five footholds is provided in SEQ ID NO: 6 wherein the track is aligned along the internal surface of an α-HL β-barrel protein nanopore.

A track with six footholds can be produced for example through use of positions 113, 115, 117, 119, 121 and 123 of the SEQ ID NO: 1 or 2 monomer. For example, appropriate amino acid residues such as cysteine or selenocysteine (e.g. cysteine) residues can be located at such points in the amino acid sequence of the protein monomer and then the monomer can be oligomerised to form a heterooligomeric or homooligomeric pore. An example of an track with six footholds is provided in SEQ ID NO: 7 wherein the track is aligned along the internal surface of an α-HL β-barrel protein nanopore.

Those skilled in the art will appreciate that other positions can be similarly modified to produce alternative tracks. Similarly, analogous positions in other protein sequences (such as the protein sequences of Msp, lysenin, CsgG, ClyA, Sp1 or haemolytic protein fragaceatoxin C (FraC)) can be used.

In the invention, a suitable substrate is a variant of a protein nanopore such as a variant of any one of SEQ ID NOs: 1 to 7. A variant of a protein pore monomer is a subunit that has an amino acid sequence which varies from that of the reference sequence (for example, from that of any of SEQ ID NOs: 1 to 7) and which retains its pore forming ability. A suitable variant may comprise additional modifications, such as introduction of positively or negatively (usually positively) charged residues, for example to facilitate interaction with analytes.

The ability of a variant to form a pore can be assayed using any method known in the art. For instance, the variant may be inserted into a membrane along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Those skilled in the art will appreciate that a protein nanopore does not necessarily comprise only naturally occurring amino acids. For example, non-naturally occurring amino acids can be introduced by any appropriate means. The resultant polymer comprising naturally occurring and/or non-naturally occurring amino acids comprises a "protein" nanopore. The track may comprise or consist of non-naturally occurring amino acids, or the substrate may be a protein comprising non-naturally occurring amino acids and the track may comprise naturally occurring amino acids, depending on the specific movement of the hopper that is required.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the pore. Similarly, other amino acids can be similarly introduced by using appropriate codons. The polynucleotide can then be expressed as discussed above.

Methods for adding or substituting non-naturally-occurring amino acids are also well known in the art. For instance, non-naturally-occurring amino acids may be introduced by including synthetic aminoacyl-tRNAs in the in vitro transcription/translation (IVTT) system used to express the pore. Alternatively, they may be introduced by expressing the pore in E. coli that are auxotrophic for specific amino acids in the presence of synthetic (i.e. non-naturally-occurring) analogues of those specific amino acids. They may also be produced by native ligation if the pore is produced using partial peptide synthesis. Modified E. coli containing genetically modified tRNA synthetase/tRNAs can be used to incorporate unnatural amino acids into proteins as described in Chin et al, Annu. Rev. Biochem. (2014) 83:379-408.

In the invention, any amino acid may be substituted with an appropriately functionalized amino acid to form a track on a protein substrate. For example, one or more amino acids may be substituted with one or more cysteine amino acids, for example when the primary functional groups are thiol groups. Selenocysteine may also be used, for example when the primary functional groups are selenol groups. Other amino acids comprising other primary functional groups can be used.

Any number of appropriately functionalized amino acids may be introduced. For instance, 1, 2, 3, 4, 5, 10, 15, 20, 25 or more appropriately functionalized amino acids may be introduced. In the case of α-HL (i.e. SEQ ID NO: 1) then a track comprising for example 2, 3, 4 or 5 appropriately functionalized amino acid residues may be generated, for example by replacing the amino acids at positions 113, 115, 117, 119, 121 and/or 123 of SEQ ID NO: 1 (as in SEQ ID NOs: 3-7). When other proteins are used, then the amino acids at the positions corresponding to the positions 113, 115, 117, 119, 121 and/or 123 of SEQ ID NO: 1 can be replaced.

Amino acid substitutions may be made to the amino acid sequence of SEQ ID NOs: 1 to 7 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2. Non-conservative replacements can be made too while the protein pore retains its structure and function.

TABLE 1

Chemical properties of amino acids

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |

TABLE 2-continued

Hydropathy scale

| Side Chain | Hydropathy |
| --- | --- |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

A variant may also include a fragment SEQ ID NOs: 1 to 7 that retains pore forming activity. Fragments may be at least 50, 100, 200 or 250 amino acids in length. A fragment typically comprises the pore forming domain of SEQ ID NOs: 1 to 7. Fragments typically include residues 113, 115, 117, 119, 121 and/or 123 of SEQ ID NOs: 1 to 7. One or more amino acids may be alternatively or additionally added to the polypeptides described above. An extension may be provided at the amino terminus or carboxy terminus of the amino acid sequence of SEQ ID NOs: 1 to 7 or a variant or fragment thereof. An extension may be provided within the amino acid sequence of SEQ ID NOs: 1 to 7 or a variant or fragment thereof, for example an extension can be incorporated to increase the length of the barrel of the pore. The extension may be quite short, for example from 1 to 10 amino acids in length. Alternatively, the extension may be longer, for example up to 50 or 100 amino acids.

The variant may be a naturally occurring variant which is expressed naturally by an organism, for instance by a Staphylococcus bacterium, or expressed recombinantly by a bacterium such as Escherichia coli. Variants also include non-naturally occurring variants produced by recombinant technology. Over the entire length of the amino acid sequence of any one of SEQ ID NOs: 1 to 7, a variant will typically be at least 50% homologous to the reference sequence based on amino acid identity. More typically, the variant polypeptide may be at least 55%, at least 60%, at least 65%, at least 70%, at least 75%, at least 80%, at least 85%, at least 90% and more usually at least 95%, 97% or 99% homologous based on amino acid identity to the amino acid sequence of any one of SEQ ID NOs: 1 to 7 over the entire sequence. There may be at least 80%, for example at least 85%, 90% or 95%, amino acid identity over a stretch of 200 or more, for example 230, 250, 270 or 280 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, typically less than about 0.1, more often less than about 0.01, and most usually less than about 0.001.

Membrane

As discussed above, in the invention the substrate may be a surface of a transmembrane pore. A transmembrane pore is a structure that crosses the membrane to some degree Any membrane may be used in accordance with the invention. Suitable membranes are well-known in the art. The membrane is typically an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units polymerized together create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. Typically the copolymer is a triblock copolymer comprising two monomer subunits A and B in an A-B-A pattern; typically the A monomer subunit is hydrophilic and the B subunit is hydrophobic.

The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is usually a planar lipid bilayer. Suitable lipid bilayers are disclosed in WO 2008/102121, WO 2009/077734 and WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers. The lipid bilayer may be formed as described in WO 2009/077734. A lipid bilayer may also be a droplet interface bilayer formed between two or more aqueous droplets each comprising a lipid shell such that when the droplets are contacted a lipid bilayer is formed at the interface of the droplets.

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in WO 2009/035647.

Hopper

In the invention, the hopper comprises a secondary functional group capable of binding to each of the plurality of primary functional groups on the track. Primary and secondary functional groups are described in more detail below.

The hopper may be any molecule capable of being directionally transferred from the first primary functional group of the track to a second primary functional group on the track thereby being moved along the track. Typically, a hopper has a single foot (i.e. comprises a single secondary functional group capable of binding to each of the plurality of primary functional groups on the track, although further functional groups that are not capable of binding to each of the plurality of primary functional groups on the track may be present). However, hoppers suitable for use in the invention may comprise two or more feet (i.e. two or more secondary functional group capable of binding to each of the plurality of primary functional groups on the track, and optionally comprising further functional groups that are not capable of binding to each of the plurality of primary functional groups on the track). A hopper comprising two or more feet may also be referred to as a walker. The motion of a hopper having a single foot does not involve stable intermediates simultaneously engaging two or more footholds (i.e. simultaneously bonding to two primary functional groups of the track to form a stable intermediate), although the movement of the hopper from a first primary functional group to a second primary functional group may involve the transient formation of a species with two or more footholds. By contrast, the motion of a walker having two or more feet involves the formation of stable intermediates engaging at least two footholds. Those skilled in the art will appreciate that although the invention refers primarily to molecular hoppers, molecular walkers are likewise embraced. Those skilled in the art will particularly recognise that invention comprises application of a the driving force so as to cause the hopper to be directionally transferred from the first primary functional group to a second primary functional group on the track thereby causing the hopper to move along the track, and the application of said driving force and the motion (typically reversible motion) of the hopper/walker is an important aspect of the invention which is applicable to both walkers and hoppers.

The hopper typically comprises a linking moiety between the secondary functional group and a cargo moiety. Any suitable linking moiety may be used. The chemistry of the linking moiety is not particularly limited providing that it can link the secondary functional group to a cargo moiety without impeding the movement of the hopper along the track.

Typically, a linking moiety comprises a linear or branched, unsubstituted or substituted alkylene, alkenylene, alkynylene, arylene, heteroarylene, carbocyclylene or heterocyclylene moiety. More often, a linking moiety comprises an unsubstituted or substituted alkylene, alkenylene, or alkynylene moiety. More usually, a linking moiety comprises an unsubstituted or substituted alkylene or alkenylene moiety. Most often, a linking moiety comprises an unsubstituted or substituted alkylene moiety. Typically, an alkylene group is a $C_{1-10}$ alkylene group. Typically, an alkenylene group is a $C_{2-10}$ alkenylene group. Typically, an alkynylene group is a $C_{2-10}$ alkynylene group. Typically, an arylene group is a $C_{6-12}$ arylene group. Typically, a heteroarylene group is a 5- to 12-membered heteroarylene group. Typically, a carbocyclylene group is a $C_{5-12}$ carbocyclylene group. Typically, a heterocyclylene group is a 5- to 12-membered heterocyclylene group.

An alkylene, alkenylene, or alkynylene moiety may be uninterrupted or interrupted by or terminate in one or more atoms or groups selected from O, N(R), S, C(O), C(O)NR, C(O)O, phosphate, thiophosphate, unsubstituted or substituted arylene, unsubstituted or substituted heteroarylene, unsubstituted or substituted carbocyclylene and unsubstituted or substituted heterocyclylene; wherein R is selected from H, unsubstituted or substituted alkyl, and unsubstituted or substituted aryl. Usually, an alkylene, alkenylene, or alkynylene moiety may be uninterrupted or interrupted by or terminate in one or more atoms or groups selected from O, N(R), S, C(O), C(O)NR, C(O)O, phosphate and thiophosphate, wherein R is selected from H and unsubstituted or substituted alkyl. More often, an alkylene, alkenylene, or alkynylene moiety may be uninterrupted or interrupted by or terminate in one or more atoms or groups selected from O, N(R), S, C(O), C(O)NR, C(O)O, phosphate and thiophosphate, wherein R is selected from H and methyl.

For example, a linking moiety is often an unsubstituted or substituted $C_{1-10}$ alkylene, $C_{2-10}$ alkenylene, or $C_{2-10}$ alkynylene moiety which is uninterrupted or interrupted by or terminates in one or more atoms or groups selected from O, N(R), S, C(O), C(O)NR, C(O)O, phosphate and thiophosphate, wherein R is selected from H and unsubstituted or substituted alkyl. More commonly, a linking moiety is an unsubstituted or substituted $C_{1-10}$ alkylene or $C_{2-10}$ alkenylene moiety which is uninterrupted or interrupted by or terminates in one or more atoms or groups selected from O, N(R), S, C(O), C(O)NR, C(O)O, phosphate and thiophosphate, wherein R is selected from H and methyl. For example, a linking moiety may be an unsubstituted or substituted $C_{1-10}$ alkylene moiety which is interrupted by one or more of O, N(R), S, C(O), C(O)NR, C(O)O, phosphate and thiophosphate, and which terminates in S or thiophosphate. An exemplary linking moiety connecting a cargo to a secondary functional group can be represented as:

[secondary functional group]-alkylene-[XPhos]-[cargo]

wherein alkylene is for example a $C_{4-10}$ alkylene group which is interrupted by C(O)NR and [XPhos] is selected from phosphate and thiophosphate. An example of such a linking group is:

[secondary functional group]-$C_2H_4$—[C(O)NH]—$C_5H_{10}$—O—P(O)(O$^-$)O-[cargo].

Typically, in such cases, the secondary functional group may be an S atom such that the hopper is capable of forming a disulfide bond to a thiol-functionalised track; for example the secondary functional group and linking group may together be

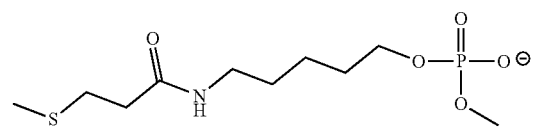 [SMILES: COP(=O)([O-])OCCCCCNC(=O)CCSC]

Another exemplary linking moiety connecting a cargo to a secondary functional group may be

[secondary functional group]-alkylene-[cargo]

wherein alkylene is for example a $C_{4-10}$ alkylene group interrupted by C(O)NR (such as, for instance, $C_2H_4$—[C(O)NH]—$C_5H_{10}$). [Cargo] may be for example, a polynucleotide wherein an oxygen atom in the terminal phosphate group of the polynucleotide may be bonded to said alkylene. The secondary functional group and the linking group may, for instance, together be

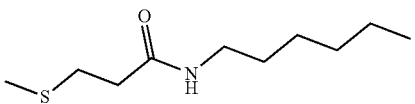

Cargo

Typically, the hopper comprises a cargo moiety. The cargo may be any suitable substance that can be carried by the hopper along the track. Suitable cargos include, but are not limited to, metal ions, inorganic salts, polymers, such as a polymeric acids or bases, dyes, bleaches, pharmaceuticals, diagnostic agents, recreational drugs, explosives and environmental pollutants. Such cargos can be beneficially analysed or characterized using the methods described herein.

The cargo can be an analyte that is secreted from cells. Alternatively, the analyte can be an analyte that is present inside cells such that the analyte must be extracted from cells. The analyte is typically a polymer. The cargo is usually charged. The cargo may be positively or negatively charged, often negatively charged. The cargo is often a polynucleotide, a polypeptide or a polysaccharide, more often a polynucleotide or a polypeptide, most often a polynucleotide. Without being bound by theory, the inventors believe that application of the driving force orientates the cargo with respect to the track and orientates the hopper for movement along the track. Without being bound by theory, the inventors believe that the movement of the cargo typically precedes the hopper; i.e. the hopper "pushes" the cargo along the track rather than "dragging" the cargo along the track.

The cargo may be a polynucleotide, i.e. a nucleic acid sequence. Nucleic acids are negatively charged. A nucleic acid is a macromolecule comprising two or more nucleotides. The nucleotides can be naturally occurring or artificial. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are usually selected from AMP, TMP, GMP, UMP, dAMP, dTMP, dGMP or dCMP.

When the cargo is a polynucleotide, the polynucleotide may be single or double stranded. Usually, when the cargo is a polynucleotide, the polynucleotide is single stranded, such as cDNA or RNA.

When the cargo is a single stranded polynucleotide, the polynucleotide may comprise from about 2 to about 1000 nucleotides, such as from about 5 to about 500 nucleotides, e.g. from about 10 to about 100 nucleotides, such as from about 20 to about 60 nucleotides e.g. from about 30 to about 50 nucleotides. When the cargo is a double stranded polynucleotide, each strand of the double stranded polynucleotide may independently comprise from about 2 to about 1000 nucleotides, such as from about 5 to about 500 nucleotides, e.g. from about 10 to about 100 nucleotides, such as from about 20 to about 60 nucleotides e.g. from about 30 to about 50 nucleotides.

The cargo may be a polypeptide. The polypeptide may be a protein or a fragment thereof. The polypeptide can be naturally-occurring or non-naturally-occurring. The polypeptide can include within it synthetic or modified amino acids. A number of different types of modification to amino acids are known in the art. Suitable amino acids and modifications thereof are discussed herein. For the purposes of the invention, it is to be understood that the polypeptide can be modified by any method available in the art. For example, the polypeptide can be modified by a post-translational modification or by sequence variation arising from alternative splicing of RNA during biological peptide synthesis.

When the cargo is a polypeptide, the polypeptide can be one that is secreted from cells. Alternatively, the polypeptide can be one that is present inside cells such that it must be extracted from the cells before the invention can be carried out. It can be extracted both by the use of antibodies or by the binding of an affinity tag introduced on the protein.

As used herein, a polypeptide may be a shorter peptide which is typically a polymer of from about 2 to about 50 amino acids or may be a longer polymer of amino acids. Proteins are typically polypeptides that are folded into a functional conformation or form part of a functional complex. For example, the polypeptide may be from about 2 to about 1000 amino acids, such as from about 5 to about 500 amino acids, e.g. from about 10 to about 100 amino acids, such as from about 20 to about 60 amino acids e.g. from about 30 to about 50 amino acids.

When the cargo is a polypeptide, any polypeptide may be used. Suitable polypeptides include, but are not limited to, proteins such as enzymes, antibodies, hormones, growth factors or growth regulatory proteins, such as cytokines; or fragments of such proteins. The polypeptide may be bacterial, archaeal, fungal, viral or derived from a parasite. The polypeptide may be derived from a plant. The polypeptide is typically mammalian, more usually human.

The cargo may be a polysaccharide. A polysaccharide is a polymeric carbohydrate molecules composed of chains of monosaccharide units bound together by glycosidic linkages. A polysaccharide may be linear or branched. A polysaccharide may be homogeneous (comprising only one repeating unit) or heterogeneous (containing modifications of the repeating unit). Polysaccharides include callose or laminarin, chrysolaminarin, xylan, arabinoxylan, mannan, fucoidan and galactomannan.

The cargo may be a polysaccharide produced by a bacterium such as a pathogenic bacterium. The polysaccharide may be a capsular polysaccharide having a molecular weight of 100-2000 kDa. The polysaccharide may be synthesized from nucleotide-activated precursors (called nucleotide sugars). The polysaccharide may be a lipopolysaccharide. The polysaccharide may be a therapeutic polysaccharide. The polysaccharide may be a toxic polysaccharide. The polysaccharide may be suitable for use as a vaccine. The polysaccharide may be for example bacterial or derived from a plant. The polysaccharide may be useful as an antibiotic, such as streptomycin, neomycins, paromomycine, kanamycin, chalcomycin, erythromycin, magnamycin, spiramycin, oleandomycin, cinerubin and amicetin, or a derivative of any one of the preceding compounds.

When the cargo is a polysaccharide, the polysaccharide may comprise from about 2 to about 1000 monosaccharide units, such as from about 5 to about 500 monosaccharide units, e.g. from about 10 to about 100 monosaccharide units, such as from about 20 to about 60 monosaccharide units e.g. from about 30 to about 50 monosaccharide units.

The cargo may comprise more than one polymer for example two or more polymers e.g. two or more polymers disclosed herein may be attached together. The two or more polymers may thus be selected from polynucleotides, polypeptides and polysaccharides.

Primary and Secondary Functional Groups

In the invention, the hopper is contacted with the track such that the secondary functional group of the hopper binds to a first primary functional group on the track.

Typically, in the invention, wherein the secondary functional group of the hopper is capable of forming a chemical bond with each of the primary functional groups on the track. The invention is not limited to covalent chemistry and includes strong non-covalent interactions. As those skilled in the art will appreciate, the main criterion is that the hopper does not dissociate from the track apart from at optional defined release points.

Usually, the chemical bond is (i) a covalent bond, preferably a dynamic covalent bond; (ii) a dative bond; (iii) a hydrogen bond; or (iv) a hydrophobic interaction. More often, the chemical bond is a covalent bond, preferably a dynamic covalent bond; a dative bond; or a hydrogen bond; still more often the chemical bond is a dynamic covalent bond.

The formation or breaking of the chemical bond may be spontaneous, catalysed by a catalyst or is driven by subjecting the primary and/or secondary functional groups to an appropriate reagent such as light. More often the formation or breaking of the chemical bond is spontaneous. An example of a spontaneously formed covalent bond within the meaning of the invention is that of a disulfide bond, a diselenide bond or a sulfide-selenide bond. Other similar chemical bonds are known to those skilled in the art.

Many examples of hopper/track chemistries suitable for use in accordance with the present invention are known in the art and the invention is not particularly limited in this regard.

For example, the chemical bond between the hopper and the track is often based on disulfide (S—S) chemistry. Selenium can be used in place of sulfur, on the track or the hopper, or both. In other words, the bond between the hopper and the track may be an S—S bond (disulphide); an S—Se bond (sulfide-selenide), the sulfur may be on the track and the selenium on the hopper or the selenium may be on the track and the sulfur on the hopper; or an Se—Se bond (diselenide bond). The primary and/or secondary functional group is typically comprised in a suitable group; for example a thiol (sulfide) group may be part of a thiophosphate or dithiophosphate group and a selenol (selenide) group may be part of a selenophosphate or diselenophosphate group. The thiophosphate, dithiophosphate, selenophosphate or diselenophosphate group is usually a terminal thiophosphate, dithiophosphate, selenophosphate or diselenophosphate group. The thiophosphate, dithiophosphate, selenophosphate or diselenophosphate group may be comprised in a DNA or RNA phosphodiester linkage.

The chemical bond between the hopper and the track may be based on As(III)-thiol chemistry. For example, the track may comprise primary thiol functional groups and the hopper may comprise an As(III) functional group such that the hopper forms an As—S bond with the track. The formation of such bonds may be catalysed e.g. by free thiol groups.

The chemical bond between the hopper and the track may be based on thioacetal chemistry, for example with thioacetal bonds formed between (di)ketone or (di)aldehyde functional groups and (di)thiol functional groups. For example, the track may comprise primary thiol groups and the hopper may comprise secondary diketone or dialdehyde functional groups or the track may comprise primary dithiol groups and the hopper may comprise secondary ketone or aldehyde functional groups such that a thioacetal bond is formed between the hopper and the track.

The chemical bond between the hopper and the track may be based on formation of boronate ester groups by reaction of boronic acid-containing secondary functional groups on the hopper with primary hydroxyl functional groups on the track; for example the track may comprise threonine, serine or tyrosine amino acids comprising hydroxyl primary functional groups for reaction with boronic acid secondary functional groups.

The chemical bond between the hopper and the track may be based on transimination chemistry. For example, the hopper may comprise an aldehyde or ketone secondary functional group and the track may comprise an amine, hydroxylamine, hydrazine or semicarbazide primary functional group such that an imine, oxime, hydrazine or semicarbazone bond (respectively) is formed between the hopper and the track. Similarly, the track may comprise an aldehyde or ketone secondary functional group and the hopper may comprise an amine, hydroxylamine, hydrazine or semicarbazide primary functional group such that an imine, oxime, hydrazine or semicarbazone bond (respectively) is formed between the hopper and the track.

The chemical bond between the hopper and the track may similarly be based on the bonding of a hopper comprising an α-methylene-4-nitrostyrene secondary functional group to a nucleophilic track such as a track comprising secondary amine functional groups.

The chemical bond between the hopper and the track may similarly be based on aldol/retroaldol chemistry; Diels Alder/retro-Diels Alder chemistry; alkene- or alkyne-catalyzed metathesis reactions; thioester or selenoester exchange reactions wherein the track comprises thiol or selenol primary functional groups, respectively; reversible urea formation by the bonding of isocyanate or isothiocyanate secondary functional groups of the hopper with primary amine functional groups on the track; cyanobenzothiazole chemistry wherein the track comprising primary thiol and/or amine functional groups; thiaMichael chemistry; dibromomaleimides and related chemistry including 5-[bis(methylthio)methylene]-2,2-dimethyl-1,3-dioxane-4,6-diones.

The chemical bond between the hopper and the track may similarly be based on the formation of metal complexes. For example, the track may comprise primary histidine or histidine functional groups and the analogue hopper may comprise metal (e.g. $Ni^{2+}$, $Co^{2+}$ etc) NTA (nitrilotriacetic acid) functional groups such that a complex forms between the track and the hopper. The track may comprise pyridine primary functional groups and the hopper may comprise Pd(II) such that a complex forms between the track and the hopper. The track may comprise chelator or π ligands and the hopper may comprise derivatised transition metal ions such that a complex forms between the track and the hopper.

Usually, in the invention, the primary functional group and the secondary functional group are independently selected from thiol groups and selenol groups; wherein optionally the thiol groups are comprised in a thiophosphate or dithiophosphate group and/or the selenol groups are comprised in a selenophosphate or diselenophosphate group. Therefore, the chemical bond between the primary and secondary functional groups is typically a covalent bond which is a disulfide bond, a diselenide bond, or a sulfide-selenide bond. Most often, the primary functional group and the secondary functional group are each thiol groups such that the chemical bond between the primary functional group and the secondary functional group is a covalent bond which is a disulfide bond. Disulfide bonds can be formed, for example, between thiol-containing amino acids. For example, an amino acid such as cysteine may be present in a protein such as in a protein nanopore and a thiol-containing group may be present on a hopper such that a disulfide bond forms between the cysteine of the pore and the thiol of the hopper. The cysteine amino acid of the pore may be present in a track as defined herein.

Typically, therefore, in the invention, the substrate is a surface of a protein nanopore and the track comprises an array of amino acid residues comprised in the protein nanopore; each amino acid residue of the track comprises a reactive side chain bearing a primary functional group; and wherein the secondary functional group of the hopper is capable of forming a chemical bond, preferably a covalent bond with each of the primary functional groups of the reactive side chains of the amino acid residues of the track.

More typically, the substrate is a surface of a protein nanopore and the track comprises an array of amino acid residues comprised in the protein nanopore wherein each amino acid residue in the track comprises a primary thiol functional group; and wherein the hopper comprises a secondary thiol functional group such that the hopper forms a disulfide bond to the amino acid residues of the track.

Positioning

Particular aspects of the invention include the ability of the hopper to be preferentially loaded at a precise point on the track. This ability is particularly useful in embodiments when the track has a plurality of potential loading points and it is desired to control the movement of the hopper between specific loading points (footholds) on the track, such as from the start of the track to an end of the track. Knowledge of the loading position of the hopper on the track can be particularly useful in methods of the invention which involve characterising a cargo analyte carried by the hopper.

The hopper may be loaded at a precise point on the track as described herein. Alternatively, the hopper may be randomly loaded onto the track. Advantageously, if the hopper is randomly loaded onto the track then the hopper can be moved along the track by application of a driving force in accordance with the invention to a defined point on the track, for example the start of the track. Once at the start of the track, the hopper is in a known position and further movement can thus be monitored accordingly. Typically, in the invention, the hopper may is loaded at a precise point on the track.

Accordingly, the invention provides for a method wherein prior to contacting the hopper with the track the hopper is attached to a positioning moiety, wherein the positioning moiety positions the hopper relative to the track such that the first primary functional group on the track binds to the secondary functional group on the hopper.

For example, in the invention, the substrate may be a surface of a transmembrane pore. A track may be comprised on the transmembrane pore such as on an internal surface of the pore. Prior to contacting the hopper with the track the secondary functional group of the hopper may be attached to a positioning moiety so that once contacted with the track the position of the hopper relative to the track can be controlled. Typically, the positioning moiety comprises a blocking entity for preventing passage of the hopper through the pore. Any suitable blocking entity can be used.

For example, the blocking entity can be a physical blocking entity which is incapable of passing through the pore, for example due to having a larger size than the internal dimensions of the pore. Size of a blocking entity can be determined in many suitable ways known in the art, including by dynamic light scattering. For examples, the blocking entity may comprise or consist of a protein, a nanoparticle, or a polymer; for example a polynucleotide, polypeptide, or organic polymer such as polyethylene glycol.

The blocking entity can be a chemical blocking entity which is incapable of passing through the pore due to chemical interactions. For example, the blocking entity can be a chemical group which binds to the pore e.g. to the opening of the pore and thus prevents passage of the hopper through the pore.

When a positioning moiety is used, the invention typically comprises contacting the hopper with the pore such that the blocking entity prevents passage of the hopper through the pore so as to hold the positioning moiety in a position such that the first primary functional group on the track binds to the secondary functional group on the hopper, thereby releasing the positioning moiety from the secondary functional group.

Most often, the blocking entity if present comprises or consists of a protein for example streptavidin, neutravidin, or traptavidin, typically traptavidin. The blocking moiety may be comprised in the positioning moiety by binding to a suitable group such as for example a biotin group.

A positioning moiety may comprise a linking moiety between a blocking entity and a functional group which bonds to the hopper, for example by bonding to the secondary functional group of the hopper. The linking moiety may be configured to position the secondary functional group of the hopper in a desired location relative to the track e.g. so that the secondary functional group of the hopper is positioned such that the first primary functional group on the track binds to the secondary functional group on the hopper. If the linking moiety of the positioning moiety is bonded to the secondary functional group on the hopper, then bonding of the first primary functional group on the track to the secondary functional group on the hopper typically releases the positioning moiety from the secondary functional group of the hopper.

Accordingly, in the invention, often
  the substrate is a surface of a transmembrane pore;
  prior to contacting the hopper with the track the secondary functional group of the hopper is attached to a positioning moiety;
  the positioning moiety comprises a blocking entity for preventing passage of the hopper through the transmembrane pore;

and step (i) of the method comprises contacting the hopper with the pore such that the blocking entity prevents passage of the hopper through the pore so as to hold the positioning moiety in a position such that the first primary functional group on the track binds to the secondary functional group on the hopper, thereby releasing the positioning moiety from the secondary functional group.

Any suitable linking moiety can be used to link the blocking entity to the hopper. The chemistry of the linking moiety is not particularly limited providing that it can link the blocking entity to the hopper. A linking moiety linking a blocking entity to the hopper is also known as a carrier.

Typically, a linking moiety comprises a linear or branched, unsubstituted or substituted alkylene, alkenylene, alkynylene, arylene, heteroarylene, carbocyclylene or heterocyclylene moiety. Such groups are as defined herein. More often, a linking moiety comprises an unsubstituted or substituted alkylene, alkenylene, or alkynylene moiety. More usually, a linking moiety comprises an unsubstituted or substituted alkylene or alkenylene moiety. Most often, a linking moiety comprises an unsubstituted or substituted alkylene moiety. The linking moiety can be interrupted by any suitable group to position the hopper in a desired position on the track. For example, an alkylene, alkenylene, or alkynylene moiety may be uninterrupted or interrupted by or terminate in one or more atoms or groups selected from prised in the positioning moiety by binding to a group such as a biotin group, the biotin group is typically a terminal group of the linking moiety.

An exemplary linking moiety connecting a blocking entity to a hopper can be represented as:

[blocking entity]-[linker1]-[PEG]-[linker2]-[functional group]-[hopper]

wherein [blocking entity] is a blocking entity such as a neutravidin, streptavidin or traptavidin protein bound to a biotin group; [linker1] and [linker2] are each independently alkylene-containing groups which are substituted or unsubstituted as defined herein and uninterrupted or interrupted as defined herein, but are typically interrupted by groups selected from NHC(O) and heterocyclylene and are often substituted by —[X] or alkylene-[X] as defined above; [PEG] is a polyethylene glycol group including between 1 and 30 ethylene glycol units; and [functional group] is a functional group which bonds to the hopper, for example by bonding to the secondary functional group of the hopper.

An example of such a group is shown below (the blocking entity, not shown, is bonded to the biotin group on the left hand end of the linking moiety as depicted, and the terminal S atom is suitable for bonding to a secondary functional group on the hopper such as a thiol group or a selenol group, typically a thiol group):

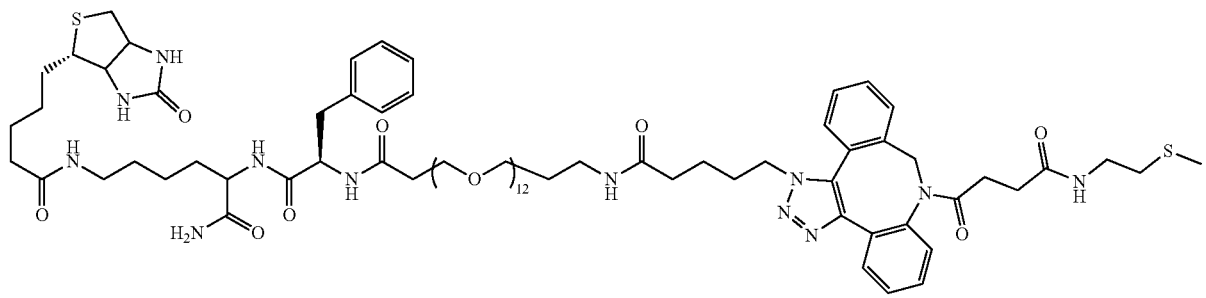

O, N(R), S, C(O), C(O)NR, C(O)O, unsubstituted or substituted arylene, arylene-alkylene, heteroarylene, heteroarylene-alkylene, carbocyclylene, carbocyclylene-alkylene, heterocyclylene and heterocyclylene-alkylene; wherein R is selected from H, unsubstituted or substituted alkyl, and unsubstituted or substituted aryl. Heterocyclyl groups such as 8,9-dihydro-1H-dibenzo[b,f][1,2,3]triazolo[4,5-d]azocine can be used to control the rigidity, geometry, length or sterics of the linking moiety. Such groups can also be used to aid synthesis of the linking moiety. Branched substituent groups on the linking moiety such as [X] or -alkylene-[X] can be used as desired wherein [X] is e.g. C(O)NR$_2$ or an aryl, heteroaryl, carbocyclyl or heterocyclyl group, wherein each R is the same or different and is as defined above.

The length of the linking moiety may be determined to position the hopper in the desired position. The length of the linking moiety can be conveniently controlled by including a polyethylene glycol (PEG) group in the linking moiety. For example, including between 1 and 30 such as between 5 and 20 e.g. between 10 and 15 e.g. 12 ethylene glycol units in the linker may allow the hopper to be preferably loaded onto the track at a desired position.

When the blocking entity is a protein such as neutravidin, streptavidin or traptavidin and the blocking moiety is com- Releasing Particular aspects of the invention include the ability of the hopper to be controllably released from the track at a predefined position. This ability is particularly useful in embodiments when the hopper is intended to carry a cargo from a loading point on the track to a position on the track and there to release from the track. For example, in accordance with the present invention the hopper can be controllably loaded at the start of a track and controllably released at the end of the track.

Controlled release of the hopper from the track can be achieved in any suitable way. For example, a tertiary functional group on the substrate can be positioned relative to the track such that when the hopper reaches a release point on the track and is thus attached to a primary functional group at that release point on the track, the tertiary functional group on the substrate bonds to the primary functional group thereby displacing the secondary functional group and so releasing the hopper. For example, the primary functional group at the release point on the track may be the final primary functional group in the track, i.e. the end of the track. Accordingly, the invention may comprise after movement of the hopper along the track, the step of (iii) contacting the primary functional group of the track bonded to the secondary functional group of the hopper with a tertiary functional group on the substrate such that the tertiary functional group bonds to the primary functional group thereby displacing the secondary functional group and so releasing the hopper.

As will be apparent from the above discussion, a typical substrate in the invention is a surface of a transmembrane pore. A track may be comprised on the transmembrane pore such as on an internal surface of the pore. A tertiary functional group may be comprised in the pore at a position close to the last of the primary functional groups on the track. For example, if the track runs from the cis side of the barrel of the pore towards the trans side of the barrel of the pore, then the tertiary functional group may be located close to the trans exit of the barrel of the pore. If the track runs from the trans side of the barrel of the pore towards the cis side of the barrel of the pore, then the tertiary functional group may be located close to the cis exit of the barrel of the pore.

Accordingly, in the invention the substrate is often a surface of a protein nanopore and the track comprises an array of amino acid residues comprised in the protein nanopore; wherein each amino acid residue of the track comprises a reactive side chain bearing a primary functional group; and wherein the secondary functional group of the hopper is capable of forming a covalent bond with each of the primary functional groups of the reactive side chains of the amino acid residues of the track; and the tertiary functional group is a further amino acid residue of the protein nanopore comprising a reactive side chain capable of forming a covalent bond to the reactive side chain of the final amino acid residue of the track thereby displacing the secondary functional group from the primary thiol group of the track and so releasing the hopper.

The tertiary functional group may be the same or different to the primary functional groups. The tertiary functional group may be comprised in an amino acid which is a natural amino acid or an unnatural amino acid. For example, the track may comprise cysteine or selenocysteine residues and the tertiary functional group may be a cysteine or selenocysteine residue. Other functional groups are within the scope of the invention. For example, in the invention, typically the substrate is a surface of a protein nanopore and the track comprises an array of amino acid residues comprised in the protein nanopore wherein each amino acid residue in the track comprises a primary thiol functional group; and the hopper comprises a secondary thiol functional group such that the hopper forms a disulfide bond to the amino acid residues of the track; and wherein the protein nanopore comprises a further amino acid residue comprising a tertiary thiol functional group and positioned such that the tertiary thiol group can form a disulfide bond to a primary thiol group of the track thereby displacing the secondary functional group from the primary thiol group of the track and so releasing the hopper.

Often, in the invention, the distance between the tertiary functional group and the primary functional group of the track at the release position (e.g. the last primary functional group in the track) is less than the step size between adjacent footholds on the track. For example, in the invention, when the substrate is a surface of a transmembrane protein pore and the track is an array of amino acids on an inner surface of the pore, the amino acid residue comprising the tertiary functional group is usually separated from the primary functional group of the final amino acid residue in the track by a distance of less than about 5 Å (Cα–Cα). Thus, for example, the track may comprise an array of amino acid residues each comprising a primary functional group and being approximately evenly spaced along one or more β-strands in the barrel of a transmembrane β-barrel protein nanopore and having a step size between adjacent amino acids comprising the primary functional groups of between about 5 Å and about 10 Å (Cα–Cα) such as between about 6 Å and about 8 Å e.g. about 7 Å; and the amino acid comprising the tertiary functional group may be located less than about 5 Å (Cα–Cα), such as between about 3 Å and about 4.5 Å such as about 4 Å, and the tertiary functional group may the same or different to the primary functional groups, typically the tertiary functional group is the same as the primary functional groups.

By way of example, an exemplary substrate comprising a track with three footholds at positions 115, 117 and 119 of the SEQ ID NO: 1 or 2 monomer may comprise appropriate amino acid residues such as cysteine or selenocysteine (e.g. cysteine) residues at such positions. An amino acid residue comprising a tertiary functional group may be positioned at position 139 of the SEQ ID NO: 1 or 2 monomer. The distance between position 119 and 139 of SEQ ID NOs: 1-7 is about 5 Å (Cα–Cα). An example of such a track is provided in SEQ ID NO: 7 wherein the track is aligned along the internal surface of an α-HL β-barrel protein nanopore.

Driving Force

The invention involves applying a driving force so as to cause the hopper to be directionally transferred from the first primary functional group to a second primary functional group on the track thereby causing the hopper to move along the track. Typically, in the invention, the driving force is an physical or chemical potential. For example, if the substrate is a transmembrane pore, then the potential may be applied across the pore so as to cause the hopper to move along the track. The applied driving force may be a physical potential such as an electrical (voltage) potential. An electrical potential may be an electrophoretic or an electroosmotic potential. Another example of a physical potential is a temperature gradient. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. Other examples of chemical potentials are pH gradients and concentration gradients.

Reversal of Direction

Because the invention involves applying a driving force so as to cause the hopper to be directionally transferred from the first primary functional group to a second primary functional group on the track thereby causing the hopper to move along the track, the direction of the hopper on the track can be altered by altering the direction of the driving force relative to the track. For example, the direction of the driving force can be reversed whilst the hopper is moving along the track, or following movement of the hopper along the track, thereby causing the direction of the motion of the hopper to be reversed. Accordingly, the invention can involve reversing the direction of the driving force relative to the track so as to cause the direction of the movement of the hopper along the track to be reversed. For example, if the track is comprised in a transmembrane pore, and the initial direction of the driving force is from the cis to the trans side of the pore so as to cause the hopper to move in the direction from the cis side to the trans side of the pore, then reversal of the direction of the driving force such that the force is applied from the trans side to the cis side of the pore can cause the movement of the hopper to be reversed, i.e. can cause the motion of the hopper to be in the direction from the trans side to the cis side of the pore. Those skilled in the art will appreciate that the motion of the hopper along the track can thus be "cycled"; i.e. the hopper can be caused to move back and forward along the track multiple times.

Methods of Characterising an Analyte

The invention also provides a method of characterising an analyte, the method comprising:
(i) providing
  (A) a detector;
  (B) a track comprising a plurality of primary functional groups aligned along a substrate; and
  (C) a molecular hopper attached to the analyte, wherein the hopper comprises a secondary functional group capable of binding to each of the plurality of primary functional groups on the track;
(ii) contacting the hopper with the track such that the secondary functional group of the hopper binds to a first primary functional group on the track;
(iii) applying a driving force so as to cause the hopper to be directionally transferred from the first primary functional group to a second primary functional group on the track thereby causing the hopper to move along the track;
wherein the track is positioned such that the movement of the hopper along the track causes the analyte to interact with the detector, thereby characterising the analyte.

The detector may be any suitable detector for characterising the analyte. Often in the invention, the detector is a transmembrane pore such as one of the pores described herein. Most often, the detector is a transmembrane protein pore as described herein. When the detector is a transmembrane pore as described herein, the substrate is typically a surface of the transmembrane pore and the track is aligned along the surface as described in more detail herein; for example the track may be array of amino acids comprising primary functional groups as defined herein.

Usually, the analyte is a polynucleotide, polypeptide or polysaccharide. More often, the analyte is a polynucleotide or polypeptide. Typically, the analyte is a polynucleotide. The analyte may for example be any of the cargos described herein.

The driving force may be a chemical or physical potential as described herein. Usually, the driving force is an electrical (voltage) potential.

Accordingly, in the method, often:
  the substrate is a surface of the transmembrane protein pore;
  the track comprises an array of amino acid residues comprised in the protein nanopore; wherein each amino acid residue of the track comprises a reactive side chain; and wherein the hopper comprises a functional group capable of forming a covalent bond to the reactive side chains of the amino acid residues of the track; optionally wherein the track and hopper are defined herein;
  the analyte is a polynucleotide, a polypeptide or a polysaccharide; and
  the driving force is a physical or chemical potential.

The method may involve cycling the movement of the hopper back and forward along the track multiple times, thereby causing the analyte to interact with the detector multiple times. This can improve the characterisation of the analyte.

In a particular aspect, therefore, the invention thus provides a method of moving a molecular hopper along a track; wherein:
(a) the track comprises a plurality of primary functional groups aligned along a substrate; wherein the substrate is a surface of a transmembrane β-barrel protein nanopore and the track comprises an array of amino acid residues comprised in the protein nanopore wherein each amino acid residue in the track comprises a primary thiol functional group; wherein optionally the amino acid residues in the track are at positions corresponding to positions 113, 115, 117, 119, 121 and/or 123 in the SEQ ID NO: 1 or 2 sequence; and
(b) the hopper comprises a thiol secondary functional group linked by a linker to a cargo moiety such that the hopper is capable of forming a disulfide bond to the track; wherein the cargo moiety is a polynucleotide and the linker is a group of form: -alkylene- or -alkylene-[XPhos]-; wherein alkylene is a $C_{4-10}$ alkylene group which is interrupted by C(O)NR and [XPhos] is selected from phosphate and thiophosphate;

the method comprising the steps of:
(i) contacting the hopper with the track such that the thiol group of the hopper binds to a first thiol group on the track;
(ii) applying an electrical potential so as to cause the hopper to be directionally and reversibly transferred from the first thiol group of the track to a second thiol group on the track thereby causing the hopper to move along the track; and
(iii) contacting the primary thiol group of the track bonded to the secondary thiol group of the hopper with a tertiary thiol group on the substrate such that the tertiary thiol group bonds to the primary thiol group thereby displacing the secondary thiol group and so releasing the hopper; wherein optionally the tertiary thiol group is comprised in an amino acid at the position corresponding to position 139 in the SEQ ID NO: 1 or 2 sequence;
wherein prior to contacting the hopper with the track the secondary thiol group of the hopper is attached to a positioning moiety of form: [blocking entity]-[linker1]-[PEG]-[linker2]-[functional group]; wherein [blocking entity] is a blocking entity such as a neutravidin, streptavidin or traptavidin protein bound to a biotin group; [linker1] and [linker2] are each independently alkylene-containing groups which are substituted or unsubstituted as defined herein and uninterrupted or interrupted as defined herein, but are typically interrupted by groups selected from NHC(O) and heterocyclylene and are typically substituted by —[X] or alkylene-[X] as defined herein; [PEG] is a polyethylene glycol group including between 1 and 30 ethylene glycol units; and [functional group] is thiol group which bonds to the secondary thiol functional group of the hopper to form a disulfide bond; and step (i) of the method comprises contacting the hopper with the pore such that the blocking entity prevents passage of the hopper through the pore so as to hold the positioning moiety in a position such that the first primary thiol group on the track binds to the secondary thiol functional group on the hopper, thereby releasing the positioning moiety from the secondary functional group.

Apparatus and Conditions

Any suitable apparatus can be used to enact the methods of the invention.

Electrical measurements may be made using standard single channel recording equipment as describe in Stoddart, D. S., et al., (2009), *Proceedings of the National Academy of Sciences of the United States of America* 106, p 7702-7707, Lieberman K R et al, J Am Chem Soc. 2010; 132(50):17961-72, and International Application WO-2000/28312. Alternatively, electrical measurements may be made using a multichannel system, for example as described in International Application WO-2009/077734 and International Application WO-2011/067559.

In embodiments of the invention which comprise the use of a nanopore (e.g. as a substrate or detector), the invention may be carried out using any apparatus that is suitable for investigating a membrane/pore system in which a pore is inserted into a membrane. The invention may be carried out using any apparatus that is suitable for transmembrane pore sensing. For example, the apparatus may comprise a chamber comprising an aqueous solution and a barrier that separates the chamber into two sections. The barrier has an aperture in which the membrane containing the pore is formed. The invention may also be carried out using droplet interface bilayers (DIBs). Two water droplets are placed on the electrodes and immersed into a oil/phospholipid mixture. The two droplets are taken in close contact and at the interface a phospholipid membrane is formed where the pores get inserted.

The invention may be carried out using the apparatus described in International Application No. PCT/GB08/000562 (WO 2008/102120).

The methods of the invention typically involve measuring the current flowing through a pore. Therefore the apparatus may also comprise an electrical circuit capable of applying a potential and measuring an electrical signal across a membrane and pore. The methods may be carried out using a patch clamp or a voltage clamp. The methods usually involve the use of a voltage clamp.

The methods may be carried out on a silicon-based array of wells where each array comprises 128, 256, 512, 1024 or more wells.

The methods may be carried out using an array of pores as described herein. The use of an array or pores may allow the monitoring of the method by monitoring a signal such an electrical or optical signal. The optical detection of analytes using an array of nanopores can be conducted using techniques known in the art, such as those described by Huang et al, Nature Nanotechnology (2015) 10: 986-992.

The methods of the invention may involve the measuring of a current flowing through a pore. Suitable conditions for measuring ionic currents through transmembrane pores are known in the art and disclosed in the Example. The method is typically carried out with a voltage applied across the membrane and pore. The voltage used is typically from +2 V to −2 V, typically −400 mV to +400 mV. The voltage used is typically in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more often in the range 100 mV to 240 mV and most usually in the range of 120 mV to 220 mV.

The methods of the invention are typically carried out in the presence of charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is typically from 150 mM to 1 M. The method is usually carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. The salt concentration used on each side of the membrane may be different, such as 0.1 M at one side and 3 M at the other. The salt and composition used on each side of the membrane may be also different.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is typically about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature.

Kit

The invention also provides a kit for characterising an analyte, the kit comprising:
(A) a detector;
(B) a track comprising a plurality of primary functional groups aligned along a substrate; and
(C) a molecular hopper for conjugating to the analyte; wherein the hopper comprises a secondary functional group capable of binding to each of the plurality of primary functional groups on the track Typically, the detector, track, primary functional groups, substrate, molecular hopper, analyte and secondary functional group are each preferably as defined herein. Usually, the analyte is a polynucleotide, polypeptide or polysaccharide, usually a polynucleotide or polypeptide, more often a polynucleotide.

Typically, in the kit the track is positioned with respect to the detector such that movement of the hopper along the track allows the analyte to interact with the detector, such that the analyte can be characterised by the detector.

System

The invention also provides a system comprising
(A) a detector;
(B) a track comprising a plurality of primary functional groups aligned along a substrate; and
(C) a molecular hopper conjugated to a polynucleotide or a polypeptide analyte; wherein the hopper comprises a secondary functional group bonded to at least one of the plurality of primary functional groups on the track.

The detector, track, primary functional groups, substrate, molecular hopper, analyte and secondary functional group are typically as defined herein.

Hopper

The invention also provides a hopper molecule as described herein. The hopper comprises:
a secondary functional group for bonding to a primary functional group on a track;
a polynucleotide, polypeptide or polysaccharide cargo moiety;
a linking moiety between the secondary functional group and the cargo moiety.

The secondary functional group, primary functional group, track, cargo, and linking moiety are typically as defined herein. The hopper may further comprise a positioning moiety for positioning the hopper relative to the track such that the first primary functional group on the track can bind to the secondary functional group on the hopper. The positioning moiety may be as defined herein. The positioning moiety may comprise a blocking entity as defined herein for preventing passage of the hopper through a transmembrane pore. Usually, the blocking entity comprises or consists of a protein.

Chemical Communication

The invention also provides a method of chemical communication across a barrier spanned by a track, the method comprising contacting the track with a molecular hopper under conditions such that the hopper moves along the track across the barrier, and wherein the movement of the hopper conveys information across the barrier.

The track and hopper are typically as defined herein. The barrier may be any suitable barrier, such as an energy barrier e.g. through a nanopore. The barrier may be between two or more compartments comprising an aqueous medium, for example between two droplets. The compartments or droplets may be for example components of a synthetic tissue or synthetic organism such as a synthetic cell. The droplets may be coated with an amphiphilic molecule as defined herein, such as a lipid or block copolymer. The droplets may therefore be or comprise droplet interface bilayers. Droplet interface bilayers are known in the art.

Typically the movement of the hopper is selectively controlled by the track. Movement of hoppers along tracks is described in more detail herein. The track may be on a substrate e.g. a surface; suitable substrates are described herein. The hopper typically carries a cargo. Suitable cargos are described herein. For example, the cargo may be a polynucleotide such as a polynucleotide which is complementary to a promoter region in a vector. The polynucleotide may be complementary to a promoter region in a vector suitable for in vitro transcription/translation and transport of said cargo across said barrier comprises initiating the in vitro transcription/translation reaction. IVTT is described in more detail herein.

The communication can be communication of any suitable information such as (but not limited to) information which can be encoded by a polynucleotide or polypeptide.

Acknowledgment

The work leading to this invention has received funding from the European Research Council under the European Union's Seventh Framework Programme (FP7/2007-2013)/ERC grant agreement no 294443.

```
                    SEQUENCE LISTING

SEQ ID NO: 1: WT
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYMSTLTYGFNGNVTGDDTGKIGGLIGANVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTN

SEQ ID NO: 2: WT-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYMSTLTYGFNGNVTGDDTGKIGGLIGANVSIGHTLKYVQ
PDFKTILESPTDKKVGWKVIFNNMVNQNWGPYDRDSWNPVYGNQLFMKTR
```

```
                 -continued
                SEQUENCE LISTING

NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH

SEQ ID NO: 3: 115C117C-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYMSCLCYGFNGNVTGDDTGKIGGLIGANVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH

SEQ ID NO: 4: 115C117C119C-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYMSCLCYCFNGNVTGDDTGKIGGLIGANVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH

SEQ ID NO: 5: 113C115C117C119C121C-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYCSCLCYCFCGNVTGDDTGKIGGLIGANVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH

SEQ ID NO: 6: 113C115C117C119C121C123C-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYCSCLCYCFCGCVTGDDTGKIGGLIGANVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH

SEQ ID NO: 7: 115C117C119C139C-D8H6
ADSDINIKTGTTDIGSNTTVKTGDLVTYDKENGMHKKVFYSFIDDKNHNK
KLLVIRTKGTIAGQYRVYSEEGANKSGLAWPSAFKVQLQLPDNEVAQISD
YYPRNSIDTKEYMSCLCYCFNGNVTGDDTGKIGGLIGACVSIGHTLKYVQ
PDFKTILESPTDKKVGWKVIFNNMVNQNWGPYDRDSWNPVYGNQLFMKTR
NGSMKAADNFLDPNKASSLLSSGFSPDFATVITMDRKASKQQTNIDVIYE
RVRDDYQLHWTSTNWKGTNTKDKWTDRSSERYKIDWEKEEMTNDDDDDD
DHHHHHH
```

The following Example illustrates the invention. The Example does not, however, limit the invention in any way. In particular, there are many methods of controlling and/or monitoring movement of a hopper along a track, and so a negative result in any specific assay is therefore not determinative.

Example 1

This Example demonstrates that a molecular hopper controlled by a chemical ratchet can move along a track processively and change direction on command. Key details are set out below and further information is provided under the heading "Supplementary Material" (SM) immediately following the main text of the Example.

Intrigued by technological potential, scientists have long attempted to control molecular motion. This Example describes how the individual 0.7-nm steps of a single molecular hopper can be monitored as it moves in an electric field along a track in a nanopore controlled by a chemical ratchet. The hopper demonstrates characteristics desired in a moving molecule: defined start- and end-points, processivity, fuel autonomy, directional motion and external control.

The hopper is readily functionalized to carry cargos. For example, DNA can be ratcheted along the track in either direction, a prerequisite for nanopore sequencing.

Processivity lies at the heart of biological machines. A replicative DNA polymerase can incorporate thousands of nucleotides before dissociating from its template (1). Molecular motors, such as kinesin and dynein, travel directionally along microtubules over hundreds of steps without detaching from the track (2-4). For years, scientists have been trying to build moving molecules that resemble their biomolecular counterparts but use simpler components (5). The ultimate goals are to achieve true processivity, which can be defined as directional motion without leaving a track, and the performance of useful work such as the transport of a cargo. Ideally, a synthetic system should exhibit the reversibility of stepping seen in various biological systems (6, 7) to enable the direction of motion to be switched through external control.

The one-legged molecular hopper reported in this Example is ratcheted by dynamic covalent chemistry along a protein track and demonstrates a level of processivity unprecedented in previous synthetic systems (Table S7), exceeding that of some biomolecular motors (FIG. 1A). Further, the direction in which the hopper moves is subject to external control by an electrical potential. The track is built inside a protein nanopore, α-hemolysin (αHL), and consists of a series of cysteine footholds facing the lumen of the transmembrane β barrel (FIG. 1B). The cysteines are evenly spaced along a R strand with an average inter-foothold distance of 6.8 Å (Cα–Cα) and an average vertical spacing of 5.6 Å. The hopper moves in the direction in which the DNA cargo has been oriented by an applied potential, by employing consecutive thiol-disulfide interchange reactions.

To execute the $S_N2$ reaction, the three participating sulfur atoms align in a near linear configuration (8-10). Under the applied potential, the DNA inside the barrel is pulled in the electric field with a force of ~10 pN (see SM section 12). The force sets the overall direction of motion by flipping the DNA (see below) and helps orient the disulfide for cleavage by the neighboring downstream cysteine thiolate, which moves the hopper one step forwards, although other forces can contribute to the forward motion (FIG. 1C). Back-stepping is disfavored and over-stepping is impossible. Release of the hopper from the linear track was not observed, presumably because the track is too rigid to accommodate the resultant disulfide bridge between adjacent footholds on the same β strand. In short, each step is chemically directional as the hopper's 'foot' is positioned to favor the forward reaction. Further, the motion is autonomous, requiring no chemical fuel.

Figure 6A:
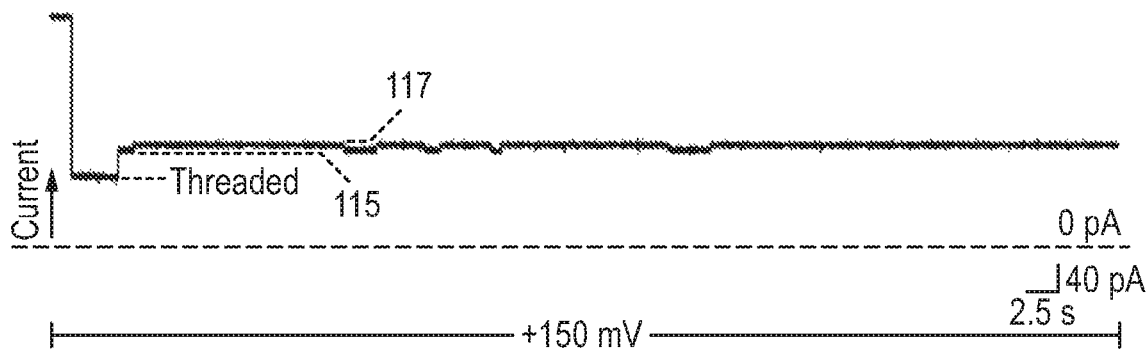
FIGS. 6A-6C show loading hopper 1 onto different tracks. Under +150 mV, a hopper-1-carrier conjugate capped with a traptavidin threaded from the cis side of the nanopore before reacting with Cys-115, which covalently attached the hopper to (FIG. 6A) a two-cysteine track (Footholds: Cys-115, 117)
Figure 6B:
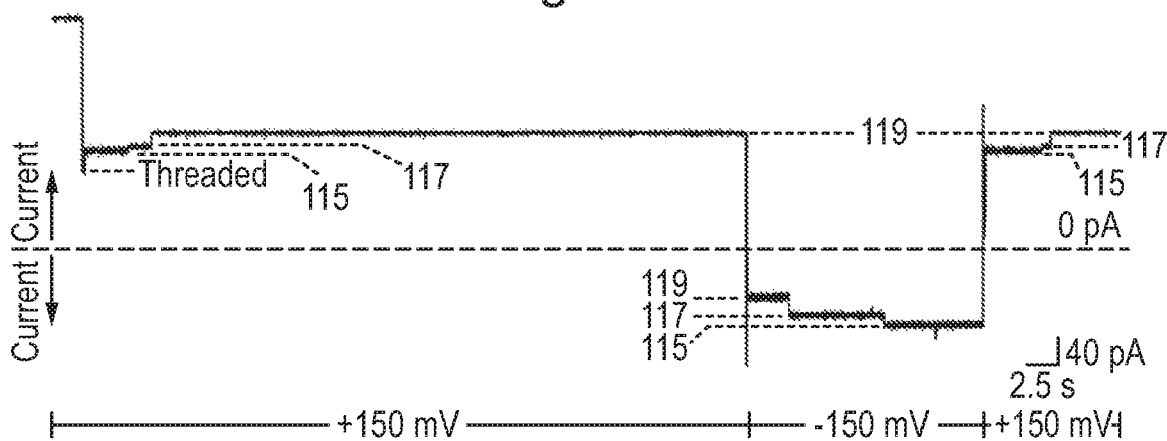
Figure 6C:
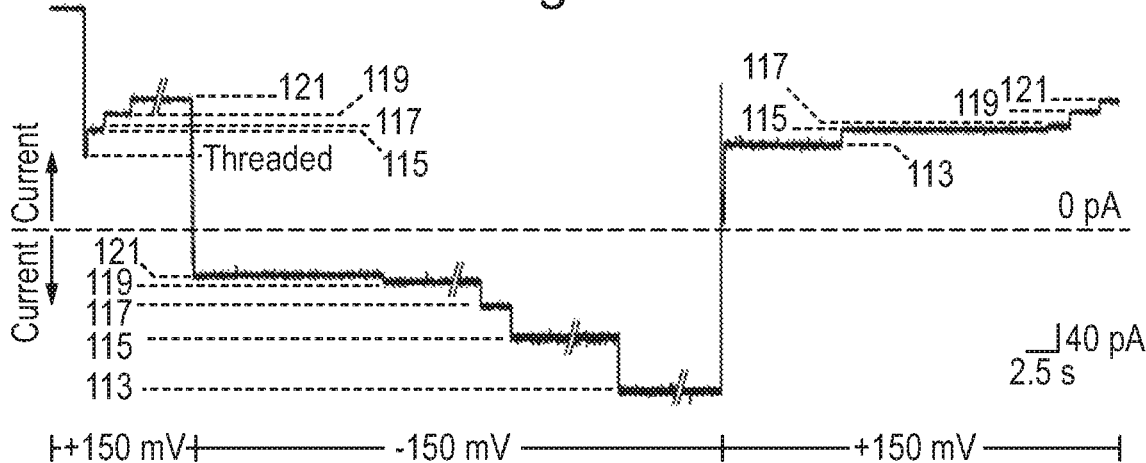

Under +150 mV, the hopper was delivered to the track from the cis compartment as a hopper-carrier conjugate (FIG. 1D) capped with a single traptavidin, which was arrested at the pore entrance (FIG. 2A). The disulfide in the construct reacted strictly regioselectively with Cys-115 releasing the carrier and placing the hopper-DNA cargo on the starting foothold (FIG. 2A, 6). The location of the hopper was ascertained from the residual current passing through the nanopore, which reflected the length of the DNA located within the R barrel when the hopper was at a particular foothold (FIG. 6). By monitoring current changes, we followed the stepwise hopping motion at the single-molecule level in real-time.

The voltage-controlled hopping motion was directional and processive. On a track containing five cysteine footholds (113, 115, 117, 119, 121), a hopper carrying an oligoadenosine 40-mer (A40, hopper 1) moved cis to trans under +150 mV, and trans to cis under −150 mV (FIG. 2B). When the hopper reached a terminal foothold, the sign of the applied potential was reversed in order to reorient (flip) the DNA cargo, and hence the hopper. Alternation between positive and negative potentials repeatedly drove the hopper towards the trans or the cis end of the track.

For the DNA to experience a force, at least one negatively-charged phosphodiester bond must lie within the electric field, which drops along the length of the pore's β barrel (11). Therefore, in the present nanopore construct, voltage-controlled hopping was demonstrated with up to six footholds (FIG. 9). The hopping direction could be changed by reversing the applied potential at any foothold, showcasing the complete control over directionality and the ability to move a hopper back to the initial foothold after an outing.

Figure 8A:
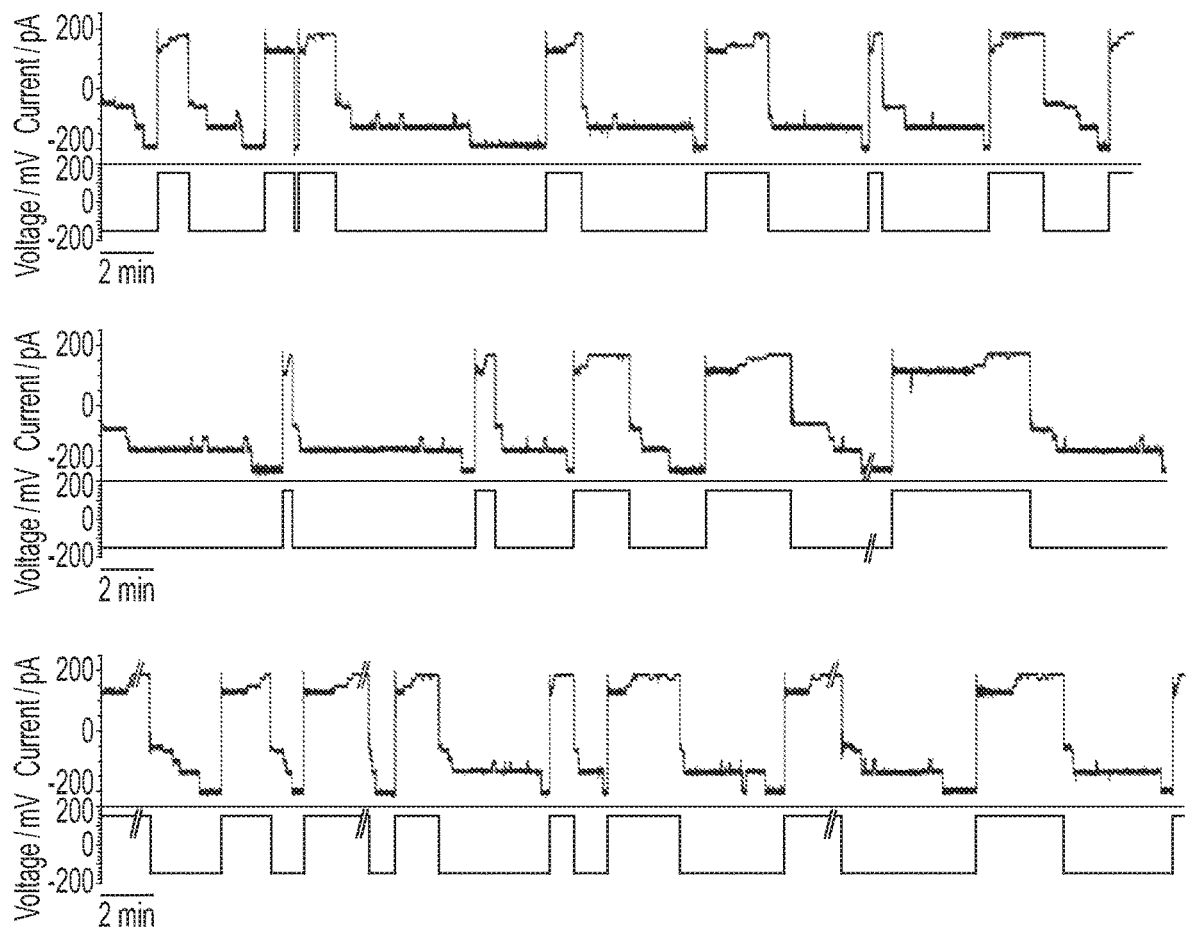
FIGS. 8A and 8B show hopping cycles on the five-cysteine track. After hopper 1 was loaded onto the five-cysteine track (Footholds: Cys-113, 115, 117, 119, 121) (FIG. 6C), it moved under external control for >20 complete cycles (from 113 to 121 at +150 mV and then from 121 to 113 at −150 mV) during a single recording.
Figure 8B:
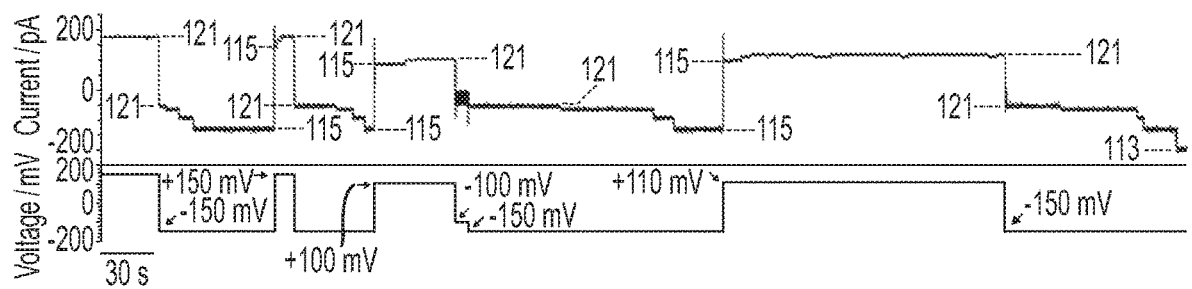

In the present system, the applied potential provides an external energy source to produce directional motion (FIG. 2C, see SM section 12). Limited only by bilayer stability, the longest records of processive hopping were documented with hopper 1, which completed 249 forward steps in 93 min on a five-cysteine track (113-121) with a mean dwell-time of ~22 s per foothold (FIG. 8). Dissociation of the hopper from the track was never seen (in >30 outings on different tracks), which implies that substantially higher step numbers would be observed with more stable bilayers. Alternative bilayer systems are described herein and can achieve significant stability improvements. In comparison, previous synthetic small-molecule walkers moved directionally for less than 10 steps (5, 12). Wild-type kinesins typically exhibit a mean step number of 75-175 before dissociation (2, 3).

The hopping rates for each of the four steps on the five-cysteine track were derived for both the cis-to-trans and trans-to-cis directions at pH 8.5 and displayed differences of less than 40-fold (0.0081 to 0.30 $s^{-1}$, Table S3). Because a thiolate is the reactive nucleophile in disulfide interchanges, the rate differences might arise from variations in the $pK_a$ values of the foothold thiols, which will be affected by neighboring residues. Previously, an arsenic(III) walker showed an up to a 50-fold difference in attachment rates with the footholds on the same five-cysteine track (113-121) at pH 8.0 (12). Tracks of thiols may be engineered with optimized inter-foothold distances and enhanced chemical reactivity to speed up the hopping process. Alternatively, the properties of the reactive sulfur atom in the hopper may be manipulated by flanking functional groups. With both the two-cysteine and the three-cysteine tracks, the influence of voltage on hopping was examined at ±100 mV, ±150 mV, and ±180 mV (Table S1, S2). The rates showed weak non-exponential voltage-dependences suggesting that the applied potential might not be the only source of propulsion (see SM section 12). However, an electrical potential is essential 1) to flip the DNA over a large barrier to set the direction of motion; 2) to aid in the orientation of the three participating sulfur atoms to favor "forward" reactions over back-steps. With respect to the latter, the estimated "effective concentrations" of participating downstream thiols are not especially high (see SM section 15) (13) and indeed need not be to produce overall forward motion (see below).

Although disfavored, back-stepping was occasionally detected and attributed to conformational lability of the hopper within the nanopore even under an applied potential. During a recording with hopper 1 on a five-cysteine track (113-121), there were 33 backward steps on the non-terminating footholds out of 282 steps in total (12%). Of the 33 backward steps, 29 occurred from 115 to 117 at −150 mV (Table S5). Despite the large forward equilibrium constant for 117 to 115 ($K=k_{117\text{-}115}/k_{115\text{-}117}=22$), 115-117 back-stepping is observed, because of the comparatively slow forward movement to the next foothold 113 (at −150 mV, $k_{115\text{-}117}=0.0094$ $s^{-1}$; $k_{115\text{-}113}=0.0081$ $s^{-1}$, Table S3, S5). Back-stepping was observed when the hopper was left on a terminal foothold as no forward footholds remained (FIG.

2B). These back-steps were quickly reversed by the hopper, which preferentially resided at the final station ($K=k_{119-121}/k_{121-119}=5.2$, Table S4). The overall motion of the hopper is governed by the product of the K values for each step. A modest value (K>1) at each step produces a considerable overall tendency towards forward movement.

Each subunit of the αHL pore offers two antiparallel β strands to the transmembrane β barrel with an inter-strand distance of ~5 Å (Cα–Cα). Given that the formation of cross-strand disulfides has been reported (14), we reasoned that the addition of a cysteine on an adjacent strand would compel hopper release from the track at a designated foothold. Indeed, with an L-shaped track consisting of cysteines at positions 115, 117, 119, and 139, the hopper attached to the track at foothold 115 by regioselective disulfide formation and dissociated from the track when it reached foothold 119. The release was initiated by Cys-139, through thiol-disulfide interchange to form a cross-strand disulfide bridge, which blocked the access of subsequent hoppers to foothold 119 (FIG. 2D). The preference for hopper release versus hopper transfer to the adjacent strand is attributed to the failure of the three participating sulfur atoms to form the co-linear alignment necessary for transfer. In the future, the engineering of footholds on a surface will allow the construction of more complex hopping pathways where hoppers are transferred to new tracks at designed junctions and cargos are released at predesignated depots.

Figure 3A:
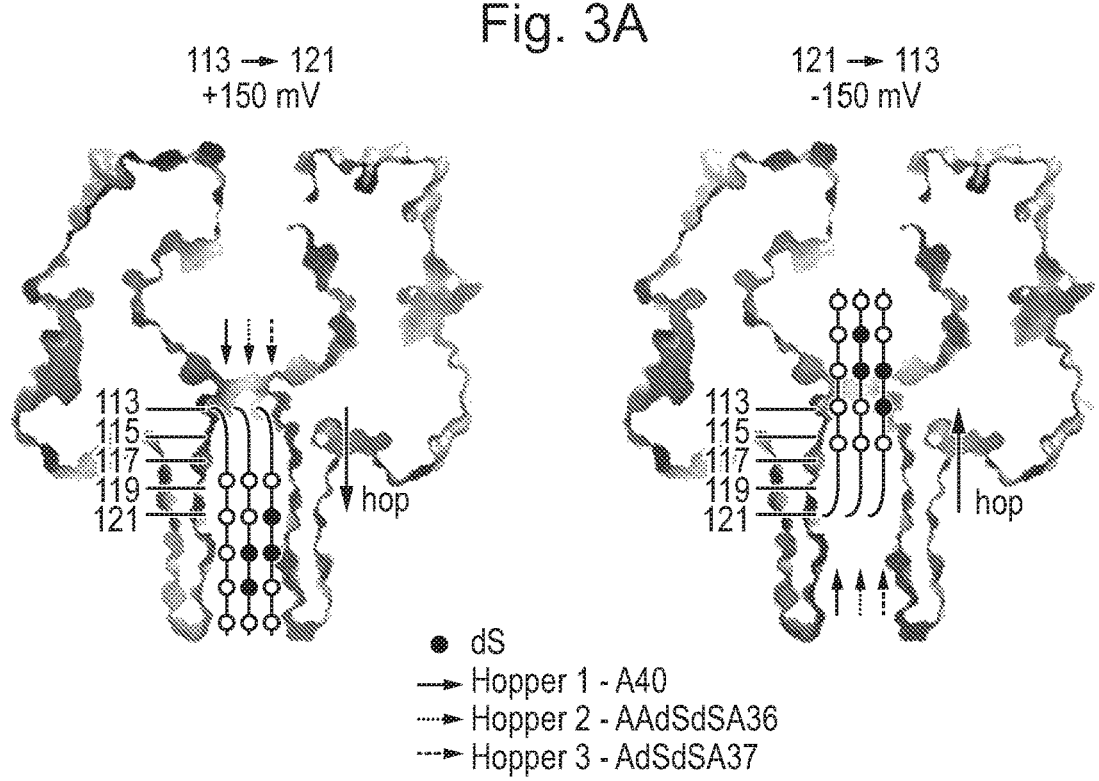
FIGS. 3A-3D show the discrimination of different DNA cargos.
Figure 3B:
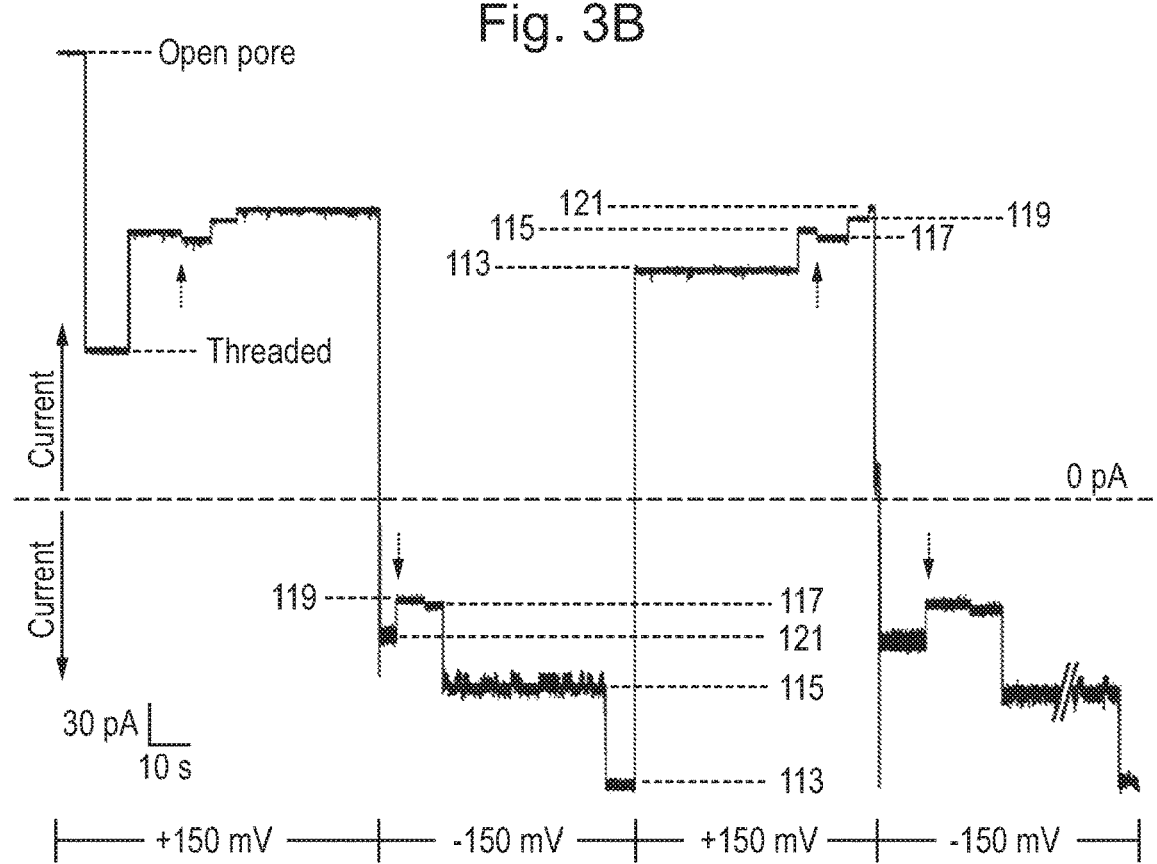
Figure 3C:
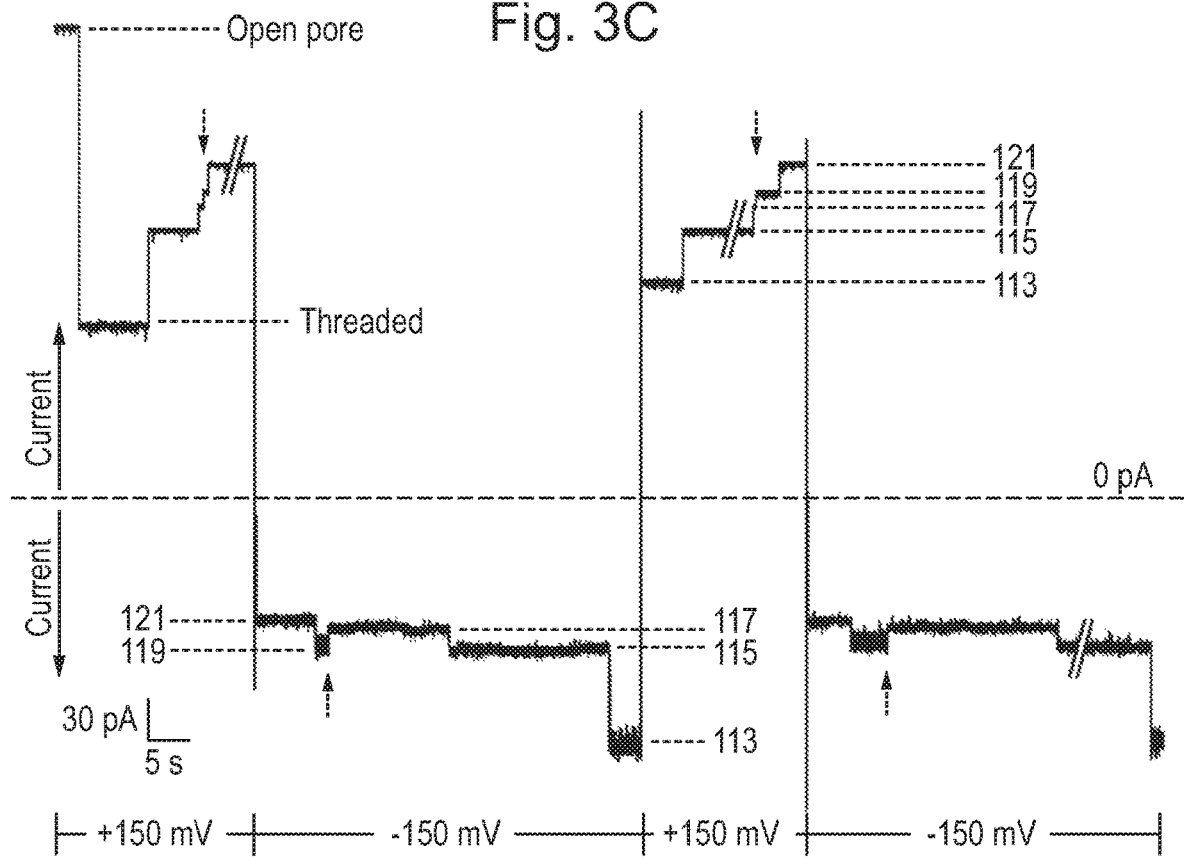
Figure 3D:
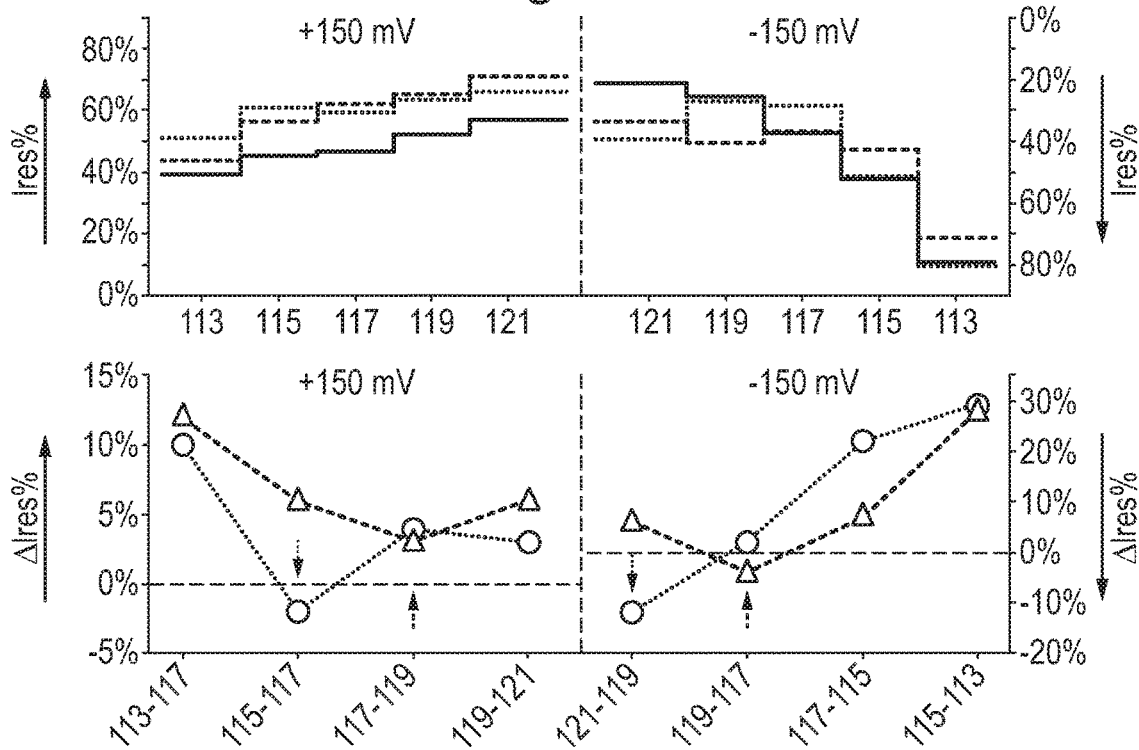

The ability to translocate a stretched DNA cargo while maintaining a covalent bond with the nanopore suggests a method for the chemical ratcheting of a nucleic acid during nanopore sequencing (15), which was explored in a proof-of-concept experiment. To provide a marker, two adjacent abasic residues (1',2'-dideoxyribose, dS) (16) were incorporated into the cargo oligos carried by hoppers 2 and 3, and current patterns were recorded during four-step hopping between Cys-113 and Cys-121 (FIG. 3A). By comparison with hopper 1, hoppers 2 and 3 showed different patterns of current modulation (FIG. 3BC, 16, Table S6). The conductance patterns generated by the four-step hopping motion could be repeated with different molecules of hopper 2 and hopper 3 (n=3 for each hopper), establishing the patterns as clear identifiers of each cargo sequence. The residual currents (Ires %, the remaining current as a percentage of the open pore current) for the three hoppers residing at each foothold were plotted for comparison (FIG. 3D). Hopper 1 and hopper 2 gave almost identical current blockades at each of footholds 115 and 113 under −150 mV, implying that the dSdS sequence had been transported well out of the sensing region by hopper 2. Moreover, hopper 2 and hopper 3 have a single nucleotide offset in the dSdS positions and we observed a one-step offset between hopper 2 and hopper 3 in ΔIres %, the difference in Ires % between two successive steps (FIG. 3D; the vertical step size, 5.6 Å, is similar to the inter-nucleotide distance in stretched single-stranded DNA, 6.9 Å (17)).

These observations demonstrate that the hopper system reported here has the potential to discriminate bases for sequencing purposes (16). An advantage of a processive hopper, which might improve sequencing accuracy, is the ability to reverse the chemical ratcheting process and thereby obtain many-fold coverage of an individual DNA strand. This could be further improved by the use of pores having longer β-barrel pores (18, 19). A viable sequencing process may involve protracted ratcheting of numerous DNA strands in parallel, perhaps by using footholds on an extended crystalline surface or internal thiophosphate feet to transport long replica strands over relatively short tracks.

Supplementary Information

1. Synthesis and Characterization of Hopper-Carrier Conjugates 1.1. Chemicals

Acetic anhydride ($Ac_2O$), acetonitrile (HPLC grade), 5-azidopentanoic acid, N,N-diisopropylethylamine (DIPEA), diethyl ether, dimethylformamide (DMF), hexafluoro-2-propanol (HFIP), N,N-hydroxybenzotriazole (HOBt), 1-methyl-2-pyrrolidinone (NMP), Nu-Fmoc-NE-biotinyl-L-lysine, piperidine, triethylamine (TEA), and trifluoroacetic acid (TFA) were purchased from Sigma-Aldrich. 2-(1H-Benzotriazole-1-yl)-1,1,3,3-tetramethyluronium hexafluorophosphate (HBTU), Fmoc-Phe-OH, and Rink Amide MBHA resin LL (100-200 mesh) were from Novabiochem. Fmoc-NH-PEG(12)-COOH was purchased from Iris Biotech GmbH.

1.2. Carrier Preparation Using Solid-Phase Peptide Synthesis

Figure 4A:
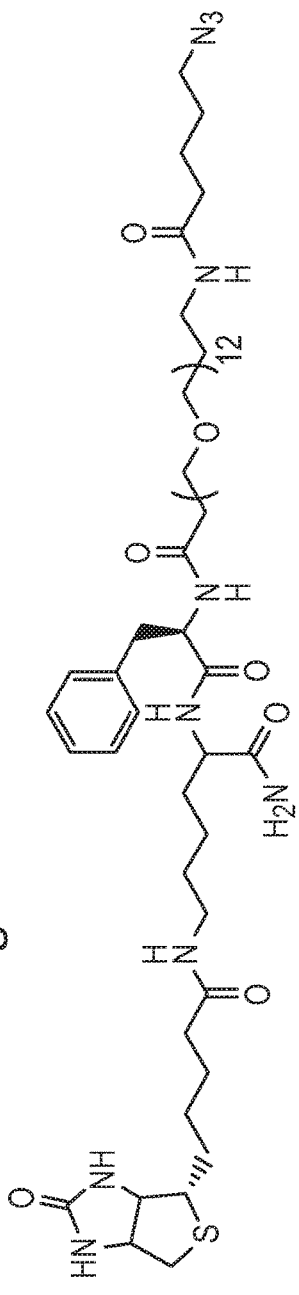
FIGS. 4A-4C show LC-MS and HPLC characterization of the carrier.
Figure 4C:
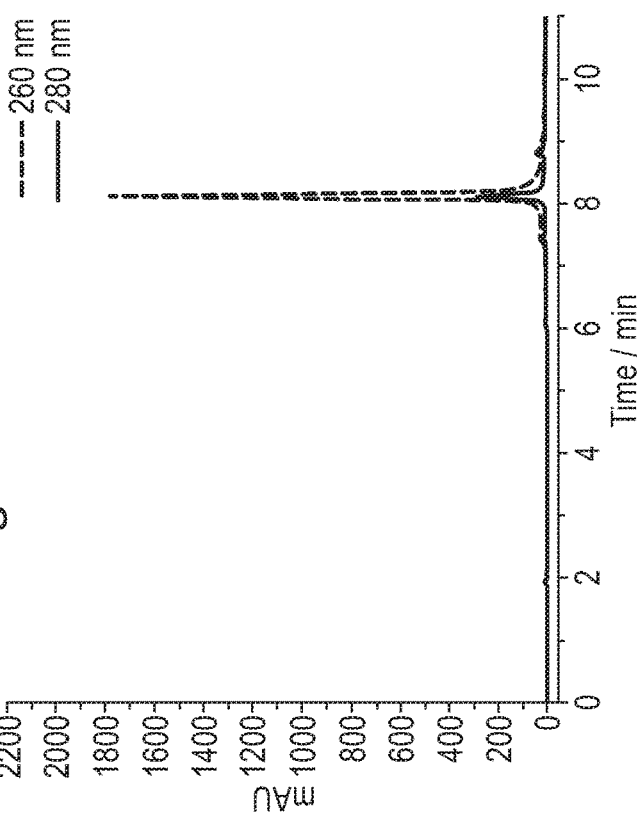

The carrier (FIG. 4A) was made by using manual solid-phase peptide synthesis, adapted from previously reported protocols (20).

Peptide elongation was carried out on 0.25 mmol Rink Amide MBHA resin LL (0.37 mmol $g^{-1}$) by the Fmoc method with HBTU and DIPEA as coupling reagents. The resin was washed and swollen overnight in DMF and Fmoc was removed by treatment with 20% (v/v) piperidine in NMP at room temperature. The carrier was assembled through standard chain elongation by using the reactants Nu-Fmoc-N&-biotinyl-L-lysine, Fmoc-Phe-OH, Fmoc-NH-PEG(12)-COOH, and 5-azidopentanoic acid. For each of the four coupling reactions, a solution of 1.0 mmol reactant, 0.95 mmol HBTU, and 2.0 mmol DIPEA in 1.9 mL DMF was added to the resin, which was then shaken for 12 min. After each coupling, the resin was washed with NMP and capped with 1.5 mmol $Ac_2O$, 0.044 mmol HOBt, and 0.39 mmol DIPEA in 3 mL DMF for 2 min. The capped resin was then washed with NMP again before the next coupling. After the completion of chain assembly, the resin was washed sequentially with DMF and ethanol and dried in vacuo. Peptides were cleaved from the resin by treatment with TFA for 2 h. The TFA was evaporated in a stream of nitrogen and the peptide was precipitated with cold diethyl ether, followed by centrifugation, and several trituration treatments with diethyl ether.

1.3. Carrier Purification and Characterization

Figure 4B:
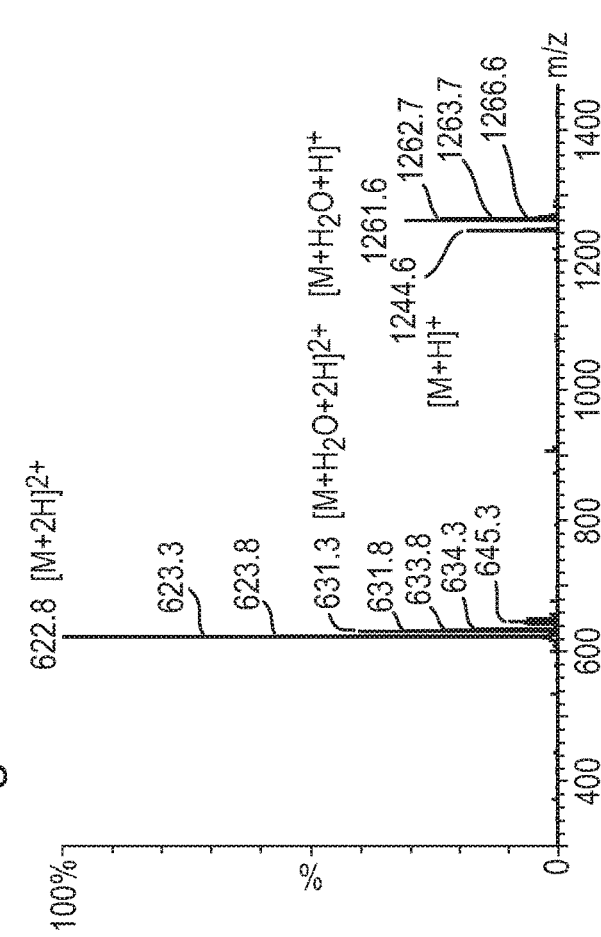

The crude peptide was dissolved in DMF and purified by preparative RP-HPLC (Dionex UltiMate 3000; Vydac C18 column: 250×22 mm, 10-15 μm (particle size); linear gradient: 5-95% eluant B in eluant A over 45 min, flow rate: 15 mL $min^{-1}$; eluant A: 0.1% TFA in water; eluant B: 0.1% TFA in acetonitrile). The identity and purity of the fractions were determined by analytical LC-MS (Waters LCT accurate-mass time-of-flight instrument (ESI-positive); Chromolith RP-18e column: 50 mm×2 mm; linear gradient: 5-100% eluant B in eluant A over 8 min, flow rate: 1 mL $min^{-1}$; eluant A: 0.1% formic acid in water; eluant B: 0.1% formic acid in acetonitrile). The fractions showing the correct mass were combined, lyophilized, and characterized by LC-MS and analytical RP-HPLC (Agilent 1260 Infinity HPLC; Polaris C18 column: 150×4.6 mm, 5 μm (particle size); linear gradient: 5-95% eluant B in eluant A over 10 min, flow rate: 1 mL $min^{-1}$; eluant A: 0.1% TFA in water; eluant B: 0.1% TFA in acetonitrile) (FIG. 4B).

1.4. Generation and Characterization of Hopper-Carrier Conjugates Oligonucleotides modified with dibenzocyclooctyne-disulfide (DBCO-SS) at the 5' terminus were purchased from biomers.net.

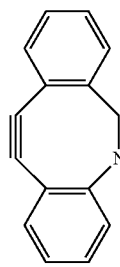
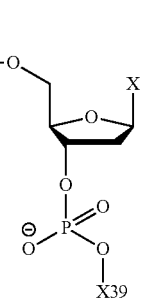

5' DBCO-SS modification

5' DBCO-SS-A40 oligo (10 µL, 1 mM in MilliQ water) was added to the carrier (1 µL, 10 mM in MilliQ water). The mixture was left at room temperature for 30 min to form the hopper-1-carrier conjugate by a copper-free click reaction. Similarly, the hopper-2-carrier and hopper-3-carrier conjugates were assembled with 5' DBCO-SS-AAdSdSA36 and 5' DBCO-SS-AdSdSA37, respectively.

The conjugates were purified by semi-preparative HPLC (Agilent 1260 Infinity; Supelco Discovery BIO Wide Pore C18 column: 250×10 mm, 10 µm (particle size); linear gradient: 10-90% eluant B in eluant A over 30 min, flow rate: 4.5 mL min$^{-1}$; eluant A: 0.1% TFA in water; eluant B: 0.1% TFA in acetonitrile) and identified by LC-MS (UPLC-MS Waters XEVO G2-QTOF (ESI-negative); ACQUITY UPLC Oligonucleotide BEH C18 Column: 2.1 mm×50 mm, 1.7 µm (particle size); linear gradient: 0-70% eluant B in eluant A over 8 min, flow rate: 0.2 mL min$^{-1}$; eluant A: 8.6 mM TEA, 200 mM HFIP in 5% methanol/water (v/v); eluant B: 20% eluant A in methanol).

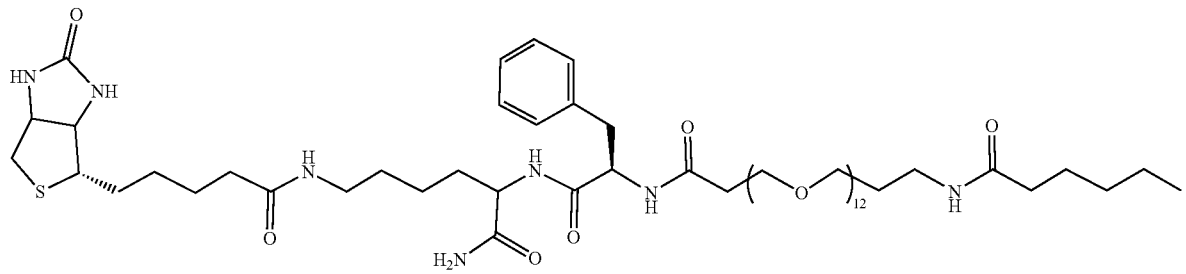

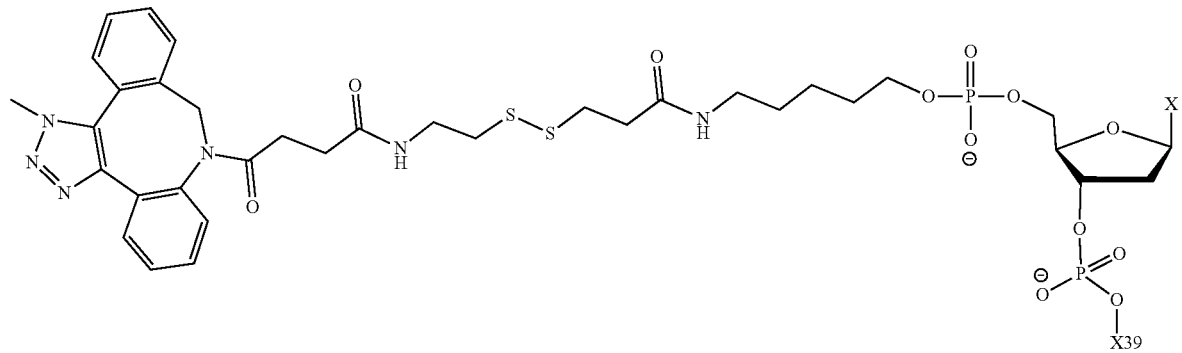

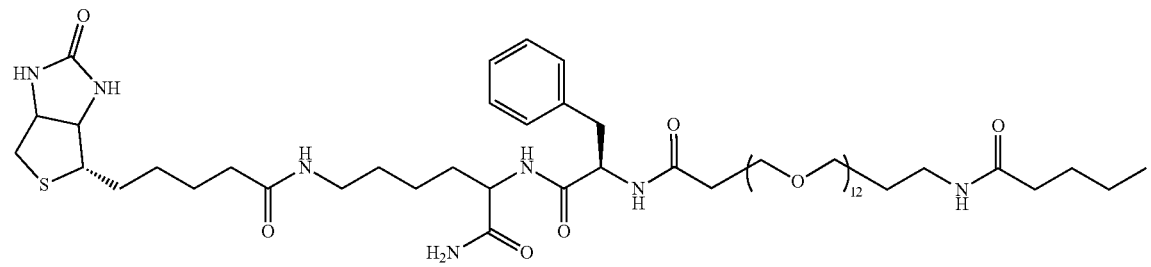

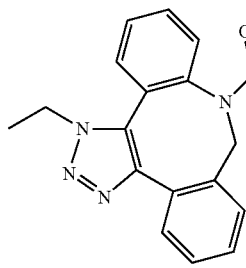
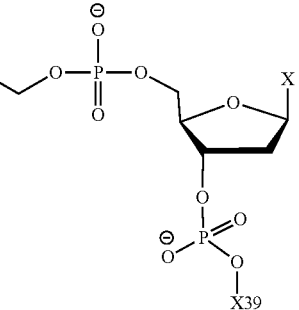

Figure 5:
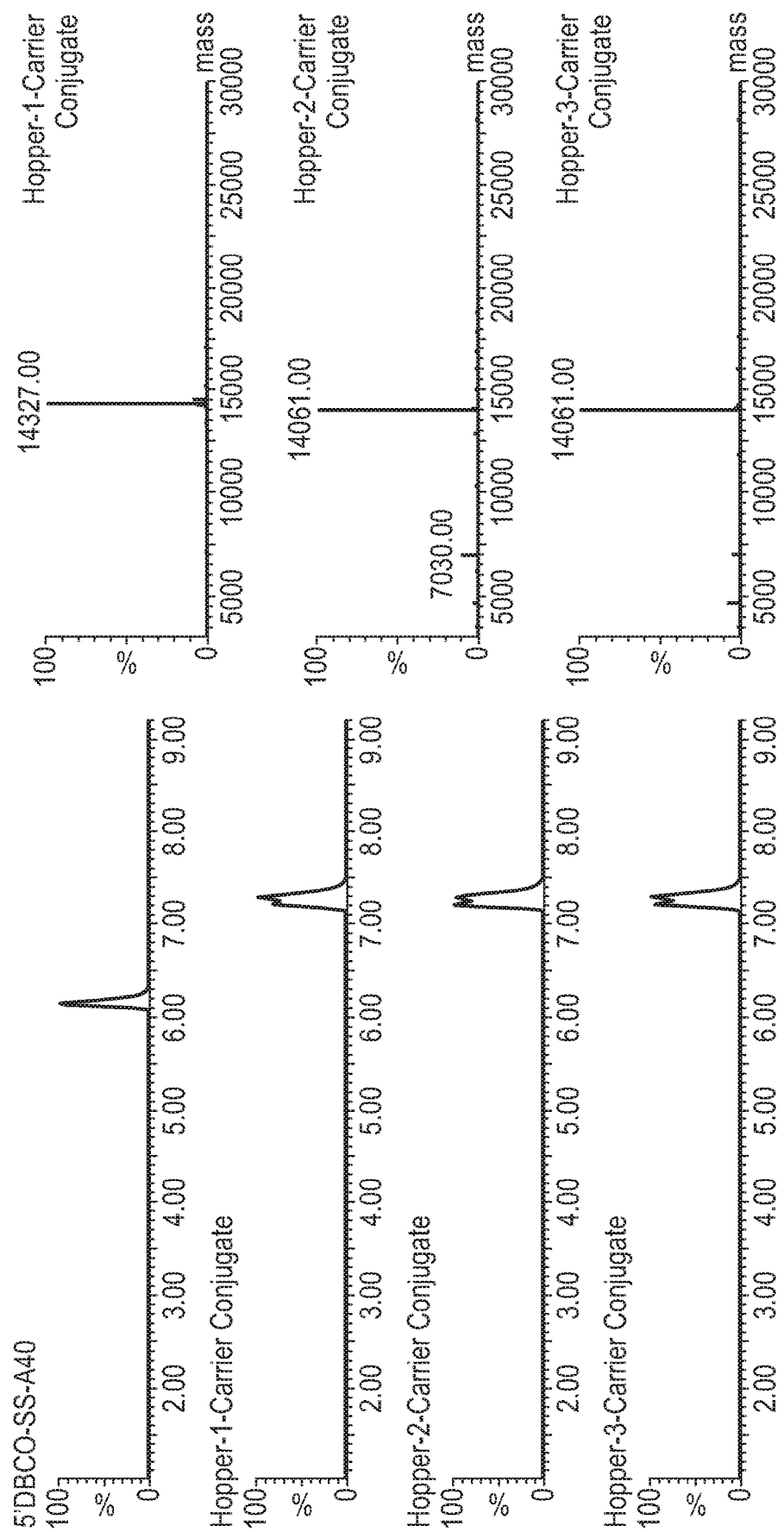
FIG. 5 shows LC-MS characterization of hopper-carrier conjugates. The two peaks in each chromatogram have the same mass, corresponding to the two regioisomeric conjugates formed by the copper-free click reaction. The mass of hopper-1-carrier conjugate was calculated to be 14327 g mol-1 and found to be 14327 g mol-1. The masses of hopper-2-carrier conjugate and hopper-3-carrier conjugate were both calculated to be 14059 g mol-1 and both found to be 14061 g mol-1. Data are described in the Example.

See FIG. 5.

2. Preparation of αHL Monomers with Multi-Cysteine Tracks

The construction of pT7-αHL-115C117C-D8H6 and pT7-αHL-113C115C117C119C121C-D8H6 (pT7-αHL-5C-D8H6), which encode αHL mutants containing cysteines either at positions 115 and 117, or at positions 113, 115, 117, 119, and 121, as well as an octa-aspartate tail and a His-tag at the C terminus, have been previously reported by our group (12).

pT7-αHL-6C-D8H6 encodes a αHL mutant containing cysteines at positions 113, 115, 117, 119, 121, and 123 as well as an octa-aspartate tail and a His-tag at the C terminus. It was generated from pT7-αHL-5C-D8H6 by in vivo homologous recombination. Two sets of PCR reactions were carried out. For the first reaction, the template was first linearized by NdeI (New England Biolabs) before PCR with the forward mutagenic primer: 5'-CTGCTTCTGCGGTTGTGTTACTGGTGATGATA-CAGG-3' (SEQ. ID NO. 8) and the reverse nonmutagenic primer (SC47): 5'-CAGAAGTGGTCCTGCAACTTTAT-3' (SEQ. ID NO. 9). For the second reaction, the template was linearized by Hind_I (New England Biolabs) before PCR with the reverse mutagenic primer: 5'-CCTGTATCAT-CACCAGTAACACAACCGCAGAAGCAG-3' (SEQ. ID NO. 10) and the forward nonmutagenic primer (SC46): 5'-ATAAAGTTGCAGGACCACTTCTG-3' (SEQ. ID NO. 11). The linearized templates and primers were mixed with 1×Phusion Flash HF Mastermix (New England Biolabs) and put through the following cycling program: 94° C. for 5 min, then 30 cycles of 94° C. (30 s), 50° C. (30 s), 72° C. (30 s), and finally 50° C. for 5 min. After PCR, 5 μL of each reaction were mixed and used to transform XL10-Gold cells (Agilent). The transformed cells were grown at 37° C. overnight on LB (Luria Broth)-carbenicillin plates. Plasmid DNA was isolated from colonies by using the QIAprep Spin Miniprep Kit (QIAGEN). Successful mutagenesis was confirmed by DNA sequencing.

Similarly, pT7-αHL-115C117C119C-D8H6 was made from pT7-αHL-WT-D8H6 with the mutagenic primer pair: 5'-CAAAAGAGTATATGAGTTGCTTATGCTATTGCTT-CAACG-3' (SEQ. ID NO. 12) (Forward); 5'-CGTT-GAAGCAATAGCATAAGCAACTCATATACTCTTTTG-3' (SEQ. ID NO. 13) (Reverse). pT7-αHL-115C117C119C139C-D8H6 was made from pT7-αHL-115C117C119C-D8H6 with the mutagenic primer pair: 5'-CCTTATTGGTGCATGTGTTTCGATTGGTCATA-CACTG-3' (SEQ. ID NO. 14) (Forward); 5'-CAGTGTATGACCAATCGAAACACATGCAC-CAATAAGG-3' (SEQ. ID NO. 15) (Reverse).

3. Preparation of an αHL Heptamer Containing a Multi-Cysteine Tracks on One of the Seven Subunits Engineered αHL polypeptides were expressed by using a commercial in vitro transcription-translation (IVTT) kit: E. coli T7 S30 Extract System for Circular DNA (Promega). To suppress transcription by E. coli RNA polymerase, the T7 S30 extract provided in the kit was treated with rifampicin prior to use (1 μg mL$^{-1}$, final concentration). A standard reaction comprised: DNA template (3.2 μg), amino acid mix minus methionine (supplied with the kit, 5 μL), S30 premix without amino acids (supplied with the kit, 20 μL), [$^{35}$S] methionine (2 μL, 1,200 Ci mmol$^{-1}$, 15 mCi mL$^{-1}$, MP Biomedicals), 15 μL T7 S30 extract (supplied with the kit. 15 μL), and nuclease-free water to a final volume of 50 μL. To make heteroheptamers, plasmids encoding the WT αHL and the mutant αHL were mixed in a ratio 6:1 (WT:mutant). The IVTT mixture was incubated at 37° C. for 1 h.

Heptamerization was carried out by the addition of rabbit erythrocyte membranes (3 μL, ~1 mg protein mL$^{-1}$) to the IVTT reaction mixture (50 μL), followed by incubation at 37° C. for another 1 h. The mixture was then centrifuged for 10 min at 25,000×g. The supernatant was removed and the pellet resuspended in MBSA buffer (200 μL, 10 mM 3-morpholinopropane-1-sulfonic acid (MOPS), 150 mM NaCl, 1 mg mL$^{-1}$ bovine serum albumin, pH 7.4). The wash with MBSA was repeated before the pellet was resuspended in 2× Laemmli sample buffer (50 μL) without heating and electrophoresed in a 5% SDS polyacrylamide gel at 70 V for 15 h.

The αHL heteroheptamers containing different numbers of mutant subunits were separated in the gel based on their different electrophoretic mobilities, which were determined by the number of octa-aspartate (D8) tails (21). The top and bottom bands corresponded to WT$_7$ and (mutant-D8H6)$_7$, respectively. The second band from the top was the desired heteroheptamer containing a single mutant subunit.

To extract heptameric pores, the gel was first dried without fixation on Whatman 3M filter paper under vacuum for 5 h at room temperature. After visualization by autoradiography with Kodak BioMax MR film, the desired bands were cut from the gel with a scalpel. Each excised band was rehydrated in TE buffer (300 μL, 10 mM Tris. HCl, 1 mM ethylenediaminetetraacetic acid (EDTA), pH 8.0) for 1 h at room temperature. The filter paper was then removed, and the rehydrated gel was macerated with a pestle. The resulting slurry was filtered through a 0.2 μm hydrophilic membrane filter (Proteus Mini Clarification Spin Column, Generon). The filtrate was stored in 10 μL aliquots at −80° C.

4. Single Channel Recordings

4.1. General 1,2-Diphytanoyl-sn-glycerol-3-phosphocholine (DPhPC) was purchased from Avanti Polar Lipids. Unless otherwise stated, the other chemicals were purchased from Sigma-Aldrich.

Planar bilayer recordings were performed following the method established by Montal and Mueller (22). Two Delrin compartments were separated by a 25 µm-thick Teflon film containing an aperture (60 µm in diameter). The aperture was pre-treated with 1% (v/v) hexadecane in pentane. Each compartment was then filled with buffer (500 µL, 2 M KCl, 20 mM N-(2-hydroxyethyl)piperazine-N'-(4-butanesulfonic acid) (HEPBS), 20 µM EDTA, pH 8.5). A drop of DPhPC in pentane (5 mg mL$^{-1}$) was added to each compartment. Repetitive up-and-down pipetting of the buffer solution resulted in the formation of a lipid bilayer across the aperture. A transbilayer potential was applied with two Ag/AgCl electrodes, each contained within a salt bridge formed from 3 M KCl in 3% (w/v) low-melt agarose.

Ionic currents were recorded by using a patch clamp amplifier (Axopatch 200B, Axon Instruments) with a 4-pole low-pass Bessel filter (80 dB/decade) at room temperature (20±1° C.). Signals were digitized with a Digidata 1320A digitizer (Molecular Devices), connected to a computer running the pCLAMP 9.2 software suite (Molecular Devices). Unless stated otherwise, the signal was filtered with a corner frequency of 5 kHz and sampled at 25 kHz.

4.2. Monitoring the Hopping Processes

The hopper-carrier conjugate (400 µM in 1 µL MilliQ water) was added to a solution of traptavidin (Kerafast) (40 µM in 10 µL phosphate-buffered saline, pH 7.4) and incubated at room temperature (20±1° C.) for 15 min to form the traptavidin-tagged hopper-carrier. The cis compartment of the apparatus, containing an engineered αHL construct in 2 M KCl, 20 mM HEPBS, 20 µM EDTA, pH 8.5 (500 µL), was stirred until a pore inserted into the bilayer. The traptavidin-tagged hopper-carrier conjugate (3 µL of a 36 µM solution) was then added to the cis compartment and driven into the pore with a transmembrane potential of +150 mV (cis at ground). In the case of hopper 1, threading of the conjugate reduced the current to Ires %=33±1% (n=20). Subsequent loading of hopper 1 onto Cys-115 by disulfide interchange gave a current increase to Ires %=45±1% (n=20). Under a positive potential (e.g. +150 mV), the hopper moved from Cys-115 towards the trans end of the track (downward). When the hopper reached the final foothold, a negative potential (e.g. −150 mV) drove the hopper back towards the cis end of the track (upward). Alternation between positive and negative potentials repeatedly drove the hopper back and forth on the track.

We define cis to trans movement as downward and trans to cis as upward. Under a positive potential (e.g. +150 mV), the forward stepping is downward; the backward stepping is upward. Under a negative potential (e.g. −150 mV), the forward stepping is upward; the backward stepping is downward.

4.3. Single-Channel Data Analysis

Figure 10:
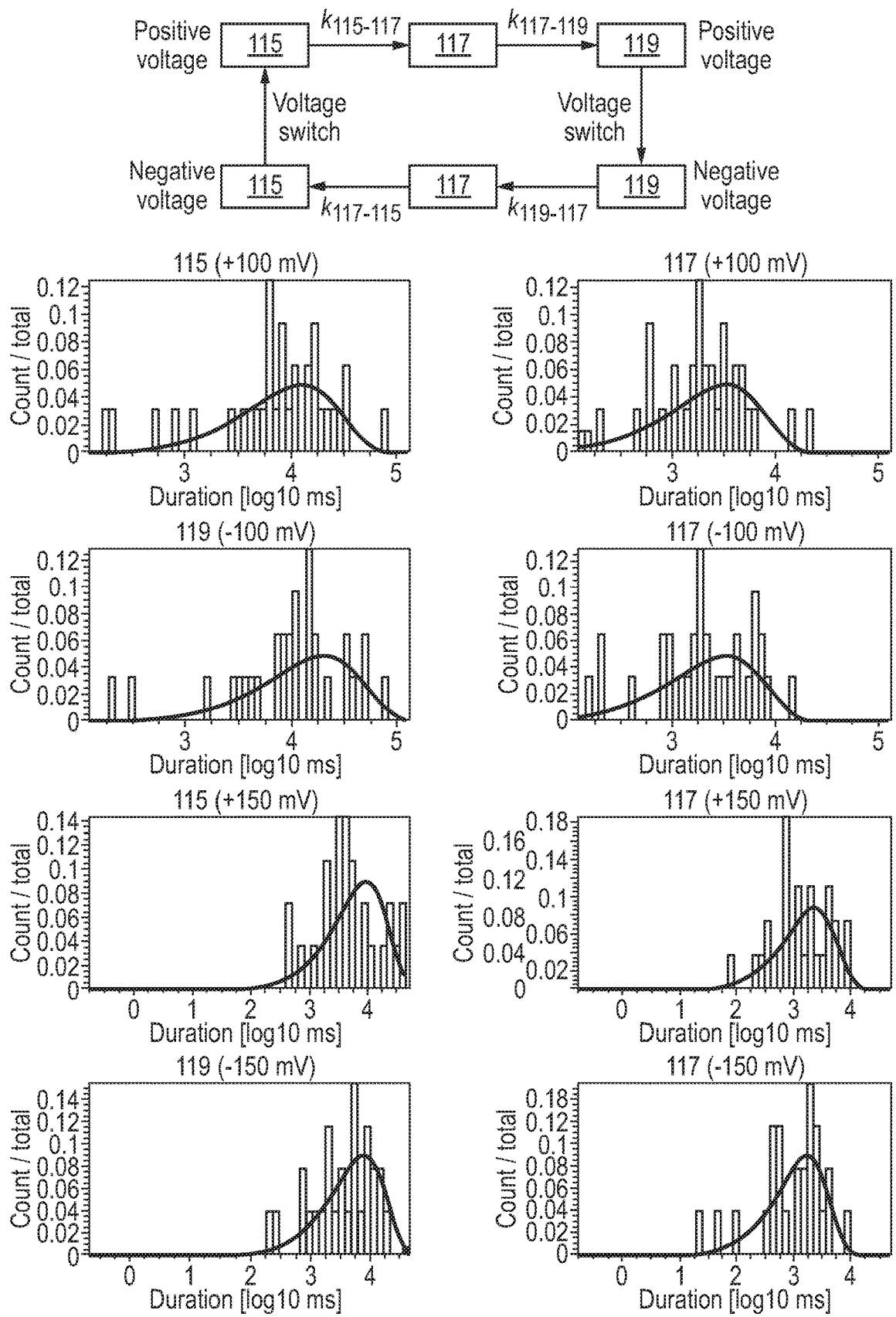
FIG. 10 shows kinetic model and duration histograms for the two steps on the three-cysteine track (Footholds: Cys-115, 117, 119) at ±100 mV, ±150 mV, ±180 mV. The kinetic model (top) links the two steps at positive voltages with the two at negative voltages to form a closed cycle. Two voltage-switch transitions were built into the model by assigning an arbitrary duration of 1 s to the final foothold (Cys-119 at positive voltages; Cys-115 at negative voltages). Given the absence of back-stepping on the middle foothold during all hopping cycles, QuB was set to treat each forward step as irreversible. QuB derived kinetic rate constants are given in Table S1. Data were collected from two separate αHL pores. Data are described in the Example.
Figure 10:
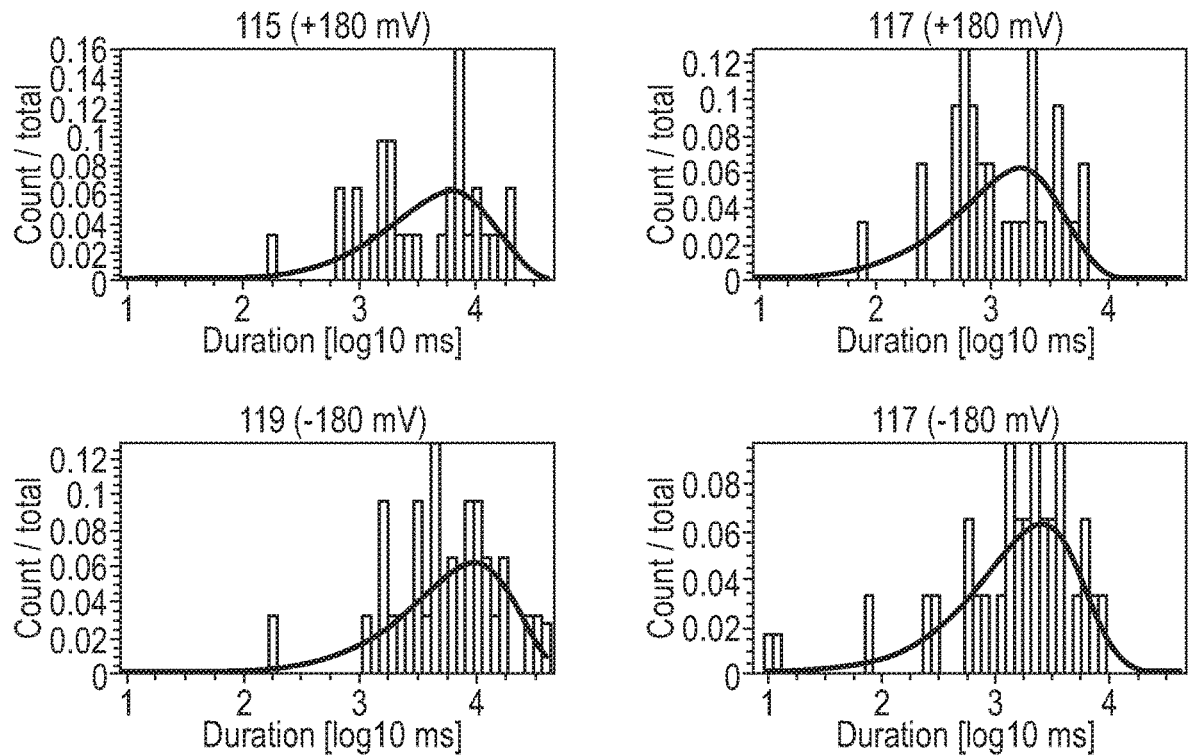
Figure 12:
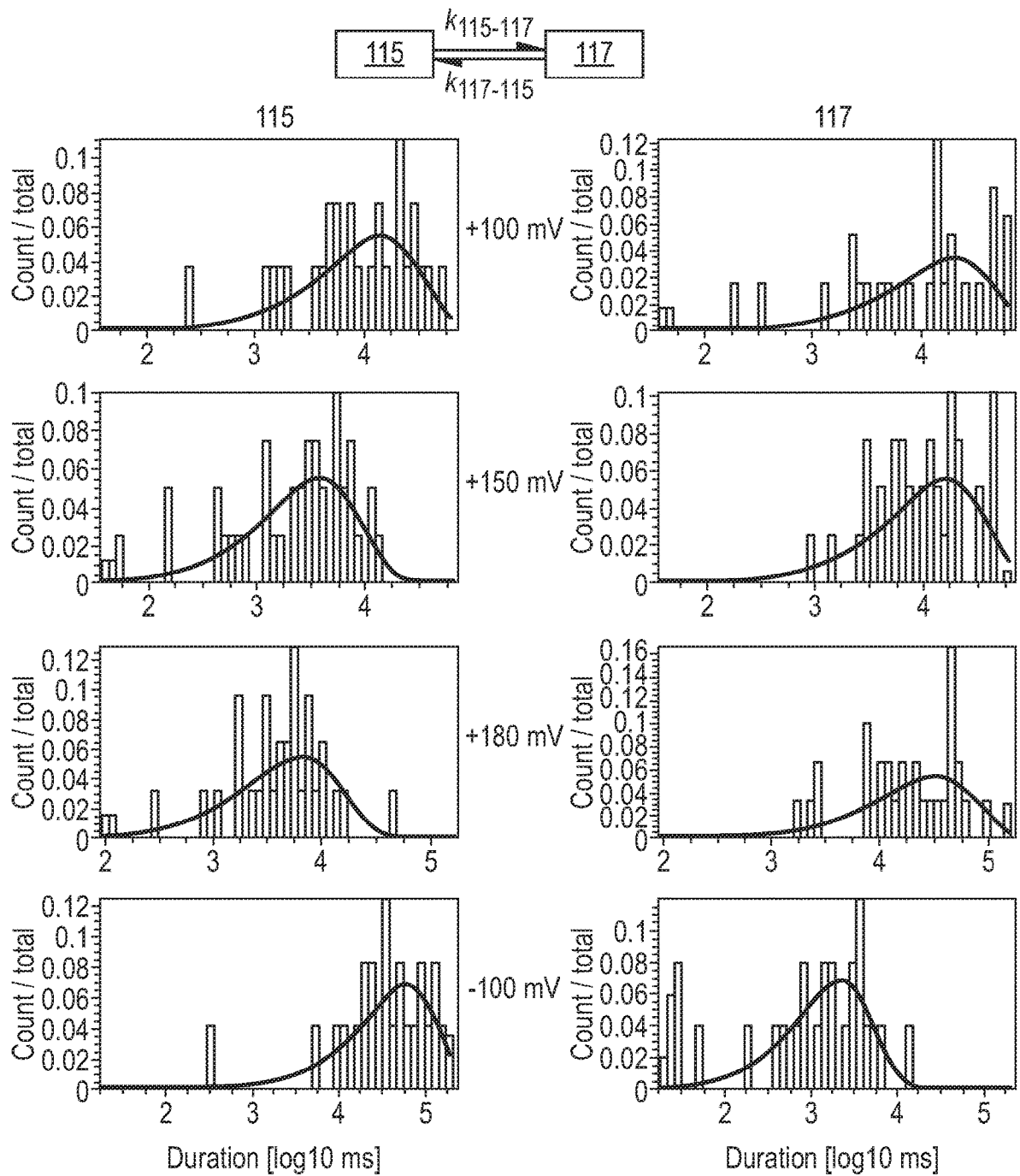
FIG. 12 shows kinetic model and duration histograms for the forward and backward steps on the two-cysteine track (Footholds: Cys-115, 117) at ±100 mV, ±150 mV, ±180 mV. The forward and backward rate constants (Table S2) were derived by using the maximum interval likelihood algorithm of QuB, according to the two-state kinetic model (top). Data were collected from four αHL pores. Data are described in the Example.
Figure 12:
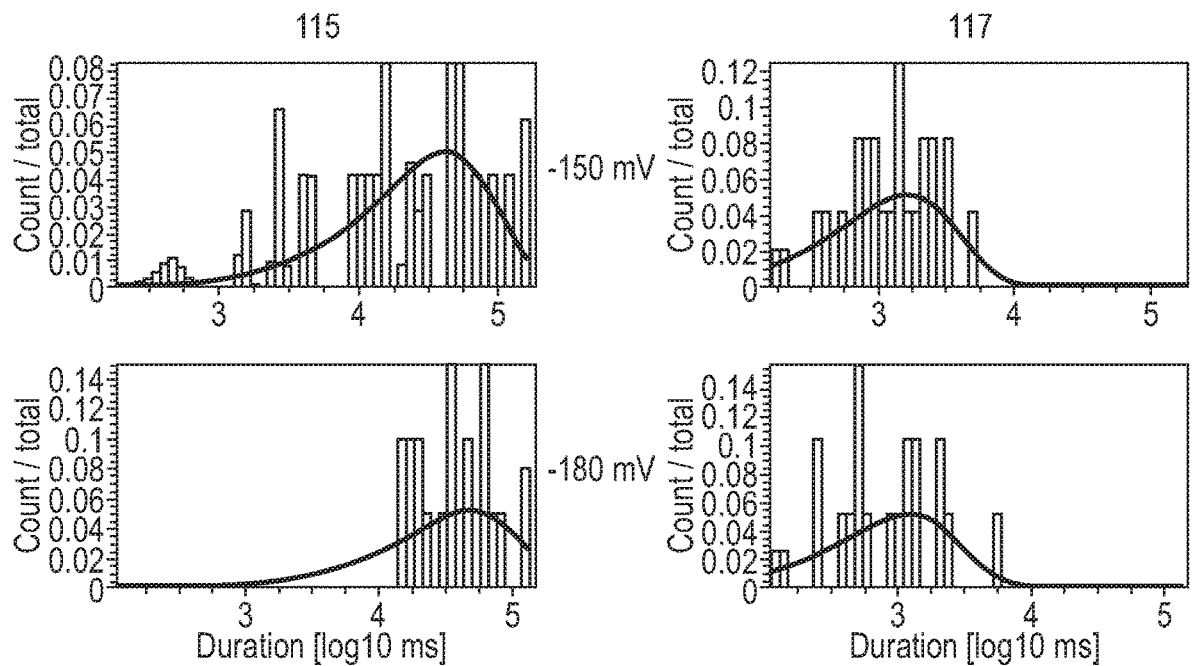

Current traces were idealized by using Clampfit 10.3 (Molecular Devices). The idealized data were analyzed with QuB 2.0 software (www.qub.buffalo.edu) (23). Dwell time analysis and rate constant estimations were performed by using the maximum interval likelihood (MIL) algorithm of QuB (24). In the cases of hopping on a three-cysteine track and a five-cysteine track, an arbitrary duration of 1 s was assigned to the final foothold in either direction (cis-trans or trans-cis) to complete the kinetic models comprising steps at both positive and negative voltages (FIG. 10, 13). A two-state kinetic model was used for hopping between two footholds (FIG. 12, 14).

5. Loading Hoppers onto Two-Cysteine, Three-Cysteine, and Five-Cysteine Tracks See FIG. 6.

6. Hopping Pattern on a Three-Cysteine Track at ±100 mV, ±150 mV, ±180 mV

Figure 7:
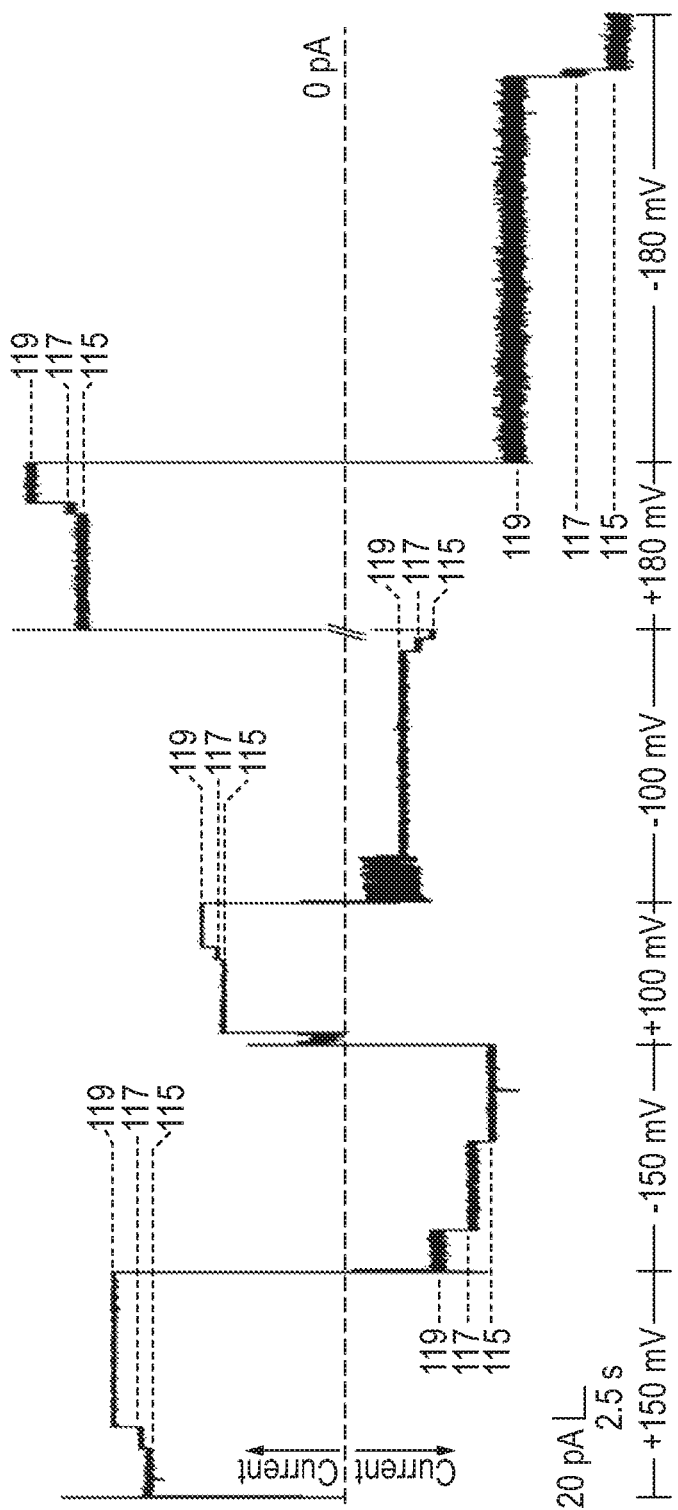
FIG. 7 shows hopping on a three-cysteine track. With a three-cysteine track (Footholds: Cys-115, 117, 119), two hopping steps were observed at ±100 mV, ±150 mV, ±180 mV with hopper 1. The hopping cycle was repeated >20 times for each voltage and QuB was used to derive the rate constants given in Table S1. The application of ±100 mV was not sufficient to quickly flip the oligo to the opposite direction and resulted in a very noisy level before the oligo was fully stretched and hopping could re-start. The noisy level was especially common at negative voltages, when it was once observed to last more than 20 min. The trace was filtered at 200 Hz. Conditions: 2 M KCl, 20 mM HEPBS, 20 µM EDTA, pH 8.5, 20±1° C. Data are described in the Example.

See FIG. 7.

7. Hopping Pattern on a Five-Cysteine Track

See FIG. 8.

8. Hopping Pattern on a Six-Cysteine Track

See FIG. 9

9. Hopping Rates at ±100 mV, ±150 mV, ±180 mV for the Two Steps of the Three-Cysteine Track

TABLE S1

Hopping rates (k) and mean dwell times (<τ>) derived by QuB[a] for hopper 1 on the three-cysteine track (Footholds: Cys-115, 117, 119) at ±100 mV, ±150 mV, and ±180 mV[b].

| | $k_{115\text{-}117}/s^{-1}$ | $<\tau>_{115\text{-}117}/s$ | n | $k_{117\text{-}119}/s^{-1}$ | $<\tau>_{117\text{-}119}/s$ | n |
|---|---|---|---|---|---|---|
| +100 mV | 0.086 ± 0.014 | 12 ± 2 | 31 | 0.33 ± 0.05 | 3.0 ± 0.5 | 31 |
| +150 mV | 0.12 ± 0.02 | 8.7 ± 1.7 | 27 | 0.46 ± 0.09 | 2.2 ± 0.4 | 27 |
| +180 mV | 0.18 ± 0.03 | 5.6 ± 1.1 | 32 | 0.63 ± 0.11 | 1.6 ± 0.3 | 32 |
| −100 mV | 0.33 ± 0.06 | 3.1 ± 0.6 | 31 | 0.053 ± 0.009 | 19 ± 3 | 31 |
| −150 mV | 0.65 ± 0.13 | 1.5 ± 0.3 | 27 | 0.15 ± 0.03 | 6.7 ± 1.3 | 27 |
| −180 mV | 0.44 ± 0.09 | 2.3 ± 0.5 | 31 | 0.12 ± 0.02 | 8.5 ± 1.3 | 31 |

[a]Dwell time analysis and rate constant estimations were performed by using the maximum interval likelihood algorithm of QuB. An arbitrary duration of 1 s was assigned to the final foothold in either direction (Cys-119 for cis-to-trans hops at positive voltages or Cys-115 for trans-to-cis hops at negative voltages) to complete the kinetic model (FIG. 10).
[b]Data were collected from two αHL pores.

See FIG. 10

10. Hopping Rates at ±100 mV, ±150 mV, ±180 mV for the One Step of the Two-Cysteine Track A two-cysteine track consisting of Cys-115 and Cys-117 was used to study the rates of forward and backward hopping under various applied potentials (±100 mV, ±150 mV, ±180 mV). Hopper 1 moved forward from foothold 115 to 117 under a positive applied potential and from foothold 117 to 115 under a negative applied potential. Occasional back-stepping was also observed. Rate constants (k) were derived for hopping steps under both positive and negative voltages (Table S2). The equilibrium constant K was then calculated for each potential, where K=$k_{forward}/k_{backward}$.

The weak voltage dependence of K under the positive applied potentials is consistent with the DNA cargo being driven towards a higher potential. The field drops primarily across the β barrel (11) and four negatively charged phosphodiesters are located inside the barrel based on PyMOL modelling (FIG. 11B). The trend is less clear at negative potentials, but in this case only one or zero phosphodiesters are located inside the barrel (FIG. 11B). Although there is a weak electric field in the αHL vestibule (11), the directionality of hopping under negative applied potentials is more likely to arise from DNA coiling in the cis vestibule which disfavors backward movement of the hopper (see section 12).

See FIG. 11

TABLE S2

Hopping rates (k) and mean dwell times (<τ>) derived by QuB[a] for hopper 1 on the two-cysteine track (Footholds: Cys-115, 117) at ±100 mV, ±150 mV, and ±180 mV[b].

| | forward stepping | | | backward stepping | | | |
|---|---|---|---|---|---|---|---|
| | $k_{115\text{-}117}$/ $s^{-1}$ | $<\tau>_{115\text{-}117}$/ s | n | $k_{117\text{-}119}$/ $s^{-1}$ | $<\tau>_{117\text{-}119}$/ s | n | $K_{115\text{-}117}$[c] |
| +100 mV | 0.075 ± 0.014 | 13 ± 3 | 28 | 0.055 ± 0.010 | 18 ± 3 | 28 | 1.4 ± 0.4 |
| +150 mV | 0.28 ± 0.05 | 3.5 ± 0.6 | 40 | 0.067 ± 0.011 | 15 ± 2 | 40 | 4.2 ± 1.0 |
| +180 mV | 0.11 ± 0.03 | 6.0 ± 1.2 | 34 | 0.034 ± 0.006 | 30 ± 5 | 34 | 4.9 ± 1.3 |
| −100 mV | 0.49 ± 0.10 | 2.0 ± 0.4 | 25 | 0.018 ± 0.004 | 55 ± 11 | 25 | 27 ± 7 |
| −150 mV | 0.66 ± 0.14 | 1.5 ± 0.3 | 24 | 0.025 ± 0.005 | 39 ± 8 | 24 | 26 ± 8 |
| −180 mV | 0.89 ± 0.23 | 1.1 ± 0.3 | 20 | 0.022 ± 0.005 | 45 ± 10 | 20 | 40 ± 14 |

[a]Dwell time analysis and rate constant estimations were performed by using the maximum interval likelihood algorithm of QuB, according to the two-state kinetic models (FIG. 12).
[b]Data were collected from four separate αHL pores.
[c]The equilibrium constant $K = k_{forward}/k_{backward}$.

See FIG. 12

11. Hopping Rates at ±150 mV for the Four Steps of the Five-Cysteine Track.

TABLE S3

Hopping rates (k) and mean dwell times (<τ>) derived by QuB[a] for hopper 1 on the five-cysteine track (Footholds: Cys-113, 115, 117, 119, 121) at ± 150 mV[b].

| Forward step at +150 mV | 113-115 | 115-117 | 117-119 | 119-121 |
|---|---|---|---|---|
| $k/s^{-1}$ | 0.027 ± 0.006 | 0.084 ± 0.017 | 0.30 ± 0.06 | 0.23 ± 0.05 |
| <τ>/s | 37 ± 8 | 12 ± 2 | 3.3 ± 0.7 | 4.3 ± 0.9 |
| n | 22 | 23 | 21 | 21 |

| Forward step at −150 mV | 121-119 | 119-117 | 117-115 | 115-113 |
|---|---|---|---|---|
| $k/s^{-1}$ | 0.086 ± 0.017 | 0.047 ± 0.010 | 0.21 ± 0.03 | 0.0081 ± 0.0017 |
| <τ>/s | 12 ± 2 | 21 ± 5 | 4.7 ± 0.7 | 124 ± 26 |
| n | 22 | 21 | 50 | 21 |

[a]Dwell time analysis and rate constant estimations were performed by using the maximum interval likelihood algorithm of QuB. An arbitrary duration of 1 s was given to the final foothold on either direction (Cys-121 for cis to trans hops at +150 mV or Cys-113 for trans to cis hops at −150 mV) to complete the kinetic model (FIG. 13).
[b]Only steps from complete cycles (from 113 to 121 at +150 mV and then from 121 to 113 at −150 mV) (FIG. 8) were used to fit the kinetic model (FIG. 13). Data were collected from a single αHL pore.

TABLE S4

Hopping rates (k) and mean dwell times (<τ>) derived by QuB[a] for hopper 1 on the last two footholds (Cys-119, 121) of the five-cysteine track (Cys-113, 115, 117, 119, 121) at +150 mV[b].

| Step at +150 mV | 119-121 | 121-119 |
|---|---|---|
| $k/s^{-1}$ | 0.23 ± 0.03 | 0.044 ± 0.005 |
| <τ>/s | 4.3 ± 0.5 | 23 ± 3 |
| n | 75 | 75 |

[a]Dwell time analysis and rate constant estimations were performed by using the maximum interval likelihood algorithm of QuB. Since there was no 119-117 back-stepping during any hopping cycles, a two-state kinetic model was used to determine the stepping kinetics on the last two footholds (FIG. 14).
[b]Data were collected from a single αHL pore.

TABLE S5

Hopping rate (k) and mean dwell time (<τ>) derived by QuB[a] for the 115-117 backward steps of hopper 1 on the five-cysteine track (Cys-113, 115, 117, 119, 121) at −150 mV[b].

| | 115-117 (−150 mV) | 119-121 (−150 mV) | 117-115 (−150 mV) | 115-113 (−150 mV) |
|---|---|---|---|---|
| $k/s^{-1}$ | 0.0094 ± 0.0019 | / | / | / |
| <τ>/s | 106 ± 21 | / | / | / |
| n | 29 | 1 | 2 | 1 |

[a]Dwell time analysis and rate constant estimations were performed by using the maximum interval likelihood algorithm of QuB. Apart from 115-117 backward steps, which occurred 29 times, the other backward steps were rare and no meaningful rate constants could be derived. QuB was hence set to treat the forward steps as irreversible; (FIG. 13).
[b]Data were collected from a single αHL pore.

Figure 14:
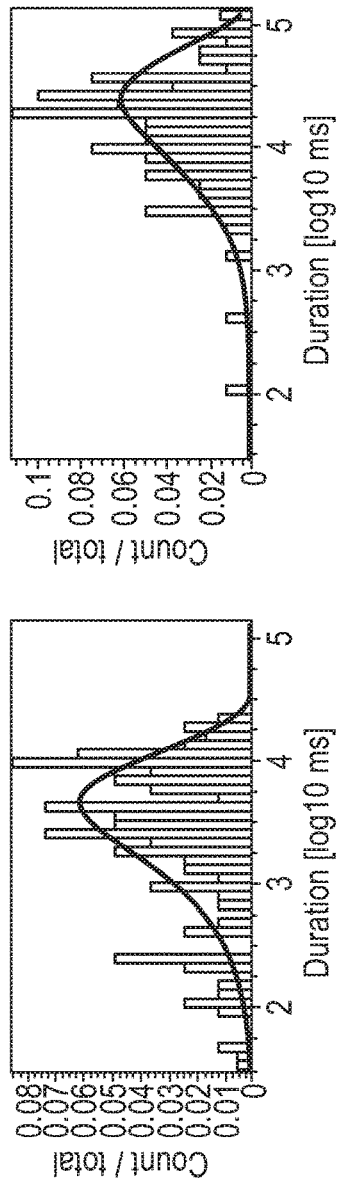
FIG. 14 shows kinetic model and duration histograms for the forward and backward steps on the last two footholds (Cys-119, 121) of the five-cysteine track (Footholds: Cys-113, 115, 117, 119, 121)+150 mV. The forward and backward rate constants were derived by using the maximum interval likelihood algorithm of QuB, according to a two-state kinetic model (top). The derived kinetic rate constants are given in Table S4. Data were collected from a single αHL pore. Data are described in the Example.

See FIGS. 13 and 14

12. Energetics of the Directional Movement

In the case of forward stepping under +150 mV from foothold 115 to 117 on a two-cysteine track (Footholds: Cys-115, 117) (as discussed in section 10), the force imparted on the hopper-oligo is $$F = n(qe)E$$

n=number of phosphodiesters in the field
q=fractional charge on a phosphodiester
e=elementary charge ($1.60 \times 10^{-19}$ C)
E=electric field Previously, it was suggested that the applied transmembrane potential drops mostly across the transmembrane β barrel (5 nm) of the αHL pore (11). At ±150 mV, E is therefore 0.03 V nm$^{-1}$.

Let n=4 (FIG. 11B) and q=1

$$F = n(qe)E = 4 \times 1.60 \times 10^{-19}\ C \times 0.03\ V\ nm^{-1} = 1.92 \times 10^{-11}\ N = 19.2\ pN$$

Let n=4 and q=0.4 (due to shielding effect of high salt (25, 26))

$$F = n(qe)E = 4 \times 0.4 \times 1.60 \times 10^{-19}\ C \times 0.03\ V\ nm^{-1} = 7.68 \times 10^{-12}\ N = 7.68\ pN$$

The work done by the electric field W=Fd per molecule=$FdN_A$ per mole (d=0.56 nm)

$$q=1,\ W=1.08 \times 10^{-20}\ J = 6.47\ kJ\ mol^{-1}$$

$$q=0.4,\ W=4.32 \times 10^{-21}\ J = 2.59\ kJ\ mol^{-1}$$

Similarly, the force applied and the work done to move the hopper-oligo from 117 to 115 under −150 mV can be calculated with n=1 (FIG. 11B).

$$q=1,\ F=4.80\ pN,\ W=1.62\ kJ\ mol^{-1}$$

$$q=0.4,\ F=1.92\ pN,\ W=0.648\ kJ\ mol^{-1}$$

From the experimentally determined equilibrium constants ($K = k_{forward}/k_{backward}$) (Table S2), the corresponding ΔG can be calculated following ΔG=−RT ln K (R=8.314 JK$^{-1}$ mol$^{-1}$, T=293.15 K).

| | 115-117 (+150 mV) | 117-115 (−150 mV) |
|---|---|---|
| K | 4.2 ± 1.0 | 26 ± 8 |
| ΔG (kJ mol$^{-1}$) | −3.5 | −7.9 |
| −W (kJ mol$^{-1}$) (q = 0.4) | −2.59 | −0.648 |

The difference between the derived ΔG and the calculated W can be accounted for by other variable thermodynamic terms (either positive or negative), which include the aforementioned DNA coiling in the pore's vestibule. After all, the system is highly complex with 1) non-uniform side-chains; 2) non-uniform cross section of the β barrel; 3) non-uniform threaded polymers.

The non-electrostatic terms will be more important to the equilibrium for each step at low applied voltages. However, processive multistep hopping only requires that the overall equilibrium constant ($K_{overall}$) is larger than 1, which can be calculated as the product of the equilibrium constants for each step (e.g. $K_{overall}=K_1K_2K_3K_4$). For example, using the experimentally derived $K_{115-117}$ at +150 mV for all four steps on a five-cysteine track, $$K_{overall}=K^4=(4.2)^4=311$$

This large $K_{overall}$ explains the observed processive and directional hopping.

Figure 15:
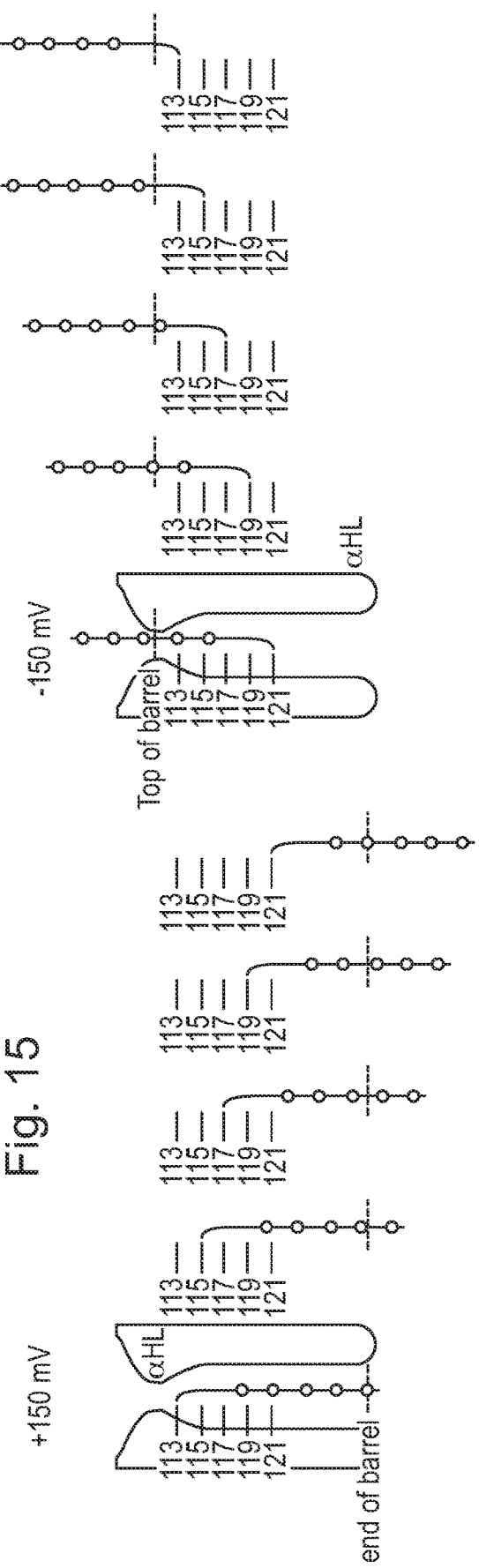
FIG. 15 shows how a charged oligo moves stepwise out of the electric field as the hopper steps forward along the track. See Example for more information.

It is worth pointing out that the calculations shown here only apply to stepping between the footholds 115 and 117. All thermodynamic contributors, including the electrostatic work, are likely to vary between footholds. For instance, as depicted in FIG. 15, the charged oligo moves stepwise out of the electric field as the hopper steps forward along the track. Consequently, the electrostatic contribution to ΔG becomes smaller as the hopper approaches the terminal foothold.

13. Residual Current Patterns for Three Hoppers on the Five-Cysteine Track.

TABLE S6

Residual current (Ires %) pattern for each hopper on the five-cysteine track (Footholds: Cys-113, 115, 117, 119, 121).

| +150 mV | Ires %[a] | | | -150 mV | Ires %[a] | | |
| --- | --- | --- | --- | --- | --- | --- | --- |
| | Hopper 1 | Hopper 2 | Hopper 3 | | Hopper 1 | Hopper 2 | Hopper 3 |
| Threading | 33% | 35% | 35% | / | / | / | / |
| 113 | 39% | 51% | 44% | 113 | 80% | 80% | 71% |
| 115 | 45% | 61% | 56% | 115 | 52% | 51% | 43% |
| 117 | 47% | 59% | 62% | 117 | 37% | 29% | 36% |
| 119 | 53% | 63% | 65% | 119 | 25% | 27% | 40% |
| 121 | 57% | 66% | 71% | 121 | 21% | 39% | 34% |

[a]The standard deviations of Ires % are less than 0.5% in all cases (derived from n = 3 separate experiments for each hopper).

14. Current Patterns of Hopper 3 on Foothold 119 at -150 mV.

Figure 16:
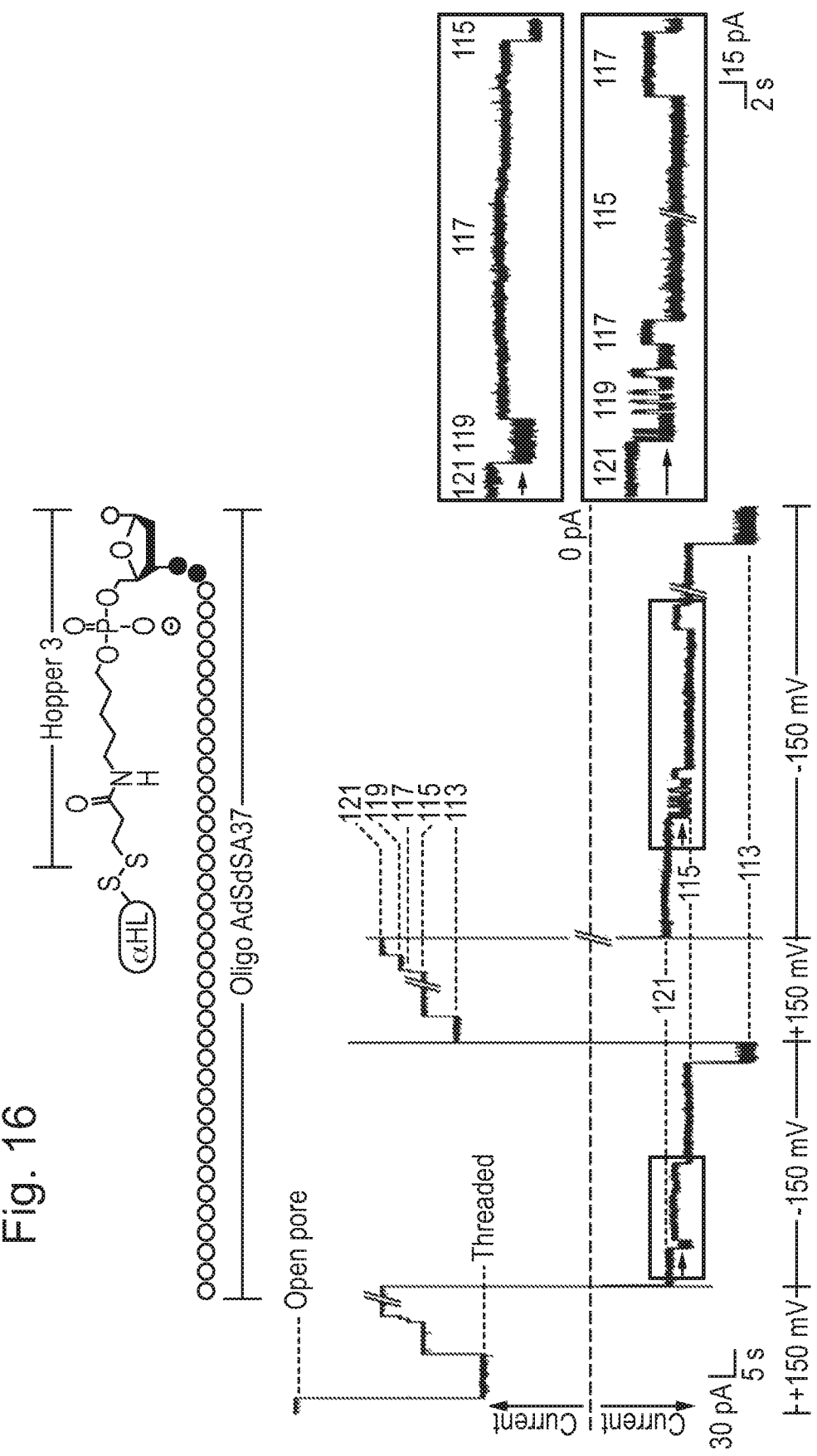
FIG. 16 shows two current patterns for hopper 3 on foothold 119 at −150 mV. Four-step hopping was observed with hopper 3 at ±150 mV (n=3 separate experiments). While the hopping generated a consistent pattern at +150 mV, hopping at −150 mV produced two ionic current signatures. In one, the current at foothold 119 was significantly noisier than the current with the hopper at neighboring footholds (top expanded trace): root mean square noise $I_{RMS}(119)=2.8\pm0.1$ pA; $I_{RMS}(121)=1.2\pm0.2$ pA; $I_{RMS}(117)=1.0\pm0.1$ pA. In the second pattern, the current with hopper 3 at foothold 119 displayed two sub-conductance levels (bottom expanded trace). The interconversion between two patterns was not observed. The ratio of dwells at foothold 119 with the noisy appearance to dwells with the two sub-conductance states was 5:2. The current amplitude is the same for the noisy level of the first pattern and the higher conductance state (larger negative current) in the second pattern (indicated with blue arrows). This value was used to plot FIG. 3D and was reported in Table S6. The two patterns must correspond to two modes of interaction of hopper 3 with the nanopore, as they were seen not only in separate experiments, but also with the same hopper molecule in the same experiment, which excludes the possibilities of an impurity in the oligo or hopper-to-hopper variation. Data are described in the Example.

See FIG. 16

15. Effective Concentrations of Thiol Footholds on the Cysteine Tracks

For a thiol-disulfide interchange:

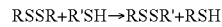

The apparent rate constant k is pH dependent (reaction occurs with the thiolate anion) and is estimated to be ~10 $M^{-1}s^{-1}$ at pH 8.5. The estimation was based on reported rate constants for thiol-disulfide interchanges between L-cysteine, DL-dithiothreitol, L-glutathione and their disulfide forms, for example (27-29).

In the case of an αHL pore, assuming that the disulfide (RSSR) is attached to the protein, and R'SH is in solution, we know:

$$<\tau>=1/(k[R'SH])$$

when R'SH is in solution.

If R'SH is attached to the protein, [R'SH] is an effective concentration in an intramolecular reaction.

For various values of <τ> (see earlier sections), assuming $k=10\ M^{-1}s^{-1}$, we find:

| <τ>/s | [RSH]$_{effective}$/mM |
| --- | --- |
| 1 | 100 |
| 5 | 20 |
| 20 | 5 |

The effective concentration of a thiol on the track with respect to an upstream disulfide is then in the mM range. Effective concentrations in this range were found for the second arm of a chelator in a nanoreactor (30) and for the intramolecular binding of an enzyme inhibitor (31).

16. Comparison with Other 'Moving Molecules'

To highlight the advances presented by our molecular hopper, a selection of its properties were compared to the best achievements across various reported examples from three different classes.

TABLE S7

Comparison of the hopper with three classes of 'moving molecules'[a]

| | | Small molecule "walkers" | Macromolecular walkers | |
| --- | --- | --- | --- | --- |
| | HOPPER (This work) | Previous small-molecule walkers (12, 32-38) | Previous DNA-walkers (39-46) | Biomolecular walkers (1-4, 6, 47) |
| Synthesis | Straightforward | Multistep chemical syntheses | DNA synthesis and assembly | Biological |
| Track chemistry | Simple, transferable between walkers | Complex for directional motion | Moderately simple, not transferable | Complex, not transferable |
| Step size | 0.7 nm | <1 nm | Typically ~10 nm (5 nm (46)) | Typically ~10 nm (Kinesin ~8 nm) |
| Processivity[b] | Processive (100s of steps[c]) | Limited (<10 steps demonstrated[d]) | Processive (<100 steps demonstrated) | Processive (100 s of steps) |

TABLE S7-continued

Comparison of the hopper with three classes of 'moving molecules'[a]

| | Small molecule "walkers" | | Macromolecular walkers | |
| --- | --- | --- | --- | --- |
| | HOPPER (This work) | Previous small-molecule walkers (12, 32-38) | Previous DNA-walkers (39-46) | Biomolecular walkers (1-4, 6, 47) |
| Directionality[b] | Directional[e] | Limited directionality | Directional (burnt-bridge mechanism) | Directional |
| Rate | Seconds per step[f] | Minutes to days per step | 10 s of minutes per step | Milliseconds per step |
| Real time step detection | Yes | No | In some cases | Yes |
| Autonomy[d] | Yes | Generally no (Autonomous (36)) | May require fuel | Requires ATP |
| Reversibility (ability to make 180° turns) | Fully reversible | Not reversible | Not reversible | Limited reversibility |
| External control | Yes | Limited | Limited | No |
| Track length | Limited based on protein nanopore (nm scale) | Limited by chemical synthesis (nm scale) | Limited by DNA biotechnology (um scale) | um to mm scale |
| Attachment and detachment points | Both precisely defined | Pre-attachment | Precisely defined | Biologically defined |
| Ability to carry molecular cargos | Yes[g] | Limited | Yes[g] | Yes |

[a]Here, we only compare molecular 'walkers'. Additional 'moving molecules' include: sleds (48), rotors (49, 50), pumps (51).
[b]Processivity is defined as directional stepping without leaving the track. A directional step has a faster forward stepping rate than the backward rate, i.e. $K = k_{forward}/k_{backward} > 1$. In previous small-molecule systems, detachment from the track has been prevented through various strategies such as the maintenance of covalent linkages between walkers and their tracks (32, 35, 36) and the exploitation of mechanically interlocked architectures (33, 34). For DNA-based walker systems, programmable hydrogen-bonding allows the walkers to remain hybridized with track components (44). Directionality has been demonstrated in small-molecule systems for short excursions on tracks terminating with thermodynamic sinks (12, 35, 36), or on tracks with switchable conformations (37), or through alternating orthogonal walker-track chemistries (32, 38), or through sequential installation and removal of stoppers on a track (33). Unidirectional motion of DNA-based walkers has been achieved through the 'burnt-bridge' mechanism by cycles of DNA hybridization and hydrolysis at the cost of reversibility (40, 41, 44).
[c]Up to 5 steps in each direction were demonstrated due to limited track length. 100 s of processive steps were achieved through 'flipping the potential' after the hopper reached the final foothold.
[d]Autonomy means motion without chemical fuel or facilitator molecules (12). Autonomous eight-step walking has been demonstrated with a nine-foothold track terminating with a thermodynamic sink through dynamic covalent chemistry-reversible Michael addition of secondary amines to an a-methylene-4-nitrostyrene unit (36). The fastest forward walking rate was reported to be $5 \times 10^{-3}$ s$^{-1}$ (~5.6 h per step). The equilibrium constants (K) for the first six steps were reported to be 1, in line with the initial random walking on the rack. The last two steps have K values of 1.3 and 2.5, respectively, to which the overall biased directionality was attributed. In comparison, the present hopper has a hopping rate of ~22 s per step and a forward equilibrium constant (K) of ~5 at +150 mV and ~20 at −150 mV.
[e]All steps demonstrated with the hopper system have an equilibrium constant larger than one, and hence are directional. On the five-cysteine track at −150 mV, hopping from 117 to 115 has a $K = k_{117-115}/k_{115-117} = 22$, which indicates that the observed back-stepping was due to a slow stepping rate for the next step to the downstream foothold 113.
[f]On the five-cysteine track, the mean step time is ~22 s at ±150 mV.
[g]Constrained by the current nanopore-based track, macromolecular cargos movable by the hopper system are limited to linear molecules such as oligonucleotides and polypeptides. DNA-walkers moving on a surface, on the other hand, are capable of transporting cargos such as nanoparticles (42, 45).

REFERENCES

1. W. A. Breyer, B. W. Matthews, A structural basis for processivity. *Protein Sci.* 10, 1699-1711 (2001).
2. R. D. Vale et al., Direct observation of single kinesin molecules moving along microtubules. *Nature* 380, 451-453 (1996).
3. R. B. Case, D. W. Pierce, N. Hom-Booher, C. L. Hart, R. D. Vale, The directional preference of kinesin motors is specified by an element outside of the motor catalytic domain. *Cell* 90, 959-66 (1997).
4. A. Gennerich, R. D. Vale, Walking the walk: how kinesin and dynein coordinate their steps. *Curr. Opin. Cell Biol.* 21, 59-67 (2009).
5. S. Erbas-Cakmak, D. A. Leigh, C. T. McTernan, A. L. Nussbaumer, Artificial molecular machines. *Chem. Rev.* 115, 10081-10206 (2015).
6. W. J. Walter, M. P. Koonce, B. Brenner, W. Steffen, Two independent switches regulate cytoplasmic dynein's processivity and directionality. *Proc. Natl. Acad. Sci. U.S.A* 109, 5289-93 (2012).
7. R. A. Cross, A. McAinsh, Prime movers: the mechanochemistry of mitotic kinesins. *Nat. Rev. Mol. Cell Biol.* 15, 257-71 (2014).
8. R. D. Bach, O. Dmitrenko, C. Thorpe, Mechanism of thiolate-disulfide interchange reactions in biochemistry. *J. Org. Chem.* 73, 12-21 (2008).
9. P. A. Fernandes, M. J. Ramos, Theoretical insights into the mechanism for thiol/disulfide exchange. *Chem.—A Eur. J.* 10, 257-266 (2004).
10. A. P. Wiita et al., Probing the chemistry of thioredoxin catalysis with force. *Nature* 450, 124-127 (2007).
11. S. Howorka, H. Bayley, Probing distance and electrical potential within a protein pore with tethered DNA. *Biophys. J.* 83, 3202-3210 (2002).

12. G. S. Pulcu, E. Mikhailova, L.-S. Choi, H. Bayley, Continuous observation of the stochastic motion of an individual small-molecule walker. *Nat. Nanotechnol.* 10, 76-83 (2015).
13. C. A. Hunter, H. L. Anderson, What is cooperativity? *Angew. Chem. Int. Ed.* 48, 7488-7499 (2009).
14. J. Venkatraman, G. A. Nagana Gowda, P. Balaram, Design and construction of an open multistranded β-sheet polypeptide stabilized by a disulfide bridge. *J. Am. Chem. Soc.* 124, 4987-94 (2002).
15. H. Bayley, Nanopore sequencing: from imagination to reality. *Clin. Chem.* 61, 25-31(2015).
16. B. Gyarfas et al., Mapping the position of DNA polymerase-bound DNA templates in a nanopore at 5 Å resolution. *ACS Nano* 3, 1457-66 (2009).
17. A. Bosco, J. Camunas-Soler, F. Ritort, Elastic properties and secondary structure formation of single-stranded DNA at monovalent and divalent salt conditions. *Nucleic Acids Res.* 42, 2064-2074 (2014).
18. I. Iacovache et al., Cryo-EM structure of aerolysin variants reveals a novel protein fold and the pore-formation process. *Nat. Commun.* 7, 12062 (2016).
19. J. Jiang, B. L. Pentelute, R. J. Collier, Z. H. Zhou, Atomic structure of anthrax protective antigen pore elucidates toxin translocation. *Nature* 521, 545-549 (2015).
20. J. Lee et al., Semisynthetic nanoreactor for reversible single-molecule covalent chemistry. *ACS Nano* 10, 8843-8850 (2016).
21. G. Miles, H. Bayley, S. Cheley, Properties of *Bacillus cereus* hemolysin II: A heptameric transmembrane pore. *Protein Sci.* 11, 1813-1824 (2009).
22. M. Montal, P. Mueller, Formation of bimolecular membranes from lipid monolayers and a study of their electrical properties. *Proc. Natl. Acad. Sci. U.S.A* 69, 3561-3566 (1972).
23. C. Nicolai, F. Sachs, Solving ion channel kinetics with the QuB software. *Biophys. Rev. Lett.* 08, 191-211 (2013).
24. F. Qin, A. Auerbach, F. Sachs, Estimating single-channel kinetic parameters from idealized patch-clamp data containing missed events. *Biophys. J.* 70, 264-280 (1996).
25. J. Nakane, M. Wiggin, A. Marziali, A nanosensor for transmembrane capture and identification of single nucleic Acid molecules. *Biophys. J.* 87, 615-21 (2004).
26. Y. Wang, K. Tian, L. L. Hunter, B. Ritzo, L.-Q. Gu, Probing molecular pathways for DNA orientational trapping, unzipping and translocation in nanopores by using a tunable overhang sensor. *Nanoscale* 6, 11372-11379 (2014).
27. R. P. Szajewski, G. M. Whitesides, Rate constants and equilibrium constants for thiol-disulfide interchange reactions involving oxidized glutathione. *J. Am. Chem. Soc.* 102, 2011-2026 (1980).
28. D. M. Rothwarf, H. A. Scheraga, Equilibrium and kinetic constants for the thiol-disulfide interchange reaction between glutathione and dithiothreitol. *Proc. Natl. Acad. Sci. U.S.A* 89, 7944-8 (1992).
29. D. A. Keire, E. Strauss, W. Guo, B. Noszal, D. L. Rabenstein, Kinetics and equilibria of thiol/disulfide interchange reactions of selected biological thiols and related molecules with oxidized glutathione. *J. Org. Chem.* 57, 123-127 (1992).
30. A. F. Hammerstein, S.-H. Shin, H. Bayley, Single-molecule kinetics of two-step divalent cation chelation. *Angew. Chem. Int. Ed.* 49, 5085-5090 (2010).
31. V. M. Krishnamurthy, V. Semetey, P. J. Bracher, N. Shen, G. M. Whitesides, Dependence of effective molarity on linker length for an intramolecular protein-ligand system. *J. Am. Chem. Soc.* 129, 1312-1320 (2007).
32. M. von Delius, E. M. Geertsema, D. A. Leigh, A synthetic small molecule that can walk down a track. *Nat. Chem.* 2, 96-101 (2010).
33. M. R. Wilson et al., An autonomous chemically fueled small-molecule motor. *Nature* 534, 235-40 (2016).
34. S. Erbas-Cakmak et al., Rotary and linear molecular motors driven by pulses of a chemical fuel. *Science* 358, 340-343 (2017).
35. A. G. Campana et al., A small molecule that walks non-directionally along a track without external intervention. *Angew. Chem. Int. Ed.* 51, 5480-5483 (2012).
36. A. G. Campana, D. A. Leigh, U. Lewandowska, One-dimensional random walk of a synthetic small molecule toward a thermodynamic sink. *J. Am. Chem. Soc.* 135, 8639-45 (2013).
37. M. J. Barrell, A. G. Campana, M. von Delius, E. M. Geertsema, D. A. Leigh, Light-driven transport of a molecular walker in either direction along a molecular track. *Angew. Chem. Int. Ed.* 50, 285-290 (2011).
38. J. E. Beves et al., Toward metal complexes that can directionally walk along tracks: controlled stepping of a molecular biped with a palladium(II) foot. *J. Am. Chem. Soc.* 136, 2094-100 (2014).
39. Y. He, D. R. Liu, Autonomous multistep organic synthesis in a single isothermal solution mediated by a DNA walker. *Nat. Nanotechnol.* 5, 778-782 (2010).
40. Y. Tian, Y. He, Y. Chen, P. Yin, C. Mao, A DNAzyme that walks processively and autonomously along a one-dimensional track. *Angew. Chem. Int. Ed.* 44, 4355-8 (2005).
41. M. You et al., An autonomous and controllable light-driven DNA walking device. *Angew. Chem. Int. Ed.* 51, 2457-2460 (2012).
42. T.-G. Cha et al., A synthetic DNA motor that transports nanoparticles along carbon nanotubes. *Nat. Nanotechnol.* 9, 39-43 (2013).
43. K. Yehl et al., High-speed DNA-based rolling motors powered by RNase H. *Nat. Nanotechnol.* 11, 184-190 (2015).
44. S. F. J. Wickham et al., Direct observation of stepwise movement of a synthetic molecular transporter. *Nat. Nanotechnol.* 6, 166-169 (2011).
45. H. Gu, J. Chao, S.-J. Xiao, N. C. Seeman, A proximity-based programmable DNA nanoscale assembly line. *Nature* 465, 202-5 (2010).
46. J.-S. Shin, N. A. Pierce, A synthetic DNA walker for molecular transport. *J. Am. Chem. Soc.* 126, 10834-5 (2004).
47. B. Ibarra et al., Proofreading dynamics of a processive DNA polymerase. *EMBO J.* 28, 2794-802 (2009).
48. A. B. C. Deutman et al., Mechanism of threading a polymer through a macrocyclic ring. *Science* 322, 1668-1671 (2008).
49. N. Koumura, R. W. J. Zijlstra, R. A. van Delden, N. Harada, B. L. Feringa, Light-driven monodirectional molecular rotor. *Nature* 401, 152-155 (1999).
50. S. Kassem et al., Stereodivergent synthesis with a programmable molecular machine. *Nature* 549, 374-378 (2017).
51. C. Cheng et al., An artificial molecular pump. *Nat. Nanotechnol.* 10, 547-553 (2015).

Example 2

This example demonstrates site-selective thiol-disulfide interchange by controlled spatial alignment.

Thiol-disulfide interchange occurs widely in cellular processes including redox sensing and homeostasis, protein folding, cell signalling, and the regulation of apoptosis. Nature exploits this chemistry in a highly selective manner, which is challenging to recapitulate in vitro. In this example the inventors report site-selective and regioselective thiol-disulfide interchange on macromolecular disulfide substrates elongated within a protein nanoreactor, where they react with cysteine thiolates presented at different locations along the length of a β strand within a tubular structure. Numerous individual reaction events were detected by promoting substrate turnover. For each substrate, the most reactive cysteines on the β strand and which sulfur atom in the disulfide is attacked are defined, demonstrating that the chemistry can be controlled with atomic precision.

The control of selectivity has been a longstanding challenge for synthetic chemists. Two important aspects of this endeavour are site-selectivity—the ability to differentiate between two (or more) similarly reactive positions within a molecule, and regioselectivity—the ability to distinguish between two (or more) sites within a given functional group[1a,2a]. The realisation of chemical selectivity often requires exploitation or subversion of the inherent steric and electronic properties of a molecule or functional group[2a]. Common strategies include the installation of a reagent-directing group on the substrate, which can be later removed[3a], or the recruitment of a catalyst (organic or transition-metal-based), which binds to the substrate to favour a particular reaction pathway[1a,2a]. Alternatively, the preorganization of reactants, in micelles[4a] or within a supramolecular cage[5a], has been used to redirect regioselectivity. Recently, site-selectivity was demonstrated to result from the spacing of reactive sites within a metal-organic framework[6a]. In the context of enzymology, selectivity has been exquisitely demonstrated[7a]. For example, a switch in the regioselectivity of nitration of L-tryptophan by a cytochrome P450 has been attributed to a change in the orientation of the substrate, which depended upon a single amino-acid substitution[8a]. Despite these remarkable achievements, the intricate molecular interactions underlying many site-selective or regioselective chemistries were only elucidated after their serendipitous discovery, and in some cases are still not fully understood[2a].

Thiol-disulfide chemistry is prevalent in nature where it underpins critical biological activities involving enzymes such as thioredoxins and protein disulfide isomerases. In this work, the inventors use a single-molecule approach to examine thiol-disulfide interchange. Previously, single-molecule force-clamp spectroscopy was used to study thiol-disulfide chemistry by monitoring the unfolding of a titin domain mutant containing two disulfides[9a]. Unfolding was initiated by L-cysteine, which reduced the more exposed disulfide. Strikingly, under an applied force, the cysteine side chain liberated from the first disulfide reacted regioselectively with the remaining disulfide, preferring one sulfur atom by ~4 times over the other. Subsequent computational simulations attributed the regioselectivity mainly to the protein conformation[10a], which would be impossible to control in bulk solution[11a-14a]. Until now, a system in which a nucleophile is programmed to react with one of two chemically equivalent sulfur atoms in a disulfide has not been reported.

Figure 17A:
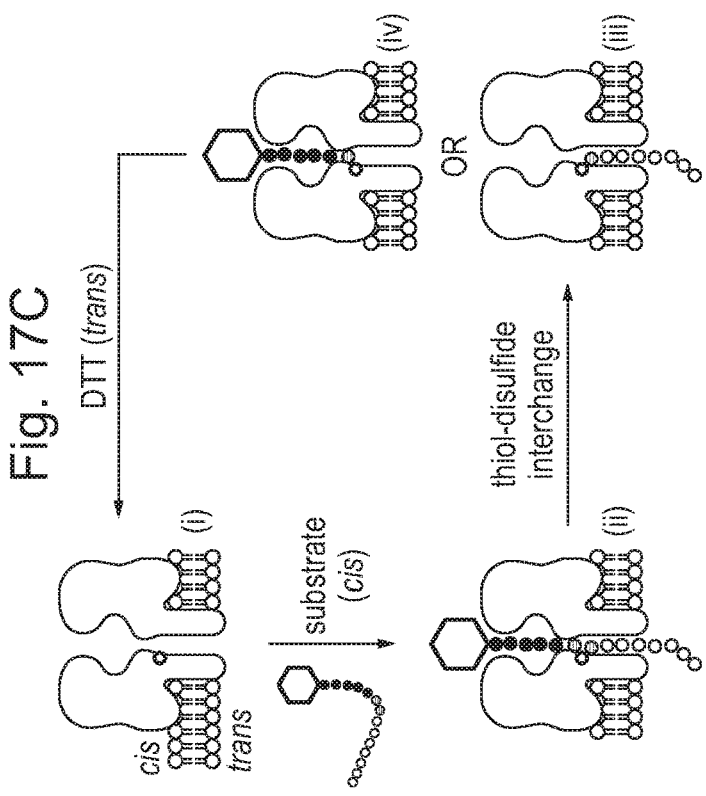
FIGS. 17A-17C show Thiol-disulfide interchange cycle.
Figure 17C:
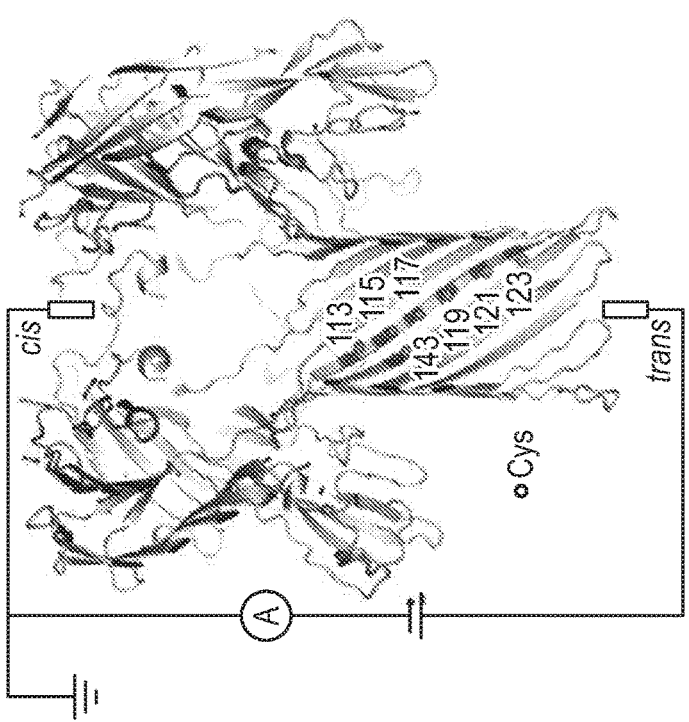
Figure 17B:
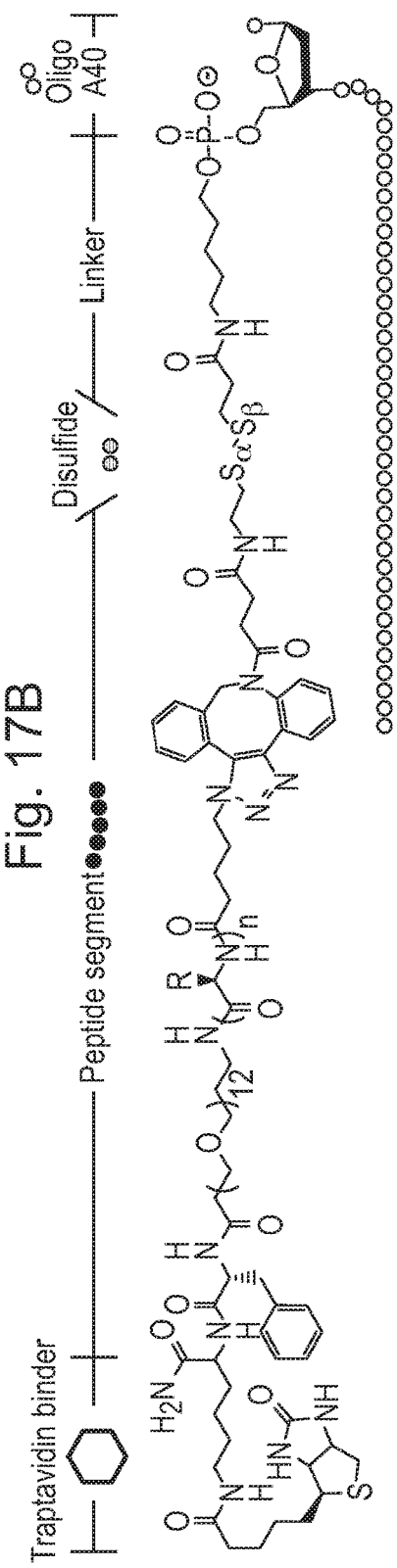

The system reported here comprises a nanoreactor—an α-hemolysin (αHL) cysteine mutant (FIG. 17a)—and linear macromolecular substrates with a disulfide bond in the backbone (FIG. 17b). The substrates consisted of biotin—a traptavidin-binding motif—at the terminus of a peptide segment, which was conjugated to a DNA oligonucleotide by strain-promoted azide-alkyne cycloaddition. The disulfide was installed between the peptide and the oligonucleotide with sulfur atom Sα proximal to the peptide segment and sulfur atom Sβ proximal to the oligonucleotide. The disulfide was flanked on both sides by ethylene groups, and therefore Sα and Sβ were expected to be closely similar both in intrinsic reactivity and steric terms.

Four substrate constructs, POC1 to POC4 (Table 1A), were tested in which the length of the peptide segment was adjusted two amino acid residues (Gly and Ser) at a time. When a substrate is fully stretched, each additional dipeptide lowers the disulfide a further ~7 Å into the barrel of the αHL pore. Seven single-cysteine αHL mutants were generated at positions 113, 115, 117, 119, 121, 123 and 143 (on one of the seven αHL subunits) in which the side chains point into the lumen of the transmembrane β barrel. Adjacent cysteines along a β strand are separated by an average distance of ~6.8 Å (Cα–Cα) and a vertical distance of ~5.6 Å, whereas Cys-143 on the antiparallel strand is vertically ~2.8 Å lower than Cys-115[15a,16a]. Given the experimental and computational evidence for a collinear trisulfide-like transition state in thiol-disulfide interchange[17a-19a], we reasoned that proximity and longitudinal alignment of the substrate disulfide with the nanoreactor cysteine side-chains would be critical in achieving site-selective and regioselective control of the reaction.

TABLE 1A

| Substrate[a] | Peptide segment[b] | Nano-reactor | Reactivity | Regioselectivity[c] | | $k_\beta/s^{-1d}$ | $k_\alpha/s^{-1d}$ | $k_{DTT}/s^{-1d}$ |
| | | | | $S_\beta$ | $S_\alpha$ | | | |
|---|---|---|---|---|---|---|---|---|
| POC1 | bKF (PEG12) | 113 | 100% | 78% | 22% | 0.077 ± 0.011 | 0.023 ± 0.006 | /[e] |
| | | 115 | 100% | 100% | 0% | 0.69 ± 0.11 | / | / |
| | | 117 | 4.5% (12/264) | 100% | 0% | 0.00053 ± 0.00031 | / | 0.011 ± 0.001 |
| | | 119 | 0% | / | / | / | / | 0.016 ± 0.004 |
| | | 143 | 100% | 100% | 0% | 0.11 ± 0.01 | / | / |
| POC2 | bKF (PEG12) GG | 113 | 100% | 44% | 56% | 0.028 ± 0.006 | 0.036 ± 0.007 | / |
| | | 115 | 100% | 79% | 21% | 1.7 ± 0.3 | 0.44 ± 0.14 | / |
| | | 117 | 100% | 89% | 11% | 0.055 ± 0.005 | 0.0069 ± 0.0018 | / |

TABLE 1A-continued

| Substrate[a] | Peptide segment[b] | Nano-reactor | Reactivity | Regioselectivity[c] | | $k_\beta/s^{-1d}$ | $k_\alpha/s^{-1d}$ | $k_{DTT}/s^{-1d}$ |
|---|---|---|---|---|---|---|---|---|
| | | | | $S_\beta$ | $S_\alpha$ | | | |
| | | 119 | 78% (72/92) | 100% | 0% | 0.032 ± 0.004 | / | 0.0090 ± 0.0020 |
| | | 121 | 0% | / | / | / | / | 0.014 ± 0.003 |
| | | 143 | 100% | 90% | 10% | 0.45 ± 0.06 | 0.05 ± 0.02 | / |
| POC3 | bKF (PEG12) SGGS | 115 | 100% | 59% | 41% | 1.8 ± 0.3 | 1.2 ± 0.3 | / |
| | | 117 | 100% | 70% | 30% | 0.17 ± 0.03 | 0.079 ± 0.019 | / |
| | | 119 | 96% (55/57) | 95% | 5% | 0.15 ± 0.01 | 0.0084 ± 0.0050 | / |
| | | 121 | 0% | / | / | / | / | 0.0092 ± 0.0009 |
| POC4 | bKF (PEG12) SGGSGG | 113 | 90% (37/41) | 19% | 81% | 0.019 ± 0.007 | 0.082 ± 0.012 | [f] |
| | | 117 | 100% | 35% | 65% | 0.094 ± 0.017 | 0.17 ± 0.02 | / |
| | | 119 | 100% | 83% | 17% | 0.36 ± 0.05 | 0.07 ± 0.02 | / |
| | | 121 | 29% (23/78) | 100% | 0% | 0.0038 ± 0.0008 | / | 0.0091 ± 0.0007 |
| | | 123 | 0% | / | / | / | / | 0.018 ± 0.004 |

[a]All substrates contained an oligoadenosine 40mer (A40).
[b]bK, biotinyl-L-lysine; F, phenylalanine; PEG, polyethylene glycol; S, serine; G, glycine.
[c]Regioselectivity is presented as the percentage of interchanges resulting in an αHL-oligo adduct ($S_\beta$) or an αHL-peptide adduct ($S_\alpha$). DTT cleavages are discounted.
[d]Dwell-time analysis and rate constant estimations were performed by using the maximum interval likelihood algorithm of QuB.
[e]/, not measurable.
[f]DTT cleavage occurred <5 times, and hence was disregarded in the kinetic model.

Results and Discussion

Turnover of thiol-disulfide interchange. To monitor the site-selectivity and regioselectivity of thiol-disulfide interchange, a means of substrate turnover was first established. When capped by traptavidin, the substrate entered the αHL pore from the cis compartment under an applied positive potential and was elongated within the electric field. Subsequent alignment-mediated thiol-disulfide interchange with the nanoreactor cysteine side chain resulted in the formation of a covalent adduct within the nanoreactor (FIG. 17c), which was revealed by a step in the ionic current passing through the pore when the top or bottom part of the substrate dissociated. The adduct was then released from the nanoreactor by the reducing reagent dithiothreitol (DTT), present in the trans compartment, which thereby allowed a new cycle to begin. No sub-steps were observed during substrate dissociation.

Figure 18A:
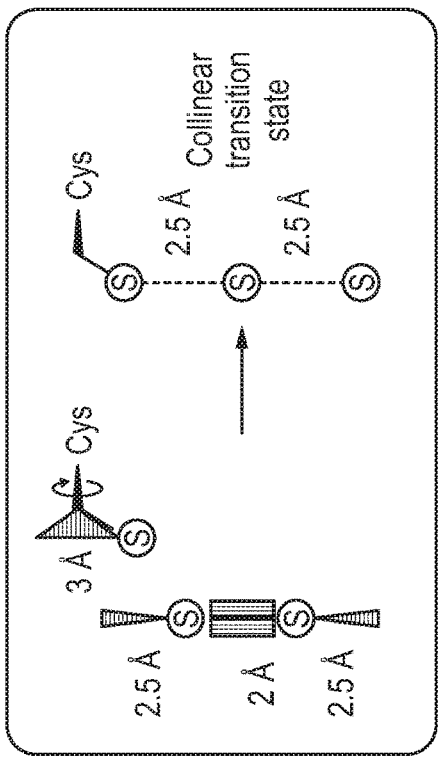
FIGS. 18A-18C show how alignment of a substrate disulfide with a nanoreactor cysteine sulfur determines reactivity.

Controlled reaction between the nanoreactor thiolate and the substrate disulfide. For the moment (see Conclusions), we assume that the system is static, i.e. that there is minimal conformational motion of the protein pore and that the substrate remains extended. In previous computational studies, thiol-disulfide interchange has been proposed to proceed through an almost linear trisulfide-like transition state with adjacent sulfur atoms separated by ~2.5 Å[18a,19a] Assuming free rotation of the nanoreactor cysteine side chains, the vertical distance (FIG. 18a) mapped out by a nucleophilic thiolate is ~3 Å (C—S bond length ~1.8 Å and C—C—S bond angle ~109.5°). For interchange to proceed, the 3 Å region must overlap with a 2.5 Å reactive zone at one end or the other of a disulfide (FIG. 18a). When the transition-state arrangement is inaccessible, with the nucleophilic thiolate residing outside the 2.5 Å radius at one end of a disulfide, the interchange is unfavourable (FIG. 18a).

Figure 18C:
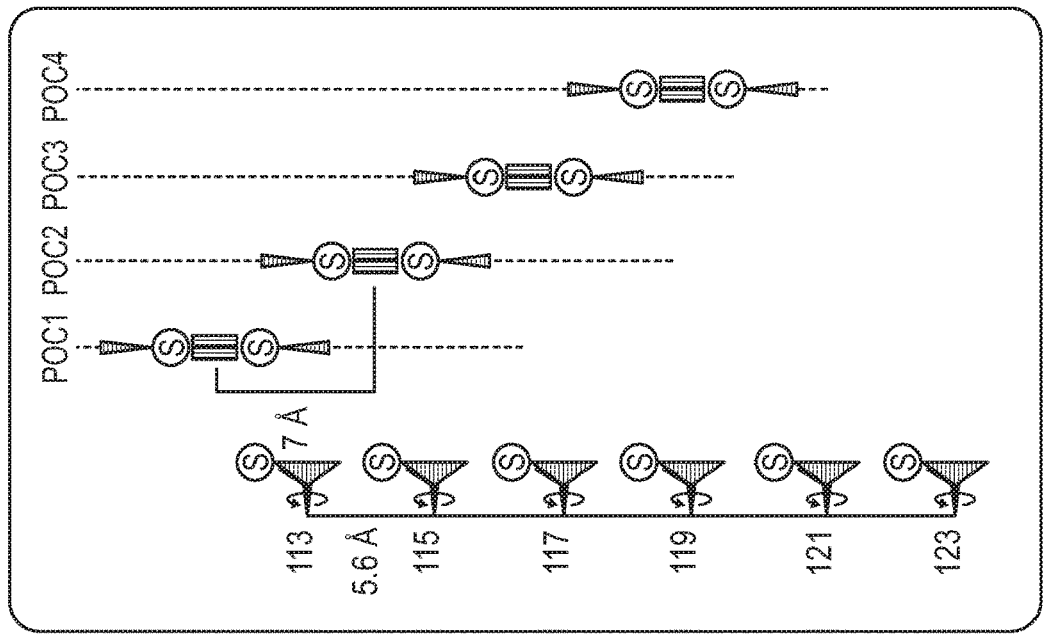
Figure 18B:
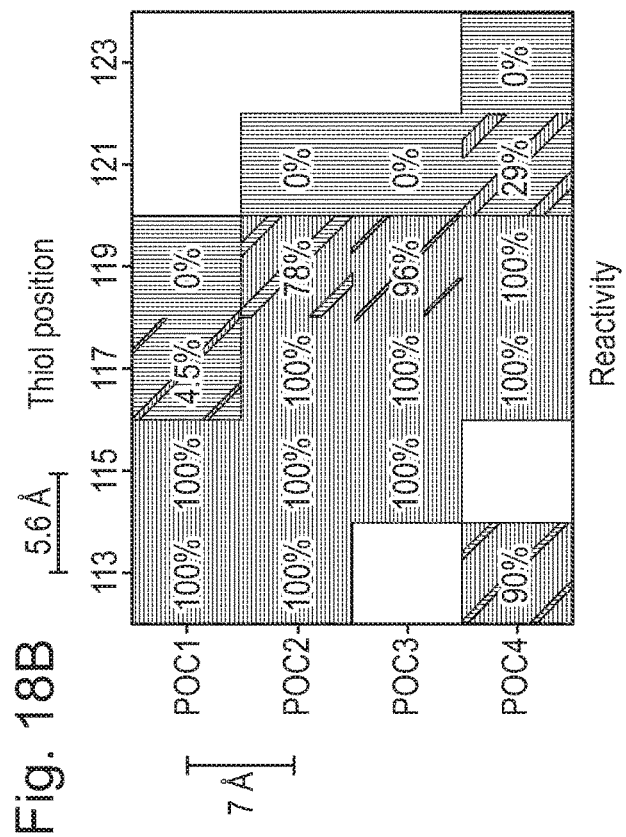

The system reported here can deliver a disulfide bond to a nucleophilic thiolate with angstrom precision. When the alignment was favourable, the interchange between the substrate disulfide and the nanoreactor thiolate generated a covalent adduct—either an αHL-peptide adduct or an αHL-oligo adduct (as discussed later)—which was subsequently released by DTT (FIG. 17c, 19a). When the alignment was unfavourable, the DTT (5 mM) diffusing into the nanopore from the trans compartment cleaved the substrate disulfide before interchange could occur and the resulting two fragments exited the pore, the DNA propelled by the applied potential and the peptide segment by diffusion (FIG. 19a). Based on these observations, reactivity was defined—regardless of regioselectivity—as the number of thiol-disulfide interchange reactions observed under specified conditions divided by the total number of substrate threading events, all of which resulted in interchange or cleavage (reactivity=$n_{react}/n_{thread}$) (FIG. 18b).

Using the aforementioned four substrates (POC1 to POC4) and seven nanoreactors (nanoreactors 113, 115, 117, 119, 121, 123, and 143), we observed a broad range of reactivity from 0% to 100% (Table 1A, FIG. 18). Notably, extension of the peptide segment by two amino acids (~7 Å) could dramatically affect reactivity. For example, once threaded into nanoreactor 117, the disulfide in POC1 was almost solely cleaved by DTT (4.5% reactivity), which suggests unfavourable alignment. In contrast, the disulfide in POC2, two amino acids longer, always formed a covalent adduct with the nanoreactor 117 (100% reactivity) (Table 1A, FIG. 18). Similar phenomena were observed with nanoreactor 119 (POC1, 0% reactivity; POC2, 78%) and nanoreactor 121 (POC3, 0% reactivity; POC4, 29%). Likewise, shifting the cysteine location by two residues along the β strand (~5.6 Å vertically) was sufficient to greatly alter or prevent reaction with substrates. For example, when nanoreactor 119 is compared with nanoreactor 121, reactivity drops from 78% to 0% with POC2, from 96% to 0% with POC3, and from 100% to 29% with POC4. Therefore, manipulation of the position of the disulfide within the substrate or the cysteine location within the nanoreactor determines whether or not thiol-disulfide interchange proceeds.

Sulfur atom selection within the substrate disulfide. The substrate disulfide connects a neutral segment (the peptide) with a negatively charged polymer (the oligonucleotide) (FIG. 17b). Upon thiol-disulfide interchange within a cysteine nanoreactor, either an αHL-peptide adduct or an αHL-oligo adduct is formed depending on whether the Sα or the Sβ atom of the disulfide bond is attacked. The two adducts showed distinctive current signatures under an applied potential (FIG. 19a), which were assigned based on their behaviour in response to voltage steps (see SI section 1). In contrast to the stable current levels associated with αHL-oligo adducts (Sβ attacked), rapid switching between three discrete levels was observed for αHL-peptide adducts (Sα attacked). We speculate that, in the electric field inside the αHL barrel20, the charged oligonucleotide experiences a constant pulling force that locks its conformation in an extended state, whereas the neutral peptide is less constrained, switching between several conformations. By counting the adducts formed over multiple substrate turnovers, we determined the sulfur regioselectivity for each nanoreactor-substrate combination, and present them as the percentage of interchanges that result in attack on Sα or Sβ (FIG. 19b, Table 1A).

In general, when a cysteine in the pore was located within the reactive zone of a substrate disulfide, lowering its position (e.g. from 113 to 115) reduced the chance of forming an αHL-peptide adduct and increased the chance of forming an αHL-oligo adduct. Complete regioselectivity towards Sβ (αHL-oligo adduct formation) was achieved with POC1 and nanoreactor 115 or 143, POC2 and nanoreactor 119, and POC4 and nanoreactor 121. In these cases, the nucleophilic thiolate could only reach the lower 2.5 Å reactive zone of the disulfide (FIG. 18a), solely permitting formation of the transition state that led to an αHL-oligo adduct.

The completely Sβ regioselective thiol-disulfide interchange between POC1 and nanoreactor 115 suggests that the thiolate resides below Sβ in the barrel. Given that the fully stretched linker (FIG. 17b) extends 13 Å and that Cys-115 is located ~40 Å from the exit of the barrel, ~4 phosphodiester bonds of POC1 must be located within the barrel's electric field. Each extension of the peptide segment by two amino acids moves one phosphodiester bond out of the field (the internucleotide distance in stretched single-stranded DNA is 6.9 Å21). The controlled positioning of a disulfide requires at least one charged residue inside the barrel to execute the pulling, which makes POC4 the longest workable construct in the present set-up. Over 80% regioselectivity towards Sα (αHL-peptide adduct formation) was achieved with POC4 and nanoreactor 113. We envisage that complete Sα regioselectivity might be achieved by using a longer peptide segment and a longer pore.

Kinetics of thiol-disulfide interchange. After a substrate threads into a nanoreactor, one of three possible reactions occurs: generation of an αHL-peptide adduct, generation of an αHL-oligo adduct, or cleavage by DTT. At the single molecule level, rate constants are related to the mean dwell times of states[22a]. For formation of a unimolecular adduct, the rate constant—kα for the formation of αHL-peptide adduct; kβ for the formation of αHL-oligo adduct—is the reciprocal of the corresponding mean dwell time (were only one of the reactions to occur) (Ta or $\tau_\beta$, e.g. $\tau_\alpha=1/k_\alpha$). For the bimolecular DTT cleavage at a fixed DTT concentration (e.g. 5 mM), $\langle\tau_{DTT}\rangle=1/k'_{DTT}=1/k_{DTT}[RS^-]_{DTT}$, where $k'_{DTT}$ is the pseudo-first order rate constant incorporating $[RS^-]_{DTT}$, the concentration of the $_{DTT}$ thiolate (at pH 8.5, the concentration of doubly ionised DTT is negligible[23a])

Over multiple turnovers, the mean waiting time before reaction ($\langle\tau\rangle$) is given by:

$$\langle\tau\rangle = \frac{1}{k_\alpha + k_\beta + k'_{DTT}} \quad (1)$$

$$\langle\tau\rangle = \frac{\langle\tau_\alpha\rangle\langle\tau_\beta\rangle\langle\tau_{DTT}\rangle}{\langle\tau_\alpha\rangle\langle\tau_\beta\rangle + \langle\tau_\beta\rangle\langle\tau_{DTT}\rangle + \langle\tau_\alpha\rangle\langle\tau_{DTT}\rangle} \quad (2)$$

Depending on the alignment, one of the three pathways may dominate, e.g. $\langle\tau_\alpha\rangle$, $\langle\tau_{DTT}\rangle>>><\tau_\beta>$, in which case $\langle\tau\rangle=\langle\tau_\beta\rangle$. In cases where more than one pathway compete, dwell-time analysis was performed to derive the independent rate constants ($k_\alpha$, $k_\beta$, $k_{DTT}'$) by using the maximum interval likelihood (MIL) algorithm of QuB software[24a] (Table 1).

Given that the thiol-disulfide interchange involves the thiolate anion, the rate constants $k_\alpha$, and $k_\beta$ depend on not only the alignment, but also on the pH and the pKa value of the nanoreactor thiol. The latter is estimated to be 8.5±1.5 in a wide β barrel[25a]. Nevertheless, when comparing different substrates reacting with the same nanoreactor (i.e. the cysteine pKa is fixed) at a fixed pH (e.g. pH 8.5), $k_\alpha$, and $k_\beta$ directly correlate with the thiolate alignment with respect to Sα and Sp, and the regioselectivity is given by $k_\beta/k_\alpha=n_\beta/n_\alpha$, where $n_\beta$ is the number of αHL-oligo adducts formed in a time interval and $n_\alpha$ the number of αHL-peptide adducts formed in the same interval. The spatial relationships between the substrates and a particular nanoreactor can be inferred from the derived rate constants (Table 1A). For each nanoreactor, optimal alignment with the substrate Sp atom was required to obtain the highest rate of αHL-oligo adduct formation ($k_\beta$). The highest $k_\beta$ values were between nanoreactor 113 and POC1, nanoreactor 115 and POC3, nanoreactor 117 and POC3 and nanoreactor 119 with POC4 (Table 1A). For example, a ~300-fold range in $k_\beta$ values was seen with nanoreactor 117, which gave 5.3×10-4 s$^{-1}$ with POC1 and 0.17 s$^{-1}$ with POC3. This shifts the overall outcome from domination by DTT cleavage with POC1 ($k'_{DTT}$=9.4×10-3 s$^{-1}$) to domination by thiol-disulfide interchange at $S_\beta$ with POC3, showcasing the influence of alignment on reaction kinetics and site selectivity. As expected, the rates of reaction of the various substrates with DTT were similar and did not vary significantly with the placement of the cysteine residues in the nanoreactor. Hence the reactivity, as determined here (FIG. 18b), and the rates of adduct formation (kα and kβ, Table 1) are correlated. Further, the kinetic data are consistent with alignments obtained from modeling studies in which the substrate chain was fully extended (FIG. 18c).

Site-selective and regioselective tandem thiol-disulfide interchanges. To recapitulate the tandem thiol-disulfide interchanges frequently seen with protein dithiols[26a,27a], we constructed two double-cysteine nanoreactors based on nanoreactor 115 with an additional cysteine on either the antiparallel strand (115/143) or on the same strand (115/117) within a single αHL subunit. Using POC1—which reacted with the three single-cysteine nanoreactors (115, 143, and 117) with complete $S_\beta$ regioselectivity—we demonstrated that the double-cysteine nanoreactors undergo consecutive thiol-disulfide interchanges.

After a POC1 molecule threaded into a double-cysteine nanoreactor, the substrate disulfide first reacted with one of the two available cysteine thiolates to form a covalent αHL-oligo adduct. The site-selectivities of the initial thiol-disulfide interchanges were determined. With nanoreactor 115/117, oligo-adducts at positions 115 and 117 can be differentiated by their residual currents (ΔIres %=Ires %(117)−Ires %(115)=+2.0%±0.5%, n=3) (FIG. 20a), which is in accord with the results obtained with single-cysteine nanoreactors (Ires %(115)=45%±1%, n=9; Ires % (117)=47%±1%, n=12). With nanoreactor 115/143, αHL-oligo adducts formed at positions 115 and 143 can also be differentiated by their residual currents (ΔIres %=Ires %(115)−Ires %(143)=+0.68%±0.03%, n=3) (FIG. 20b and FIG. S23), which again is consistent with the results obtained with single-cysteine nanoreactors (Ires % (115)=45%±1%, n=9; Ires %(143)=46%±1%, n=6). With nanoreactor 115/117, we found that the substrate disulfide reacted site-selectively (100%) with Cys-115 to form the αHL-oligo adduct (n=30), which is in accord with the kinetics of the single-cysteine nanoreactors: $k_\beta(115)$ $k_\beta(117)$. In contrast, we observed 81% reaction with Cys-115 and 19% reaction with Cys-143 with nanoreactor 115/143, also in accord with the kinetics of the single-cysteine nanoreactors (Table 1A, FIG. 20b, S23).

Figure 20A:
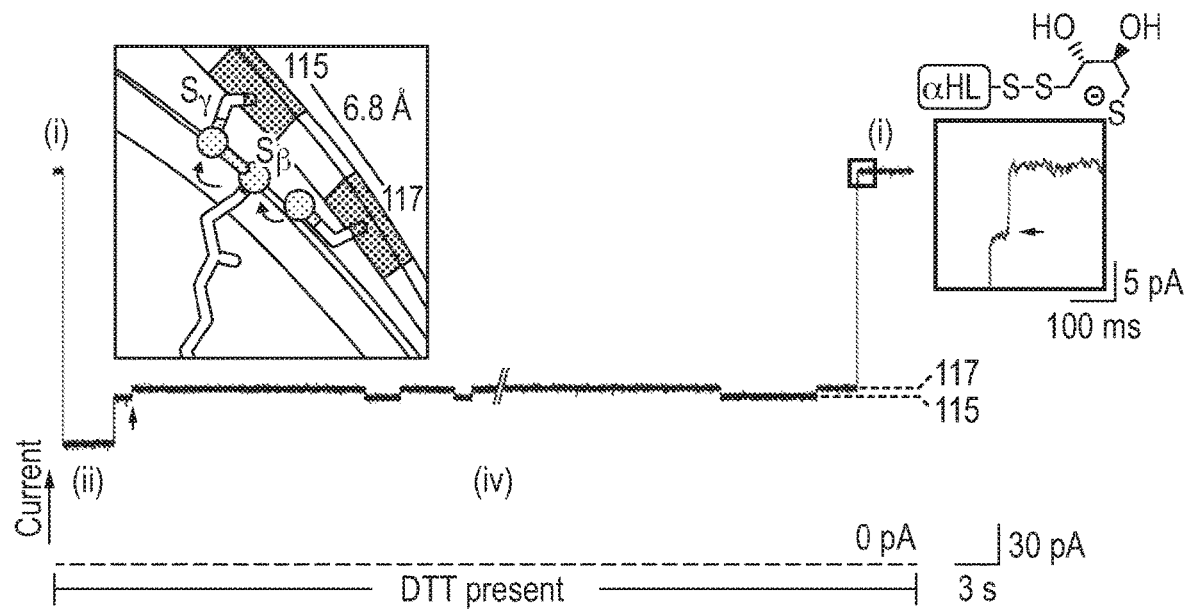
FIGS. 20A and 20B show Tandem thiol-disulfide interchanges with double-cysteine nanoreactors.
Figure 20B:
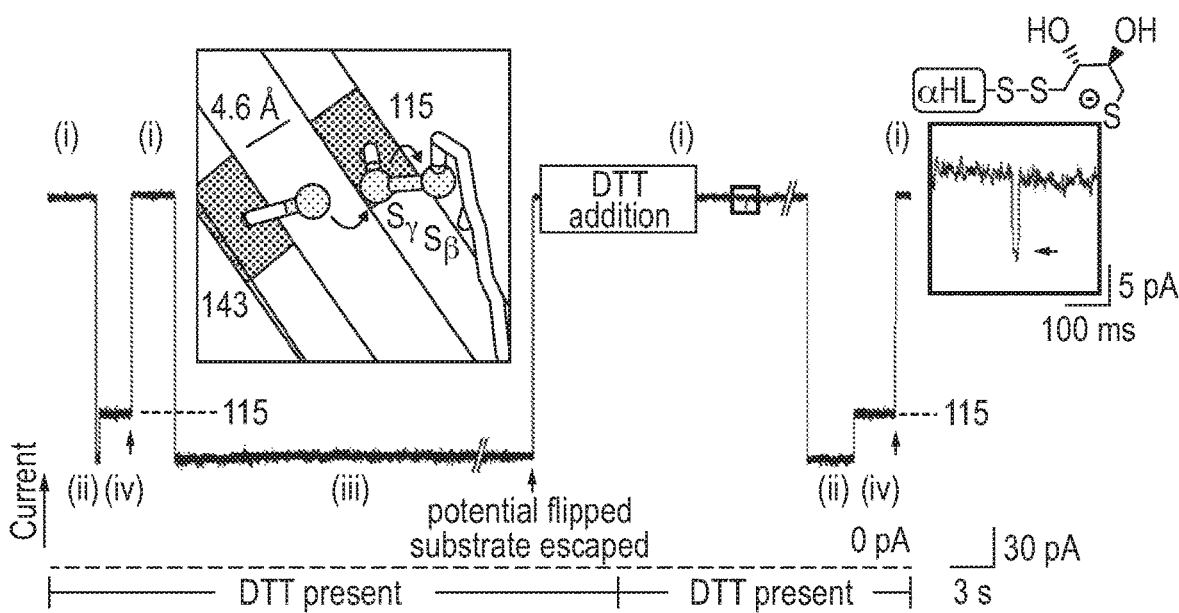

Once the adduct had been formed, the free cysteine on nanoreactor 115/117 or nanoreactor 115/143 initiated a second thiol-disulfide interchange by attacking either the sulfur contributed by the nanoreactor cysteine ($S_\gamma$) or the sulfur contributed by the oligonucleotide (Sp) (FIG. 20). Interestingly, the regioselectivities of these two intramolecular reactions differed. When the free cysteine was on the same strand (115/117), complete $S_\beta$ regioselectivity resulted in transfer of the oligonucleotide back and forth from one site to another (FIG. 20a). In the presence of DTT, the average number of transfers per cycle before adduct release by DTT (FIG. 20a) was 11 (n=40 cycles), and up to 29 successive transfers were recorded in a single cycle. When the free cysteine was on the antiparallel strand (115/143), we observed thiolate attack on both Sβ and Sγ (see below), the latter of which led to the irreversible release of the oligonucleotide from the nanoreactor and formation of a cross-strand disulfide in the absence of DTT (FIG. 20b). The subsequent addition of DTT regenerated free cysteines through a transient αHL-DTT intermediate28 (FIG. 20b, see SI section 3). The average number of transfers before intramolecular release depended on which site an αHL-oligo adduct initially formed: 0.54 transfers per cycle (n=48 cycles) for the αHL-oligo adducts initially formed on Cys-115 and 1.36 (n=11 cycles) for those initially formed on Cys-143. The difference of ~1 implies that release was exclusively from Cys-115, which was indeed the case. Up to 6 transfers have been seen within a single cycle (FIG. 232). Among the αHL-oligo adducts formed on Cys-115, 85% were immediately released through intramolecular Sγ attack by Cys-143 without transfer.

Figure 23C:
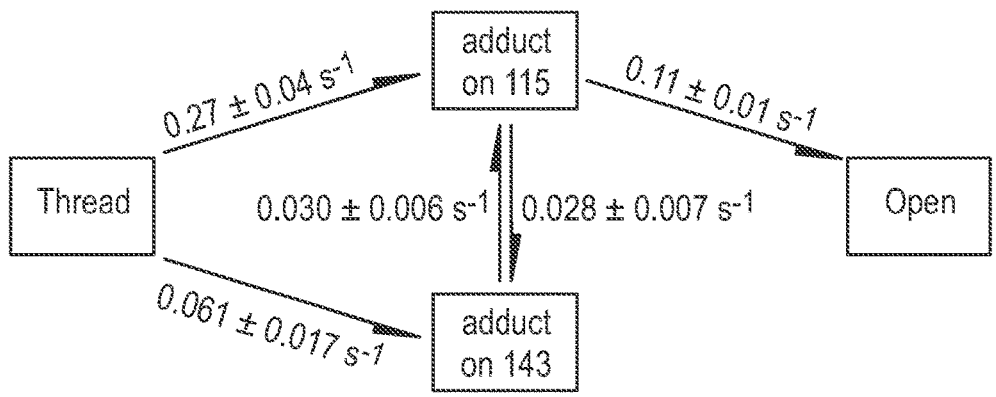

The regioselectivities of the second thiol-disulfide interchanges were attributed to the Cα–Cα distances between the two cysteines involved (FIG. 20 and FIG. 23). For nanoreactor 115/117, in which Cα–Cα=6.8 Å, Sβ attack occurred exclusively (FIG. 20). For nanoreactor 115/143, in which Cα–Cα=4.6 Å, Sγ attack predominated and was more favourable when the adduct was on Cys-115 (FIGS. 20 and 279 FIG. 23).

Conclusions

In biology, thiol-disulfide interchange in proteins is highly site-selective and regioselective as a result of the accessibility or the altered chemical properties of the reactive groups[26a,29a-31a]. Until now, no artificial system has been constructed to mediate precise site selective control over this important chemistry. In the present work, we examined the influence of spatial alignment on thiol-disulfide interchange between nanoreactor cysteines and disulfides consisting of chemically equivalent sulfur atoms ($S_\alpha$ and $S_\beta$). Our results show that thiol-disulfide interchange is sensitive towards alignment, and indeed can be controlled with Angstrom precision. By manipulating the relative position of the substrate disulfide and the thiolate in single-cysteine nanoreactors, we steered the interchange between complete $S_\beta$ regioselectivity and >80% Sα regioselectivity. Tandem thiol-disulfide interchanges with double-cysteine nanoreactors exhibited remarkable site-selectivity and regioselectivity simultaneously, which is present in biological systems but unprecedented in synthetic systems. The ability of an αHL-oligo adduct to move back and forth between Cys-115 and Cys-117 has been further developed to construct a molecular "hopper" that can advance up and down a 5- or 6-cysteine track[32a].

To aid description, we have so far assumed that our reaction system is static. However, we expect significant molecular motion of the components, especially the confined polymer substrate[33a]. In a static system, site-selectivity and regioselectivity could be achieved by accurate alignment and would then occur at the fastest reaction rates. However, just as in host-guest systems, strict organization can be difficult to achieve, and a degree of conformational flexibility might be advantageous. Indeed, we found that complete $S_\beta$ regioselectivity was always achieved among substrates with the lowest $k_\beta$ values (Table 1, FIG. 19b, c). In these cases, it seems likely that the reactive thiol in the nanoreactor is positioned on average below the substrate disulfide (i.e. towards the trans side). Then, rare encounters in a collinear arrangement resulting from conformational flexibility result in $S_\beta$ regioselectivity, while $S_\alpha$ is inaccessible (FIG. 19c).

Figure 21:
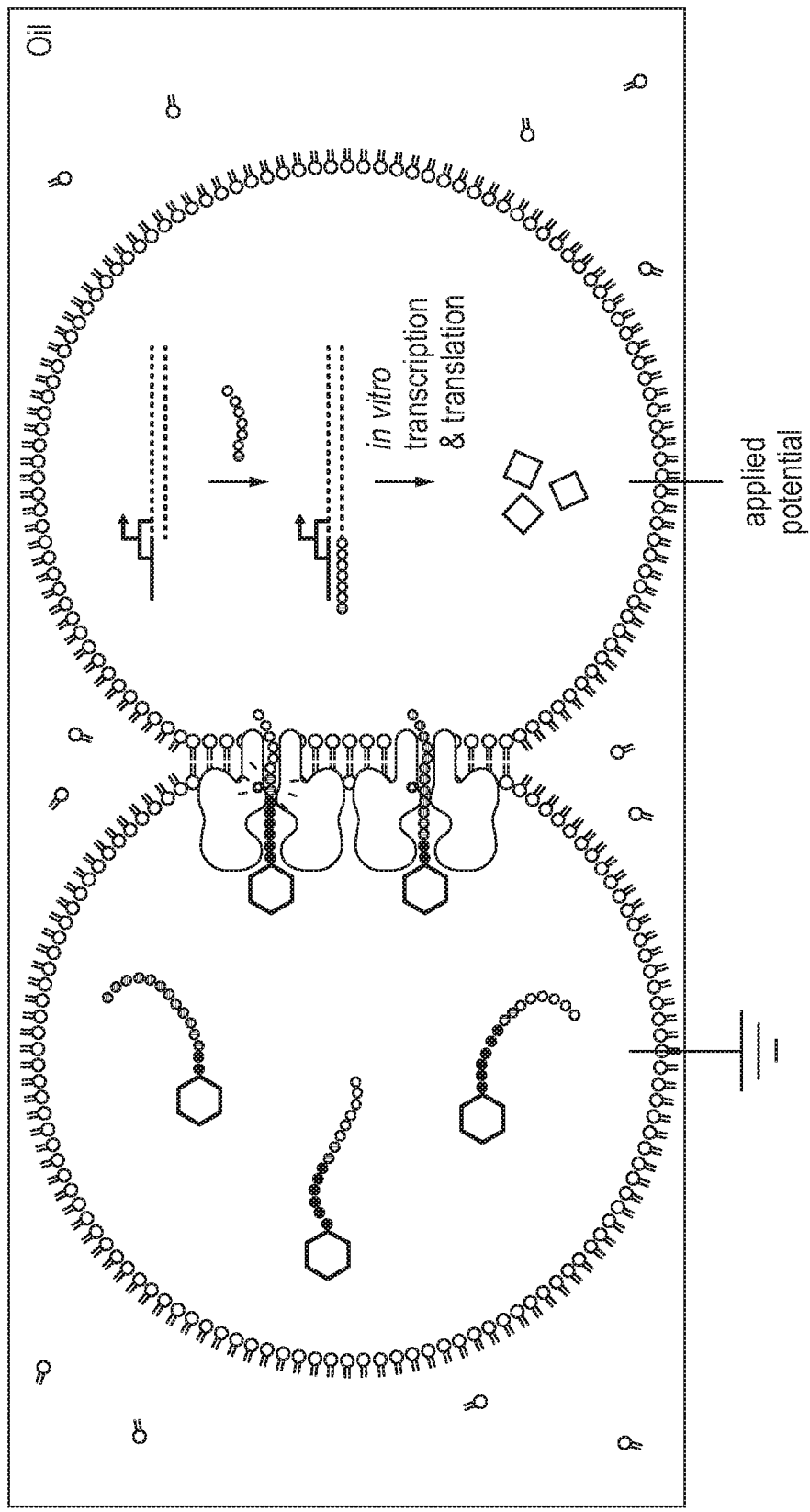
FIG. 21 shows Transmembrane communication. In a droplet interface bilayer (DIB) system, a component of mixed substrates in the left droplet is recognized by selective reaction with nanoreactors embedded in the bilayer and under an applied potential. Substrate turnover releases the oligonucleotide segments (brown) into the right droplet to trigger a variety of downstream responses. For example, the translocated oligonucleotides might complement a single-stranded promoter region to initiate in vitro transcription and translation. Results are described in Example 2.

Based on this study, we envisage transmembrane communication based on substrate alignment and site-selective and regioselective chemistry. Previously, in the bottom-up fabrication of synthetic cells[34a] and tissues[35a], signalling based on thiol-disulfide interchange has not been used, presumably because it has been hard to control. The results described herein show that selective vectorial cargo movement across membranes, which will include the controlled transport of a variety of chemical signals (FIG. 21) is achievable. The fact that the system is catalytic and permits multiple turnovers (FIG. 17c) will increase the sensitivity of signalling. Transmembrane communication has been achieved with pore-forming proteins, such as αHL[36a,37a] or with synthetic membrane transducers or transmitters[38a-42a]. The system reported here can be directly incorporated into droplet-based synthetic tissues scaffolded with lipid bilayers[35a] to allow internal (intercompartment) or external communication.

Steric and electronic properties of functional groups flanking the disulfide in the substrate can be manipulated during synthesis to produce innate regioselectivity. In addition, the spatial alignment of reactants within a narrow 'tube' can be generalised for the site-selective and regioselective control of other chemistries. Indeed, a click reaction with a dialkyne becomes site-selective when reactive azides are suitably spaced within the porous structure of a metal-organic framework[6a].

Methods

Single-molecule monitoring of thiol-disulfide interchange

The substrate (400 μM in 1 μL MilliQ water) was added to a solution of traptavidin (Kerafast) (40 μM in 10 μL phosphate-buffered saline, pH 7.4) and incubated at room temperature (20±1° C.) for 15 min to form the traptavidin-tagged substrate. The cis compartment of a planar bilayer recording apparatus containing the αHL nanoreactor was stirred until a single pore inserted into the bilayer. The traptavidin-tagged substrate (3 μL, 36 μM) was then added to the cis compartment, which contained 500 μL of recording buffer (2 M KCl, 20 mM HEPBS, 20 μM EDTA, pH 8.5). The trans compartment contained the same buffer supplemented with 5 mM DTT. To drive the macromolecular substrate into the nanopore, a potential of +150 mV was applied to the trans side of the bilayer. The threaded substrate reduced the current to an Ires % of ~33% (see SI section 4 for each substrate-nanoreactor combination). After the thiol-disulfide interchange between the substrate and the nanoreactor, the current increased as one segment of the substrate departed from the nanoreactor (see SI section 4 for Ires % for each substrate-nanoreactor combination). Subsequent reaction with DTT released the adduct and returned the nanoreactor to its initial state ready for another round of thiol-disulfide interchange.

REFERENCES

1a. Davis, H. J. & Phipps, R. J. Harnessing non-covalent interactions to exert control over regioselectivity and site-selectivity in catalytic reactions. *Chem. Sci.* 8, 864-877 (2017).

2a. Mahatthananchai, J., Dumas, A. M. & Bode, J. W. Catalytic selective synthesis. *Angew. Chem. Int. Ed.* 51, 10954-10990 (2012).

3a. Rousseau, G. & Breit, B. Removable directing groups in organic synthesis and catalysis. *Angew. Chem. Int. Ed.* 50, 2450-2494 (2011).

4a. Su, D. & Jaeger, D. A. High regioselectivity in the Diels-Alder reaction of a surfactant 1,3-diene with a surfactant dienophile resulting from a short tether between their functional groups and head groups. *Tetrahedron Lett.* 40, 7871-7874 (1999).

5a. Yoshizawa, M., Tamura, M. & Fujita, M. Diels-Alder in aqueous molecular hosts: unusual regioselectivity and efficient catalysis. *Science* 312, 251-4 (2006).

6a. Huxley, M. T. et al. Protecting-group-free site-selective reactions in a metal-organic framework reaction vessel. *J. Am. Chem. Soc.* 140, 6416-6425 (2018).

7a. Wang, J. bo, Li, G. & Reetz, M. T. Enzymatic site-selectivity enabled by structure-guided directed evolution. *Chem. Commun.* 53, 3916-3928 (2017).

8a. Dodani, S. C. et al. Discovery of a regioselectivity switch in nitrating P450s guided by molecular dynamics simulations and Markov models. *Nat. Chem.* 8, 419-425 (2016).

9a. Alegre-Cebollada, J., Kosuri, P., Rivas-Pardo, J. A. & Fernindez, J. M. Direct observation of disulfide isomerization in a single protein. *Nat. Chem.* 3, 882-887 (2011).

10a. Kolšek, K., Aponte-Santamaria, C. & Gräter, F. Accessibility explains preferred thiol-disulfide isomerization in a protein domain. *Sci. Rep.* 7, 9858 (2017).

11a. Beedle, A. E. M. et al. Forcing the reversibility of a mechanochemical reaction. *Nat. Commun.* 9, 3155 (2018).

12a. Beedle, A. E. M., Mora, M., Lynham, S., Stirnemann, G. & Garcia-Manyes, S. Tailoring protein nanomechanics with chemical reactivity. *Nat. Commun.* 8, 15658 (2017).

13a. Beedle, A. E. M., Lynham, S. & Garcia-Manyes, S. Protein S-sulfenylation is a fleeting molecular switch that regulates non-enzymatic oxidative folding. *Nat. Commun.* 7, 1-10 (2016).

14a. Garcia-Manyes, S. & Beedle, A. E. M. Steering chemical reactions with force. *Nat. Rev. Chem.* 389 1, 0083 (2017). 90

15a. Murzin, A. G., Lesk, A. M. & Chothia, C. Principles determining the structure of β-sheet barrels in proteins. *J Mol Biol* 236, 1382-1400 (1994).

16a. Song, L. et al. Structure of staphylococcal α-hemolysin, a heptameric transmembrane pore. *Science* 274, 1859-66 (1996).

17a. Wiita, A. P. et al. Probing the chemistry of thioredoxin catalysis with force. *Nature* 450, 124-395 127 (2007).

18a. Fernandes, P. A. & Ramos, M. J. Theoretical insights into the mechanism for thiol/disulfide exchange. *Chem.—A Eur. J.* 10, 257-266 (2004).

19a. Bach, R. D., Dmitrenko, O. & Thorpe, C. Mechanism of thiolate-disulfide interchange reactions in biochemistry. *J. Org. Chem.* 73, 12-21 (2008).

20a. Howorka, S. & Bayley, H. Probing distance and electrical potential within a protein pore with tethered DNA. *Biophys. J.* 83, 3202-3210 (2002).

21a. Bosco, A., Camunas-Soler, J. & Ritort, F. Elastic properties and secondary structure formation of single-stranded DNA at monovalent and divalent salt conditions. *Nucleic Acids Res.* 42, 2064-2074 (2014).

22a. Bayley, H., Luchian, T., Shin, S.-H. & Steffensen, M. B. Single-molecule covalent chemistry in a protein nanoreactor. in *Single Molecules and Nanotechnology Springer Series in Biophysics* 12 (eds. Rigler, R. & Vogel, H.) 251-277 (2008).

23a. Whitesides, G. M., Lilburn, J. E. & Szajewski, R. P. Rates of thiol-disulfide interchange reactions between mono and dithiols and Ellman's reagent. *J. Org. Chem.* 42, 332-338 (1977).

24a. Qin, F., Auerbach, A. & Sachs, F. Estimating single-channel kinetic parameters from idealized patch-clamp data containing missed events. *Biophys. J.* 70, 264-280 (1996).

25a. Pace, C. N., Grimsley, G. R. & Scholtz, J. M. Protein ionizable groups: pK values and their contribution to protein stability and solubility. *J. Biol. Chem.* 284, 13285-9 (2009).

26a. Depuydt, M., Messens, J. & Collet, J.-F. How proteins form disulfide bonds. *Antioxid. Redox Signal.* 15, 49-66 (2011).

27a. Ukuwela, A. A., Bush, A. I., Wedd, A. G. & Xiao, Z. Glutaredoxins employ parallel monothiol-dithiol mechanisms to catalyze thiol-disulfide exchanges with protein disulfides. *Chem. Sci.* 9, 1173-1183 (2018).

28a. Luchian, T., Shin, S.-H. & Bayley, H. Single-molecule covalent chemistry with spatially separated reactants. *Angew. Chem. Int. Ed.* 42, 3766-71 (2003).

29a. Messens, J. et al. How thioredoxin can reduce a buried disulphide bond. *J. Mol. Biol.* 339, 527-37 (2004).

30a. Roos, G. et al. How thioredoxin dissociates its mixed disulfide. *PLoS Comput. Biol.* 5, (2009).

31a. Roos, G., Foloppe, N. & Messens, J. Understanding the pKa of redox cysteines: the key role of hydrogen bonding. Antioxid. Redox *Signal.* 18, 94-127 (2013).

32a. Qing, Y., Ionescu, S. A., Pulcu, G. S. & Bayley, H. Directional control of a processive molecular hopper. *Science* 361, 908-912 (2018).

33a. Lu, B., Fleming, S., Szalay, T. & Golovchenko, J. Thermal motion of DNA in an MspA pore. *Biophys. J.* 109, 1439-1445 (2015).

34a. Noireaux, V. & Libchaber, A. A vesicle bioreactor as a step toward an artificial cell assembly. *Proc. Natl. Acad. Sci.* 101, 17669-17674 (2004).

35a. Villar, G., Graham, A. D. & Bayley, H. A tissue-like printed material. *Science* 340, 48-52 (2013).

36a. Booth, M. J., Schild, V. R., Graham, A. D., Olof, S. N. & Bayley, H. Light-activated communication in synthetic tissues. *Sci. Adv.* 2, (2016).

37a. Lentini, R. et al. Integrating artificial with natural cells to translate chemical messages that direct E. coli behaviour. *Nat. Commun.* 5, 1-6 (2014).

38a. Langton, M. J., Keymeulen, F., Ciaccia, M., Williams, N. H. & Hunter, C. A. Controlled membrane translocation provides a mechanism for signal transduction and amplification. *Nat. Chem.* 9, 426-430 (2017).

39a. Lister, F. G. A., Le Bailly, B. A. F., Webb, S. J. & Clayden, J. Ligand-modulated conformational switching in a fully synthetic membrane-bound receptor. *Nat. Chem.* 9, 420-425 (2017).

40a. De Poli, M. et al. Conformational photoswitching of a synthetic peptide foldamer bound within a phospholipid bilayer. *Science* 352, 575-580 (2016).

41a. Janout, V. & Regen, S. L. Bioconjugate-based molecular umbrellas. *Bioconjug. Chem.* 20, 183-92 (2009).

42a. Janout, V., Jing, B. & Regen, S. L. Molecular umbrella-assisted transport of thiolated AMP and ATP across phospholipid bilayers. *Bioconjug. Chem.* 13, 351-356 (2002).

Supplementary Information for Example 2

1. IDENTIFYING THE COVALENT ADDUCTS BY CURRENT PATTERNS

Figure 22A:
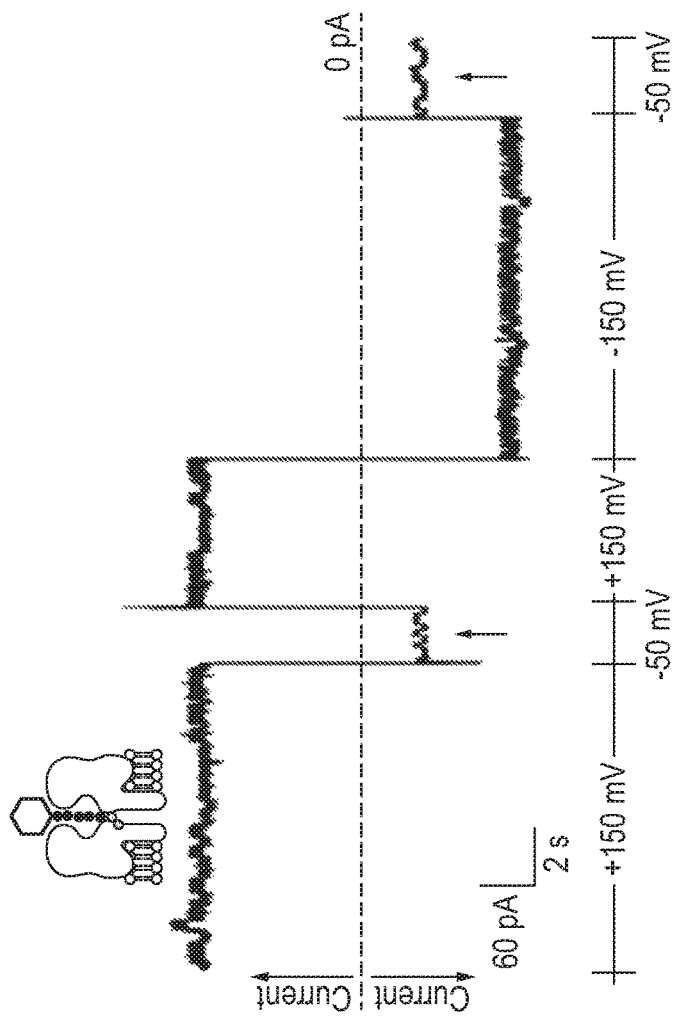
FIGS. 22A and 22B show Current changes caused by αHL-polymer adducts in response to voltage steps.
Figure 22B:
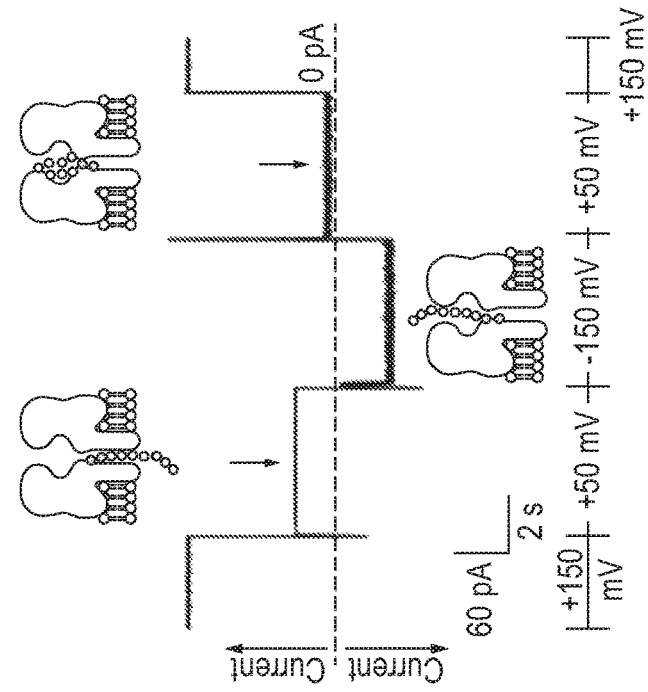

To confirm the identity of adducts formed upon thiol-disulfide interchange, we probed their behaviour in response to voltage steps (FIG. 22).

For an αHL-oligo adduct (FIG. 22a), the negative charges on the oligonucleotide within the barrel re-orientated the chain upon switching the applied potential between high positive and negative values (e.g. ±150 mV). At low potentials (e.g. +50 mV), the pulling force was insufficient to overcome the energy barrier for re-orientation. Therefore, due to condensation of the oligonucleotide, the current level recorded at a low potential (e.g. +50 mV) was lower if the immediately previous applied potential was of opposite polarity.

For an αHL-peptide adduct (FIG. 22b), the peptide fragment was locked inside the upper vestibule of the αHL pore with traptavidin acting as a stopper. In this case, the current pattern at a low applied potential (e.g. −50 mV) was the same following high potentials of opposite polarity (e.g. ±150 mV), which indicates that the conformation was unaffected.

See FIG. 22

2. SITE-SELECTIVITY AND REGIOSELECTIVITY OF THIOL-DISULFIDE INTERCHANGES BETWEEN NANOREACTOR 115/143 AND POC1

See FIG. 23

3. REGIOSELECTIVITY OF THIOL-DISULFIDE INTERCHANGE BETWEEN DTT AND αHL ADDUCTS

Previously, a transient intermediate was detected upon DTT reduction of a mixed-disulfide formed between an αHL pore with a single Cys-117 and 5,5'-dithiobis-(2-nitrobenzoic acid) (DTNB)[1b].

Figure 24A:
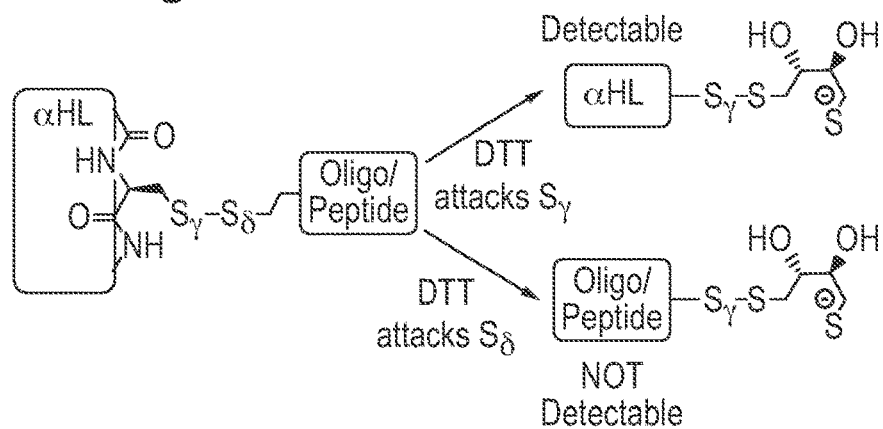
FIGS. 24A and 24B show regioselectivity of thiol-disulfide interchange between DTT and αHL adducts. A mixed-disulfide is formed (FIG. 24A) with a macromolecular substrate to give either an αHL-oligo adduct or an αHL-peptide adduct, or (FIG. 24B) with DTNB. When the DTT attacks the cysteine sulfur (Sγ), the transient intermediate can be detected by single-channel electrical recording. Results are described in Example 2.
Figure 25:
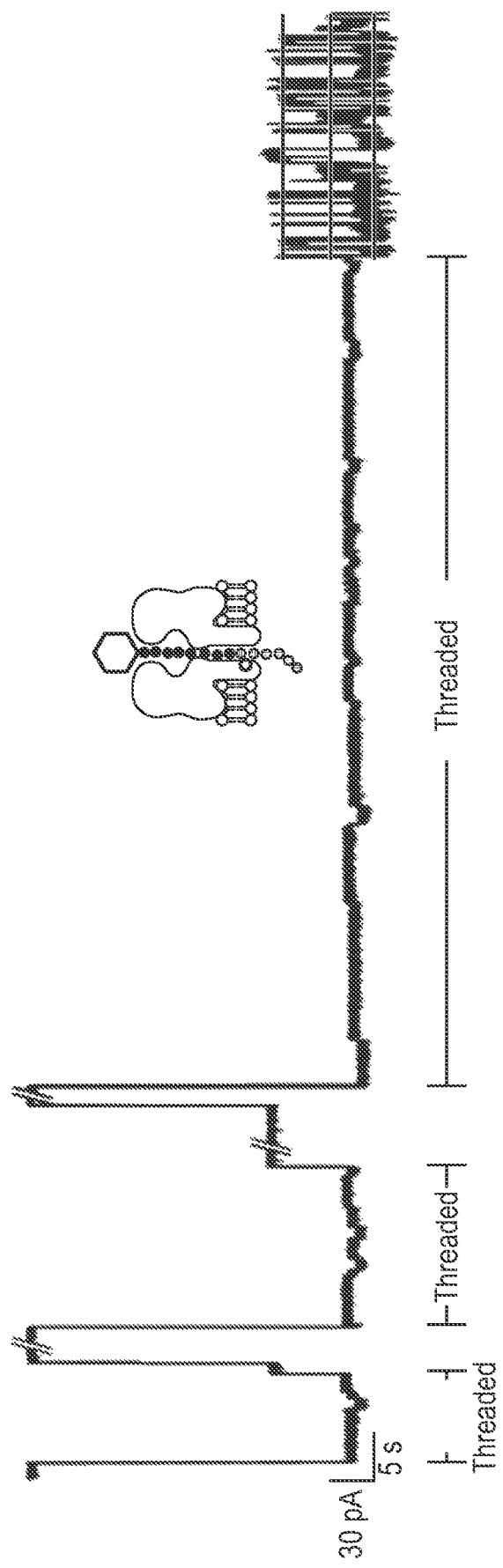
FIG. 25 shows Interchanging current levels recorded with POC3 threaded into nanoreactor 119. Three interchanging current levels were observed. Neither the αHL-oligo adduct nor the αHL-peptide adduct was formed specifically from one of the three levels. Traces were filtered at 200 Hz. Conditions: 2 M KCl, 20 mM HEPBS, 20 μM EDTA, 5 mM DTT (trans), pH 8.5, 20±1° C. Results are described in Example 2.

In the present work, DTT was used to release covalent disulfide adducts—either αHL-oligo adducts or αHL-peptide adducts—from nanoreactors. The DTT thiolate can attack either the nanoreactor cysteine sulfur (Sγ) or the sulfur atom donated by the polymer: an oligonucleotide or a peptide (Sδ) (FIG. 24a). When Sδ is attacked, an αHL-DTT adduct is formed, which has a distinctive breakdown signal (FIG. 25). We investigated the regioselectivity of release of αHL-polymer adducts by DTT, by monitoring the formation of the αHL-DTT adduct (Table S1, FIG. 24a). The Sγ regioselectivity is defined as the number of αHL-DTT adducts detected against the overall number of events:

$$regioselectivity(\%) = \frac{n(S_\gamma)}{n(S_\gamma) + n(S_\delta)} \cdot 100$$

Figure 24B:
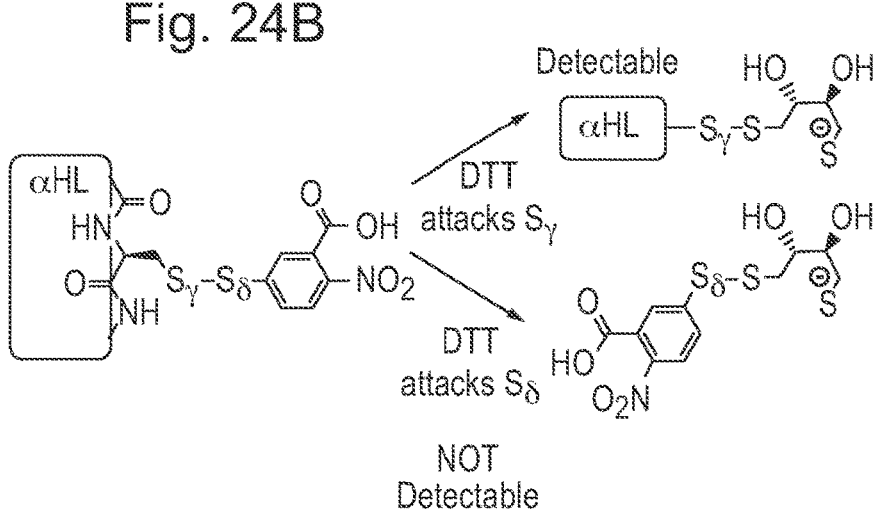

In general, DTT attacked Sδ more frequently than Sγ (Table S1). Complete Sδ regioselectivity was seen when the mixed disulfide was formed between nanoreactor 113 or nanoreactor 143 and the polymer (an oligonucleotide or a peptide). In contrast, complete Sγ regioselectivity was seen when a mixed disulfide was formed between nanoreactor 113 and DTNB (Table S1, FIG. 24b), and over 80% reaction at Sγ was seen when the mixed disulfide was formed between nanoreactor 143 and DTNB. This ruled out the possibility that the αHL-DTT adducts were too short-lived to be detected.

For the thiol-disulfide interchange between DTT and covalent adducts, the constituent sulfurs are not chemically and sterically equivalent and the DTT is freely diffusing in solution. Therefore, no spatial control was exerted on the attacking thiolate and innate regioselectivity was observed (Table S1).

The lifetime of an αHL-DTT adduct (<ταHL-DTT>)—the mean waiting times before cyclization (Table S1)-varied between the nanoreactors. This implies that the nanoreactor cysteine thiols, which are the leaving groups upon DTT thiolate attack, have different pKa values[2b].

See FIG. 24

| | DTT/αHL adducts (αHL-oligo adducts and αHL-peptide adducts combined) | | DTT/DTNB | |
|---|---|---|---|---|
| | Regioselectivity $\frac{n(S_\gamma)}{n(S_\gamma)+n(S_\delta)}$ | $<\tau_{\alpha HL\text{-}DTT}>$/ms[a] | Regioselectivity $\frac{n(S_\gamma)}{n(S_\gamma)+n(S_\delta)}$ | $<\tau_{\alpha HL\text{-}DTT}>$/ms[a] |
| 113 | 0/137 (0%) | /[b] | 47/47 (100%) | 85 ± 8 |
| 115 | 41/143 (29%) | 220 ± 30 | 85/85 (100%) | 150 ± 20 |
| 143 | 0/133 (0%) | / | 82/100 (82%) | 18 ± 2 |
| 117 | 59/220 (27%) | 73 ± 6 | 63/63 (100%) | 66 ± 6 |
| 119 | 3/198 (1.5%) | 34 ± 30[c] | 0/145 (0%)[d] | / |
| 121 | 3/23 (13%) | 110 ± 80[c] | 0/60 (0%)[d] | / |
| | Detection of αHL-DTT adducts | $<\tau_{\alpha HL\text{-}DTT}>$/ms[a] | Detection of αHL-DTT adducts | $<\tau_{\alpha HL\text{-}DTT}>$/ms[a] |
| 115/143 | 59/59 (100%) | 9.4 ± 1.7 | Not tested | |

[a] Dwell-time analysis was performed by using the maximum interval likelihood algorithm of QuB unless stated otherwise.
[b] /, not measurable
[c] $<\tau DTT\text{-}\alpha HL>$ was calculated as the arithmetic mean due to insufficient events with nanoreactor 119 or 121.
[d] We speculate that the current levels of the adducts formed upon DTNB reaction with nanoreactor 119 or 121 cannot be distinguished from the current level of the αHL-DTT adduct. Future experiments with alternative reducing reagents (e.g. dihydrolipoic acid) might give identifiable current steps for the transient intermediates.

4. CURRENT LEVELS FOR EACH SUBSTRATE/NANOREACTOR COMBINATION

TABLE S2

Residual current levels (Ires %) for individual substrate/nanoreactor combination

| +150 mV[a] | | $I_{res}$ % | |
|---|---|---|---|
| POC1 | Threading[b] | αHL-Oligo[b] | αIL-Peptide[c] |
| 113 | 33% | 39% | 43%-51% |
| 115 | 31% | 45% | / |
| 117 | 34% | 47% | / |
| 143 | 31% | 44% | / |
| 115/117 | 30% | 45%, 47% | / |
| 115/143 | 30% | 45% | / |
| POC2 | Threading | αHL-Oligo | αHL-Peptide |
| 113 | 33% | 39% | 39%-56% |
| 115 | 32% | 45% | 27%-50% |
| 117 | 33% | 47% | 42%-49% |
| 119 | 34% | 53% | / |
| 143 | 32% | 44% | 27-54% |
| POC3 | Threading | αHL-Oligo | α-IL-Peptide |
| 115 | 32%, 33%, 34%[d] | 45% | 24%-52% |
| 117 | 32%, 33%, 34%[d] | 47% | 29%-56% |
| 119 | 32%, 33%. 34%[d] | 53% | 28%-48% |
| 121 | 32%, 33%, 34%[d] | / | / |
| POC4 | Threading | αHL-Oligo | αHL-Peptide |
| 113 | 33%, 34%, 35%[d] | 39% | 28%-56% |
| 117 | 33%, 34%, 35%[d] | 47% | 29%-54% |
| 119 | 33%, 34%, 35%[d] | 53% | 33%-54% |
| 121 | 33%, 34%, 35%[d] | / | / |
| 123 | 34%, 35%, 36%[d] | / | / |

[a]. All the measurements in the Table were carried out at +150 mV.
[b]. The standard deviations of Ires % are less than 0.5% (derived from n > 3 separate experiments for each substrate/nanoreactor combination).
[c]. Three discrete interchanging levels were recorded for each adduct. However, adduct to adduct variation in Ires % was seen. The observed range of Ires % for all experiments is reported here.
[d]. Three discrete interchanging levels were recorded at the threading stage.

5. CONFORMATIONAL FLEXIBILITY OF MACROMOLECULAR SUBSTRATES AT THE THREADED STAGE

Interchanging current levels were observed during the substrate-threaded stage, and were more prominent with substrates containing a longer peptide segment (i.e. POC3 and POC4) (FIG. 25).

Conformational switching during the threaded stage was correlated with fewer phosphodiester units remaining within the electric field for POC3 and POC4. Consequently, less pulling force was imparted to the peptide, resulting in greater conformational freedom.

See FIG. 25

6. SYNTHESIS AND CHARACTERIZATION OF MACROMOLECULAR SUBSTRATES 6.1. Chemicals Acetic anhydride ($Ac_2O$), acetonitrile (HPLC grade), 5-azidopentanoic acid, N,N-diisopropylethylamine (DIPEA), diethyl ether, dimethylformamide (DMF), hexafluoro-2-propanol (HFIP), N,N-hydroxybenzotriazole (HOBt), 1-methyl-2-pyrrolidinone (NMP), Nα-Fmoc-NE-biotinyl-L-lysine, piperidine, triethylamine (TEA), and trifluoroacetic acid (TFA) were purchased from Sigma-Aldrich. 2-(1H-Benzotriazole-1-yl)-1,1,3,3-tetramethyluronium hexafluorophosphate (HBTU), Fmoc-Phe-OH, and Rink Amide MBHA resin LL (100-200 mesh) were from Novabiochem. Fmoc-NH-polyethylene glycol (PEG)(12)-COOH and Fmoc-Gly-Gly-OH were purchased from Iris Biotech GmbH.

6.2. Peptide Segment Preparation Using Solid-Phase Peptide Synthesis

Figure 26A:
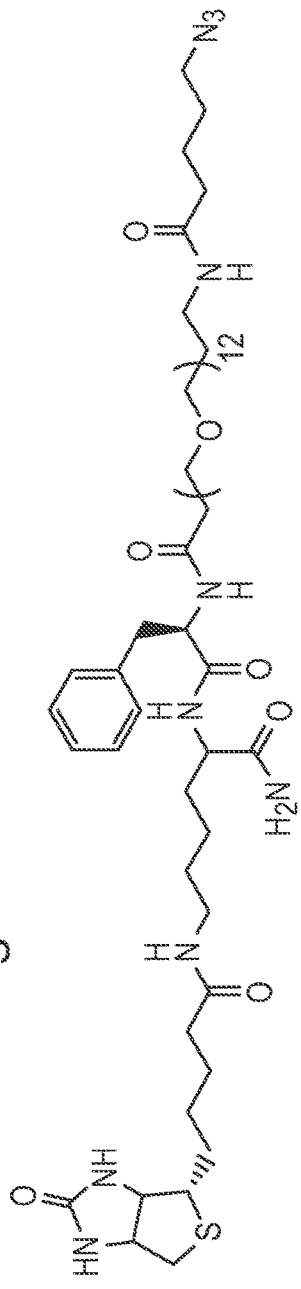
FIGS. 26A-26C show LC-MS and HPLC characterization of the POC1 peptide segment.
Figure 26C:
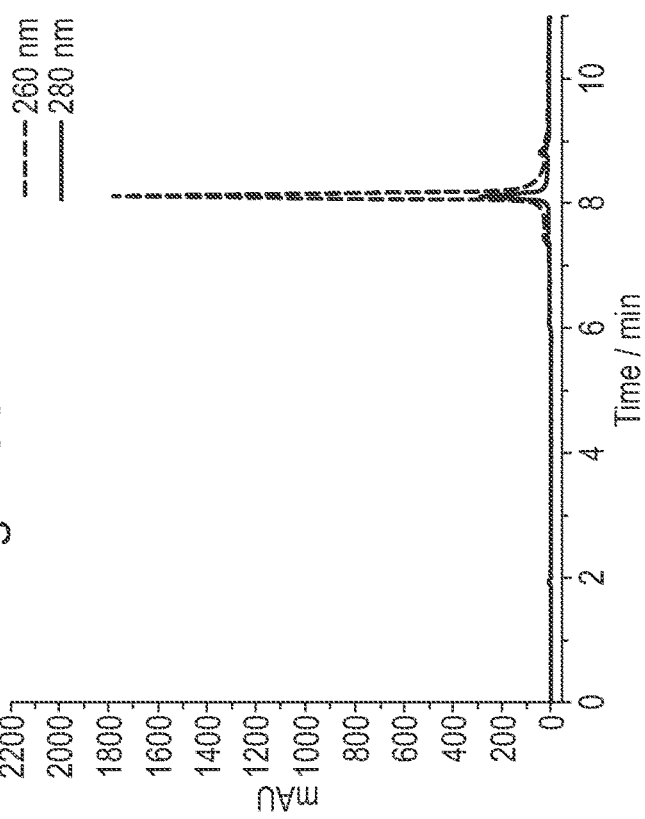
Figure 26B:
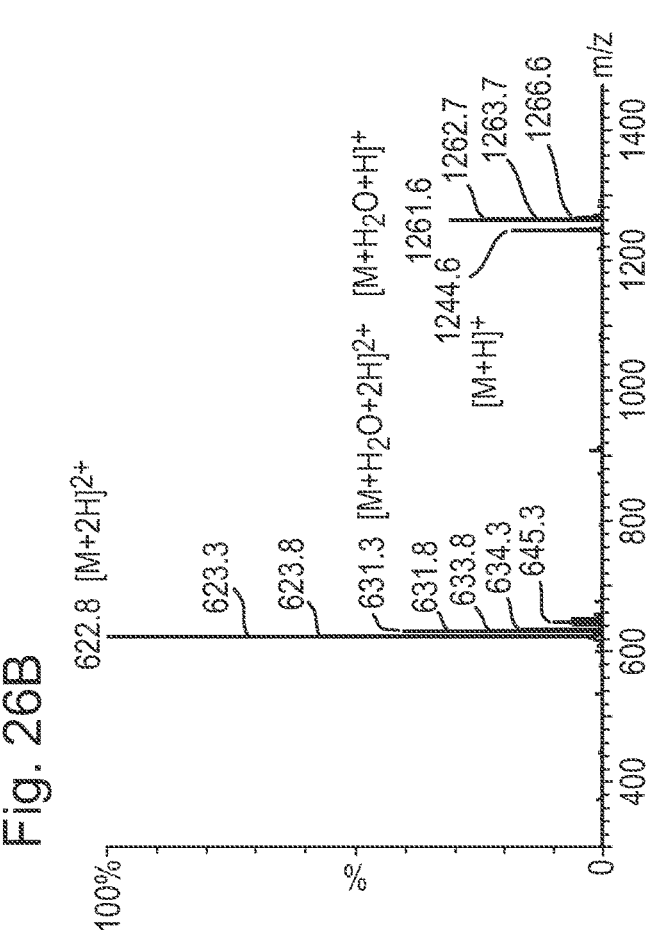
Figure 27A:
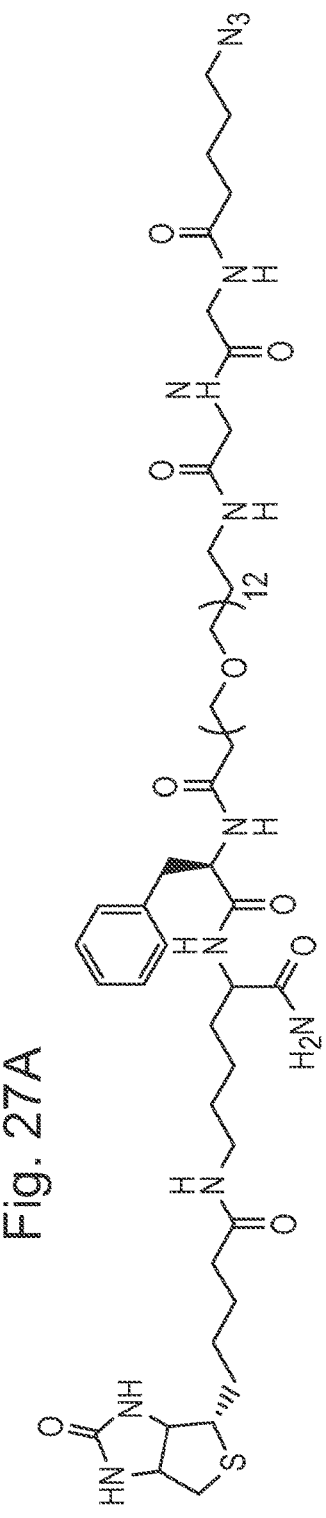
FIGS. 27A-27C show LC-MS and HPLC characterization of the POC2 peptide segment.
Figure 27C:
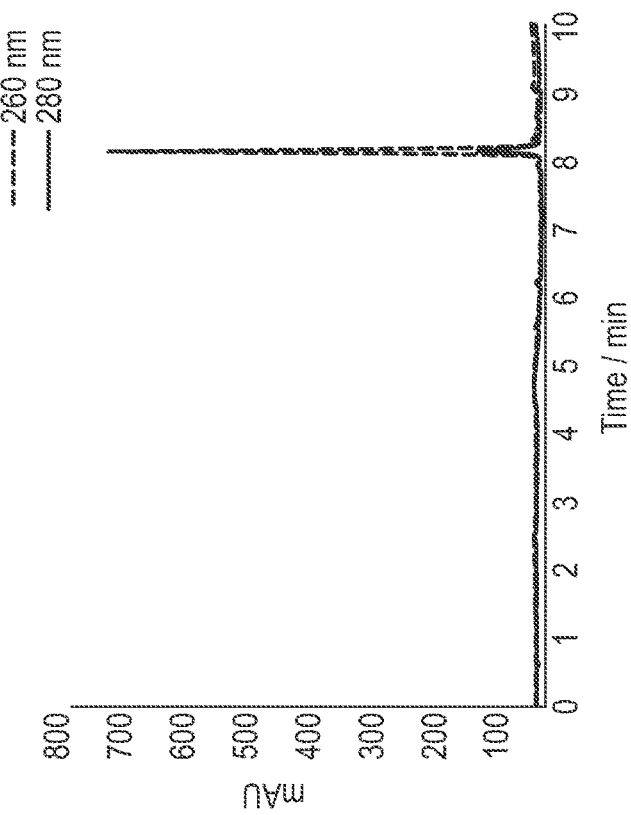
Figure 27B:
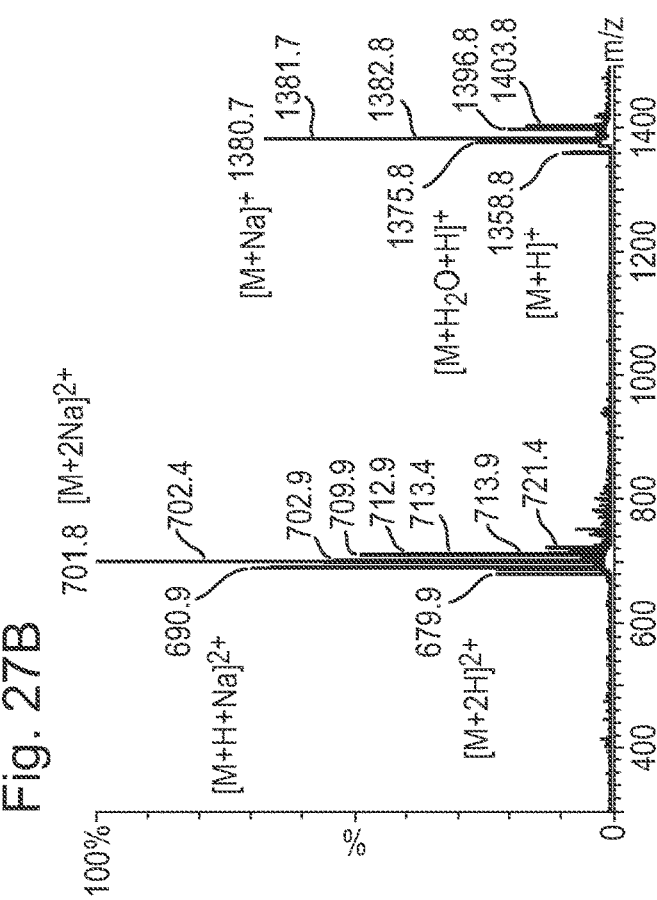

The peptide segments for POC1 and POC2 (FIG. 26a, 27a) were synthesized by using manual solid-phase peptide synthesis, adapted from previously reported protocols[3b]. Peptide segments for POC3 and POC4 were purchased from Peptide Protein Research Ltd.

Peptide elongation was carried out on 0.25 mmol Rink Amide MBHA resin LL (0.37 mmol g-1) by the Fmoc method with HBTU and DIPEA as coupling reagents. The resin was washed and swollen overnight in DMF and Fmoc was removed by treatment with 20% (v/v) piperidine in NMP at room temperature. The peptide segments were assembled through standard chain elongation by using the reactants Nα-Fmoc-Nε-biotinyl-L-lysine, Fmoc-Phe-OH, Fmoc-NH-PEG(12)—COOH, Fmoc-Gly-Gly-OH (for POC2 peptide segment) and 5-azidopentanoic acid. For each of the coupling reactions, a solution of 1.0 mmol reactant, 0.95 mmol HBTU, and 2.0 mmol DIPEA in 1.9 mL DMF was added to the resin, which was then shaken for 12 min. After each coupling, the resin was washed with NMP and capped with 1.5 mmol Ac2O, 0.044 mmol HOBt, and 0.39 mmol DIPEA in 3 mL DMF for 2 min. The capped resin was then washed with NMP again before the next coupling. After the completion of chain assembly, the resin was washed sequentially with DMF and ethanol and dried in vacuo. Peptides were cleaved from the resin by treatment with TFA for 2 h. The TFA was evaporated in a stream of nitrogen and the peptide was precipitated with cold diethyl ether, followed by centrifugation, and several trituration treatments with diethyl ether.

6.3. Peptide Segment Purification and Characterization

The crude peptide segment for POC1 or POC2 was dissolved in DMF and purified by preparative RP-HPLC (Dionex UltiMate 3000; Vydac C18 column: 250×22 mm, 10-15 m (particle size); linear gradient: 5-95% eluant B in eluant A over 45 min, flow rate: 15 mL min-1; eluant A: 0.1% TFA in water; eluant B: 0.1% TFA in acetonitrile). The identity and purity of the fractions were determined by analytical LC-MS (Waters LCT accurate-mass time-of-flight instrument (ESI-positive); Chromolith RP-18e column: 50 mm×2 mm; linear gradient: 5-100% eluant B in eluant A over 8 min, flow rate: 1 mL min-1; eluant A: 0.1% formic acid in water; eluant B: 0.1% formic acid in acetonitrile). The fractions with the correct mass were combined, lyophilized, and characterized by LC-MS and analytical RP-HPLC (Agilent 1260 Infinity HPLC; Polaris C18 column: 150×4.6 mm, 5 m (particle size); linear gradient: 5-95% eluant B in eluant A over 10 min, flow rate: 1 mL min-1; eluant A: 0.1% TFA in water; eluant B: 0.1% TFA in acetonitrile) (FIG. 26b, 26c, 27b, 27c).

See FIGS. 26 and 27

6.4. Generation and Characterization of Macromolecular Substrates

Oligonucleotides modified with dibenzocyclooctyne-disulfide (DBCO-SS) at the 5' terminus were purchased from biomers.net.

Figure 28:
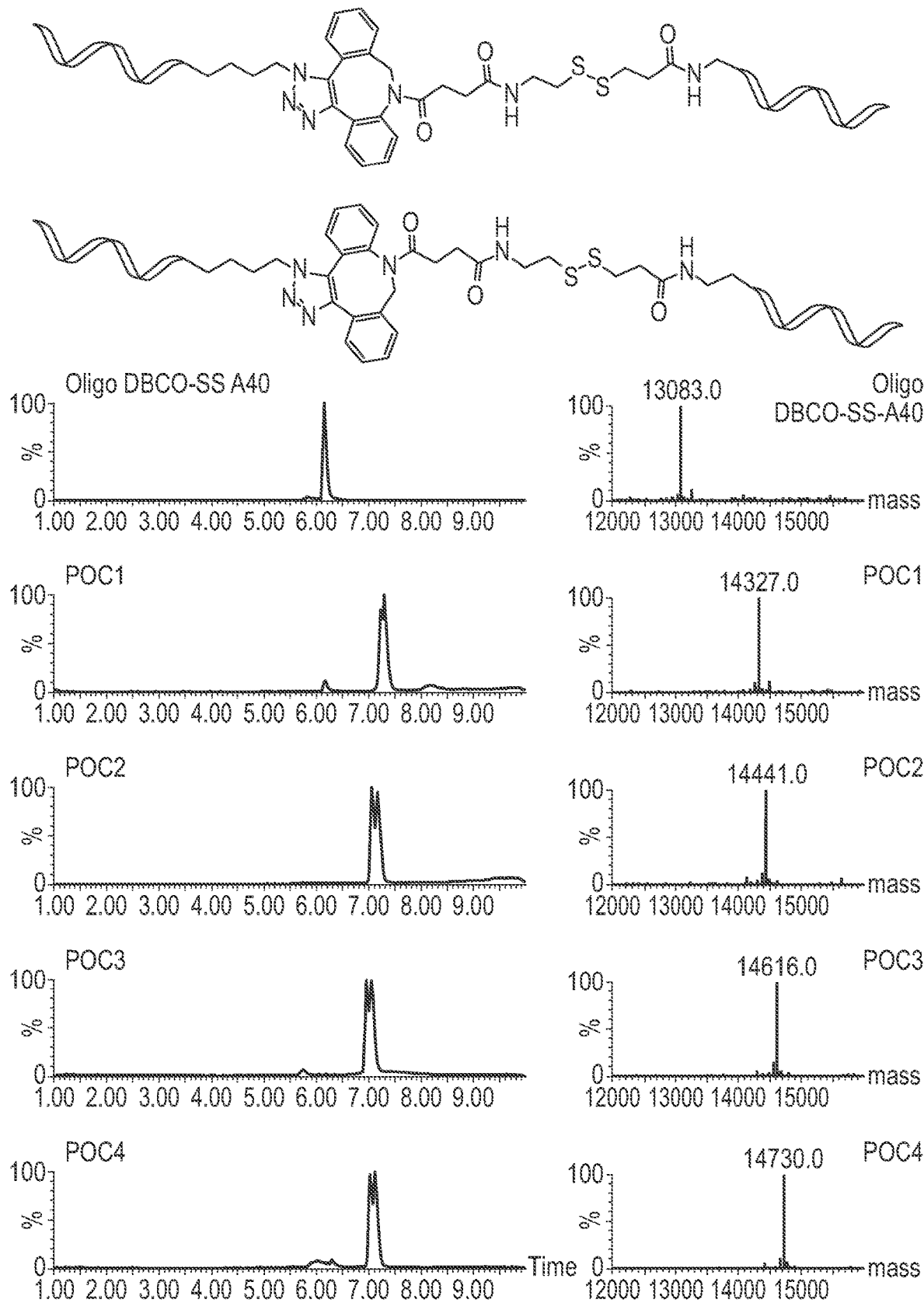
FIG. 28 shows LC-MS characterization of macromolecular substrates POC1-4. The two peaks in each chromatogram have the same mass, corresponding to the two regioisomeric conjugates formed by the copper-free click chemistry between the peptide segment (blue) and the oligonucleotide (green). The mass of POC1 was calculated to be 14327 g mol-1 and found to be 14327 g mol-1. The mass of POC2 was calculated to be 14440 g mol-1 and found to be 14441 g mol-1. The mass of POC3 was calculated to be 14615 g mol-1 and found to be 14616 g. The mass of POC4 was calculated to be 14729 g mol-1 and found to be 14730 g mol-1. Results are described in Example 2.

5' DBCO-SS-A40 oligo (10 μL, 1 mM in MilliQ water) was added to each peptide segment (1 μL, 10 mM in MilliQ water). The mixtures were left at room temperature for 30 min to form the peptide-oligo conjugates (POC1-4) by a copper-free click reaction (FIG. 28).

The conjugates were purified by semi-preparative HPLC (Agilent 1260 Infinity; Supelco Discovery BIO Wide Pore C18 column: 250×10 mm, 10 m; linear gradient: 10-90% eluant B in eluant A over 30 min, flow rate: 4.5 mL min-1; eluant A: 0.1% TFA in water; eluant B: 0.1% TFA in acetonitrile) and identified by LC-MS (UPLC-MS Waters XEVO G2-QTOF (ESI-negative); ACQUITY UPLC Oligonucleotide BEH C18 Column: 2.1 mm×50 mm, 1.7 m (particle size); linear gradient: 0-70% eluant B in eluant A over 8 min, flow rate: 0.2 mL min-1; eluant A: 8.6 mM TEA, 200 mM HFIP in 5% methanol/water (v/v); eluant B: 20% eluant A in methanol).

7. PREPARATION OF CYSTEINE-CONTAINING αHL MONOMERS

The construction of single-cysteine nanoreactors 113, 115, 117, 119, 121 and the double-cysteine nanoreactor 115/117 based on pT7-αHL-D8H6, which encodes the wild-type αHL with an octa-aspartate tail and a His-tag at the C terminus, have been previously reported[4b].

Plasmid pT7-αHL-143C-D8H6 encodes an αHL mutant containing a cysteine at position 143 as well as an octa-aspartate tail and a His-tag at the C terminus. It was generated from pT7-αHL-D8H6 by in vivo homologous recombination. Two sets of PCR reactions were carried out. For the first reaction, the template was first linearized by NdeI (New England Biolabs) before PCR with the forward mutagenic primer: 5'-CAAATGTTTCGATTTGTCATACACTGAAATATGTTC-3' (SEQ. ID NO. 16) and the reverse nonmutagenic primer (SC47): 5'-CAGAAGTGGTCCTGCAACTTTAT-3' (SEQ. ID NO. 9). For the second reaction, the template was linearised by HindIII (New England Biolabs) before PCR with the reverse mutagenic primer: 5'-GAACATATTTCAGTGTATGACAAATCGAAACATTTG-3' (SEQ. ID NO. 17) and the forward nonmutagenic primer (SC46): 5'-ATAAAGTTGCAGGACCACTTCTG-3' (SEQ. ID NO. 11). The linearized templates and primers were mixed with 1×Phusion Flash HF Mastermix (New England Biolabs) and put through the following cycling program: 94° C. for 5 min, then 30 cycles of 94° C. (30 s), 50° C. (30 s), 72° C. (30 s), and then 50° C. for 5 min. After PCR, 5 μL of each reaction

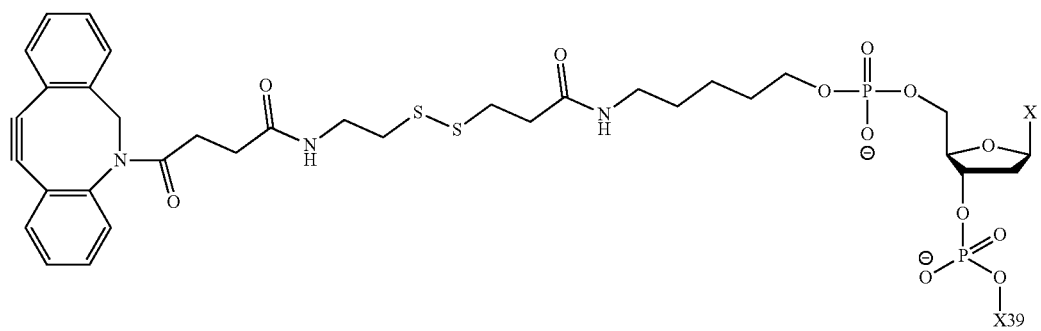

5' DBCO-SS modification were mixed and transformed into *E. coli* XL10-Gold cells (Agilent). The transformed cells were allowed to grow at 37° C. overnight on LB (Luria Broth)-carbenicillin plates. Plasmid DNA was isolated from colonies by using the QIAprep Spin Miniprep Kit (QIAGEN). Successful mutagenesis was confirmed by DNA sequencing. Similarly, pT7-αHL-115C143C-D8H6 was made from pT7-αHL-115C-D8H6 with the same two mutagenic primers. pT7-αHL-123C-D8H6 was made from pT7-αHL-WT-D8H6 with the two mutagenic primers: 5'-CGGATTCAACGGTTGTGT-TACTGGTGATGATACAGG-3' (SEQ. ID NO. 18) (Forward); 5'-CCTGTATCATCACCAGTAACACAACCGTT-GAATCCG-3' (SEQ. ID NO. 19) (Reverse).

8. PREPARATION OF αHL HEPTAMERS CONTAINING CYSTEINE(S) ON ONE OF THE SEVEN SUBUNITS

Engineered αHL polypeptides were expressed by using a commercial in vitro transcription-translation (IVTT) kit: *E. coli* T7 S30 Extract System for Circular DNA (Promega). To suppress transcription by *E. coli* RNA polymerase, the T7 S30 extract provided in the kit was treated with rifampicin prior to use (1 µg mL-1, final concentration). A standard reaction comprised: DNA template (3.2 µg), amino acid mix minus methionine (supplied with the kit, 5 L), S30 premix without amino acids (supplied with the kit, 20 µL), [35S] methionine (2 µL, 1,200 Ci mmol-1, 15 mCi mL-1, MP Biomedicals), T7 S30 extract (supplied with the kit. 15 L), and nuclease-free water to a final volume of 50 µL. To make heteroheptamers, a mixture of plasmids encoding the WT αHL and the mutant monomer were mixed in a ratio 6:1 (WT: mutant). The IVTT mixture was incubated at 37° C. for 1 h.

Heptamerization was carried out by the addition of rabbit erythrocyte membranes (3 µL, ~1 mg protein mL-1) to the IVTT reaction mixture (50 µL), followed by incubation at 37° C. for another 1 h. The mixture was then centrifuged for 10 min at 25,000×g. The supernatant was removed and the pellet resuspended in MBSA buffer (200 µL, 10 mM 3-morpholinopropane-1-sulfonic acid (MOPS), 150 mM NaCl, 1 mg mL-1 bovine serum albumin, pH 7.4). The wash with MBSA was repeated before the pellet was resuspended in 2× Laemmli sample buffer (50 L) and electrophoresed in a 5% SDS polyacrylamide gel at 70 V for 15 h.

The αHL heteroheptamers containing different numbers of mutant subunits were separated in the gel based on their different electrophoretic mobilities, which were determined by the number of octa-aspartate (D8) tails[5b]. The top and bottom bands corresponded to WT7 and (mutant-D8H6)7, respectively. The second band from the top was the desired heteroheptamer containing a single mutant subunit.

To extract heptameric pores, the gel was first dried without fixation on Whatman 3M filter paper under vacuum for 5 h at room temperature. After visualization by autoradiography with Kodak BioMax MR film, the desired bands were cut from the gel with a scalpel. Each excised band was rehydrated in TE buffer (300 µL; 10 mM Tris-HCl, 1 mM ethylenediaminetetraacetic acid (EDTA), pH 8.0) for 1 h at room temperature. The filter paper was then removed, and the rehydrated gel was macerated with a pestle. The resulting slurry was filtered through a 0.2 m hydrophilic membrane filter (Proteus Mini Clarification Spin Column, Generon). The filtrate was stored in 10 µL aliquots at −80° C.

9. SINGLE CHANNEL RECORDING

9.1. General 1,2-Diphytanoyl-sn-glycerol-3-phosphocholine (DPhPC) was purchased from Avanti Polar Lipids. Unless otherwise stated, all other chemicals were purchased from Sigma-Aldrich. Planar bilayer recordings were performed following the method established by Montal and Mueller[6b]. Two Delrin compartments were separated by a 25 µm-thick Teflon film containing an aperture (60 m in diameter). The aperture was pre-treated with 1% (v/v) hexadecane in pentane. Each compartment was then filled with buffer (500 µL, 2 M KCl, 20 mM N-(2-hydroxyethyl)piperazine-N'-(4-butanesulfonic acid) (HEPBS), 20 µM EDTA, pH 8.5). The trans compartment contained an additional 5 mM DTT. Drops of DPhPC in pentane (5 mg mL-1) were added to both compartments. Repetitive up-and-down pipetting of the buffer solution resulted in the formation of a lipid bilayer across the aperture. A transbilayer potential was applied with two Ag/AgCl electrodes, each contained within a salt bridge formed from 3 M KCl in 3% (w/v) low-melt agarose.

Ionic currents were recorded by using a patch clamp amplifier (Axopatch 200B, Axon Instruments) with a 4-pole low-pass Bessel filter (80 dB/decade) at room temperature (20±1° C.). Signals were digitized with a Digidata 1320A digitizer (Molecular Devices), connected to a computer running the pCLAMP 10.3 software suite (Molecular Devices). Unless stated otherwise, the signal was filtered with a corner frequency of 5 kHz and sampled at 25 kHz.

9.2. Monitoring Turnovers

The substrate (400 µM in 1 µL MilliQ water) was added to a solution of traptavidin (Kerafast) (40 µM in 10 µL phosphate-buffered saline, pH 7.4) and incubated at room temperature (20±1° C.) for 15 min to form the traptavidin-tagged substrate. The cis compartment of a planar bilayer recording apparatus containing the αHL nanoreactor was stirred until a single pore inserted into the bilayer. The traptavidin-tagged substrate (3 µL, 36 µM) was then added to the cis compartment, which contained 500 µL of recording buffer (2 M KCl, 20 mM HEPBS, 20 M EDTA, pH 8.5). The trans compartment contained an additional 5 mM DTT. To drive the macromolecular substrate into the nanopore, a potential of +150 mV was applied to the trans side. The threaded substrate reduced the current to an Ires % of ~33% (see Table S2 for each substrate-nanoreactor combination). After the thiol-disulfide interchange between the substrate and the nanoreactor, the current increased as one segment of the substrate departed the nanoreactor (I res % of 39%-53% for αHL-oligo adducts and ~24-56% for αHL-peptide adducts, see section 3, Table S2). DTT later released the adduct and returned the nanoreactor to its initial state ready for another round of thiol-disulfide interchange.

9.3. Single-Channel Data Analysis Current traces were idealized by using Clampfit 10.3 (Molecular Devices). The idealized data were analyzed with QuB 2.0 software (www.qub.buffalo.edu)[7b]. Dwell time analysis and rate constant estimations were performed by using the maximum interval likelihood (MIL) algorithm of QuB[8b].

10. REFERENCES

1b. Luchian, T., Shin, S.-H. & Bayley, H. Single-molecule covalent chemistry with spatially separated reactants. *Angew. Chem. Int. Ed.* 42, 3766-71 (2003).
2b. Singh, R. & Whitesides, G. M. Thiol-disulfide interchange. in *Sulphur-Containing Functional Groups* 633-658 (John Wiley & Sons, Inc., 1993).

3b. Lee, J. et al. Semisynthetic nanoreactor for reversible single-molecule covalent chemistry. *ACS Nano* 10, 8843-8850 (2016).

4b. Pulcu, G. S., Mikhailova, E., Choi, L.-S. & Bayley, H. Continuous observation of the stochastic motion of an individual small-molecule walker. *Nat. Nanotechnol.* 10, 76-83 (2015).

5b. Miles, G., Bayley, H. & Cheley, S. Properties of *Bacillus cereus* hemolysin II: A heptameric transmembrane pore. *Protein Sci.* 11, 1813-1824 (2009).

6b. Montal, M. & Mueller, P. Formation of bimolecular membranes from lipid monolayers and a study of their electrical properties. *Proc. Natl. Acad. Sci. U.S.A* 69, 3561-3566 (1972).

7b. Nicolai, C. & Sachs, F. Solving ion channel kinetics with the QuB software. *Biophys. Rev. Lett.* 08, 191-211 (2013).

8b. Qin, F., Auerbach, A. & Sachs, F. Estimating single-channel kinetic parameters from idealized patch-clamp data containing missed events. *Biophys. J.* 70, 264-280 (1996).

The invention claimed is:

1. A method of moving a molecular hopper along a track, wherein:
   (a) the track comprises a plurality of primary functional groups aligned along a substrate,
   (b) the hopper comprises a secondary functional group capable of binding to each of the plurality of primary functional groups on the track, and
   (c) the hopper comprises a cargo moiety,
and wherein the method comprises the steps of:
   (i) contacting the hopper with the track such that the secondary functional group of the hopper binds to a first primary functional group on the track, and
   (ii) applying a driving force so as to cause the hopper to be directionally transferred from the first primary functional group to a second primary functional group on the track, thereby causing the hopper to move along the track.

2. The method of claim 1, wherein the direction of the driving force relative to the track determines the direction of the movement of the hopper along the track.

3. The method of claim 1, wherein the transfer of the hopper from the first primary functional group to the second primary functional group on the track is independent of the addition of exogenous fuel.

4. The method of claim 1, wherein step (ii) comprises applying a driving force to the hopper so as to cause the hopper to be sequentially transferred between each of the plurality of primary functional groups on the track, thereby causing the hopper to move along the track.

5. The method of claim 1, wherein the substrate is an organic or inorganic surface comprising plurality of primary functional groups.

6. The method of claim 1, wherein the substrate is a surface of a transmembrane pore.

7. The method of claim 6, wherein the transmembrane pore is a protein nanopore, a solid state nanopore, a DNA nanopore, a polymer nanopore, or a synthetic or semi-synthetic nanopore.

8. The method of claim 7, wherein the track comprises an array of natural and/or unnatural amino acid residues comprised in the barrel and/or lumen of a transmembrane β-barrel protein nanopore, wherein each amino acid residue in the track comprises a primary functional group.

9. The method of claim 8, wherein the track comprises an array of amino acid residues evenly spaced along one or more β-strands in the barrel of a transmembrane β-barrel protein nanopore, wherein each amino acid residue in the track comprises a primary functional group.

10. The method of claim 1, wherein the hopper comprises a linking moiety between the secondary functional group and the cargo moiety.

11. The method of claim 10, wherein the linking moiety comprises an unsubstituted or substituted alkylene, alkenylene, alkynylene, arylene, heteroarylene, carbocyclylene, or heterocyclylene moiety, wherein an alkylene, alkenylene, or alkynylene moiety may be uninterrupted or interrupted by or terminate in one or more atoms or groups selected from the group consisting of: O, N(R), S, C(O), C(O)NR, C(O)O, phosphate, thiophosphate, dithiophosphate, selenophosphate, diselenophosphate, unsubstituted or substituted arylene, unsubstituted or substituted heteroarylene, unsubstituted or substituted carbocyclylene, and unsubstituted or substituted heterocyclylene, wherein R is selected from the group consisting of: H, unsubstituted or substituted alkyl, and unsubstituted or substituted aryl.

12. The method of claim 1, wherein the cargo moiety is a polynucleotide, a polypeptide, or a polysaccharide.

13. The method of claim 1, wherein the secondary functional group of the hopper is capable of forming a chemical bond with each of the primary functional groups on the track.

14. The method of claim 13, wherein the chemical bond is a disulfide bond, a diselenide bond, or a sulfide-selenide bond.

15. The method of claim 1, wherein the substrate is a surface of a protein nanopore and the track comprises an array of amino acid residues comprised in the protein nanopore, wherein each amino acid residue of the track comprises a reactive side chain bearing a primary functional group, and wherein the secondary functional group of the hopper is capable of forming a covalent bond with each of the primary functional groups of the reactive side chains of the amino acid residues of the track.

16. The method of claim 1, wherein prior to contacting the hopper with the track the hopper is attached to a positioning moiety, wherein the positioning moiety positions the hopper relative to the track such that the first primary functional group on the track binds to the secondary functional group on the hopper.

17. The method of claim 16, wherein:
the substrate is a surface of a transmembrane pore,
prior to contacting the hopper with the track the secondary functional group of the hopper is attached to a positioning moiety, and
the positioning moiety comprises a blocking entity for preventing passage of the hopper through the transmembrane pore,
and wherein step (i) of the method comprises contacting the hopper with the pore such that the blocking entity prevents passage of the hopper through the pore so as to hold the positioning moiety in a position such that the first primary functional group on the track binds to the secondary functional group on the hopper, thereby releasing the positioning moiety from the secondary functional group.

18. The method of claim 17, wherein the blocking entity comprises or consists of a protein, a nanoparticle, or a polymer.

19. The method of claim 1, the method further comprising after movement of the hopper along the track, the step of (iii) contacting the primary functional group of the track bonded to the secondary functional group of the hopper with a tertiary functional group on the substrate such that the tertiary functional group bonds to the primary functional group, thereby displacing the secondary functional group and so releasing the hopper.

20. The method of claim 19, wherein the substrate is a surface of a protein nanopore and the track comprises an array of amino acid residues comprised in the protein nanopore, wherein each amino acid residue of the track comprises a reactive side chain bearing a primary functional group, and wherein the secondary functional group of the hopper is capable of forming a covalent bond with each of the primary functional groups of the reactive side chains of the amino acid residues of the track,
and wherein the tertiary functional group is a further amino acid residue of the protein nanopore comprising a reactive side chain capable of forming a covalent bond to the reactive side chain of the final amino acid residue of the track, thereby displacing the secondary functional group and so releasing the hopper.

21. The method of claim 20, wherein the amino acid residue comprising the tertiary functional group is separated from the primary functional group of the final amino acid residue in the track by a distance which is less than the distance between primary functional groups on the track.

22. The method of claim 21, wherein adjacent amino acid residues in the track are separated by a distance of from about 5 to about 10 Å and/or wherein the amino acid residue comprising the tertiary functional group is separated from the primary functional group of the final amino acid residue in the track by a distance of less than about 5 Å.

23. The method of claim 1, wherein the driving force is selected from the group consisting of a physical potential, a chemical potential, and an electrical potential.

24. The method of claim 1, further comprising reversing the direction of the driving force relative to the track so as to cause the direction of the movement of the hopper along the track to be reversed.

25. A method of chemical communication across a barrier spanned by a track, the method comprising contacting the track with a molecular hopper under conditions such that the hopper moves along the track as defined in claim 1, thereby moving the hopper across the barrier, and wherein the movement of the hopper conveys information across the barrier.

26. The method of claim 25, wherein the barrier is (i) a barrier between two or more compartments comprising an aqueous medium or (ii) a barrier between components of a synthetic tissue or synthetic organism.

27. The method of claim 1, wherein the cargo moiety is charged.

28. The method of claim 1, wherein the cargo moiety comprises a polymer.

29. The method of claim 1, wherein the driving force is an electrical potential.

30. The method of claim 1, wherein the driving force is a chemical potential.

31. A product comprising:
(A) a detector,
(B) a track comprising a plurality of primary functional groups aligned along a substrate, and
(C) a molecular hopper comprising a secondary functional group capable of binding to each of the plurality of primary functional groups on the track,
wherein (i) the product is a kit for characterising a peptide, polypeptide, or protein analyte and the hopper is configured for conjugating to the analyte, or (ii) the product is a system and the hopper is conjugated to a peptide, polypeptide, or protein analyte.

32. A molecular hopper comprising:
a secondary functional group for bonding to a primary functional group on a track,
a polynucleotide, polypeptide, or polysaccharide cargo moiety, and
a linking moiety between the secondary functional group and the cargo moiety.

33. The molecular hopper of claim 32, comprising a positioning moiety for positioning the hopper relative to the track such that the first primary functional group on the track can bind to the secondary functional group on the hopper.

* * * * *